US007601505B2

(12) United States Patent
Monahan et al.

(10) Patent No.: US 7,601,505 B2
(45) Date of Patent: Oct. 13, 2009

(54) COMPOSITIONS, KITS, AND METHODS FOR IDENTIFICATION, ASSESSMENT, PREVENTION, AND THERAPY OF BREAST CANCER

(75) Inventors: John E. Monahan, Walpole, MA (US); Sebastian Hoersch, Arlington, MA (US); Dustin L. Anderson, Brighton, MA (US); Wilson O. Endege, Norwood, MA (US); Donna Ford, Plainville, MA (US); Karen Glatt, Natick, MA (US); Bella O. Gorbatcheva, Boston, MA (US); Shubhangi Kamatkar, Newton, MA (US); Yong Yao Xu, Belmont, MA (US); Manjula Gannavarapu, Acton, MA (US); Xumei Zhao, Wayland, MA (US); Robert Schlegel, Auburndale, MA (US); Maureen Mertens, Stow, MA (US); Robert C. Bast, Jr., Houston, TX (US); Gabriel N. Hortobagyi, Bellaire, TX (US); Lajos Pusztai, Pearland, TX (US)

(73) Assignees: Millennium Pharmaceuticals, Inc., Cambridge, MA (US); Board of Regents, The University of Texas Systems, Austin, TX (US)

( * ) Notice: Subject to any disclaimer, the term of this patent is extended or adjusted under 35 U.S.C. 154(b) by 753 days.

(21) Appl. No.: 10/855,588

(22) Filed: May 26, 2004

(65) Prior Publication Data

US 2005/0042642 A1 Feb. 24, 2005

Related U.S. Application Data

(60) Provisional application No. 60/474,281, filed on May 29, 2003, provisional application No. 60/555,557, filed on Mar. 23, 2004.

(51) Int. Cl.
*G01N 33/53* (2006.01)
*C12Q 1/70* (2006.01)

(52) U.S. Cl. .......................................... 435/7.1; 435/5

(58) Field of Classification Search ...................... None
See application file for complete search history.

(56) References Cited

U.S. PATENT DOCUMENTS

| | | | |
|---|---|---|---|
| 5,872,235 | A | 2/1999 | Chen et al. |
| 6,171,816 | B1 | 1/2001 | Yu et al. |
| 2002/0006616 | A1 | 1/2002 | Gish et al. |

FOREIGN PATENT DOCUMENTS

| | | | |
|---|---|---|---|
| WO | WO-00/55629 | A2 | 9/2000 |
| WO | WO-01/63289 | A1 | 8/2001 |
| WO | WO-01/98543 | A2 | 12/2001 |
| WO | WO-02/00690 | A2 | 1/2002 |
| WO | WO-03/000012 | A2 | 1/2003 |
| WO | WO-03/004989 | A2 | 1/2003 |
| WO | WO-03/016471 | A2 | 2/2003 |
| WO | WO-03/029271 | A2 | 4/2003 |
| WO | WO-2004/112829 | A2 | 12/2004 |

OTHER PUBLICATIONS

Duffy et al (Clinical Cancer 2006 52(3):345-351).*
Rudikoff et al (Proc Natl Acad Sci USA 1982 vol. 79 p. 1979).*
Panka et al (Proc Natl Acad Sci USA vol. 85 3080-3084 May 1988).*
Amit et al Science vol. 233 747-753 1986.*
International Search Report Docket No. PCT/US04/16793, dated Nov. 21, 2005.
European Communication for Application No. 04753595.0-2403, dated Mar. 26, 2008.

* cited by examiner

*Primary Examiner*—Christopher H Yaen
(74) *Attorney, Agent, or Firm*—McCarter & English, LLP; Maria Laccotripe Zacharakis; Marcie B. Clarke

(57) ABSTRACT

The invention relates to nucleic acid molecules and proteins associated with breast cancer. Compositions, kits, and methods for detecting, characterizing, preventing, and treating human breast cancers are provided.

24 Claims, No Drawings

COMPOSITIONS, KITS, AND METHODS FOR IDENTIFICATION, ASSESSMENT, PREVENTION, AND THERAPY OF BREAST CANCER

CROSS REFERENCE TO RELATED APPLICATIONS

This application claims the benefit of U.S. Provisional Application No. 60/474,281, filed May 29, 2003, and U.S. Provisional Application No. 60/555,557, filed Mar. 23, 2004, the contents of which are incorporated herein by this reference.

FIELD OF THE INVENTION

The field of the invention is breast cancer, including diagnosis, characterization, management, and therapy of breast cancer.

BACKGROUND OF THE INVENTION

The increased number of cancer cases reported in the United States, and, indeed, around the world, is a major concern. Currently there are only a handful of treatments available for specific types of cancer, and these provide no absolute guarantee of success. In order to be most effective, these treatments require not only an early detection of the malignancy, but a reliable assessment of the severity of the malignancy.

The incidence of breast cancer, a leading cause of death in women, has been gradually increasing in the United States over the last thirty years. In 1997, it was estimated that 181,000 new cases were reported in the U.S., and that 44,000 people would die of breast cancer (Parker et al., 1997, *CA Cancer J. Clin.* 47:5-27; Chu et al., 1996, *J. Nat. Cancer Inst.* 88:1571-1579). While the pathogenesis of breast cancer is unclear, transformation of normal breast epithelium to a malignant phenotype may be the result of genetic factors, especially in women under 30 (Miki et al., 1994, *Science,* 266:66-71). The discovery and characterization of BRCA1 and BRCA2 has recently expanded our knowledge of genetic factors which can contribute to familial breast cancer. Germline mutations within these two loci are associated with a 50 to 85% lifetime risk of breast and/or ovarian cancer (Casey, 1997, *Curr. Opin. Oncol.* 9:88-93; Marcus et al., 1996, *Cancer* 77:697-709). However, it is likely that other, non-genetic factors also have a significant effect on the etiology of the disease. Regardless of its origin, breast cancer morbidity and mortality increases significantly if it is not detected early in its progression. Thus, considerable effort has focused on the early detection of cellular transformation and tumor formation in breast tissue.

Currently, the principal manner of identifying breast cancer is through detection of the presence of dense tumorous tissue. This may be accomplished to varying degrees of effectiveness by direct examination of the outside of the breast, or through mammography or other X-ray imaging methods (Jatoi, 1999, *Am. J Surg.* 177:518-524). The latter approach is not without considerable cost, however. Every time a mammogram is taken, the patient incurs a small risk of having a breast tumor induced by the ionizing properties of the radiation used during the test. In addition, the process is expensive and the subjective interpretations of a technician can lead to imprecision, e.g., one study showed major clinical disagreements for about one-third of a set of mammograms that were interpreted individually by a surveyed group of radiologists. Moreover, many women find that undergoing a mammogram is a painful experience. Accordingly, the National Cancer Institute has not recommended mammograms for women under fifty years of age, since this group is not as likely to develop breast cancers as are older women. It is compelling to note, however, that while only about 22% of breast cancers occur in women under fifty, data suggests that breast cancer is more aggressive in pre-menopausal women.

It would therefore be beneficial to provide specific methods and reagents for the diagnosis, staging, prognosis, monitoring, and treatment of diseases associated with breast cancer, or to indicate a predisposition to such for preventative measures.

SUMMARY OF THE INVENTION

The invention relates to cancer markers (hereinafter "markers" or "markers of the inventions"), which are listed in Table 1 and Table 2. The invention provides nucleic acids and proteins that are encoded by or correspond to the markers (hereinafter "marker nucleic acids" and "marker proteins," respectively). The invention further provides antibodies, antibody derivatives and antibody fragments which bind specifically with such marker proteins and/or fragments of the marker proteins.

The invention also relates to various methods, reagents and kits for diagnosing, staging, prognosing, monitoring and treating breast cancer. In one embodiment, the invention provides a diagnostic method of assessing whether a patient has breast cancer or has higher than normal risk for developing breast cancer, comprising comparing the level of expression of at least one marker of the invention in a patient sample and the normal level of expression of the marker or markers in a control, e.g., a sample from a patient without breast cancer. Elevated expression of the marker or markers in the patient sample can be indicative of a patient having or at risk for developing breast cancer.

In another embodiment, the invention provides a diagnostic method of assessing whether a patient has an aggressive breast tumor or is likely to develop an aggressive breast tumor, comprising comparing the level of expression of at least one marker of the invention in a patient sample and the level of expression of the marker in a sample from a control subject having an indolent breast tumor or no breast tumor. Elevated expression of the marker can be indicative of aggressive breast cancer.

Thus, the methods of the present invention can be of use in identifying patients having an enhanced risk of developing breast cancer (e.g., patients having a familial history of breast cancer, patients identified as having a mutant oncogene). The methods are also useful diagnostics for assessing whether a patient has an aggressive breast cancer or is likely to develop an aggressive breast tumor.

The methods of the present invention may be useful in predicting the specific stage of breast cancer, as well as in assessing whether the cancer has metastasized (e.g., metastasis to the lymph nodes). Still further, the methods of the present invention are also useful in predicting the clinical outcome for a patient with breast cancer, or for a patient who has undergone therapy to eradicate breast cancer. Additionally, the methods of the present invention are also useful in assessing the efficacy of treatment of a breast cancer patient (e.g., the efficacy of chemotherapy).

According to the invention, the markers are selected such that the positive predictive value of the methods of the invention is at least about 10%, preferably about 25%, more preferably about 50% and most preferably about 90%. Also preferred are embodiments of the method wherein the marker is over-expressed by at least five-fold in at least about 15% of breast cancer patients (including, e.g., stage 0 breast cancer patients, stage I breast cancer patients, stage IIA breast cancer patients, stage IIB breast cancer patients, stage IIIA breast cancer patients, stage IIIB breast cancer patients, stage IV breast cancer patients, grade I breast cancer patients, grade II breast cancer patients, grade III breast cancer patients, malignant breast cancer patients, ductal carcinoma breast cancer patients, and lobular carcinoma breast cancer patients, and any other types of cancers, malignancies and transformations associated with the breast) as compared to normal non-breast cancer patients.

In one aspect, a diagnostic method of assessing whether a patient is afflicted with breast cancer (e.g., new detection "screening," detection of recurrence, reflex testing) is provided. Such method comprises comparing the level of expression of at least one marker listed in Table 1 in a sample from the patient, and the level of expression of the marker or markers in a control subject not having breast cancer. A significantly higher level of expression of the marker in the patient sample, as compared to the level in the control subject, is an indication that the patient is afflicted with breast cancer.

The invention additionally provides a diagnostic method for assessing whether a patient is afflicted with an aggressive breast cancer, comprising the steps of:

determining the level of expression of at least one marker in a patient sample, wherein the marker is selected from the group consisting of the markers listed in Table 2;

determining the level of expression of the marker or markers in a sample from a control subject having an indolent breast tumor or no breast tumor; and comparing the level of expression of the marker in the patient sample and in the sample from a control subject. A significantly higher level of expression of the marker or markers in the patient sample, as compared to the level in the sample from the control subject, is an indication that the patient has an aggressive breast cancer or is likely to develop an aggressive breast tumor. No difference in expression between the patient sample and the control sample, or a significantly lower level of expression in the patient sample, as compared to the control level, indicates that the patient has an indolent breast cancer.

The invention further provides a diagnostic method of assessing whether a patient is afflicted with a breast cancer which has metastasized or is likely to metastasize, the method comprising comparing the level of expression of at least one marker listed in Table 2 in a sample from the patient, and the level of expression of the marker or markers in a sample from a control subject having a non-metastasized breast tumor or no breast tumor. A significantly higher level of expression in the patient sample as compared to the level in the sample from the control subject is an indication that the breast cancer has metastasized or is likely to metastasize.

In another embodiment, the present invention includes a method for determining whether a patient has breast cancer that has metastasized to lymph nodes, or is likely to metastasize to lymph nodes, the method comprising comparing the level of expression of a marker listed in Table 2 in a sample from the patient, and the level of expression in a sample from a control subject having a non-metastasized breast tumor or no breast tumor. A significantly higher level of expression in the patient sample as compared to the level in the sample from the control subject, is an indication that the patient is afflicted with metastatic breast cancer that has metastasized to lymph nodes, or is likely to metastasize to lymph nodes.

The invention also provides a method for predicting the clinical outcome of a breast cancer patient, comprising comparing the level of expression of at least one marker listed in Table 2 in a sample from the patient and the level of expression of the marker or markers in a sample for a control subject having a good clinical outcome (e.g., a former breast cancer patient having greater than five years of disease free survival level). A significantly higher level of expression in the patient sample as compared to the expression level in the sample from the control subject is an indication that the patient has a poor outcome (e.g., less than three years of disease free survival).

The invention also provides methods for assessing the efficacy of a therapy for inhibiting breast cancer in a patient. Such methods comprise comparing expression of at least one marker of the invention in a first sample obtained from the patient prior to providing at least a portion of the therapy to the patient, and expression of the marker or markers in a second sample obtained from the patient following provision of the portion of the therapy. A significantly lower level of expression of the marker or markers in the second sample relative to that in the first sample is an indication that the therapy is efficacious for inhibiting breast cancer in the patient.

It will be appreciated that in these methods the "therapy" may be any therapy for treating breast cancer including, but not limited to, chemotherapy, radiation therapy, surgical removal of tumor tissue, gene therapy and biologic therapy, such as the administering of antibodies and chemokines. Thus, the methods of the invention may be used to evaluate a patient before, during and after therapy, for example, to evaluate the reduction in tumor burden.

In a preferred embodiment, the methods are directed to therapy using a chemical or biologic agent. These methods comprise comparing expression of at least one marker of the invention in a first sample obtained from the patient and maintained in the presence of the chemical or biologic agent, and expression of the marker in a second sample obtained from the patient and maintained in the absence of the agent. A significantly lower level of expression of the marker or markers in the second sample relative to that in the first sample is an indication that the agent is efficacious for inhibiting breast cancer, in the patient. In certain embodiments, the first and second samples can be portions of a single sample obtained from the patient, or portions of pooled samples obtained from the patient.

The invention additionally provides a monitoring method for assessing progression of breast cancer in a patient, the method comprising:

detecting in a sample from the patient at a first time point, the expression of at least one marker of the invention;

repeating the detection of expression step at a subsequent time point in time; and comparing the level of expression detected in the first and second detection steps, thereby monitoring the progression of breast cancer in the patient. A significantly higher level of expression of the marker in the sample at the subsequent time point from that of the sample at the first time point is an indication that the breast cancer has progressed in the patient, whereas a significantly lower level of expression is an indication that the breast cancer has regressed. In one embodiment, the patient has undergone surgery to remove a tumor between the first point in time and the subsequent point in time.

The invention moreover provides a test method for selecting a candidate composition for inhibiting breast cancer in a patient. This method comprises the steps of obtaining a sample comprising cancer cells from the patient;

separately maintaining at least one sample comprising cancer cells from the patient in the presence of at least one test composition;

comparing expression of at least one marker of the invention in each of the aliquots; and selecting a test composition as a candidate composition for inhibition of breast cancer where the composition significantly reduces the level of expression of at least one marker of the invention in the aliquot containing that test composition, relative to the levels of expression of the marker in the presence of the other test compositions.

The invention additionally provides a test method of assessing the breast carcinogenic potential of a compound. This method comprises the steps of: maintaining separate aliquots of breast cells in the presence and absence of a compound; and comparing expression of a marker of the invention in each of the aliquots. A significantly higher level of expression of the marker in the aliquot maintained in the presence of the compound, relative to that of the aliquot maintained in the absence of the compound, is an indication that the compound possesses breast carcinogenic potential.

In addition, the invention further provides a method of inhibiting breast cancer in a patient. This method comprises the steps of:

obtaining a sample comprising cancer cells from a patient;

separately maintaining at least one sample comprising cancer cells from a patient in the presence of a test composition;

comparing expression of a marker of the invention in each of the aliquots;

identifying a composition as an inhibitor of breast cancer where the composition significantly lowers the level of expression of a marker of the invention in the aliquot containing the composition relative to the levels of expression of the marker in the presence of the other compositions; and administering to the patient at least one of the compositions which are identified as an inhibitor of breast cancer.

According to the invention, the level of expression of a marker of the invention in a sample can be assessed, for example, by detecting the presence in the sample of:

the corresponding marker protein (e.g., a protein having any one of the sequences of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, and SEQ ID NO: 96) or a fragment of the protein (e.g., by using a reagent, such as an antibody, an antibody derivative, an antibody fragment or single-chain antibody, which binds specifically with the protein or protein fragment);

the corresponding marker nucleic acid (e.g., a nucleotide transcript having one of the sequences of the SEQ ID NOs (e.g., SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, and SEQ ID NO: 95), or a complement thereof), or a fragment of the nucleic acid (e.g., by contacting transcribed polynucleotides obtained from the sample with a substrate having affixed thereto one or more nucleic acids having the entire or a segment of the sequence of any of the SEQ ID NOs (e.g., SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, and SEQ ID NO: 95)), or a complement thereof, or a metabolite which is produced directly (i.e., catalyzed) or indirectly by the corresponding marker protein.

According to the invention, any of the aforementioned methods may be performed using or detecting a plurality (e.g., 2, 3, 5, or 10 or more) of breast cancer markers, including a combination of the provided markers of the invention with additional breast cancer markers known in the art. In such methods, the level of expression in the sample of each of a plurality of markers, at least one of which is a marker of the invention, is compared with the normal level of expression of each of the plurality of markers in samples of the same type obtained from control humans not afflicted with breast cancer. A significantly altered (i.e., increased or decreased as specified in the described methods using a single marker) level of expression in the sample of one or more markers of the invention, or some combination thereof, relative to that marker's corresponding normal or control level, is an indication that the patient is afflicted with breast cancer. For all of the aforementioned methods, the marker(s) are preferably selected such that the positive predictive value of the method is at least about 10%.

In a further aspect, the invention provides an antibody, an antibody derivative, or an antibody fragment, which binds specifically with a marker protein (e.g., a protein having the sequence of any of SEQ ID NO: 2, SEQ ID NO: 4, SEQ ID NO: 6, SEQ ID NO: 8, SEQ ID NO: 10,. SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, and SEQ ID NO: 96) or a fragment of the protein. The invention also provides methods for making such antibody, antibody derivative, and antibody fragment. Such methods may comprise immunizing a mammal with a protein or peptide comprising the entirety, or a segment of 10 or more amino acids, of a marker protein (e.g., a protein having the sequence of any of SEQ ID NO:2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, and SEQ ID NO: 96), wherein the protein or peptide may be obtained from a cell or by chemical synthesis. The methods of the invention also encompass producing monoclonal and single-chain antibodies, which would further comprise isolating splenocytes from the immunized mammal, fusing the isolated splenocytes with an immortalized cell line to form hybridomas, and screening individual hybridomas for those that produce an antibody that binds specifically with a marker protein or a fragment of the protein.

In another aspect, the invention relates to various diagnostic and test kits. In one embodiment, the invention provides a kit for assessing whether a patient is afflicted with a breast tumor. In another aspect, the kit may be used for assessing whether a patient is at risk of developing a breast tumor. The kit comprises a reagent for assessing expression of at least one marker of the invention. Yet another embodiment provides a kit which may be used for assessing whether a patient is afflicted with an aggressive breast tumor. The kit comprises a reagent for assessing expression of at least one marker of the invention. In another embodiment, the invention provides a kit for assessing the suitability of a chemical or biologic agent for inhibiting breast cancer in a patient. Such a kit comprises reagents for assessing expression of at least one marker of the invention, and may also comprise one or more of such agents. In a further embodiment, the invention provides kits for assessing the presence of breast cancer cells or treating breast cancers. Such kits may comprise an antibody, an antibody derivative, or an antibody fragment, which binds specifically with a marker protein, or a fragment of the protein. Such kits may also comprise a plurality of antibodies, antibody derivatives, or antibody fragments wherein the plurality of such antibody agents binds specifically with a marker protein, or a fragment of the protein.

In an additional embodiment, the invention provides a kit for assessing the presence of breast cancer cells, wherein the kit comprises at least one nucleic acid probe that binds specifically with at least one marker nucleic acid or a fragment of the nucleic acid. The kit may further comprise a plurality of probes, wherein each of the probes binds specifically with a marker nucleic acid, or a fragment of the nucleic acid.

In a further aspect, the invention relates to methods for treating a patient afflicted with breast cancer or at risk of developing breast cancer. Such methods may comprise reducing the expression and/or interfering with the biological function of at least one marker of the invention. In one embodiment, the method comprises providing to the patient an antisense oligonucleotide or polynucleotide complementary to a marker nucleic acid, or a segment thereof. For example, an antisense polynucleotide may be provided to the patient through the delivery of a vector that expresses an anti-sense polynucleotide of a marker nucleic acid or a fragment thereof. In another embodiment, the method comprises providing to the patient an antibody, an antibody derivative, or antibody fragment, which binds specifically with a marker protein or a fragment of the protein. In a preferred embodiment, the antibody, antibody derivative or antibody fragment binds specifically with a protein having the sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, and SEQ ID NO: 96, or a fragment of the protein.

It will be appreciated that the methods and kits of the present invention may also include known cancer markers including known breast cancer markers. It will further be appreciated that the methods and kits may be used to identify cancers other than breast cancer.

In another aspect the invention features nucleic acid molecules which encode marker proteins or marker polypeptides, e.g., a biologically active portion of the marker protein. In a preferred embodiment, the isolated nucleic acid molecules encode marker polypeptides having the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, and SEQ ID NO: 96. In other embodiments, the invention provides isolated marker nucleic acid molecules having the nucleotide sequences shown in any one selected from SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, or SEQ ID NO: 95. In still other embodiments, the invention provides nucleic acid molecules that are substantially identical (e.g., naturally occurring allelic variants) to the nucleotide sequences shown in SEQ ID NO: 1, SEQ ID NO: 3, SEQ ID NO: 5, SEQ ID NO: 7, SEQ ID NO: 9, SEQ ID NO: 1, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, or SEQ ID NO: 95. In other embodiments, the invention provides nucleic acid molecules which hybridize under stringent hybridizatlon conditions as described herein to nucleic acid molecules comprising the nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, and SEQ ID NO: 95, wherein the nucleic acid encodes a full length marker protein or an active fragment thereof.

In a related aspect, the invention further provides nucleic acid constructs which include marker nucleic acid molecules described herein. In certain embodiments, the nucleic acid molecules of the invention are operatively linked to native or heterologous regulatory sequences. Also included are vectors and host cells containing marker nucleic acid molecules of the invention e.g., vectors and host cells suitable for producing polypeptides.

In another related aspect, the invention provides nucleic acid fragments suitable as primers or hybridization probes for the detection of marker-encoding nucleic acids.

In still another related aspect, isolated nucleic acid molecules that are antisense to a marker encoding nucleic acid molecule are provided.

In other embodiments, the invention provides marker polypeptides, e.g., marker polypeptides having the amino acid sequences shown in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, and SEQ ID NO: 96; an amino acid sequence that is substantially identical to the amino acid sequences shown in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, and SEQ ID NO: 96; or amino acid sequences encoded by nucleic acid molecules having a nucleotide sequence which hybridizes under a stringent hybridization condition as described herein to nucleic acid molecules comprising the nucleotide sequences of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, and SEQ ID NO: 95, wherein the nucleic acid encodes a full length marker protein or an active fragment thereof.

In a related aspect, the invention further provides protein or peptide constructs which include polypeptide molecules described herein. In certain embodiments the marker polypeptides or fragments of the invention are operatively linked to native or heterologous non-marker polypeptide sequences to form fusion protein sequences.

In yet another aspect, the invention features antibodies and antigen-binding fragments thereof, that react with, or more preferably specifically or selectively bind marker polypeptides.

DETAILED DESCRIPTION OF THE INVENTION

The invention relates to newly discovered breast cancer markers set forth in Table 1, associated with the cancerous state of breast cells. It has been discovered that a higher than normal level of expression of any of these markers or combination of these markers correlates with breast cancer in a patient. Additionally, the invention relates to newly discovered breast cancer markers set forth in Table 2, associated with the cancerous state of breast cells. It has been discovered that a higher than normal level of expression of any of these markers or combination of these markers correlates with aggressiveness of breast cancer in a patient. Methods are provided for detecting the presence of breast cancer in a sample, the absence of breast cancer in a sample, the stage of breast cancer, assessing whether a breast cancer has metastasized, predicting the likely clinical outcome of a breast cancer patient, and with other characteristics of breast cancer that are relevant to prevention, diagnosis, characterization, and therapy of breast cancer in a patient. Methods of treating breast cancer are also provided.

Table 1 lists markers of the invention which are over-expressed in breast cancer patient samples compared to non-breast cancer patient samples (e.g., non-breast cancer patient samples, non-cancerous breast cells, other non-breast cancer patient samples). Table 1 lists markers particularly useful in screening for the presence of breast cancer ("screening markers"). Table 2 lists markers of the invention, which are over-expressed in poor outcome breast cancer patient samples compared to normal samples (e.g., good outcome breast cancer patient samples, non-breast cancer patient samples, non-cancerous breast cells). Table 2 lists markers particularly useful in assessing the stage of the breast cancer ("staging markers"). Table 1 and Table 2 provide the sequence listing identifiers of the cDNA sequence of a nucleotide transcript and the amino acid sequence of a protein encoded by or corresponding to each marker, as well as the location of the protein coding sequence within the cDNA sequence. Tables 1 identifies markers of the invention (SEQ ID NOS:1-66) and Table 2 identifies markers of the invention (SEQ ID NOS: 67-96), which are designated with a name ("Marker"), the name the gene is commonly known by, if applicable ("Gene Name"), the Sequence Listing identifier of the cDNA sequence of the nucleotide transcript encoded by or corresponding to the marker ("SEQ ID NO (nts)"), the Sequence Listing identifier of the amino acid sequence of the protein encoded by the nucleotide transcript ("SEQ ID NO (AAs)"), and the location of the protein coding sequence within the cDNA sequence ("CDS").

TABLE 1

Breast Cancer Screening Markers

| Marker | Gene Name | SEQ ID NO (nts) | SEQ ID NO (AAs) | CDS |
|---|---|---|---|---|
| M196A | BCMP11: breast cancer membrane protein 11, variant 1 | 1 | 2 | 48 . . . 548 |
| M725 | BCMP11: breast cancer membrane protein 11, variant 2 | 3 | 4 | 49 . . . 501 |
| M726 | BCMP11: breast cancer membrane protein 11, variant 3 | 5 | 6 | 98 . . . 412 |
| M727 | BCMP11: breast cancer membrane protein 11, variant 4 | 7 | 8 | 49 . . . 465 |
| M156 | CXCL9: chemokine (C-X-C motif) ligand 9 | 9 | 10 | 40 . . . 417 |
| M419 | CXCL10: chemokine (C-X-C motif) ligand 10 | 11 | 12 | 67 . . . 363 |
| M728 | DNAJC1: DNAJ (hsp40) homolog, subfamily C, member 1, variant 1 | 13 | 14 | 244 . . . 1152 |
| M729 | DNAJC1: DNAJ (hsp40) homolog, subfamily C, member 1, variant 2 | 15 | 16 | 244 . . . 1134 |
| M111 | DNAJC1: DNAJ (hsp40) homolog, subfamily C, member 1, variant 3 | 17 | 18 | 108 . . . 1772 |
| M428A | FLJ22774: hypothetical protein FLJ22774 | 19 | 20 | 528 . . . 3053 |
| M149A | LIV-1: LIV-1 protein, estrogen regulated, variant 1 | 21 | 22 | 282 . . . 2549 |
| M730 | LIV-1: LIV-1 protein, estrogen regulated, variant 2 | 23 | 24 | 309 . . . 1751 |
| M158A | MMP11: matrix metalloproteinase 11 (stromelysin 3) | 25 | 26 | 23 . . . 1489 |
| M165A | NPY1R: neuropeptide Y receptor Y1, variant 1 | 27 | 28 | 272 . . . 1426 |
| M731 | NPY1R: neuropeptide Y receptor Y1, variant 2 | 29 | 30 | 241 . . . 1005 |
| M732 | NPY1R: neuropeptide Y receptor Y1, variant 3 | 31 | 32 | 272 . . . 700 |
| M235 | NY-BR-1: breast cancer antigen NY-BR-1 | 33 | 34 | 100 . . . 4125 |
| M56A | OSF-2: osteoblast specific factor 2 (fasciclin I-like), variant 1 | 35 | 36 | 12 . . . 2522 |
| M733 | OSF-2: osteoblast specific factor 2 (fasciclin I-like), variant 2 | 37 | 38 | 12 . . . 2438 |
| M734 | OSF-2: osteoblast specific factor 2 (fasciclin I-like), variant 3 | 39 | 40 | 12 . . . 2441 |
| M735 | OSF-2: osteoblast specific factor 2 (fasciclin I-like), variant 4 | 41 | 42 | 12 . . . 2357 |
| M491A | OSF-2: osteoblast specific factor 2 (fasciclin I-like), variant 5 | 43 | 44 | 12 . . . 2351 |
| M736 | OSF-2: osteoblast specific factor 2 (fasciclin I-like), variant 6 | 45 | 46 | 12 . . . 2267 |
| M737 | OSF-2: osteoblast specific factor 2 (fasciclin I-like), variant 7 | 47 | 48 | 12 . . . 2261 |
| M738 | OSF-2: osteoblast specific factor 2 (fasciclin I-like), variant 8 | 49 | 50 | 12 . . . 2177 |
| M562 | PIP: prolactin-induced protein | 51 | 52 | 37 . . . 477 |
| M96A | SCUBE2: signal peptide, CUB domain, EGF-like 2, variant 1 | 53 | 54 | 81 . . . 3077 |
| M739 | SCUBE2: signal peptide, CUB domain, EGF-like 2, variant 2 | 55 | 56 | 81 . . . 2837 |
| M740 | SCUBE2: signal peptide, CUB domain, EGF-like 2, variant 3 | 57 | 58 | 81 . . . 2699 |
| M741 | SCUBE2: signal peptide, CUB domain, EGF-like 2, variant 4 | 59 | 60 | 81 . . . 3164 |
| M242 | TFF1: trefoil factor 1 (breast cancer, estrogen-inducible sequence expressed in) | 61 | 62 | 41 . . . 295 |
| M716 | WFDC2: WAP four-desulfide core domain 2, variant 1 | 63 | 64 | 28 . . . 402 |
| M717 | WFDC2: WAP four-desulfide core domain 2, variant 2 | 65 | 66 | 67 . . . 288 |

TABLE 2

Breast Cancer Staging Markers

| Marker | Gene Name | SEQ ID NO (nts) | SEQ ID NO (AAs) | CDS |
|---|---|---|---|---|
| M672A | ASS: argininosuccinate synthetase | 67 | 68 | 81 . . . 1319 |
| M675A | CAB2: hypothetical protein MGC9753 | 69 | 70 | 18 . . . 980 |
| M367 | CD24: CD24 antigen (small cell lung carcinoma cluster 4 antigen) | 71 | 72 | 57 . . . 299 |
| M514 | DARPP-32: dopamine and cAMP regulated phosphoprotein, (PPP1R1B: protein phosphatase 1, regulatory (inhibitor) subunit 1B), variant 1 | 73 | 74 | 236 . . . 742 |
| M708 | DARPP-32: dopamine and cAMP regulated phosphoprotein, (PPP1R1B: protein phosphatase 1, regulatory (inhibitor) subunit 1B), variant 2 | 75 | 76 | 468 . . . 1082 |
| M709 | FACL2: fatty-acid-Coenzyme A ligase, long-chain 2, variant 1 | 77 | 78 | 124 . . . 2220 |
| M710 | FACL2: fatty-acid-Coenzyme A ligase, long-chain 2, variant 2 | 79 | 80 | 188 . . . 2284 |
| M495 | GSTP1: glutathione S-transferase pi | 81 | 82 | 30 . . . 662 |
| M674 | HN1: hematological and neurological expressed 1 | 83 | 84 | 104 . . . 568 |
| M234A | MGC14832: hypothetical protein MGC14832 | 85 | 86 | 8 . . . 355 |
| M408 | NDRG1: N-myc downstream regulated protein | 87 | 88 | 111 . . . 1295 |
| M711 | ORMDL3: ORM1-like 3 (*S. cerevisiae*) | 89 | 90 | 301 . . . 762 |
| M678A | PSMB9: proteasome subunit, beta type, 9 | 91 | 92 | 52 . . . 711 |
| M421A | SERHL: kraken-like | 93 | 94 | 103 . . . 1047 |
| M185A | SLPI: secretory leukocyte protease inhibitor (antileukoproteinase) | 95 | 96 | 23 . . . 421 |

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

A "marker" is a gene whose altered level of expression in a tissue or cell from its expression level in normal or healthy tissue or cell is associated with a disease state, such as cancer. A "marker nucleic acid" is a nucleic acid (e.g., mRNA, cDNA) encoded by or corresponding to a marker of the invention. Such marker nucleic acids include DNA (e.g., cDNA) comprising the entire or a partial sequence of any of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, or SEQ ID NO: 95 or the complement of such a sequence. The marker nucleic acids also include RNA comprising the entire or a partial sequence of any of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, or SEQ ID NO: 95 or the complement of such a sequence, wherein all thymidine residues are replaced with uridine residues. A "marker protein" is a protein encoded by or corresponding to a marker of the invention. A marker protein comprises the entire or a partial sequence of any of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, and SEQ ID NO: 96. The terms "protein" and "polypeptide' are used interchangeably.

A "marker set" is a group of more than one marker.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

"Breast cancer" as used herein includes carcinomas, (e.g., carcinoma in situ, invasive carcinoma, metastatic carcinoma) and pre-malignant conditions.

A "breast-associated" body fluid is a fluid which, when in the body of a patient, contacts or passes through breast cells or into which cells, nucleic acids or proteins shed from breast cells are capable of passing. Exemplary breast-associated body fluids include blood fluids, lymph, cystic fluid, and nipple aspirates.

A "sample" or "patient sample" comprises cells obtained from the patient, e.g., a lump biopsy, body fluids including blood fluids, lymph and cystic fluids, as well as nipple aspirates. In a further embodiment, the patient sample is in vivo.

The "normal" level of expression of a marker is the level of expression of the marker in breast cells of a human subject or patient not afflicted with breast cancer.

An "over-expression" or "significantly higher level of expression" of a marker refers to an expression level in a test sample that is greater than the standard error of the assay employed to assess expression, and is preferably at least twice, and more preferably three, four, five or ten times the expression level of the marker in a control sample (e.g., sample from a healthy subjects not having the marker associated disease) and preferably, the average expression level of the marker in several control samples.

A "significantly lower level of expression" of a marker refers to an expression level in a test sample that is at least twice, and more preferably three, four, five or ten times lower than the expression level of the marker in a control sample (e.g., sample from a healthy subjects not having the marker associated disease) and preferably, the average expression level of the marker in several control samples.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue-specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "transcribed polynucleotide" or "nucleotide transcript" is a polynucleotide (e.g., an mRNA, hnRNA, a cDNA, or an analog of such RNA or cDNA) which is complementary to or homologous with all or a portion of a mature mRNA made by transcription of a marker of the invention and normal post-transcriptional processing (e.g., splicing), if any, of the RNA transcript, and reverse transcription of the RNA transcript.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

A molecule is "fixed" or "affixed" to a substrate if it is covalently or non-covalently associated with the substrate such the substrate can be rinsed with a fluid (e.g., standard saline citrate, pH 7.4) without a substantial fraction of the molecule dissociating from the substrate.

As used herein, a "naturally-occurring" nucleic acid molecule refers to an RNA or DNA molecule having a nucleotide sequence that occurs in an organism found in nature.

A cancer is "inhibited" if at least one symptom of the cancer is alleviated, terminated, slowed, or prevented. As used herein, breast cancer is also "inhibited" if recurrence or metastasis of the cancer is reduced, slowed, delayed, or prevented.

A kit is any manufacture (e.g., a package or container) comprising at least one reagent, e.g., a probe, for specifically detecting the expression of a marker of the invention. The kit may be promoted, distributed, or sold as a unit for performing the methods of the present invention.

"Proteins of the invention" encompass marker proteins and their fragments; variant marker proteins and their fragments; peptides and polypeptides comprising an at least 15 amino acid segment of a marker or variant marker protein; and fusion proteins comprising a marker or variant marker protein, or an at least 15 amino acid segment of a marker or variant marker protein.

Unless otherwise specified herewithin, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The present invention is based, in part, on newly identified markers which are over-expressed in breast cancer cells as compared to their expression in normal (i.e., non-cancerous) breast cells. The enhanced expression of one or more of these markers in breast cells is herein correlated with the cancerous state of the tissue. The invention provides compositions, kits, and methods for assessing the cancerous state of breast cells (e.g., cells obtained from a human, cultured human cells, archived or preserved human cells and in vivo cells) as well as treating patients afflicted with breast cancer.

The compositions, kits, and methods of the invention have the following uses, among others:

assessing the status of breast cancer in a human patient;

assessing the stage of breast cancer in a human patient;

assessing the grade of breast cancer in a patient;

assessing the benign or malignant nature of breast cancer in a patient;

assessing the metastatic potential of breast cancer in a patient;

determining if breast cancer has metastasized to lymph nodes;

predicting the clinical outcome of a breast cancer patient;

assessing whether a patient is afflicted with breast cancer;

assessing the histological type of neoplasm associated with breast cancer in a patient;

making antibodies, antibody fragments or antibody derivatives that are useful for treating breast cancer and/or assessing whether a patient is afflicted with breast cancer;

assessing the presence of breast cancer cells;

assessing the efficacy of one or more test compounds for inhibiting breast cancer in a patient;

assessing the efficacy of a therapy for inhibiting breast cancer in a patient;

monitoring the progression of breast cancer in a patient;

selecting a composition or therapy for inhibiting breast cancer in a patient;

treating a patient afflicted with breast cancer;

inhibiting breast cancer in a patient;

assessing the breast carcinogenic potential of a test compound; and preventing the onset of breast cancer in a patient at risk for developing breast cancer.

The invention thus includes a method of assessing breast cancer cells in a patient afflicted with breast cancer. This method comprises comparing the level of expression of a marker of the invention (listed in Table 1) in a patient sample and the normal level of expression of the marker in a control, e.g., a non-breast cancer sample or a non-cancer, normal sample. A significantly higher level of expression of the marker in the patient sample as compared to the normal level of expression is an indication that the patient is afflicted with a breast tumor.

Additionally provided is a method of assessing aggressiveness of breast cancer cells in a patient afflicted with breast cancer. The method comprises comparing the level of expression of a marker of the invention (listed in Table 2) in a patient sample and the normal level of expression of the marker in a control, e.g., a non-breast cancer sample or an indolent breast cancer sample. A significantly higher level of expression of the marker in the patient sample as compared to the normal level of expression is an indication that the patient is afflicted with an aggressive breast tumor.

Gene delivery vehicles, host cells and compositions (all described herein) containing nucleic acids comprising the entirety, or a segment of 15 or more nucleotides, of any of the sequences of the invention (e.g., SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO:, 15, SEQ ID NO: 17, SEQ ID NO: 19, SEQ ID NO: 21, SEQ ID NO: 23, SEQ ID NO: 25, SEQ ID NO: 27, SEQ ID NO:29, SEQ ID NO: 31, SEQ ID NO: 33, SEQ ID NO:35, SEQ ID NO:37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, and SEQ ID NO: 65) or the complement of such sequences, and polypeptides comprising the entirety, or a segment of 10 or more amino acids, of any of the sequences of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, and SEQ ID NO: 96 are also provided by this invention.

As described herein, breast cancer in patients is associated with an increased level of expression of one or more markers of the invention. While, as discussed above, some of these changes in expression level result from occurrence of the breast cancer, others of these changes induce, maintain, and promote the cancerous state of breast cancer cells. Thus, breast cancer characterized by an increase in the level of expression of one or more markers of the invention can be inhibited by reducing and/or interfering with the expression of the markers and/or function of the proteins encoded by those markers.

Expression of a marker of the invention can be inhibited in a number of ways generally known in the art. For example, an RNA interference oligonucleotide or an antisense oligonucleotide can be provided to the breast cancer cells in order to inhibit transcription, translation, or both, of the marker(s). Alternately, a polynucleotide encoding an antibody, an antibody derivative, or an antibody fragment which specifically binds a marker protein, and operably linked with an appropriate promoter/regulator region, can be provided to the cell in order to generate intracellular antibodies which will inhibit the function or activity of the protein. The expression and/or function of a marker may also be inhibited by treating the breast cancer cell with a peptide or an antibody, antibody derivative or antibody fragment that specifically binds a marker protein. Using the methods described herein, a variety of molecules, particularly including molecules sufficiently small that they are able to cross the cell membrane, can be screened in order to identify molecules which inhibit expression of a marker or inhibit the function of a marker protein.

The compound so identified can be provided to the patient in order to inhibit breast cancer cells of the patient.

Any marker or combination of markers of the invention, as well as any known markers in combination with the markers of the invention, may be used in the compositions, kits, and methods of the present invention. In general, it is preferable to use markers for which the difference between the level of expression of the marker in breast cancer cells and the level of expression of the same marker in normal breast cells is as great as possible. Although this difference can be as small as the limit of detection of the method for assessing expression of the marker, it is preferred that the difference be at least greater than the standard error of the assessment method, and preferably a difference of at least 2-, 3-, 4-, 5-, 6-, 7-, 8-, 9-, 10-, 15-, 20-, 25-, 100-, 500-, 1000-fold or greater than the level of expression of the same marker in normal breast tissue.

It is recognized that certain marker proteins are secreted from breast cells (i.e., one or both of normal and cancerous cells) to the extracellular space surrounding the cells. These markers are preferably used in certain embodiments of the compositions, kits, and methods of the invention, owing to the fact that the such marker proteins can be detected in a breast-associated body fluid sample, which may be more easily collected from a human patient than a tissue biopsy sample. In addition, preferred in vivo techniques for detection of a marker protein include introducing into a subject a labeled antibody directed against the protein. For example, the antibody can be labeled with a radioactive marker whose presence and location in a subject can be detected by standard imaging techniques.

It is a simple matter for the skilled artisan to determine whether any particular marker protein is a secreted protein. In order to make this determination, the marker protein is expressed in, for example, a mammalian cell, preferably a human breast cell line, extracellular fluid is collected, and the presence or absence of the protein in the extracellular fluid is assessed (e.g., using a labeled antibody which binds specifically with the protein).

The following is one example of a method which can be used to detect secretion of a protein: About $8\times10^5$ 293T cells are incubated at 37° C. in wells containing growth medium (Dulbecco's modified Eagle's medium {DMEM} supplemented with 10% fetal bovine serum) under a 5% (v/v) $CO_2$, 95% air atmosphere to about 60-70% confluence. The cells are then transfected using a standard transfection mixture comprising 2 micrograms of DNA comprising an expression vector encoding the protein and 10 microliters of LipofectAMINE™ (GIBCO/BRL Catalog no. 18342-012) per well. The transfection mixture is maintained for about 5 hours, and then replaced with fresh growth medium and maintained in an air atmosphere. Each well is gently rinsed twice with DMEM which does not contain methionine or cysteine (DMEM-MC; ICN Catalog no. 16-424-54). About 1 milliliter of DMEM-MC and about 50 microcuries of Trans-$^{35}$S™ reagent (ICN Catalog no. 51006) are added to each well. The wells are maintained under the 5% $CO_2$ atmosphere described above and incubated at 37° C. for a selected period. Following incubation, 150 microliters of conditioned medium is removed and centrifuged to remove floating cells and debris. The presence of the protein in the supernatant is an indication that the protein is secreted. Additional and alternative methods for detection of secreted proteins are known in the art and can be used in addition to, or alternative to this method.

It will be appreciated that patient samples containing breast cells may be used in the methods of the present invention. In these embodiments, the level of expression of the marker can be determined by assessing the amount (e.g., absolute amount or concentration) of the marker in a breast cell sample, e.g., breast biopsies obtained from a patient. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, breast biopsies may also be subjected to post-collection preparative and storage techniques, e.g., fixation.

The compositions, kits, and methods of the invention can be used to detect expression of marker proteins having at least one portion which is displayed on the surface of cells which express it. It is a simple matter for the skilled artisan to determine whether a marker protein, or a portion thereof, is exposed on the cell surface. For example, immunological methods may be used to detect such proteins on whole cells, or well known computer-based sequence analysis methods may be used to predict the presence of at least one extracellular domain (i.e., including both secreted proteins and proteins having at least one cell-surface domain). Expression of a marker protein having at least one portion which e is displayed on the surface of a cell which expresses it may be detected without necessarily lysing the cell (e.g., using a labeled antibody which binds specifically with a cell-surface domain of the protein).

Expression of a marker of the invention may be assessed by any of a wide variety of well known methods for detecting expression of a transcribed nucleic acid or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In a preferred embodiment, expression of a marker is assessed using an antibody (e.g., a radio-labeled, chromophore-labeled, fluorophore-labeled, or enzyme-labeled antibody), an antibody derivative (e.g., an antibody conjugated with a substrate or with the protein or ligand of a protein-ligand pair {e.g., biotin-streptavidin}), or an antibody fragment (e.g., a single-chain antibody, an isolated antibody hypervariable domain, etc.) which binds specifically with a marker protein or fragment thereof, including a marker protein which has undergone all or a portion of its normal post-translational modification.

In another preferred embodiment, expression of a marker is assessed by preparing mRNA/cDNA (i.e., a transcribed polynucleotide) from cells in a patient sample, and by hybridizing the mRNA/cDNA with a reference polynucleotide which is a complement of a marker nucleic acid, or a fragment thereof. cDNA can, optionally, be amplified using any of a variety of polymerase chain reaction methods prior to hybridization with the reference polynucleotide; preferably, it is not amplified. Expression of one or more markers can likewise be detected using quantitative PCR to assess the level of expression of the marker(s). Alternatively, any of the many known methods of detecting mutations or variants (e.g., single nucleotide polymorphisms, deletions, etc.) of a marker of the invention may be used to detect occurrence of a marker in a patient.

In a related embodiment, a mixture of transcribed polynucleotides obtained from the sample is contacted with a substrate having fixed thereto a polynucleotide complementary to or homologous with at least a portion (e.g., at least 7, 10, 15, 20, 25, 30, 40, 50, 100, 500, or more nucleotide residues) of a marker nucleic acid. If polynucleotides complementary to or homologous with are differentially detectable on the substrate (e.g., detectable using different chromophores or fluorophores, or fixed to different selected positions), then the levels of expression of a plurality of markers can be assessed simultaneously using a single substrate (e.g., a "gene chip" microarray of polynucleotides fixed at selected positions). When a method of assessing marker expression is used which involves hybridization of one nucleic acid with another, it is preferred that the hybridization be performed under stringent hybridization conditions.

Because the compositions, kits, and methods of the invention rely on detection of a difference in expression levels of one or more markers of the invention, it is preferable that the level of expression of the marker is significantly greater than the minimum detection limit of the method used to assess expression in at least one of normal breast cells and cancerous breast cells.

It is understood that by routine screening of additional patient samples using one or more of the markers of the invention, it will be realized that certain of the markers are over-expressed in cancers of various types, including specific breast cancers, as well as other cancers such as lung cancer, ovarian cancer, etc. For example, it will be confirmed that some of the markers of the invention are over-expressed in most (i.e., 50% or more) or substantially all (i.e., 80% or more) of breast cancer. The compositions, kits, and methods of the invention are thus useful for characterizing the benign or malignant nature of breast tumors in patients.

Furthermore, it will be confirmed that certain of the markers of the invention are associated with breast cancer of various stages (i.e., stage 0, I, II, II, and IV breast cancers, as well as subclassifications IIA, IIB, IIIA, and IIIB, using the FIGO Stage Grouping system for primary carcinoma of the breast; (see Breast, In: *American Joint Committee on Cancer: AJCC Cancer Staging Manual*. Lippincott-Raven Publishers, 5th ed., 1997, pp. 171-180), of various histologic subtypes (e.g., serous, mucinous, endometroid, and clear cell subtypes, as well as subclassifications and alternate classifications adenocarcinoma, papillary adenocarcinoma, papillary cystadenocarcinoma, surface papillary carcinoma, malignant adenofibroma, cystadenofibroma, adenocarcinoma, cystadenocarcinoma, adenoacanthoma, endometrioid stromal sarcoma, mesodermal (Muillerian) mixed tumor, mesonephroid tumor, malignant carcinoma, Brenner tumor, mixed epithelial tumor, and undifferentiated carcinoma, using the WHO/FIGO system for classification of malignant breast tumors; Scully, *Atlas of Tumor Pathology,* 3d series, Washington D.C.), and various grades (i.e., grade I {well differentiated}, grade II {moderately well differentiated}, and grade III {poorly differentiated from surrounding normal tissue})). In addition, as a greater number of patient samples are assessed for expression of the markers of the invention and the outcomes of the individual patients from whom the samples were obtained are correlated, it will also be confirmed that altered expression of certain of the markers of the invention are strongly correlated with malignant cancers and that altered expression of other markers of the invention are strongly correlated with benign tumors. The compositions, kits, and methods of the invention are thus useful for characterizing one or more of the stage, grade, histological type, and benign/malignant nature of breast cancer in patients.

When the compositions, kits, and methods of the invention are used for characterizing the one or more of the stage, grade, histological type, and benign or malignant nature of breast tumors in a patient, it is preferred that the marker or panel of markers of the invention is selected such that a positive result is obtained in at least about 20%, and preferably at least about 40%, 60%, or 80%, and more preferably in substantially all patients afflicted with a breast tumor of the corresponding stage, grade, histological type, or benign or malignant nature. Preferably, the marker or panel of markers of the invention is selected such that a positive predictive value (PPV) of greater than about 10% is obtained for the general population (more preferably coupled with an assay specificity greater than 80%).

When a plurality of markers of the invention are used in the compositions, kits, and methods of the invention, the level of expression of each marker in a patient sample can be compared with the normal level of expression of each of the plurality of markers in non-cancerous samples of the same type, either in a single reaction mixture (i.e., using reagents, such as different fluorescent probes, for each marker) or in individual reaction mixtures corresponding to one or more of the markers. In one embodiment, a significantly increased level of expression of more than one of the plurality of markers in the sample, relative to the corresponding normal levels, is an indication that the patient is afflicted with breast cancer. When a plurality of markers is used, it is preferred that 2, 3, 4, 5, 8, 10, 12, or 15, or more individual markers be used. Still further markers can be used to include a marker set wherein at least 20, 25, 30, 40, 50, or more individual markers are used.

In order to maximize the sensitivity of the compositions, kits, and methods of the invention (i.e., by interference attributable to cells of non-breast origin in a patient sample), it is preferable that the marker of the invention used therein be a marker which has a restricted tissue distribution, e.g., normally not expressed in a non-breast tissue.

Only a small number of markers are known to be associated with breast cancers (e.g., BRCA1 and BRCA2). These markers are not, of course, included among the markers of the invention, although they may be used together with one or more markers of, the invention in a panel of markers, for example. It is well known that certain types of genes, such as oncogenes, tumor suppressor genes, growth factor-like genes, protease-like genes, and protein kinase-like genes are often involved with development of cancers of various types. Thus, among the markers of the invention, use of those which correspond to proteins which resemble known proteins encoded by known oncogenes and tumor suppressor genes, and those which correspond to proteins which resemble growth factors, proteases, and protein kinases are preferred.

It is recognized that the compositions, kits, and methods of the invention will be of particular utility to patients having an enhanced risk of developing breast cancer and their medical advisors. Patients recognized as having an enhanced risk of developing breast cancer include, for example, patients having a familial history of breast cancer, patients identified as having a mutant oncogene (i.e., at least one allele), and patients of advancing age (i.e., women older than about 50 or 60 years).

The level of expression of a marker in normal (i.e., non-cancerous) breast tissue can be assessed in a variety of ways. In one embodiment, this normal level of expression is determined by assessing the level of expression of the marker in a portion of breast cells which appears to be non-cancerous and by comparing this normal level of expression with the level of expression in a portion of the breast cells which is suspected of being cancerous. Alternately, and particularly as further information becomes available as a result of routine performance of the methods described herein, population-average values for normal expression of the markers of the invention may be used. In other embodiments, the 'normal' level of expression of a marker may be determined by assessing expression of the marker in a patient sample obtained from a non-cancer-afflicted patient, from a patient sample obtained from a patient before the suspected onset of breast cancer in the patient, from archived patient samples, and the like.

The invention includes compositions, kits, and methods for assessing the presence of breast cancer cells in a sample (e.g., an archived tissue sample or a sample obtained from a patient). These compositions, kits, and methods are substantially the same as those described above, except that, where necessary, the compositions, kits, and methods are adapted for use with samples other than patient samples. For example, when the sample to be used is a parafinized, archived human tissue sample, it can be necessary to adjust the ratio of compounds in the compositions of the invention, in the kits of the invention, or the methods used to assess levels of marker expression in the sample. Such methods are well known in the art and within the skill of the ordinary artisan.

The invention includes a kit for assessing the presence of breast cancer cells (e.g., in a sample such as a patient sample). The kit comprises a plurality of reagents, each of which is capable of binding specifically with a marker nucleic acid or protein. Suitable reagents for binding with a marker protein include antibodies, antibody derivatives, antibody fragments, and the like. Suitable reagents for binding with a marker nucleic acid (e.g., a genomic DNA, an mRNA, a spliced mRNA, a cDNA, or the like) include complementary nucleic acids. For example, the nucleic acid reagents may include oligonucleotides (labeled or non-labeled) fixed to a substrate, labeled oligonucleotides not bound with a substrate, pairs of PCR primers, molecular beacon probes, and the like.

The kit of the invention may optionally comprise additional components useful for performing the methods of the invention. By way of example, the kit may comprise fluids (e.g., SSC buffer) suitable for annealing complementary nucleic acids or for binding an antibody with a protein with which it specifically binds, one or more sample compartments, an instructional material which describes performance of a method of the invention, a sample of normal breast cells, a sample of breast cancer cells, and the like.

The invention also includes a method of making an isolated hybridoma which produces an antibody useful for assessing whether a patient is afflicted with breast cancer. In this method, a protein or peptide comprising the entirety or a segment of a marker protein is synthesized or isolated (e.g., by purification from a cell in which it is expressed or by transcription and translation of a nucleic acid encoding the protein or peptide in vivo or in vitro using known methods). A vertebrate, preferably a mammal such as a mouse, rat, rabbit, or sheep, is immunized using the protein or peptide. The vertebrate may optionally (and preferably) be immunized at least one additional time with the protein or peptide, so that the vertebrate exhibits a robust immune response to the protein or peptide. Splenocytes are isolated from the immunized vertebrate and fused with an immortalized cell line to form hybridomas, using any of a variety of methods well known in the art. Hybridomas formed in this manner are then screened using standard methods to identify one or more hybridomas which produce an antibody which specifically binds with the marker protein or a fragment thereof. The invention also includes hybridomas made by this method and antibodies made using such hybridomas.

The invention also includes a method of assessing the efficacy of a test compound for inhibiting breast cancer cells. As described above, differences in the level of expression of the markers of the invention correlate with the cancerous state of breast cells. Although it is recognized that changes in the levels of expression of certain of the markers of the invention likely result from the cancerous state of breast cells, it is likewise recognized that changes in the levels of expression of other of the markers of the invention induce, maintain, and promote the cancerous state of those cells. Thus, compounds which inhibit a breast cancer in a patient will cause the level of expression of one or more of the markers of the invention to change to a level nearer the normal level of expression for that marker (i.e., the level of expression for the marker in non-cancerous breast cells).

This method thus comprises comparing expression of a marker in a first breast cell sample and maintained in the presence of the test compound and expression of the marker in a second breast cell sample and maintained in the absence of the test compound. A significantly reduced expression of a marker of the invention in the presence of the test compound is an indication that the test compound inhibits breast cancer. The breast cell samples may, for example, be aliquots of a single sample of normal breast cells obtained from a patient, pooled samples of normal breast cells obtained from a patient, cells of a normal breast cell line, aliquots of a single sample of breast cancer cells obtained from a patient, pooled samples of breast cancer cells obtained from a patient, cells of a breast cancer cell line, or the like. In one embodiment, the samples are breast cancer cells obtained from a patient and one or more of a plurality of compounds known to be effective for inhibiting various breast cancers are tested in order to identify the compound which is likely to best inhibit the breast cancer in the patient.

This method may likewise be used to assess the efficacy of a therapy for inhibiting breast cancer in a patient. In this method, the level of expression of one or more markers of the invention in a pair of samples (one subjected to the therapy, the other not subjected to the therapy) is assessed. As with the method of assessing the efficacy of test compounds, if the therapy induces a significantly lower level of expression of a marker of the invention, then the therapy is efficacious for inhibiting breast cancer. As above if samples from a selected patient are used in this method, then alternative therapies can be assessed in vitro in order to select a therapy most likely to be efficacious for inhibiting breast cancer in the patient.

As described above, the cancerous state of human breast cells is correlated with changes in the levels of expression of the markers of the invention. The invention includes a method for assessing the human breast cell carcinogenic potential of a test compound. This method comprises maintaining separate aliquots of human breast cells in the presence and absence of the test compound. Expression of a marker of the invention in each of the aliquots is compared. A significantly higher level of expression of a marker of the invention in the aliquot maintained in the presence of the test compound (relative to the aliquot maintained in the absence of the test compound) is an indication that the test compound possesses human breast cell carcinogenic potential. The relative carcinogenic potentials of various test compounds can be assessed by comparing the degree of enhancement or inhibition of the level of expression of the relevant markers, by comparing the number of markers for which the level of expression is enhanced or inhibited, or by comparing both.

Various aspects of the invention are described in further detail in the following subsections.

Isolated Nucleic Acid Molecules

One aspect of the invention pertains to isolated nucleic acid molecules, including nucleic acids which encode a marker protein or a portion thereof. Isolated nucleic acids of the invention also include nucleic acid molecules sufficient for use as hybridization probes to identify marker nucleic acid molecules, and fragments of marker nucleic acid molecules, e.g., those suitable for use as PCR primers for the amplification or mutation of marker nucleic acid molecules. As used herein, the term “nucleic acid molecule” is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An “isolated” nucleic acid molecule is one which is separated from other nucleic acid molecules which are present in the natural source of the nucleic acid molecule. Preferably, an “isolated” nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an “isolated” nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual, 2nd ed.*, Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, nucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which has a nucleotide sequence complementary to the nucleotide sequence of a marker nucleic acid or to the nucleotide sequence of a nucleic acid encoding a marker protein. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence, wherein the full length nucleic acid sequence comprises a marker nucleic acid or which encodes a marker protein. Such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a nucleic acid of the invention.

Probes based oil the sequence of a nucleic acid molecule of the invention can be used to detect transcripts or genomic sequences corresponding to one or more markers of: the invention. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

The invention further encompasses nucleic acid molecules that differ, due to degeneracy of the genetic code, from the nucleotide sequence of nucleic acids encoding a marker protein (e.g., protein having the sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, and SEQ ID NO: 96), and thus encode the same protein.

It will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

As used herein, the phrase “allelic variant” refers to a nucleotide sequence which occurs at a given locus or to a polypeptide encoded by the nucleotide sequence.

As used herein, the terms “gene” and “recombinant gene” refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, an isolated nucleic acid molecule of the invention is at least 7, 15, 20, 25, 30, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or more nucleotides in length and hybridizes under stringent conditions to a marker nucleic acid or to a nucleic acid encoding a marker protein. As used herein, the term “hybridizes under stringent conditions” is intended to describe conditions for hybridization and washing under which nucleotide sequences at least 60% (65%, 70%, preferably 75%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a variant marker protein that contain changes in amino acid residues that are not essential for activity. Such variant marker proteins differ in amino acid sequence from the naturally-occurring marker proteins, yet retain biological activity. In one embodiment, such a variant marker protein has an amino acid sequence that is at least about 40% identical, 50%, 60%, 70%, 80%, 90%, 95%, or 98% identical to the amino acid sequence of a marker protein.

An isolated nucleic acid molecule encoding a variant marker protein can be created by introducing one or more nucleotide substitutions, additions or deletions into the nucleotide sequence of marker nucleic acids, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

The present invention encompasses antisense nucleic acid molecules, i.e., molecules which are complementary to a sense nucleic acid of the invention, e.g., complementary to the coding strand of a double-stranded marker cDNA molecule or complementary to a marker mRNA sequence. Accordingly, an antisense nucleic acid of the invention can hydrogen bond to (i.e., anneal with) a sense nucleic acid of the invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a marker protein. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, -5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a marker protein to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific Interactions in the major groove of the double helix. Examples of a route of administration of antisense nucleic acid molecules of the invention includes direct injection at a tissue site or infusion of the antisense nucleic acid into a breast-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a marker protein can be designed based upon the nucleotide sequence of a cDNA corresponding to the marker. For example, a derivative of a *Tetrahymena* L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the invention can be used to select a catalytic RNA having a specific ribonuclease activity from a pool of RNA molecules (see. e.g., Bartel and Szostak, 1993, *Science* 261:1411-1418).

The invention also encompasses nucleic acid molecules which form triple helical structures. For example, expression of a marker of the invention can be inhibited by targeting nucleotide sequences complementary to the regulatory region of the gene encoding the marker nucleic acid or protein (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Peny-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl) amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

The invention also includes molecular beacon nucleic acids having at least one region which is complementary to a nucleic acid of the invention, such that the molecular beacon is useful for quantitating the presence of the nucleic acid of the invention in a sample. A "molecular beacon" nucleic acid is a nucleic acid comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid are not annealed with one another, fluorescence of the fluorophore is quenched to a lesser degree. Molecular beacon nucleic acids are described, for example, in U.S. Pat. No. 5,876,930.

Isolated Proteins and Antibodies

One aspect of the invention pertains to isolated marker proteins and biologically active portions thereof, as well as polypeptide fragments suitable for use as immunogens to raise antibodies directed against a marker protein or a fragment thereof. In one embodiment, the native marker protein can be isolated from cells or tissue sources by an appropriate purification scheme using standard protein purification techniques. In another embodiment, a protein or peptide comprising the whole or a segment of the marker protein is produced by recombinant DNA techniques. Alternative to recombinant expression, such protein or peptide can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from, chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a marker protein include polypeptides comprising amino acid sequences sufficiently identical to or derived from the amino acid sequence of the marker protein, which include fewer amino acids than the full length protein, and exhibit at least one activity of the corresponding full-length protein. Typically, biologically active portions comprise a domain or motif with at least one activity of the corresponding full-length protein. A biologically active portion of a marker protein of the invention can be a polypeptide which is, for example, 10, 25, 50, 100 or more amino acids in length. Moreover, other biologically active portions, in which other regions of the marker protein are deleted, can be prepared by recombinant techniques and evaluated for one or more of the functional activities of the native form of the marker protein.

Preferred marker proteins are encoded by nucleotide sequences encoding proteins comprising the sequence of any one of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, and SEQ ID NO: 96. Other useful proteins are substantially identical (e.g., at least about 40%, preferably 50%, 60%, 70%, 80%, 90%, 95%, or 99%) to one of these sequences and retain the functional activity of the corresponding naturally-occurring marker protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the BLASTN and BLASTX programs of Altschul, et al. (1990) *J. Mol. Biol.* 215:403-410. BLAST nucleotide searches can be performed with the BLASTN program, score=100, wordlength=12 to obtain nucleotide sequences homologous to a nucleic acid molecules of the invention. BLAST protein searches can be performed with the BLASTP program, score=50, wordlength=3 to obtain amino acid sequences homologous to a protein molecules of the invention. To obtain gapped alignments for comparison purposes, a newer version of the BLAST algorithm called Gapped BLAST can be utilized as described in Altschul et al. (1997) *Nucleic Acids Res.* 25:3389-3402, which is able to perform gapped local alignments for the programs BLASTN, BLASTP and BLASTX. Alternatively, PSI-Blast can be used to perform an iterated search which detects distant relationships between molecules. When utilizing BLAST, Gapped BLAST, and PSI-Blast programs, the default parameters of the respective programs (e.g., BLASTX and BLASTN) can be used. Another preferred, non-limiting example of a mathematical algorithm utilized for the comparison of sequences is the algorithm of Myers and Miller, (1988) *CABIOS* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The invention also provides chimeric or fusion proteins comprising a marker protein or a segment thereof. As used herein, a "chimeric protein" or "fusion protein" comprises all or part (preferably a biologically active part) of a marker protein operably linked to a heterologous polypeptide (i.e., a polypeptide other than the marker protein). Within the fusion protein, the term "operably linked" is intended to indicate that the marker protein or segment thereof and the heterologous polypeptide are fused in-frame to each other. The heterologous polypeptide can be fused to the amino-terminus or the carboxyl-terminus of the marker protein or segment.

One useful fusion protein is a GST fusion protein in which a marker protein or segment is fused to the carboxyl terminus of GST sequences. Such fusion proteins can facilitate the purification of a recombinant polypeptide of the invention.

In another embodiment, the fusion protein contains a heterologous signal sequence at its amino terminus. For example, the native signal sequence of a marker protein can be removed and replaced with a signal sequence from another protein. For example, the gp67 secretory sequence of the baculovirus envelope protein can be used as a heterologous signal sequence (Ausubel et al., ed., *Current Protocols in Molecular Biology*, John Wiley & Sons, NY, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a marker protein is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a marker protein. Inhibition of ligand/receptor interaction can be useful therapeutically, both for treating proliferative and differentiative disorders and for modulating (e.g., promoting or inhibiting) cell survival. Moreover, the immunoglobulin fusion proteins of the invention can be used as immunogens to produce antibodies directed against a marker protein in a subject, to purify ligands and in screening assays to identify molecules which inhibit the interaction of the marker protein with ligands.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence can be used to facilitate secretion and isolation of marker proteins. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to marker proteins, fusion proteins or segments thereof having a signal sequence, as well as to such proteins from which the signal sequence has been proteolytically cleaved (i.e., the cleavage products). In one embodiment, a nucleic acid sequence encoding a signal sequence can be operably linked in an expression vector to a protein of interest, such as a marker protein or a segment thereof. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the marker proteins. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a marker protein which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the marker proteins from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of segments of a marker protein can be used to generate a variegated population of polypeptides for screening and subsequent selection of variant marker proteins or segments thereof. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with SI nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (RFM), a technique which enhances the frequency of functional mutants in the libraries, can be used in combination with the screening assays to identify variants of a protein of the invention (Arkin and Yourvan, 1992, *Proc. Natl. Acad. Sci. USA* 89:7811-7815; Delgrave et al., 1993, *Protein Engineering* 6(3):327-331).

Another aspect of the invention pertains to antibodies directed against a protein of the invention. In preferred embodiments, the antibodies specifically bind a marker protein or a fragment thereof. The terms "antibody" and "antibodies" as used interchangeably herein refer to immunoglobulin molecules as well as fragments and derivatives thereof that comprise an immunologically active portion of an immunoglobulin molecule, (i.e., such a portion contains an antigen binding site which specifically binds an antigen, such as a marker protein, e.g., an epitope of a marker protein). An antibody which specifically binds to a protein of the invention is an antibody which binds the protein, but does not substantially bind other molecules in a sample, e.g., a biological sample, which naturally contains the protein. Examples of an immunologically active portion of an immunoglobulin molecule include, but are not limited to, single-chain antibodies (scAb), F(ab) and $F(ab')_2$ fragments.

An isolated protein of the invention or a fragment thereof can be used as an immunogen to generate antibodies. The full-length protein can be used or, alternatively, the invention provides antigenic peptide fragments for use as immunogens. The antigenic peptide of a protein of the invention comprises at least 8 (preferably 10, 15, 20, or 30 or more) amino acid residues of the amino acid sequence of one of the proteins of the invention, and encompasses at least one epitope of the protein such that an antibody raised against the peptide forms a specific immune complex with the protein. Preferred epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions. In preferred embodiments, an isolated marker protein or fragment thereof is used as an immunogen.

An immunogen typically is used to prepare antibodies by immunizing a suitable (i.e., immunocompetent) subject such as a rabbit, goat, mouse, or other mammal or vertebrate. An appropriate immunogenic preparation can contain, for example, recombinantly-expressed or chemically-synthesized protein or peptide. The preparation can further include an adjuvant, such as Freund's complete or incomplete adjuvant, or a similar immunostimulatory agent. Preferred immunogen compositions are those that contain no other human proteins such as, for example, immunogen compositions made using a non-human host cell for recombinant expression of a protein of the invention. In such a manner, the resulting antibody compositions have reduced or no binding of human proteins other than a protein of the invention.

The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope. Preferred polyclonal and monoclonal antibody compositions are ones that have been selected for antibodies directed against a protein of the invention. Particularly preferred polyclonal and monoclonal antibody preparations are ones that contain only antibodies directed against a marker protein or fragment thereof.

Polyclonal antibodies can be prepared by immunizing a suitable subject with a protein of the invention as an immunogen The antibody titer in the immunized subject can be monitored over time by standard techniques, such as with an enzyme linked immunosorbent assay (ELISA) using immobilized polypeptide. At an appropriate time after immunization, e.g., when the specific antibody titers are highest, antibody-producing cells can be obtained from the subject and used to prepare monoclonal antibodies (mAb) by standard techniques, such as the hybridoma technique originally described by Kohler and Milstein (1975) *Nature* 256:495-497, the human B cell hybridoma technique (see Kozbor et al., 1983, *Immunol. Today* 4:72), the EBV-hybridoma technique (see Cole et al., pp. 77-96 In *Monoclonal Antibodies and Cancer Therapy*, Alan R. Liss, Inc., 1985) or trioma techniques. The technology for producing hybridomas is well known (see generally *Current Protocols in Immunology*, Coligan et al. ed., John Wiley & Sons, New York, 1994). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a protein of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene *SurfZAP Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

The invention also provides recombinant antibodies that specifically bind a protein of the invention. In preferred embodiments, the recombinant antibodies specifically binds a marker protein or fragment thereof. Recombinant antibodies include, but are not limited to, chimeric and humanized monoclonal antibodies, comprising both human and non-human portions, single-chain antibodies and multi-specific antibodies. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Single-chain antibodies have an antigen binding site and consist of a single polypeptides. They can be produced by techniques known in the art, for example using methods described in Ladner et. al U.S. Pat. No. 4,946,778 (which is incorporated herein by reference in its entirety); Bird et al., (1988) *Science* 242:423-426; Whitlow et al., (1991) *Methods in Enzymology* 2:1-9; Whitlow et al., (1991) *Methods in Enzymology* 2:97-105; and Huston et al., (1991) *Methods in Enzymology Molecular Design and Modeling: Concepts and Applications* 203:46-88. Multi-specific antibodies are antibody molecules having at least two antigen-binding sites that specifically bind different antigens. Such molecules can be produced by techniques known in the art, for example using methods described in Segal, U.S. Pat. No. 4,676,980 (the disclosure of which is incorporated herein by reference in its entirety); Holliger et al., (1993) *Proc. Natl. Acad. Sci. USA* 90:6444-6448;. Whitlow et al., (1994) *Protein Eng.* 7:1017-1026 and U.S. Pat. No. 6,121,424.

Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

More particularly, humanized antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide corresponding to a marker of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995) *Int. Rev. Immunol.* 13:65-93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope (Jespers et al., 1994, *Bio/technology* 12:899-903).

The antibodies of the invention can be isolated after production (e.g., from the blood or serum of the subject) or synthesis and further purified by well-known techniques. For example, IgG antibodies can be purified using protein A chromatography. Antibodies specific for a protein of the invention can be selected or (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those of the desired protein of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein of the invention.

In a preferred embodiment, the substantially purified antibodies of the invention may specifically bind to a signal peptide, a secreted sequence, an extracellular domain, a transmembrane or a cytoplasmic domain or cytoplasmic membrane of a protein of the invention. In a particularly preferred embodiment, the substantially purified antibodies of the invention specifically bind to a secreted sequence or an extracellular domain of the amino acid sequences of a protein of the invention. In a more preferred embodiment, the substantially purified antibodies of the invention specifically bind to a secreted sequence or an extracellular domain of the amino acid sequences of a marker protein.

An antibody directed against a protein of the invention can be used to isolate the protein by standard techniques, such as affinity chromatography or immunoprecipitation. Moreover, such an antibody can be used to detect the marker protein or fragment thereof (e.g., in a cellular lysate or cell supernatant) in order to evaluate the level and pattern of s expression of the marker. The antibodies can also be used diagnostically to monitor protein levels in tissues or body fluids (e.g., in a breast-associated body fluid) as part of a clinical testing procedure, e.g., to, for example, determine the efficacy of a given treatment regimen. Detection can be facilitated by the use of an antibody derivative, which comprises an antibody of the invention coupled to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies of the invention may also be used as therapeutic agents in treating cancers. In a preferred embodiment, completely human antibodies of the invention are used for therapeutic treatment of human cancer patients, particularly those having a breast cancer. In another preferred embodiment, antibodies that bind specifically to a marker protein or fragment thereof are used for therapeutic treatment. Further, such therapeutic antibody may be an antibody derivative or immunotoxin comprising an antibody conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugated antibodies of the invention can be used for modifying a given biological response, for the drug moiety is not to be construed as limited to classical chemical therapeutic agents. For example, the drug moiety may be a protein or polypeptide possessing a desired biological activity. Such proteins may include, for example, a toxin such as ribosome-inhibiting protein (see Better et al., U.S. Pat. No. 6,146,631, the disclosure of which is incorporated herein in its entirety), abrin, ricin A, pseudomonas exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 (“IL-1”), interleukin-2 (“IL-2”), interleukin-6 (“IL-6”), granulocyte macrophase colony stimulating factor (“GM-CSF”), granulocyte colony stimulating factor (“G-CSF”), or other growth factors.

Techniques for conjugating such therapeutic moiety to antibodies are well known, see, e.g., Arnon et al., “Monoclonal Antibodies For Immunotargeting Of Drugs In Cancer Therapy”, in Monoclonal Antibodies And Cancer Therapy, Reisfeld et al. (eds.), pp. 243-56 (Alan R. Liss, Inc. 1985); Hellstrom et al., “Antibodies For Drug Delivery”, in Controlled Drug Delivery (2nd Ed.), Robinson et al. (eds.), pp. 623-53 (Marcel Dekker, Inc. 1987); Thorpe, “Antibody Carriers Of Cytotoxic Agents In Cancer Therapy: A Review”, in Monoclonal Antibodies ’84: Biological And Clinical Applications, Pinchera et al. (eds.), pp. 475-506 (1985); “Analysis, Results, And Future Prospective Of The Therapeutic Use Of Radiolabeled Antibody In Cancer Therapy”, in Monoclonal Antibodies For Cancer Detection And Therapy, Baldwin et al. (eds.), pp. 303-16 (Academic Press 1985), and Thorpe et al., “The Preparation And Cytotoxic Properties Of Antibody-Toxin Conjugates”, Immunol. Rev., 62:119-58 (1982).

Accordingly, in one aspect, the invention provides substantially purified antibodies, antibody fragments and derivatives, all of which specifically bind to a protein of the invention and preferably, a marker protein. In various embodiments, the substantially purified antibodies of the invention, or fragments or derivatives thereof, can be human, non-human, chimeric and/or humanized antibodies. In another aspect, the invention provides non-human antibodies, antibody fragments and derivatives, all of which specifically bind to a protein of the invention and preferably, a marker protein. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies. In still a further aspect, the invention provides monoclonal antibodies, antibody fragments and derivatives, all of which specifically bind to a protein of the invention and preferably, a marker protein. The monoclonal antibodies can be human, humanized, chimeric and/or non-human antibodies.

The invention also provides a kit containing an antibody of the invention conjugated to a detectable substance, and instructions for use. Still another aspect of the invention is a pharmaceutical composition comprising an antibody of the invention and a pharmaceutically acceptable carrier. In one embodiment, the pharmaceutical composition comprises an antibody of the invention, a therapeutic moiety, and a pharmaceutically acceptable carrier.

Recombinant Expression Vectors and Host Cells

Another aspect of the invention pertains to vectors, preferably expression vectors, containing a nucleic acid encoding a marker protein (or a portion of such a protein). As used herein, the term “vector” refers to a nucleic acid molecule capable of transporting another nucleic acid to which it has been linked. One type of vector is a “plasmid”, which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This; means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors of the invention can be designed for expression of a marker protein or a segment thereof in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein: 2) to increase the solubility of the recombinant protein; and 3) to aid in the purification or the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expression Technology: Methods in Enzymology* vol. 185, Academic Press, San Diego, Calif., 1991). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, p. 119-128, In *Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid of the invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which e direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., 1986, *Trends in Genetics*, Vol. 1(1).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker will survive, while the other cells die).

A host cell of the invention, such as a prokarotic or eukaryotic host cell in culture, can be used to produce a marker protein or a segment thereof. Accordingly, the invention further provides methods for producing a marker protein or a segment thereof using the host cells of the invention. In one embodiment, the method comprises culturing the host cell of the invention (into which a recombinant expression vector encoding a marker protein or a segment thereof has been introduced) in a suitable medium such that the is produced. In another embodiment, the method further comprises isolating the a marker protein or a segment thereof from the medium or the host cell.

The host cells of the invention can also be used to produce nonhuman transgenic animals. For example, in one embodiment, a host cell of the invention is a fertilized oocyte or an embryonic stem cell into which a sequences encoding a marker protein or a segment thereof have been introduced. Such host cells can then be used to create non-human transgenic animals in which exogenous sequences encoding a marker protein of the invention have been introduced into their genome or homologous recombinant animals in which endogenous gene(s) encoding a marker protein have been altered. Such animals are useful for studying the function and/or activity of the marker protein and for identifying and/or evaluating modulators of marker protein. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a nucleic acid encoding a marker protein into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, 4,873,191 and in Hogan, *Manipulating the Mouse Embryo*, Cold Spring Harbor Laboratory Press, Cold Spring Harbor, N.Y., 1986. Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding a marker protein into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi, 1987, *Cell* 51:503 for a description of homologous recombination vectors). The vector is introduced into an embryonic stem cell line (e.g., by electroporation) and cells in which the introduced gene has homologously reconbined with the endogenous gene are selected (see, e.g., Li et al., 1992, *Cell* 69:915). The selected cells are then injected into a blastocyst of an animal (e.g., a mouse) to form aggregation chimeras (see, e.g., Bradley, *Teratocarcinomas and Embryonic Stem Cells: A Practical Approach*, Robertson. Ed., IRL Oxford, 1987, pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication NOS. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al., 1991, *Science* 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT Publication NOS. WO 97/07668 and WO 97/07669.

Pharmaceutical Compositions

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a marker nucleic acid or protein. Such methods comprise formulating a pharmaceutically acceptable carrier with an agent which modulates expression or activity of a marker nucleic acid or protein. Such compositions can further include additional active agents. Thus, the invention further includes methods for preparing a pharmaceutical composition by formulating a pharmaceutically acceptable carrier with an agent which modulates expression or activity of a marker nucleic acid or protein and one or more additional active compounds.

The invention also provides methods (also referred to herein as "screening assays") for identifying modulators, i.e., candidate or test compounds or agents (e.g., peptides, peptidomimetics, peptoids, small molecules or other drugs) which (a) bind to the marker, or (b) have a modulatory (e.g., stimulatory or inhibitory) effect on the activity of the marker or, more specifically, (c) have a modulatory effect on the interactions of the marker with one or more of its natural substrates (e.g., peptide, protein, hormone, co-factor, or nucleic acid), or (d) have a modulatory effect on the expression of the marker. Such assays typically comprise a reaction between the marker and one or more assay components. The other components may be either the test compound itself, or a combination of test compound and a natural binding partner of the marker.

The test compounds of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten, 1992, *Biotechniques* 13-412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al., 1992, *Proc Natl Acad Sci USA* 89:1865-1869) or on phage (Scott and Smith, 1990, *Science* 249:386-390; Devlin, 1990, *Science* 249:404-406; Cwirla et al., 1990, *Proc. Natl. Acad. Sci.* 87:6378-6382; Felici, 1991, *J. Mol. Biol.* 222:301-310; Ladner, supra.).

In one embodiment, the invention provides assays for screening candidate or test compounds which are substrates of a protein encoded by or corresponding to a marker or biologically active portion thereof. In another embodiment, the invention provides assays for screening candidate or test compounds which bind to a protein encoded by or corresponding to a marker or biologically active portion thereof. Determining the ability of the test compound to directly bind to a protein can be accomplished, for example, by coupling the compound with a radioisotope or enzymatic label such that binding of the compound to the marker can be determined by detecting the labeled marker compound in a complex. For example, compounds (e.g., marker substrates) can be labeled with $^{125}I$, $^{35}S$, $^{14}C$, or $^{3}H$, either directly or indirectly, and the radioisotope detected by direct counting of radioemission or by scintillation counting. Alternatively, assay components can be enzymatically labeled with, for example, horseradish peroxidase, alkaline phosphatase, or luciferase, and the enzymatic label detected by determination of conversion of an appropriate substrate to product.

In another embodiment, the invention provides assays for screening candidate or test compounds which modulate the expression of a marker or the activity of a protein encoded by or corresponding to a marker, or a biologically active portion thereof. In all likelihood, the protein encoded by or corresponding to the marker can, in vivo, interact with one or more molecules, such as but not limited to, peptides, proteins, hormones, cofactors and nucleic acids. For the purposes of this discussion, such cellular and extracellular molecules are referred to herein as "binding partners" or marker "substrate".

One necessary embodiment of the invention in order to facilitate such screening is the use of a protein encoded by or corresponding to marker to identify the protein's natural in vivo binding partners. There are many ways to accomplish this which are known to one skilled in the art. One example is the use of the marker protein as "bait protein" in a two-hybrid assay or three-hybrid assay (see, e.g., U.S. Pat. No. 5,283,317; Zervos et al., 1993, *Cell* 72:223-232; Madura et al., 1993, *J. Biol. Chem.* 268:12046-12054; Bartel et al ,1993, *Biotechniques* 14:920-924; Iwabuchi et al., 1993 *Oncogene* 8:1693-1696; Brent WO94/10300) in order to identify other proteins which bind to or interact with the marker (binding partners) and, therefore, are possibly involved in the natural function of the marker. Such marker binding partners are also likely to be involved in the propagation of signals by the marker protein or downstream elements of a marker protein-mediated signaling pathway. Alternatively, such marker protein binding partners may also be found to be inhibitors of the marker protein.

The two-hybrid system is based on the modular nature of most transcription factors, which consist of separable DNA-binding and activation domains. Briefly, the assay utilizes two different DNA constructs. In one construct, the gene that encodes a marker protein fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a marker-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be readily detected and cell colonies containing the functional transcription factor can be isolated and used to obtain the cloned gene which encodes the protein which interacts with the marker protein.

In a further embodiment, assays may be devised through the use of the invention for the purpose of identifying compounds which modulate (e.g., affect either positively or negatively) interactions between a marker protein and its substrates and/or binding partners. Such compounds can include, but are not limited to, molecules such as antibodies, peptides, hormones, oligonucleotides, nucleic acids, and analogs thereof. Such compounds may also be obtained from any available source, including systematic libraries of natural and/or synthetic compounds. The preferred assay components for use in this embodiment is a breast cancer marker protein identified herein, the known binding partner and/or substrate of same, and the test compound. Test compounds can be supplied from any, source.

The basic principle of the assay systems used to identify compounds that interfere with the interaction between the marker protein and its binding partner involves preparing a reaction mixture containing the marker protein and its binding partner under conditions and for a time sufficient to allow the two products to interact and bind, thus forming a complex. In order to test an agent for inhibitory activity, the reaction mixture is prepared in the presence and absence of the test compound. The test compound can be initially included in the reaction mixture, or can be added at a time subsequent to the addition of the marker protein and its binding partner. Control reaction mixtures are incubated without the test compound or with a placebo. The formation of any complexes between the marker protein and its binding partner is then detected. The formation of a complex in the control reaction, but less or no such formation in the reaction mixture containing the test compound, indicates that the compound interferes with the interaction of the marker protein and its binding partner. Conversely, the formation of more complex in the presence of compound than in the control reaction indicates that the compound may enhance interaction of the marker protein and its binding partner.

The assay for compounds that interfere with the interaction of the marker protein with its binding partner may be conducted in a heterogeneous or homogeneous format. Heterogeneous assays involve anchoring either the marker protein or its binding partner onto a solid phase and detecting complexes anchored to the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the marker proteins and the binding partners (e.g., by competition) can be identified by conducting the reaction in the presence of the test substance, i.e., by adding the test substance to the reaction mixture prior to or simultaneously with the marker and its interactive binding partner. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the marker protein or its binding partner is anchored onto a solid surface or matrix, while the other corresponding non-anchored component may be labeled, either directly or indirectly. In practice, microtitre plates are often utilized for this approach. The anchored species can be immobilized by a number of methods, either non-covalent or covalent, that are typically well known to one who practices the art. Non-covalent attachment can often be accomplished simply by coating the solid surface with a solution of the marker protein or its binding partner and drying. Alternatively, an immobilized antibody specific for the assay component to be anchored can be used for this purpose. Such surfaces can often be prepared in advance and stored.

In related embodiments, a fusion protein can be provided which adds a domain that allows one or both of the assay components to be anchored to a matrix. For example, glutathione-S-transferase/marker fusion proteins or glutathione- S-transferase/binding partner can be adsorbed onto glutathione sepharose beads (Sigma Chemical, St. Louis, Mo.) or glutathione derivatized microtiter plates, which are then combined with the test compound or the test compound and either the non-adsorbed marker or its binding partner, and the mixture incubated under conditions conducive to complex formation (e.g., physiological conditions). Following incubation, the beads or microtiter plate wells are washed to remove any unbound assay components, the immobilized complex assessed either directly or indirectly, for example, as described above. Alternatively, the complexes can be dissociated from the matrix, and the level of marker binding or activity determined using standard techniques.

Other techniques for immobilizing proteins on matrices can also be used in the screening assays of the invention. For example, either a marker protein or a marker protein binding partner can be immobilized utilizing conjugation of biotin and streptavidin. Biotinylated marker protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the protein-immobilized surfaces can be prepared in advance and stored.

In order to conduct the assay, the corresponding partner of the immobilized assay component is exposed to the coated surface with or without the test compound. After the reaction is complete, unreacted assay components are removed (e.g., by washing) and any complexes formed will remain immobilized on the solid surface. The detection of complexes anchored on the solid surface can be accomplished in a number of ways. Where the non-immobilized component is prelabeled, the detection of label immobilized on the surface indicates that complexes were formed. Where the non-immobilized component is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds which modulate (inhibit or enhance) complex formation or which disrupt preformed complexes can be detected.

In an alternate embodiment of the invention, a homogeneous assay may be used. This is typically a reaction, analogous to those mentioned above, which is conducted in a liquid phase in the presence or absence of the test compound. The formed complexes are then separated from unreacted components, and the amount of complex formed is determined. As mentioned for heterogeneous assay systems, the order of addition of reactants to the liquid phase can yield information about which test compounds modulate (inhibit or enhance) complex formation and which disrupt preformed complexes.

In such a homogeneous assay, the reaction products may be separated from unreacted assay components by any of a number of standard techniques, including but not limited to: differential centrifugation, chromatography, electrophoresis and immunoprecipitation. In differential centrifugation, complexes of molecules may be separated from uncomplexed molecules through a series of centrifugal steps, due to the different sedimentation equilibria of complexes based on their different sizes and densities (see, for example, Rivas, G., and Minton, A. P., *Trends Biochem Sci* 1993 August; 18(8): 284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the complex as compared to the uncomplexed molecules may be exploited to differentially separate the complex from the remaining individual reactants., for example through the use of ion-exchange chromatography resins. Such resins and chromatographic techniques are well known to one skilled in the art (see, e.g., Heegaard, 1998, *J. Mol. Recognit.* 11:141-148; Hage and Tweed, 1997, *J. Chromatogr. B. Biomed. Sci. Appl.,* 699:499-525). Gel electrophoresis may also be employed to separate complexed molecules from unbound species (see, e.g., Ausubel et al (eds.), In: Current Protocols in Molecular Biology, J. Wiley & Sons, New York. 1999). In this technique, protein or nucleic acid complexes are separated based on size or charge, for example. In order to maintain the binding interaction during the electrophoretic process, nondenaturing gels in the absence of reducing agent are typically preferred, but conditions appropriate to the particular interactants will be well known to one skilled in the art. Immunoprecipitation is another common technique utilized for the isolation of a protein-protein complex from solution (see, e.g., Ausubel et al (eds.), In: Current Protocols in Molecular Biology, J. Wiley & Sons, New York. 1999). In this technique, all proteins binding to an antibody specific to one of the binding molecules are precipitated from solution by conjugating the antibody to a polymer bead that may be readily collected by centrifugation. The bound assay components are released from the beads (through a specific proteolysis event or other technique well known in the art which will not disturb the protein-protein interaction in the complex), and a second immunoprecipitation step is performed, this time utilizing antibodies specific for the correspondingly different interacting assay component. In this manner, only formed complexes should remain attached to the beads. Variations in complex formation in both the presence and the absence of a test compound can be compared, thus offering information about the ability of the compound to modulate interactions between the marker protein and its binding partner.

Also within the scope of the present invention are methods for direct detection of interactions between the marker protein and its natural binding partner and/or a test compound in a homogeneous or heterogeneous assay system without further sample manipulation. For example, the technique of fluorescence energy transfer may be utilized (see, e.g., Lakowicz et al.; U.S. Pat. No. 5,631,169; Stavrianopoulos et al., U.S. Pat. No. 4,868,103). Generally, this technique involves the addition of a fluorophore label on a first ‘donor’ molecule (e.g., marker or test compound) such that its emitted fluorescent energy will be absorbed by a fluorescent label on a second, ‘acceptor’ molecule (e.g., marker or test compound), which in turn is able to fluoresce due to the absorbed energy. Alternately, the ‘donor’ protein molecule may simply utilize the natural fluorescent energy of tryptophan residues. Labels are chosen that emit different wavelengths of light, such that a the ‘acceptor’ molecule label may be differentiated from that of the ‘donor’. Since the efficiency of energy transfer between the labels is related to the distance separating the molecules, spatial relationships between the molecules can be assessed. In a situation in which binding occurs between the molecules, the fluorescent emission of the ‘acceptor’ molecule label in the assay should be maximal. An FET binding event can be conveniently measured through standard fluorometric detection means well known in the art (e.g., using a fluorimeter). A test substance which either enhances or hinders participation of one of the species in the preformed complex will result in the generation of a signal variant to that of background. In this way, test substances that modulate interactions between a marker and its binding partner can be identified in controlled assays.

In another embodiment, modulators of marker expression are identified in a method wherein a cell is contacted with a candidate compound and the expression of marker mRNA or protein in the cell, is determined. The level of expression of marker mRNA or protein in the presence of the candidate compound is compared to the level of expression of marker mRNA or protein in the absence of the candidate compound. The candidate compound can then be identified as a modulator of marker expression based on this comparison. For example, when expression of marker mRNA or protein is greater (statistically significantly greater) in the presence of the candidate compound than in its absence, the candidate compound is identified as a stimulator of marker mRNA or protein expression. Conversely, when expression of marker mRNA or protein is less (statistically significantly less) in the presence of the candidate compound than in its absence, the candidate compound is identified as an inhibitor of marker mRNA or protein expression. The level of marker mRNA or protein expression in the cells can be determined by methods described herein for detecting marker mRNA or protein.

In another aspect, the invention pertains to a combination of two or more of the assays described herein. For example, a modulating agent can be identified using a cell-based or a cell free assay, and the ability of the agent to modulate the activity of a marker protein can be further confirmed in vivo, e.g., in a whole animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein (e.g., an marker modulating agent an antisense marker nucleic acid molecule, an marker-specific antibody, or an marker-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

It is understood that appropriate doses of small molecule agents and protein or polypeptide agents depends upon a number of factors within the knowledge of the ordinarily skilled physician, veterinarian, or researcher. The dose(s) of these agents will vary, for example, depending upon the identity, size, and condition of the subject or sample being treated, further depending upon the route by which the composition is to be administered, if applicable, and the effect which the practitioner desires the agent to have upon the nucleic acid or polypeptide of the invention. Exemplary doses of a small molecule include milligram or microgram amounts per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). Exemplary doses of a protein or polypeptide include gram, milligram or microgram amounts per kilogram of subject or sample weight (e.g., about 1 microgram per kilogram to about 5 grams per kilogram, about 100 micrograms per kilogram to about 500 milligrams per kilogram, or about 1 milligram per kilogram to about 50 milligrams per kilogram). It is furthermore understood that appropriate doses of one of these agents depend upon the potency of the agent with respect to the expression or activity to be modulated. Such appropriate doses can be determined using the assays described herein. When one or more of these agents is to be administered to an animal (e.g., a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific agent employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediamine-tetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium, and then incorporating the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches, and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes having monoclonal antibodies incorporated therein or thereon) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration. A method for lipidation of antibodies is described by Cruikshank et al. (1997) *J. Acquired Immune Deficiency Syndromes and Human Retrovirology* 14:193.

The invention also provides vaccine compositions for the prevention and/or treatment of breast cancer. The invention provides breast cancer vaccine compositions in which a protein of a marker of Table 1, or a combination of proteins of the markers of Table 1 . are introduced into a subject in order to stimulate an immune response against the breast cancer. The invention also provides breast cancer vaccine compositions in which a gene expression construct, which expresses a marker or fragment of a marker identified in Table 1, is introduced into the subject such that a protein or fragment of a protein encoded by a marker of Table J is produced by transfected cells in the subject at a higher than normal level and elicits an immune response.

In one embodiment, a breast cancer vaccine is provided and employed as an immunotherapeutic agent for the prevention of breast cancer. In another embodiment, a breast cancer vaccine is provided and employed as an immunotherapeutic agent for the treatment of breast cancer.

By way of example, a breast cancer vaccine comprised of the proteins of the markers of Table 1, may be employed for the prevention and/or treatment of breast cancer in a subject by administering the vaccine by a variety of routes, e.g., intradermally, subcutaneously, or intramuscularly. In addition, the breast cancer vaccine can be administered together with adjuvants and/or immunomodulators to boost the activity of the vaccine and the subject's response. In one embodiment, devices and/or compositions containing the vaccine, suitable for sustained or intermittent release could be, implanted in the body or topically applied thereto for the relatively slow release of such materials into the body. The breast cancer vaccine can be introduced along with immunomodulatory compounds, which can alter the type of immune response produced in order to produce a response which will be more effective in eliminating the cancer.

In another embodiment, a breast cancer vaccine comprised of an expression construct of the markers of Table 1, may be introduced by injection into muscle or by coating onto microprojectiles and using a device designed for the purpose to fire the projectiles at high speed into the skin. The cells of the subject will then express the protein(s) or fragments of proteins of the markers of Table 1 and induce an immune response. In addition, the breast cancer vaccine may be introduced along with expression constructs for immunomodulatory molecules, such as cytokines, which may increase the immune response or modulate the type of immune response produced in order to produce a response which will be more effective in eliminating the cancer.

The marker nucleic acid molecules can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al., 1994, *Proc. Natl. Acad Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Predictive Medicine

The present invention pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining the level of expression of one or more marker proteins or nucleic acids, in order to determine whether an individual is at risk of developing breast cancer. Such assays can be used for prognostic or predictive purposes to thereby prophylactically treat an individual prior to the onset of the cancer.

Yet another aspect of the invention pertains to monitoring the influence of agents (e.g., drugs or other compounds administered either to inhibit breast cancer or to treat or prevent any other disorder {i.e., in order to understand any breast carcinogenic effects that such treatment may have}) on the expression or activity of a marker of the invention in clinical trials. These and other agents are described in further detail in the following sections.

Diagnostic Assays

An exemplary method for detecting the presence or absence of a marker protein or nucleic acid in a biological sample involves obtaining a biological sample (e.g., a breast associated body fluid) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. For example, in vitro techniques for detection of mRNA include Northern hybridizations and in situ hybridizations. In vitro techniques for detection of a marker protein include enzyme linked immunosorbent assays (ELISAs), Western blots, immunoprecipitations and immunofluorescence. In vitro techniques for detection of genomic DNA include Southern hybridizations. Furthermore, in vivo techniques for detection of a marker protein include introducing into a subject a labeled antibody directed against the protein or fragment thereof. For example, the antibody can be labeled with a radioactive marker whose presence and location in a subject can be detected by standard imaging techniques.

A general principle of such diagnostic and prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In a preferred embodiment, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C., 1991, *Anal. Chem.* 63:2338-2345 and Szabo et al., 1995, *Curr. Opin. Struct. Biol.* 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P., 1993, *Trends Biochem Sci.* 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, *J. Mol. Recognit. Winter* 11(1-6):141-8; Hage, D. S., and Tweed, S. A. *J Chromatogr B Biomed Sci Appl Oct.* 10, 1997;699(1-2):499-525). Gel electrophoresis may also be employed to separate complexed assay components from unbound components (see, e.g., Ausubel et al., ed., *Current Protocols in Molecular Biology*, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of marker mRNA can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from breast cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

An alternative method for determining the level of mRNA marker in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA,* 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the breast cells prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker.

Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-breast cancer sample, or between samples from different sources.

Alternatively, the expression level can be provided as a relative expression level. To determine a relative expression level of a marker, the level of expression of the marker is determined for 10 or more samples of normal versus cancer cell isolates, preferably 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

Preferably, the samples used in the baseline determination will be from breast lancer or from non-breast cancer cells of breast tissue. The choice of the cell source is dependent on the use of the relative expression level. Using expression found in normal tissues as a mean expression score aids in validating whether the marker assayed is breast specific (versus normal cells). In addition, as more data is accumulated, the mean expression value can be revised, providing improved relative expression values based on accumulated data. Expression data from breast cells provides a means for grading the severity of the breast cancer state.

In another embodiment of the present invention, a marker protein is detected. A preferred agent for detecting marker protein of the invention is an antibody capable of binding to such a protein or a fragment thereof, preferably an antibody with a detectable label. Antibodies can be polyclonal, or more preferably, monoclonal. An intact antibody, or a fragment or derivative thereof (e.g., Fab or $F(ab')_2$) can be used. The term “labeled”, with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Proteins from breast cells can be isolated using techniques that are well known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether breast cells express a marker of the present invention.

In one format, antibodies, or antibody fragments or derivatives, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an, antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from breast cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

The invention also encompasses kits for detecting the presence of a marker protein or nucleic acid in a biological sample (e g., a breast-associated body fluid such as a nipple aspirate). Such kits can be used to determine if a subject is suffering from or is at increased risk of developing breast cancer. For example, the kit can comprise a labeled compound or agent capable of detecting a marker protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include instructions for interpreting the results obtained using the kit.

For antibody-based kits, the kit can comprise, for example: (1) a first antibody (e.g., attached to a solid support) which binds to a marker protein; and, optionally, (2) a second, different antibody which binds to either the protein or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a marker protein or (2) a pair of primers useful for amplifying a marker nucleic acid molecule. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

Pharmacogenomics

The markers of the invention are also useful as pharmacogenomic markers. As used herein, a “pharmacogenomic marker” is an objective biochemical marker whose expression level correlates with a specific clinical drug response or susceptibility in a patient (see, e.g., McLeod et al. (1999) *Eur. J. Cancer* 35(12): 1650-1652). The presence or quantity of the pharmacogenomic marker expression is related to the predicted responsive of the patient and more particularly the patient’s tumor to therapy with a specific drug or class of drugs. By assessing the presence or quantity of the expression of one or more pharmacogenomic markers in a patient, a drug therapy which is most appropriate for the patient, or which is predicted to have a greater degree of success, may be selected. For example, based on the presence or quantity of RNA or protein encoded by specific tumor markers in a patient, a drug or course of treatment may be selected that is optimized for the treatment of the specific tumor likely to be present in the patient. The use of pharmacogenomic markers therefore permits selecting or designing the most appropriate treatment for each cancer patient without trying different drugs or regimes.

Another aspect of pharmacogenomics deals with genetic conditions that alters the way the body acts on drugs. These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gYene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the level of expression of a marker of the invention in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of expression of a marker of the invention.

Monitoring Clinical Trials

Monitoring the influence of agents (e.g., drug compounds) on the level of expression of a marker of the invention can be applied not only in basic drug screening, but also in clinical trials. For example, the effectiveness of an agent to affect marker expression can be monitored in clinical trials of subjects receiving treatment for breast cancer. In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting the level of expression of one or more selected markers of the invention in the pre-administration sample; (iii) obtaining one or more post-administration samples from the subject; (iv) detecting the level of expression of the marker(s) in the post-administration samples; (v) comparing the level of expression of the marker(s) in the pre-administration sample with the level of expression of the marker(s) in the post-administration sample or samples; and (vi) altering the administration of the agent to the subject accordingly. For example, increased expression of marker gene(s) during the course of treatment may indicate ineffective dosage and the desirability of increasing the dosage. Conversely, decreased expression of the marker gene(s) may indicate efficacious treatment and no need to change dosage.

Electronic Apparatus Readable Media and Arrays

Electronic apparatus readable media comprising a marker of the present invention is also provided. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon a marker of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the markers of the present invention.

A variety of software programs and formats can be used to store the marker information of the present invention on the electronic apparatus readable medium. For example, the marker nucleic acid sequence can be represented in a word processing text file, formatted in commercially-available software such as WordPerfect and MicroSoft Word, or represented in the form of an ASCII file, stored in a database application, such as DB2, Sybase, Oracle, or the like, as well as in other forms. Any number of data processor structuring formats (e.g., text file or database) may be employed in order to obtain or create a medium having recorded thereon the markers of the present invention.

By providing the markers of the invention in readable form, one can routinely access the marker sequence information for a variety of purposes. For example, one skilled in the art can use the nucleotide or amino acid sequences of the present invention in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has breast cancer or a pre-disposition to breast cancer, wherein the method comprises the steps of determining the presence or absence of a marker and based on the presence or absence of the marker, determining whether the subject has breast cancer or a pre-disposition to breast cancer and/or recommending a particular treatment for breast cancer or pre-breast cancer condition.

The present invention further provides in an electronic system and/or in a network, a method for determining whether a subject has breast cancer or a pre-disposition to breast cancer associated with a marker wherein the method comprises the steps of determining the presence or absence of the marker, and based on the presence or absence of the marker, determining whether the subject has breast cancer or a pre-disposition to breast cancer, and/or recommending a particular treatment for the breast cancer or pre-breast cancer condition. The method may further comprise the step of receiving phenotypic information associated with the subject and/or acquiring from a network phenotypic information associated with the subject.

The present invention also provides in a network, a method for determining whether a subject has breast cancer or a pre-disposition to breast cancer associated with a marker, said method comprising the steps of receiving information associated with the marker receiving phenotypic information associated with the subject, acquiring information from the network corresponding to the marker and/or breast cancer, and based on one or more of the phenotypic information, the marker, and the acquired information, determining whether the subject has a breast cancer or a pre-disposition to breast cancer. The method may further comprise the step of recommending a particular treatment for the breast cancer or pre-breast cancer condition.

The present invention also provides a business method for determining whether a subject has breast cancer, an aggressive breast tumor or a pre-disposition to breast cancer, said method comprising the steps of receiving information associated with the marker, receiving phenotypic information associated with the subject, acquiring information from the network corresponding to the marker and/or breast cancer, and based on one or more of the phenotypic information, the marker, and the acquired information, determining whether the subject has breast cancer or a pre-disposition to breast cancer. The method may further comprise the step of recommending a particular treatment for the breast cancer or pre-breast cancer condition.

The invention also includes an array comprising a marker of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of breast cancer, progression of breast cancer, and processes, such a cellular transformation associated with breast cancer.

The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that could serve as a molecular target for diagnosis or therapeutic intervention.

Surrogate Markers

The markers of the invention may serve as surrogate markers for one or more disorders or disease states or for conditions leading up to disease states, and in particular, breast cancer. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The markers of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker transcription or expression, the amplified marker may be in a quantity which is more readily detectable than the drug itself. Also, the marker may be more easily detected due to the nature of the marker itself; for example, using the methods described herein, antibodies may be employed in an immune-based detection system for a protein marker, or marker-specific radiolabeled probes may be used to detect a mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am, J. Health-Syst. Pharm.* 56 Suppl. 3: S16-S20.

EXAMPLE 1

Identification of Breast Cancer Markers by cDNA and Tissue Microarrays

I. Materials and Methods

Sample Collection and RNA Preparation

Breast tissues were collected and snap frozen in liquid nitrogen. The histology and cellular composition of tissues were confirmed before RNA extraction was performed. Total RNA was extracted from the frozen tissues using Trizol Reagent (Invitrogen, San Diego, Calif.) followed by a secondary clean up step with Qiagen's RNeasy kit to increase RNA probe labeling efficiency (Qiagen, Valencia Calif.). Only RNA with a 28S/18S ribosomal RNA ratio of at least 1.0, calculated from ethidium staining of the RNA after electrophoresis on agarose gels, was used in this study.

cDNA Microarray Hybridization cDNA microarrays containing 30,732 Unigene clones from Research Genetics (Hunstville, Ala.) were generated on nylon filters. A total of 4-6 ug of total RNA was used as template to generate radioactively labeled cDNA by reverse transcription with $^{33}$P-dCTP, oligo dT-30 primer and Superscript II Reverse Transcriptase (Life Technologies). $^{33}$P-labeled first strand cDNA was preannealed with cot-1 DNA and poly-dA 40-60 (Pharmacia, Peapack, N.J.) to reduce non-specific hybridization. Each filter was hybridized at 65° C. for 16 hours with approximately $6\times10^6$ counts of labeled probe in a buffer containing 7% sodium dodecyl sulfate (SDS), 250 mM $Na_3PO_4$ (pH 7.2), 1 mM EDTA, 0.5% Casein-Hammerstein and 0.1 mg/ml of denatured salmon sperm DNA. After the filters were washed with 4% and 1% SDS wash buffer (20 mM $Na_3PO_4$ (pH 7.2), 1 mM EDTA and 4% or 1% SDS), they were exposed to Fuji Phosphoimager screens and scanned using a Fuji scanner BAS 2500. Spots were quantitated using an automated array analysis program, Grid Guru v1.0, developed at Millennium Pharmaceuticals, Inc.

Marker Scoring Algorithm and Data Analysis

To correct for differences in hybridization efficiency, the digitized data from each microarray filter was normalized by the median intensity of all spots on that filter. Both array-based and gene-based hierarchical clustering was performed and visualized using Stanford's Gene Cluster and Tree View software. Differentially expressed genes were ranked by calculating the Marker Score for each gene.

Samples were divided into control and tester groups for computation of Marker Score. The starting point for the Marker Score is average fold change (ratio) of the tester samples above the control samples. The score was designed to reflect both the degree of change (the expression ratio) and the number of tester samples showing differential expression, while not being dominated by a small fraction of tester samples with very high values. To reduce this "outlier" effect, genes were treated with expression ratios greater than 10 as not meaningfully different from those with ratios of 10. This desired performance from a Marker Score was accomplished by transforming the tester:control expression ratio using an asymptotic compression function before taking the average fold-change across tester samples. A Marker Score has a value of 1 when the testers do not appear to be expressed more highly than the controls and a value greater than 1 otherwise. A Marker Score cannot exceed a value of 10 for any gene.

The Marker Score Sg for gene g is therefore computed as the average of the ratios of weighted intensities of the individual testers and a control level as follows:

$$S_g=(\Sigma\, S_{gs})/N_{tester}$$

$S_{gs}=C(x_{gs}/(k+x_g^Q))$, where $S_{gs}$ represents the Marker Score for gene g and the sample s, C(r) is the compression function $C(r)=A(1-e^{r/A})$ for $r\geqq1$, and $C(r)=1$ for $r<1$, A is an upper asymptote on the fold-change value (we used 10), $X_{gs}$ is the expression value of gene g on sample s, $x_g^Q$ is the Qth percentile of the control samples' expression value; typically Q=50.

k is a constant reflecting the additive noise in the data, i.e., the fixed component of the variance in repeated measurements. A value of 0.25 was derived for this parameter from calibration experiments using microarray technology.

$N_{tester}$ is the number of tester samples

In situ Hybridization of Tissue Microarrays

Formalin-fixed, paraffin embedded breast tissue microarrays were provided. Prehybridization treatment was performed with an automatic Tissue-Tek DRS 2000 Slide Stainer (Sakura, Torrance, Calif.) using a previously described protocol (Duncan, L. M., et al., 2001, *J. Clin. Oncol.* 19(2): 568-576). The breast tissues were deparaffinized, rehydrated and postfixed with 4% paraformaldehyde in PBS for 15 minutes. After washing with PBS, the tissue microarrays were digested with 2 ug/ml proteinase K at 37° C. for 15 minutes and again incubated with 4% paraformaldehyde/PBS for 10 minutes. Tissue sections were subsequently incubated with 0.2N HCL for 10 minutes, 0.25% acetic anhydride/0.1 mol/L triethanolamine for 10 minutes, and dehydrated with graded ethanol. Antisense probes were labeled with $^{35}$S-UTP in an in vitro transcription reaction (Riboprobe Combination System, Promega, Madison, Wis.) using 500 ng of linearized plasmid DNA derived from IMAGE clones. Hybridizations were performed at 50° C. for 18 hours using probes labeled at $5\times10^7$ cpm/ml in 10 mM Tris-HCl (pH 7.6) buffer containing 50% formamide, 10% dextran sulfate, 1× Denhardt's solution, 0.6 M NaCl, 10 mM DTT, 0.25% SDS and 200 ug/ml tRNA. After hybridization, slides were washed with 5× standard saline citrate (SSC) at 50° C. for 10 minutes, 50% formamide/2×SSC at 50° C. for 30 minutes, 10 mM Tris-HCl (pH 7.6)/500 mM NaCl/1 mM EDTA (TNE) at 37° C. for 10 minutes, incubated in 10 ug/ml Rnase A in TNE at 37° C. for 30 minutes, washed in TNE at 37° C. for 10 minutes, incubated once in 2×SSC at 50° C. for 20 minutes, twice in 0.2×SSC at 50° C. for 20 minutes, and dehydrated with graded ethanol. Localization of mRNA transcripts was determined by dipping slides in Kodak NTB2 photoemulsion (Eastman Kodak, Rochester, N.Y.) and exposing for 14-21 days at 4° C. The slides were counterstained using Myers hematoxylin and alcoholic eosin Y.

Gene Expression Analysis Using Quantitative PCR

Gene expression was measured by TAQMAN® quantitative PCR (Applied Biosystems) in cDNA prepared from normal and diseased (e.g., cancerous) human tissue samples. Briefly, total RNA was prepared from patient samples by a single step extraction method using TRIZOL Reagent according to the manufacturer's instructions (Invitrogen). Each RNA preparation was treated with DNase I (Ambion) at 37° C. for 1 hour. DNAse I treatment was determined to be complete if the sample required at least 38 PCR amplification cycles to reach a threshold level of fluorescence using β-2 microglobulin as an internal amplicon reference (or 35 PCR amplification cycles for 18s ribosome gene). The integrity of the RNA samples following DNase I treatment was confirmed by agarose gel electrophoresis and ethidium bromide staining. After phenol extraction cDNA was prepared from the sample using the Taqman Reverse Transcription Reagents following the manufacturer's instructions (Applied Biosytems). A negative control of RNA without reverse transcriptase was mock reverse transcribed for each RNA sample.

Probes were designed by PrimerExpress software (Applied Biosystems) based on the sequence of the specific genes and their related transcripts. Each target gene probe was labeled using FAM (6-carboxyfluorescein), and the 18s reference probe was labeled with a different fluorescent dye, VIC. The differential labeling of the target gene and internal reference gene thus enabled measurement in same well. Primer and probes were checked for their sensitivity and specificity for each transcript of the specific gene. Forward and reverse primers and the probes for both 18s and target gene were added to the TAQMAN® Universal PCR Master Mix (Applied Biosystems). Although the final concentration of primer and probe could vary, each was internally consistent within a given experiment. A typical experiment contained 100 nM of forward and reverse primers plus 200 nM probe for 18s and 900 nM forward and reverse primers plus 250 nM probe for the target gene. TAQMAN® matrix experiments were carried out on an ABI PRISM 7700 Sequence Detection System (Applied Biosystems). The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate gene expression in the various tissues relative to 18s expression in the same tissue. The threshold cycle (Ct) value is defined as the cycle at which a statistically significant increase in fluorescence is detected. A lower Ct value is indicative of a higher mRNA concentration. The Ct value of the gene is normalized by subtracting the Ct value of the 18s cibosome gene to obtain a ΔCt value using the following formula: ΔCt=Ct (target transcript)−Ct (18s). Relative expression is then calculated using the arithmetic formula given by 2−ΔCt.

II. Results

Screening Marker Selection

All of the markers listed in Table 1 were identified by transcription profiling as defined in the materials and methods section above using mRNA from a breast screening panel consisting of patient samples of a "breast tumor pool" (3 breast tumor patient samples), a "breast normal pool" (3 normal breast epithelium patient samples), an "other normals pool" (one sample from normal heart, kidney, small intestine, spleen, white blood cells, lung, liver, brain, bone marrow and colon patient tissue samples) and an "others tumors pool" (4 cervical carcinoma, 5 colon tumor, 8 lung carcinoma patient samples of various types, 4 ovarian tumor samples, and 5 prostate tumor samples). Clones having expression of at least three-fold higher in at least 25% of breast tumors, compared to their expression breast normal, other normal or other tumors, were designated as breast tumor specific screening markers. These cDNA clones were selected to have their protein-encoding transcript sequences determined.

In order to determine the full-length protein-encoding transcripts for the selected cDNA clones, the sequence(s) of the selected clones were used to query the public and proprietary sequence databases in order to identify other EST sequences or clusters with significant overlap. Thus, contiguous EST sequences and/or clusters were assembled into protein-encoding transcripts. Alternative transcript analysis for all of the claimed markers was undertaken as follows.

Using existing mappings of known nucleotide sequences for any given marker gene to the human genome sequence and by additionally mapping novel nucleotide sequences for any given marker gene onto the human genome sequence (e.g., using resources like the "UCSC genome browser" or in-house resources of similar functionality in conjunction with algorithms like BLAT that allow a rapid and precise mapping of search sequences onto genomic sequence), the exon-intron structure of a marker gene was established, taking additionally into account EST sequences matching the same gene.

PCR primers were designed to amplify the coding sequence of a given marker gene from the tissue of interest and control samples. Any alternative 5' or 3' ends of a marker gene arising from this analysis with the potential to alter the coding sequence led to the design of an additional primer specific for this alternative end.

PCR products obtained with cDNA templates derived from breast tumor specimens were cloned into a plasmid vector and characterized by DNA sequence analysis. Typically, 96 clones were analyzed by restriction digestion and gel electrophoresis of the PCR products or by DNA sequence analysis.

Clones representative of alternative gene transcripts occurring at a frequency of 2% or greater were sequenced. The identification of protein sequence corresponding to these alternative transcripts was accomplished by the identification of the open reading frame (ORF) contained within a manually curated assembly (contig) based on all available sequences. The identified sequences are designated in Table 1 and the sequence listing.

Differential gene expression of genes with identified alternative transcripts was confirmed by TAQMAN® quantitative PCR (Applied Biosystems) in cDNA prepared from the patient tissue specimens. Gene specific TAQMAN® reagents which were sensitive for all transcripts identified for a given gene were prepared in certain instances (e.g., BCMP11, DNAJC1 and NPY1R). Additionally, splice-form specific TAQMAN® reagent sets were developed for each transcript of certain markers separately (e.g., M725, M726, M727, M111, M149, M730, M165A, M731, M732, M96A, M739, M740, M741, M716, M717). With one exception, gene-specific as well as transcript-specific expression profiles demonstrating differential tumor-normal expression, with similar amplification efficiencies were found. In one case (M731, a NPY1R transcript), expression was not demonstrated with TAQMAN® PCR, presumably due to low abundance of this transcript.

Staging Marker Selection

All of the markers listed in Table 2 were identified by transcription profiling as defined in the materials and methods section using mRNA from 23 IDC node negative breast tumors with good outcome, defined as greater than five years of disease-free survival, and 16 IDC node negative breast tumors with poor clinical outcome, defined as less than three years of disease free survival. Clones having expression of at least three-fold higher in at least 25% of poor clinical outcome tumors, compared to their expression in good clinical outcome tumors, were designated as poor clinical outcome tumor specific markers. These cDNA clones were selected to have their protein-encoding transcript sequences determined.

Determination of the full-length protein encoding transcripts for selected cDNA clones was carried out as described above for the screening markers. The identified sequences are designated in Table 2 and the sequence listing. The differential gene expression of the identified alternative transcripts was confirmed by TAQMAN® quantitative PCR (Applied Biosystems) in cDNA prepared from patient tissue specimens from invasive ductal carcinoma (IDC) tumors with good outcome and poor outcome. Splice-form specific TaqMan primers and probe reagent sets were developed for each transcript and similar amplification efficiencies were obtained with all reagent sets for each gene (see Table 3).

The identification of protein sequences corresponding to these alternative transcripts was accomplished by the identification of the open reading frame (ORF) contained within a manually curated assembly (contig) based on all available sequences. The identified protein sequences are designated in Table 2 and the sequence listing.

TABLE 3

Breast Cancer Staging Marker Differential Expression

| Marker | Gene Name | GOP Pos/ Total | GOP Freq | POP Pos/ Total | POP Freq |
|---|---|---|---|---|---|
| M672A | ASS: argininosuccinate synthetase | 0 of 25 | 0.0% | 0 of 39 | 0.0% |
| M675A | CAB2: hypothetical protein MGC9753 | 2 of 28 | 7.1% | 3 of 37 | 8.1% |
| M367 | CD24: CD24 antigen (small cell lung carcinoma cluster 4 antigen) | 6 of 32 | 18.8% | 16 of 38 | 42.1% |
| M709 M710 | FACL2: fatty-acid-Coenzyme A ligase, long-chain 2 | 0 of 25 | 0.0% | 0 of 39 | 0.0% |
| M495 | GSTP1: glutathione S-transferase pi | 0 of 25 | 0.0% | 0 of 39 | 0.0% |
| M674 | HN1: hematological and neurological expressed 1 | 0 of 25 | 0.0% | 0 of 39 | 0.0% |
| M234A | MGC14832: hypothetical protein MGC14832 | 0 of 25 | 0.0% | 0 of 39 | 0.0% |
| M408 | NDRG1: N-myc downstream regulated protein | 5 of 35 | 14.3% | 12 of 39 | 30.8% |
| M711 | ORMDL3: ORM1-like 3 (*S. cerevisiae*) | 5 of 28 | 17.9% | 13 of 35 | 37.1% |
| M514 M708 | DARPP-32: dopamine and cAMP regulated phosphoprotein, (PPP1R1B: protein phosphatase 1, regulatory (inhibitor) subunit 1B) | 0 of 25 | 0.0% | 0 of 39 | 0.0% |
| M678A | PSMB9: proteasome subunit, beta type, 9 | 0 of 25 | 0.0% | 0 of 39 | 0.0% |
| M421A | SERHL: kraken-like | 5 of 33 | 15.2% | 9 of 37 | 24.3% |
| M185A | SLPI: secretory leukocyte protease inhibitor (antileukoproteinase) | 3 of 25 | 12.0% | 4 of 36 | 11.1% |

EXAMPLE 2

Gene Expression Analysis by End-Point PCR

I. Materials and Methods

Briefly, total RNA from different samples was pooled to be used as template to generate first strand cDNA. Equal amounts of each sample were included in the pool. The breast screening panel consisted of patient samples of a "breast tumor pool" (3 breast tumor patient samples), a "breast normal pool" (3 normal breast epithelium patient samples), an "other normals pool" (one sample from normal heart, kidney, small intestine, spleen, white blood cells, lung, liver, brain, bone marrow and colon patient tissue samples) and an "others tumors pool" (4 cervical carcinoma, 5 colon tumor, 8 lung carcinoma patient samples of various types, 4 ovarian tumor samples, and 5 prostate tumor samples) (see, e.g., Table 2). The breast staging panel consisted of patient samples of a "tumor good outcome pool" (4 adenocarcinoma patient samples), a "tumor poor outcome pool" (5 adenocardinoma patient samples), a "breast normal pool" (4 normal breast epithelium patient samples), an "other normals pool" (one patient sample from normal heart, kidney, small intestine, spleen, white blood cells, lung, liver brain, bone marrow and colon) and an "others tumors pool" (cervical, colon, lung, ovarian and prostate tumors) (see, e.g., Table 3).

Total RNA was prepared from patient samples by a single step extraction method using TRIZOL Reagent according to the manufacturer's instructions (Invitrogen). Each RNA preparation was treated with DNase I (Ambion) at 37° C. for 1 hour. RNA from each patient sample was pooled into one of the four patient pools, e.g., breast normal pool, breast tumor pool, other normals pool, others tumors pool. ThermoScript RT-PCR System (Invitrogen, San Diego, Calif.) was used to obtain cDNA from each of the five patient pools. Briefly, 1 μg RNA was denatured at 65° C. for 5 min with 1 μl of 50 μM oligo (dT)20 primer in a 10 μl volume according to the manufacturer's instructions. The reaction was terminated by incubation at 85° C. for 5 min. The final product was diluted with water to a final volume of 100 μl.

Gene specific primers were designed just outside the Open Reading Frame (as shown in Table 2 categories "Endpoint PCR Primer 1" and "Endpoint PCR Primer 2"). The PCR conditions were optimized for the primers and the size of the product expected. 2 μl of cDNA was used in a 20 μl reaction with touchdown cycling conditions. Products were run on an ethidium bromide containing agarose gel, and resulting gel pictures were semi-quantitatively analyzed and scored. The gel pictures of the end-point PCR on the tissue panel were scored on a scale of 1-5. Each picture was scored independently by three people based on visual band intensity and results compiled, scores were compared to confirm all three agreed on the relative intensities of the bands and modifications were made where needed. The median of the three scores was then recorded as the final score.

II. Results

TABLE 4

Breast Screening Endpoint PCR Data

| Marker | Gene Name | Endpoint PCR Primer 1 | Endpoint PCR Primer 2 | Normal Pool | Tumor Pool | Breast Normal | Breast Tumor |
|---|---|---|---|---|---|---|---|
| M196A | BCMP11 | 1-20 | 243-262 | 3 | 3 | 3 | 5 |
| M725 | BCMP11 | 2-21 | 523-543 | 0 | 0 | 0 | 2 |
| M726 | BCMP11 | 1-20 | 107-126 | 3 | 3 | 3 | 5 |
| M727 | BCMP11 | 1-20 | 244-263 | 3 | 3 | 3 | 5 |
| M156 | CXCL9 | 12-38 | 479-498 | 0 | 3 | 0 | 4 |
| M419 | CXCL10 | 29-51 | 366-385 | 1 | 1 | 2 | 4 |
| M728 | DNAJC1 | 388-410 | 1155-1179 | 0 | 0 | 0 | 2 |
| M729 | DNAJC1 | 388-410 | 1137-1161 | 0 | 0 | 0 | 2 |
| M111 | DNAJC1 | 252-274 | 1775-1799 | 1 | 1 | 2 | 3 |
| M428A | FLJ22774 | 528-553 | 3028-3050 | | | 0 | 2 |
| M149A | LIV-1 | 266-283 | 2612-2638 | 0 | 3 | 2 | 5 |
| M730 | LIV-1 | 309-324 | 1748-1719 | | | 2 | 3 |
| M158A | MMP11 | 433-450 | 1518-1536 | 0 | 0 | 0 | 3 |
| M165A | NPY1R | 195-215 | 1440-1459 | 2 | 2 | 3 | 5 |
| M731 | NPY1R | 164-184 | 1506-1525 | 2 | 2 | 3 | 5 |
| M732 | NPY1R | 195-215 | 1154-1173 | 2 | 2 | 3 | 5 |
| M235 | NY-BR-1 | 3539-3560 | 4171-4195 | 1 | 0 | 3 | 4 |
| M562 | PIP | 4-22 | 494-509 | 0 | 3 | 4 | 5 |
| M96A | SCUBE2 | 342-365 | 3272-3294 | 0 | 0 | 3 | 5 |
| M739 | SCUBE2 | 342-365 | 3032-3054 | 0 | 0 | 3 | 5 |
| M740 | SCUBE2 | 342-365 | 2894-2916 | 0 | 0 | 3 | 5 |
| M741 | SCUBE2 | 342-365 | 3359-3381 | 0 | 0 | 3 | 5 |
| M242 | TFF1 | 22-42 | 351-371 | 0 | 0 | 2 | 5 |

Markers were expressed at higher levels in the breast tumor samples than those obtained from the other tumor samples or the normal sample groups (Table 4). Particular strong expression was observed with M725, M728, M729, M158A, M242, M156, M419, and M149A in the breast tumor group when compared to those obtained from the breast normal, other normal, or the other tumor group.

TABLE 5

Breast Staging Endpoint PCR Data

| Marker | Gene Symbol | Endpoint PCR Primer 1 | Endpoint PCR Primer 2 | Tum Out Good | Tum Out Poor |
|---|---|---|---|---|---|
| M672A | ASS | 69-88 | 1323-1344 | 1 | 5 |
| M675A | CAB2 | 1-21 | 1153-1177 | 0 | 3 |
| M367 | CD24 | 6-29 | 361-384 | 3 | 4 |
| M514 | DARPP-32, variant 1 | 179-198 | 1201-1220 | 1 | 5 |

TABLE 5-continued

Breast Staging Endpoint PCR Data

| Marker | Gene Symbol | Endpoint PCR Primer 1 | Endpoint PCR Primer 2 | Tum Out Good | Tum Out Poor |
|---|---|---|---|---|---|
| M708 | DARPP-32, variant 2 | 137-156 | 1541-1560 | 1 | 4 |
| M709 M710 | FACL2 | 1-24 | 2307-2332 | 0 | 3 |
| M495 | GSTP1 | 3-22 | 676-697 | 1 | 3 |
| M674 | HN1 | 54-72 | 601-622 | 2 | 5 |
| M234A | MGC14832 | 2-19 | 374-396 | 2 | 5 |
| M408 | NDRG1 | 66-85 | 1374-1393 | 1 | 3 |
| M711 | ORMDL3 | 287-308 | 874-896 | 0 | 4 |
| M678A | PSMB9 | 1-18 | 739-761 | 1 | 3 |

TABLE 5-continued

Breast Staging Endpoint PCR Data

| Marker | Gene Symbol | Endpoint PCR Primer 1 | Endpoint PCR Primer 2 | Tum Out Good | Tum Out Poor |
|---|---|---|---|---|---|
| M421A | SERHL | 51-69 | 1103-1122 | 3 | 5 |
| M185A | SLPI | 13-33 | 519-538 | N/A | 4 |

The markers were expressed at higher levels in the breast tumor samples of the poor outcome group than those obtained from the good outcome group (Table 5). Particular strong expression was observed with M672A, M675A, M514, M708, M710, M674, M234A, M711, and M421A in the poor outcome group when compared to those obtained from the good outcome group.

EXAMPLE 3

Characterization of OST-2 Splice Variants

I. Materials and Methods cDNA Synthesis

Total RNA was isolated from 3 normal and 12 tumor breast tissue samples similar to procedures described above in Examples 1 and 2. Briefly, using the TRIZOL Reagent (Invitrogen, San Diego, Calif.) System according to manufacturer instructions, followed by RNAeasy (Qiagen, Valencia, Calif.) or DNase I (Ambion) treatment according to manufacturers instructions. 1 μg from each sample was combined into normal and tumor pools. ThermoScript RT-PCR System (Invitrogen, San Diego, Calif.) was used to obtain cDNA as described in Example 2 above. The final product was diluted with water to a final volume of 400-8300 μl.

cDNA was amplified using OSF-2 gene specific primers from exon 16 and exon 23 to cover the region involved in splice variation. Primers for PCR amplification were designed using Primer Version 5.0 software (Whitehead Institute, Cambridge, Mass.). PCR conditions were optimized for the primers and product size expected. 0.5 μl of diluted RT reaction was used in a 30 μl reaction with PCR conditions, after an initial 95° C. denaturing step of 2 minutes, consisting of 55 cycles of 95° C. for 30 sec, annealing@60° C. for 35 sec and elongation temp of 72° C. for 30 sec and a final elongation step of 72° C. for 7 min.

Cloning Colony PCR and Sequencing

PCR products for both reactions derived from RT/PCR were gel-purified and cloned into pCR2.1 using TOPO TA cloning kit and transforming into *E. coli* One-Shot Chemically Competent cells (Invitrogen, San Diego, Calif.) according to manufacturer's instructions. Resulting colonies were selected and colony PCR was carried out in 30 μL volume as described under above using colony cells originating from the normal and the tumor pools as template. Resulting PCR product was purified using QIAquick 96 multiwell kit (Qiagen Inc., Valencia Calif.), and submitted for sequencing. Sequencing was preformed using ABI 3700 Automated Sequencer with Big Dye Terminators version 1.1.

The program BLAST [Kent, 2002] was used to align all clone sequences to genomic sequence of the OSF-2 locus. Only sequences matching the entire variable region of OSF-2, i.e., spanning at least from exon 17 to exon 22 or from exon 21 to exon 16 ("qualifying sequences'), were considered. Sequences were then grouped according to their presence-absence pattern of the variable exons 17-21.

II. Results

OSF-2 expression is subject to alternative splicing events creating eight transcript variants, which are characterized by different combinations of exons 17 to 21 (of 23 total exons) (see Table 6). Variable exons 17-19 and 21 are positioned within the coding sequence and can be present or absent without changing the transcripts' reading frame, giving rise to different protein products in a modular fashion.

TABLE 6

Schematic Representation of OSF-2 Alternative Splice Variants

| Marker ID | Exon | Exon | Exon | Exon | Exon | Exon | Exon |
|---|---|---|---|---|---|---|---|
| M56A | 16 | 17 | 18 | 19 | 20 | 21 | 22 |
| M733 | 16 | 17 | 18 | 19 | 20 | | 22 |
| M734 | 16 | | 18 | 19 | 20 | 21 | 22 |
| M735 | 16 | | 18 | 19 | 20 | | 22 |
| M491A | 16 | | | 19 | 20 | 21 | 22 |
| M736 | 16 | | | 19 | 20 | | 22 |
| M737 | 16 | | | | 20 | 21 | 22 |
| M738 | 16 | | | | 20 | | 22 |

The relative expression levels of the eight listed splice variants of OSF-2 are different between normal and tumor tissue. Table 7 depicts the relative frequencies of each transcript in normal, and breast tumor tissue as obtained by analyzing qualifying sequences of clones derived from normal breast tissue and breast tumor tissue.

TABLE 7

Relative frequencies of OSF-2 splice variant transcripts in tissue

| Marker ID | Description of transcript | % of all transcripts in normal | % of all transcripts in tumor |
|---|---|---|---|
| M56A | (1) all exons, +21 | 10.09 | 3.50 |
| M733 | (2) all exons, no 21 | 4.28 | 2.33 |
| M734 | (3) no 17, +21 | 31.50 | 23.03 |
| M735 | (4) no 17, no 21 | 24.46 | 32.07 |
| M491A | (5) no (17, 18), +21 | 11.62 | 11.95 |
| M736 | (6) no (17, 18), no 21 | 12.54 | 19.83 |
| M737 | (7) no (17-19), +21 | 0.61 | 2.33 |
| M738 | (8) no (17-19), no 21 | 2.45 | 4.67 |
| | Other transcripts | 2.45 | 0.29 |
| ALL | | 100 | 100 |

There is an increased level exon 21 containing transcripts in normal breast tissue, and increased level of transcripts lacking exon 21 in breast tumor tissue (e.g., a total of 59% of all transcripts in breast tumor tissue lacking exon 21, compared to only 45% of all transcripts lacking exon 21 in normal breast tissue in samples analyzed).

Expression levels were determined for transcripts either containing or lacking exon 21 for OSF-2. Two reagent sets were used: one specific for transcripts containing exon 21 and a second one specific for transcripts that do not. A significant tumor/normal increased expression was observed. For example, an average 2.5-fold over-expression in tumor samples, is observed with the reagent set specific for OSF-2 transcripts lacking exon 21. This increase is not observed in assessing the OSF-2 transcripts containing exon 21. These results reflect both the differences in relative transcript frequencies between normal and tumor tissue as described above and a general overexpression of OSF-2 in tumor tissue as originally observed with transcriptional profiling microarray experiments using probes unable to distinguish between the OSF-2 variants described.

The references cited herein, including journal articles, patents, published patent applications, and database records including GenBank, IMAGE consortium and Derwent cited throughout this application, are hereby incorporated by reference.

Other Embodiments

Those skilled in the art will recognize, or be able to ascertain using no more than routine experimentation, many equivalents to the specific embodiments of the invention described herein. Such equivalents are intended to be encompassed by the following claims:

---

What is claimed:

1. A method for predicting the clinical outcome of a breast cancer patient, the method comprising:

a) determining the level of expression of marker M708 in a patient sample, wherein the M708 marker is selected from the group consisting of a marker that is at least 95% identical to the entire sequence of SEQ ID NO:75 or a marker that is at least 95% identical to the entire sequence of SEQ ID NO:76;

b) determining the level of expression of marker M708 in a sample from a control subject having a good clinical outcome; and c) comparing the level of expression of marker M708 in the patient sample and in the sample from the control subject;

wherein a higher level of expression of marker M708 in the patient sample as compared to the expression level in the sample from the control subject predicts that the patient will have a poor clinical outcome.

2. The method of claim 1, wherein marker M708 corresponds to a protein.

3. The method of claim 1, wherein marker M708 comprises a transcribed polynucleotide or portion thereof.

4. The method of claim 1, wherein the patient sample comprises cells obtained from the patient.

5. The method of claim 1, wherein the patient sample comprises a fluid selected from the group consisting of blood fluid, lymph, cystic fluid, nipple aspirates, and fluid collected from a lump biopsy.

6. The method of claim 1, wherein the level of expression of marker M708 in the patient sample is assessed by detecting the presence in the sample of a protein corresponding to marker M708.

7. The method of claim 6, wherein the presence of marker M708 protein is detected using a reagent which specifically binds the protein.

8. The method of claim 7, wherein the reagent is selected from the group consisting of an antibody, an antibody derivative, and an antigen-binding antibody fragment.

9. The method of claim 1, wherein the level of expression of marker M708 is determined by detecting the amount of protein corresponding to marker M708.

10. The method of claim 8, wherein the antibody or fragment thereof is a monoclonal antibody or antigen-binding antibody fragment thereof.

11. The method of claim 8, wherein the antibody or fragment thereof is a polyclonal antibody or antigen-binding antibody fragment thereof.

12. The method of claim 8, wherein the antibody or antigen-binding antibody fragment thereof is labelled.

13. The method of claim 12, wherein the antibody or antigen-binding antibody fragment thereof is radio-labelled.

14. The method of claim 12, wherein the antibody or antigen-binding antibody fragment thereof is biotin-labelled.

15. The method of claim 12, wherein the antibody or antigen-binding antibody fragment thereof is labelled with a label selected from the group consisting of a chromophore label, a fluorophore label and an enzyme label.

16. The method of claim 6, wherein the marker M708 protein is detected using a non-antibody peptide which specifically binds the protein.

17. The method of claim 1, wherein said marker M708 is a marker comprising the sequence of SEQ ID NO:75.

18. The method of claim 1, wherein said marker M708 is a marker comprising the sequence of SEQ ID NO:76.

19. The method of claim 1, wherein the level of expression of marker M708 in the sample is assessed by detecting the presence in the sample of a transcribed polynucleotide or portion thereof, corresponding to marker M708.

20. The method of claim 19, wherein the transcribed polynucleotide is a mRNA or a cDNA.

21. The method of claim 19, wherein the step of detecting a transcribed polynucleotide further comprises amplifying the transcribed polynucleotide.

22. The method of claim 1, wherein the level of expression of marker M708 in the sample is assessed by detecting the presence in the sample of a transcribed polynucleotide which anneals with a nucleic acid marker or a portion thereof under stringent hybridization conditions.

23. The method of claim 1, wherein the level of expression of marker M708 in the patient sample differs from the level of expression of marker M708 in the sample from the control subject by a factor of at least about 2 or at least about 5.

24. The method of claim 1, wherein the level of expression of the marker M708 in the sample is assessed using a technique selected from the group consisting of Northern hybridization, polymerase chain reaction analysis, RT-PCR, probe array, and in situ hybridization.

* * * * *

UNITED STATES PATENT AND TRADEMARK OFFICE

CERTIFICATE OF CORRECTION

| | | |
|---|---|---|
| PATENT NO. | : 7,601,505 B2 | Page 1 of 1 |
| APPLICATION NO. | : 10/855588 | |
| DATED | : October 13, 2009 | |
| INVENTOR(S) | : Monahan et al. | |

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 753 days Delete the phrase "by 753 days" and insert -- by 1131 days --

Signed and Sealed this

Twentieth Day of April, 2010

David J. Kappos

*Director of the United States Patent and Trademark Office*

UNITED STATES PATENT AND TRADEMARK OFFICE

CERTIFICATE OF CORRECTION

PATENT NO. : 7,601,505 B2
APPLICATION NO. : 10/855588
DATED : October 13, 2009
INVENTOR(S) : Monahan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1131 days.

Signed and Sealed this
Twenty-ninth Day of March, 2011

David J. Kappos
*Director of the United States Patent and Trademark Office*

```
                              SEQUENCE LISTING


<160> NUMBER OF SEQ ID NOS: 96

<210> SEQ ID NO 1
<211> LENGTH: 623
<212> TYPE: DNA
<213> ORGANISM: human
<220> FEATURE:
<221> NAME/KEY: CDS
<222> LOCATION: (48)...(548)

<400> SEQUENCE: 1

aagagcactg gccaagtcag cttcttctga gagagtctct agaagac atg atg cta        56
                                                    Met Met Leu
                                                     1

cac tca gct ttg ggt ctc tgc ctc tta ctc gtc aca gtt tct tcc aac       104
His Ser Ala Leu Gly Leu Cys Leu Leu Leu Val Thr Val Ser Ser Asn
    5                   10                  15

ctt gcc att gca ata aaa aag gaa aag agg cct cct cag aca ctc tca       152
Leu Ala Ile Ala Ile Lys Lys Glu Lys Arg Pro Pro Gln Thr Leu Ser
 20                  25                  30                  35

aga gga tgg gga gat gac atc act tgg gta caa act tat gaa gaa ggt       200
Arg Gly Trp Gly Asp Asp Ile Thr Trp Val Gln Thr Tyr Glu Glu Gly
                40                  45                  50

ctc ttt tat gct caa aaa agt aag aag cca tta atg gtt att cat cac       248
Leu Phe Tyr Ala Gln Lys Ser Lys Lys Pro Leu Met Val Ile His His
            55                  60                  65

ctg gag gat tgt caa tac tct caa gca cta aag aaa gta ttt gcc caa       296
Leu Glu Asp Cys Gln Tyr Ser Gln Ala Leu Lys Lys Val Phe Ala Gln
        70                  75                  80

aat gaa gaa ata caa gaa atg gct cag aat aag ttc atc atg cta aac       344
Asn Glu Glu Ile Gln Glu Met Ala Gln Asn Lys Phe Ile Met Leu Asn
    85                  90                  95

ctt atg cat gaa acc act gat aag aat tta tca cct gat ggg caa tat       392
Leu Met His Glu Thr Thr Asp Lys Asn Leu Ser Pro Asp Gly Gln Tyr
100                 105                 110                 115

gtg cct aga atc atg ttt gta gac cct tct tta aca gtt aga gct gac       440
Val Pro Arg Ile Met Phe Val Asp Pro Ser Leu Thr Val Arg Ala Asp
                120                 125                 130

ata gct gga aga tac tct aac aga ttg tac aca tat gag cct cgg gat       488
Ile Ala Gly Arg Tyr Ser Asn Arg Leu Tyr Thr Tyr Glu Pro Arg Asp
            135                 140                 145

tta ccc cta ttg ata gaa aac atg aag aaa gca tta aga ctt att cag       536
Leu Pro Leu Leu Ile Glu Asn Met Lys Lys Ala Leu Arg Leu Ile Gln
        150                 155                 160

tca gag cta taa gagatgatag aaaaaagcct tcacttcaaa gaagtcaaat           588
Ser Glu Leu  *
    165

ttcatgaaga aaacctctgg cacattgaca aatac                                623


<210> SEQ ID NO 2
<211> LENGTH: 166
```

-continued

```
<212> TYPE: PRT
<213> ORGANISM: human

<400> SEQUENCE: 2

Met Met Leu His Ser Ala Leu Gly Leu Cys Leu Leu Leu Val Thr Val
 1               5                  10                  15

Ser Ser Asn Leu Ala Ile Ala Ile Lys Lys Glu Lys Arg Pro Pro Gln
            20                  25                  30

Thr Leu Ser Arg Gly Trp Gly Asp Asp Ile Thr Trp Val Gln Thr Tyr
        35                  40                  45

Glu Glu Gly Leu Phe Tyr Ala Gln Lys Ser Lys Lys Pro Leu Met Val
    50                  55                  60

Ile His His Leu Glu Asp Cys Gln Tyr Ser Gln Ala Leu Lys Lys Val
65                  70                  75                  80

Phe Ala Gln Asn Glu Glu Ile Gln Glu Met Ala Gln Asn Lys Phe Ile
                85                  90                  95

Met Leu Asn Leu Met His Glu Thr Thr Asp Lys Asn Leu Ser Pro Asp
            100                 105                 110

Gly Gln Tyr Val Pro Arg Ile Met Phe Val Asp Pro Ser Leu Thr Val
        115                 120                 125

Arg Ala Asp Ile Ala Gly Arg Tyr Ser Asn Arg Leu Tyr Thr Tyr Glu
    130                 135                 140

Pro Arg Asp Leu Pro Leu Leu Ile Glu Asn Met Lys Lys Ala Leu Arg
145                 150                 155                 160

Leu Ile Gln Ser Glu Leu
                165


<210> SEQ ID NO 3
<211> LENGTH: 543
<212> TYPE: DNA
<213> ORGANISM: human
<220> FEATURE:
<221> NAME/KEY: CDS
<222> LOCATION: (49)...(501)

<400> SEQUENCE: 3

caagagcact ggccaagtca gcttcttctg agagagtctc tagaagac atg atg cta      57
                                                     Met Met Leu
                                                      1

cac tca gct ttg ggt ctc tgc ctc tta ctc gtc aca gtt tct tcc aac      105
His Ser Ala Leu Gly Leu Cys Leu Leu Leu Val Thr Val Ser Ser Asn
     5                  10                  15

ctt gcc att gca ata aaa aag gaa aag agg cct cct cag aca ctc tca      153
Leu Ala Ile Ala Ile Lys Lys Glu Lys Arg Pro Pro Gln Thr Leu Ser
 20                  25                  30                  35

aga gga tgg gga gat gac atc act tgg gta caa act tat gaa gaa ggt      201
Arg Gly Trp Gly Asp Asp Ile Thr Trp Val Gln Thr Tyr Glu Glu Gly
                 40                  45                  50

ctc ttt tat gct caa aaa agt aag aag cca tta atg gtt att cat cac      249
Leu Phe Tyr Ala Gln Lys Ser Lys Lys Pro Leu Met Val Ile His His
             55                  60                  65

ctg gag gat tgt caa tac tct caa gca cta aag aaa gta ttt gcc caa      297
Leu Glu Asp Cys Gln Tyr Ser Gln Ala Leu Lys Lys Val Phe Ala Gln
         70                  75                  80

aat gaa gaa ata caa gaa atg gct cag aat aag ttc atc atg cta aac      345
Asn Glu Glu Ile Gln Glu Met Ala Gln Asn Lys Phe Ile Met Leu Asn
     85                  90                  95

ctt atg cat gaa acc act gat aag aat tta tca cct gat ggg caa tat      393
Leu Met His Glu Thr Thr Asp Lys Asn Leu Ser Pro Asp Gly Gln Tyr
```

-continued

```
100                 105                 110                 115

gtg cct aga atc atg ttt gta gac cct tct tta aca gtt aga gct gac      441
Val Pro Arg Ile Met Phe Val Asp Pro Ser Leu Thr Val Arg Ala Asp
                120                 125                 130

ata gct gga aga tac tct aac aga ttg tac aca tat gag cct cgg gat      489
Ile Ala Gly Arg Tyr Ser Asn Arg Leu Tyr Thr Tyr Glu Pro Arg Asp
            135                 140                 145

tta ccc cta taa gaaatttgga tacagagaca tgcatacaga aggaatgcca          541
Leu Pro Leu  *
        150

tg                                                                   543
```

<210> SEQ ID NO 4
<211> LENGTH: 150
<212> TYPE: PRT
<213> ORGANISM: human

<400> SEQUENCE: 4

```
Met Met Leu His Ser Ala Leu Gly Leu Cys Leu Leu Leu Val Thr Val
 1               5                  10                  15

Ser Ser Asn Leu Ala Ile Ala Ile Lys Lys Glu Lys Arg Pro Pro Gln
            20                  25                  30

Thr Leu Ser Arg Gly Trp Gly Asp Asp Ile Thr Trp Val Gln Thr Tyr
        35                  40                  45

Glu Glu Gly Leu Phe Tyr Ala Gln Lys Ser Lys Lys Pro Leu Met Val
    50                  55                  60

Ile His His Leu Glu Asp Cys Gln Tyr Ser Gln Ala Leu Lys Lys Val
65                  70                  75                  80

Phe Ala Gln Asn Glu Glu Ile Gln Glu Met Ala Gln Asn Lys Phe Ile
                85                  90                  95

Met Leu Asn Leu Met His Glu Thr Thr Asp Lys Asn Leu Ser Pro Asp
            100                 105                 110

Gly Gln Tyr Val Pro Arg Ile Met Phe Val Asp Pro Ser Leu Thr Val
        115                 120                 125

Arg Ala Asp Ile Ala Gly Arg Tyr Ser Asn Arg Leu Tyr Thr Tyr Glu
    130                 135                 140

Pro Arg Asp Leu Pro Leu
145                 150
```

<210> SEQ ID NO 5
<211> LENGTH: 577
<212> TYPE: DNA
<213> ORGANISM: human
<220> FEATURE:
<221> NAME/KEY: CDS
<222> LOCATION: (98)...(412)

<400> SEQUENCE: 5

```
aagagcactg gccaagtcag gatggggaga tgacatcact tgggtacaaa cttatgaaga      60

aggtctcttt tatgctcaaa aaagtaagaa gccatta atg gtt att cat cac ctg      115
                                         Met Val Ile His His Leu
                                          1               5

gag gat tgt caa tac tct caa gca cta aag aaa gta ttt gcc caa aat      163
Glu Asp Cys Gln Tyr Ser Gln Ala Leu Lys Lys Val Phe Ala Gln Asn
            10                  15                  20

gaa gaa ata caa gaa atg gct cag aat aag ttc atc atg cta aac ctt      211
Glu Glu Ile Gln Glu Met Ala Gln Asn Lys Phe Ile Met Leu Asn Leu
        25                  30                  35
```

-continued

```
atg cat gaa acc act gat aag aat tta tca cct gat ggg caa tat gtg      259
Met His Glu Thr Thr Asp Lys Asn Leu Ser Pro Asp Gly Gln Tyr Val
     40                  45                  50

cct aga atc atg ttt gta gac cct tct tta aca gtt aga gct gac ata      307
Pro Arg Ile Met Phe Val Asp Pro Ser Leu Thr Val Arg Ala Asp Ile
 55                  60                  65                  70

gct gga aga tac tct aac aga ttg tac aca tat gag cct cgg gat tta      355
Ala Gly Arg Tyr Ser Asn Arg Leu Tyr Thr Tyr Glu Pro Arg Asp Leu
                 75                  80                  85

ccc cta ttg ata gaa aac atg aag aaa gca tta aga ctt att cag tca      403
Pro Leu Leu Ile Glu Asn Met Lys Lys Ala Leu Arg Leu Ile Gln Ser
             90                  95                 100

gag cta taa gagatgatgg aaaaaagcct tcacttcaaa gaagtcaaat              452
Glu Leu  *

ttcatgaaga aaacctctgg cacattgaca aatactaaat gtgcaagtat atagattttg    512

taatattact atttagtttt tttaatgtgt ttgcaatagt cttattaaaa taaatgtttt    572

ttaaa                                                                577


<210> SEQ ID NO 6
<211> LENGTH: 104
<212> TYPE: PRT
<213> ORGANISM: human

<400> SEQUENCE: 6

Met Val Ile His His Leu Glu Asp Cys Gln Tyr Ser Gln Ala Leu Lys
 1               5                  10                  15

Lys Val Phe Ala Gln Asn Glu Glu Ile Gln Glu Met Ala Gln Asn Lys
            20                  25                  30

Phe Ile Met Leu Asn Leu Met His Glu Thr Thr Asp Lys Asn Leu Ser
        35                  40                  45

Pro Asp Gly Gln Tyr Val Pro Arg Ile Met Phe Val Asp Pro Ser Leu
    50                  55                  60

Thr Val Arg Ala Asp Ile Ala Gly Arg Tyr Ser Asn Arg Leu Tyr Thr
65                  70                  75                  80

Tyr Glu Pro Arg Asp Leu Pro Leu Leu Ile Glu Asn Met Lys Lys Ala
                85                  90                  95

Leu Arg Leu Ile Gln Ser Glu Leu
            100


<210> SEQ ID NO 7
<211> LENGTH: 630
<212> TYPE: DNA
<213> ORGANISM: human
<220> FEATURE:
<221> NAME/KEY: CDS
<222> LOCATION: (49)...(465)

<400> SEQUENCE: 7

aagagcactg gccaagtcag gcttcttctg agagagtctc tagaagac atg atg cta      57
                                                     Met Met Leu
                                                      1

cac tca gct ttg ggt ctc tgc ctc tta ctc gtc aca gtt tct tcc aac      105
His Ser Ala Leu Gly Leu Cys Leu Leu Leu Val Thr Val Ser Ser Asn
     5                  10                  15

ctt gcc att gca ata aaa aag gaa aag agg cct cct cag aca ctc tca      153
Leu Ala Ile Ala Ile Lys Lys Glu Lys Arg Pro Pro Gln Thr Leu Ser
 20                  25                  30                  35

aga gga tgg gga gat gac atc act tgg gta caa act tat gaa gaa ggt      201
Arg Gly Trp Gly Asp Asp Ile Thr Trp Val Gln Thr Tyr Glu Glu Gly
```

-continued

```
                40                  45                  50

ctc ttt tat gct caa aaa agt aag aag cca tta atg gtt att cat cac      249
Leu Phe Tyr Ala Gln Lys Ser Lys Lys Pro Leu Met Val Ile His His
             55                  60                  65

ctg gag gat tgt caa tac tct caa gca cta aag aaa gta ttt gcc caa      297
Leu Glu Asp Cys Gln Tyr Ser Gln Ala Leu Lys Lys Val Phe Ala Gln
         70                  75                  80

aat gaa gaa ata caa gaa atg gct cag aat aag ttc atc atg cta aac      345
Asn Glu Glu Ile Gln Glu Met Ala Gln Asn Lys Phe Ile Met Leu Asn
     85                  90                  95

ctt atg cat gaa acc act gat aag aat tta tca cct gat ggg caa tat      393
Leu Met His Glu Thr Thr Asp Lys Asn Leu Ser Pro Asp Gly Gln Tyr
100                 105                 110                 115

gtg cct aga atc atg ttt gta gtg ata gaa aac atg aag aaa gca tta      441
Val Pro Arg Ile Met Phe Val Val Ile Glu Asn Met Lys Lys Ala Leu
                120                 125                 130

aga ctt att cag tca gag cta taa gagatgatgg aaaaaagcct tcacttcaaa     495
Arg Leu Ile Gln Ser Glu Leu  *
            135

gaagtcaaat ttcatgaaga aaacctctgg cacattgaca aatactaaat gtgcaagtat    555

atagattttg taatattact atttagtttt tttaatgtgt ttgcaatagt cttattaaaa    615

taaatgtttt ttaaa                                                     630


<210> SEQ ID NO 8
<211> LENGTH: 138
<212> TYPE: PRT
<213> ORGANISM: human

<400> SEQUENCE: 8

Met Met Leu His Ser Ala Leu Gly Leu Cys Leu Leu Leu Val Thr Val
 1               5                  10                  15

Ser Ser Asn Leu Ala Ile Ala Ile Lys Lys Glu Lys Arg Pro Pro Gln
            20                  25                  30

Thr Leu Ser Arg Gly Trp Gly Asp Asp Ile Thr Trp Val Gln Thr Tyr
        35                  40                  45

Glu Glu Gly Leu Phe Tyr Ala Gln Lys Ser Lys Lys Pro Leu Met Val
    50                  55                  60

Ile His His Leu Glu Asp Cys Gln Tyr Ser Gln Ala Leu Lys Lys Val
65                  70                  75                  80

Phe Ala Gln Asn Glu Glu Ile Gln Glu Met Ala Gln Asn Lys Phe Ile
                85                  90                  95

Met Leu Asn Leu Met His Glu Thr Thr Asp Lys Asn Leu Ser Pro Asp
            100                 105                 110

Gly Gln Tyr Val Pro Arg Ile Met Phe Val Val Ile Glu Asn Met Lys
        115                 120                 125

Lys Ala Leu Arg Leu Ile Gln Ser Glu Leu
    130                 135


<210> SEQ ID NO 9
<211> LENGTH: 2545
<212> TYPE: DNA
<213> ORGANISM: human
<220> FEATURE:
<221> NAME/KEY: CDS
<222> LOCATION: (40)...(417)

<400> SEQUENCE: 9

atccaataca ggagtgactt ggaactccat tctatcact atg aag aaa agt ggt        54
```

-continued

```
                                              Met Lys Lys Ser Gly
                                               1               5

gtt ctt ttc ctc ttg ggc atc atc ttg ctg gtt ctg att gga gtg caa      102
Val Leu Phe Leu Leu Gly Ile Ile Leu Leu Val Leu Ile Gly Val Gln
                 10                  15                  20

gga acc cca gta gtg aga aag ggt cgc tgt tcc tgc atc agc acc aac      150
Gly Thr Pro Val Val Arg Lys Gly Arg Cys Ser Cys Ile Ser Thr Asn
             25                  30                  35

caa ggg act atc cac cta caa tcc ttg aaa gac ctt aaa caa ttt gcc      198
Gln Gly Thr Ile His Leu Gln Ser Leu Lys Asp Leu Lys Gln Phe Ala
         40                  45                  50

cca agc cct tcc tgc gag aaa att gaa atc att gct aca ctg aag aat      246
Pro Ser Pro Ser Cys Glu Lys Ile Glu Ile Ile Ala Thr Leu Lys Asn
     55                  60                  65

gga gtt caa aca tgt cta aac cca gat tca gca gat gtg aag gaa ctg      294
Gly Val Gln Thr Cys Leu Asn Pro Asp Ser Ala Asp Val Lys Glu Leu
 70                  75                  80                  85

att aaa aag tgg gag aaa cag gtc agc caa aag aaa aag caa aag aat      342
Ile Lys Lys Trp Glu Lys Gln Val Ser Gln Lys Lys Lys Gln Lys Asn
                 90                  95                 100

ggg aaa aaa cat caa aaa aag aaa gtt ctg aaa gtt cga aaa tct caa      390
Gly Lys Lys His Gln Lys Lys Lys Val Leu Lys Val Arg Lys Ser Gln
            105                 110                 115

cgt tct cgt caa aag aag act aca taa gagaccactt caccaataag            437
Arg Ser Arg Gln Lys Lys Thr Thr  *
        120                 125

tattctgtgt taaaaatgtt ctattttaat tataccgcta tcattccaaa ggaggatggc    497

atataataca aaggcttatt aatttgacta gaaaatttaa aacattactc tgaaattgta    557

actaaagtta gaaagttgat tttaagaatc caaacgttaa gaattgttaa aggctatgat    617

tgtctttgtt cttctaccac ccaccagttg aatttcatca tgcttaaggc catgatttta    677

gcaataccca tgtctacaca gatgttcacc caaccacatc ccactcacaa cagctgcctg    737

gaagagcagc cctaggcttc cacgtactgc agcctccaga gagtatctga ggcacatgtc    797

agcaagtcct aagcctgtta gcatgctggt gagccaagca gtttgaaatt gagctggacc    857

tcaccaagct gctgtggcca tcaacctctg tatttgaatc agcctacagg cctcacacac    917

aatgtgtctg agagattcat gctgattgtt attgggtatc accactggag atcaccagtg    977

tgtggctttc agagcctcct ttctggcttt ggaagccatg tgattccatc ttgcccgctc   1037

aggctgacca ctttatttct ttttgttccc ctttgcttca ttcaagtcag ctcttctcca   1097

tcctaccaca atgcagtgcc tttcttctct ccagtgcacc tgtcatatgc tctgatttat   1157

ctgagtcaac tcctttctca tcttgtcccc aacaccccac agaagtgctt tcttctccca   1217

attcatcctc actcagtcca gcttagttca agtcctgcct cttaaataaa cctttttgga   1277

cacacaaatt atcttaaaac tcctgtttca cttggttcag taccacatgg gtgaacactc   1337

aatggttaac taattcttgg gtgtttatcc tatctctcca accagattgt cagctccttg   1397

agggcaagag ccacagtata tttccctgtt tcttccacag tgcctaataa tactgtggaa   1457

ctaggtttta ataatttttt aattgatgtt gttatgggca ggatggcaac cagaccattg   1517

tctcagagca ggtgctggct ctttcctggc tactccatgt tggctagcct ctggtaacct   1577

cttacttatt atcttcagga cactcactac agggaccagg gatgatgcaa catccttgtc   1637

tttttatgac aggatgtttg ctcagcttct ccaacaataa gaagcacgtg gtaaaacact   1697

tgcggatatt ctggactgtt tttaaaaaat atacagttta ccgaaaatca tataatctta   1757
```

-continued

```
caatgaaaag gactttatag atcagccagt gaccaacctt ttcccaacca tacaaaaatt   1817

ccttttcccg aaggaaaagg gctttctcaa taagcctcag ctttctaaga tctaacaaga   1877

tagccaccga gatccttatc gaaactcatt ttaggcaaat atgagtttta ttgtccgttt   1937

acttgtttca gagtttgtat tgtgattatc aattaccaca ccatctccca tgaagaaagg   1997

gaacggtgaa gtactaagcg ctagaggaag cagccaagtc ggttagtgga agcatgattg   2057

gtgcccagtt agcctctgca ggatgtggaa acctccttcc aggggaggtt cagtgaattg   2117

tgtaggagag gttgtctgtg gccagaattt aaacctatac tcactttccc aaattgaatc   2177

actgctcaca ctgctgatga tttagagtgc tgtccggtgg agatcccacc cgaacgtctt   2237

atctaatcat gaaactccct agttccttca tgtaacttcc ctgaaaaatc taagtgtttc   2297

ataaatttga gagtctgtga cccacttacc ttgcatctca caggtagaca gtatataact   2357

aacaaccaaa gactacatat tgtcactgac acacacgtta taatcattta tcatatatat   2417

acatacatgc atacactctc aaagcaaata atttttcact tcaaaacagt attgacttgt   2477

ataccttgta atttgaaata ttttctttgt taaaatagaa tggtatcaat aaatagacca   2537

ttaatcag                                                            2545
```

<210> SEQ ID NO 10
<211> LENGTH: 125
<212> TYPE: PRT
<213> ORGANISM: human

<400> SEQUENCE: 10

```
Met Lys Lys Ser Gly Val Leu Phe Leu Leu Gly Ile Ile Leu Leu Val
 1               5                  10                  15

Leu Ile Gly Val Gln Gly Thr Pro Val Val Arg Lys Gly Arg Cys Ser
            20                  25                  30

Cys Ile Ser Thr Asn Gln Gly Thr Ile His Leu Gln Ser Leu Lys Asp
        35                  40                  45

Leu Lys Gln Phe Ala Pro Ser Pro Ser Cys Glu Lys Ile Glu Ile Ile
    50                  55                  60

Ala Thr Leu Lys Asn Gly Val Gln Thr Cys Leu Asn Pro Asp Ser Ala
65                  70                  75                  80

Asp Val Lys Glu Leu Ile Lys Lys Trp Glu Lys Gln Val Ser Gln Lys
                85                  90                  95

Lys Lys Gln Lys Asn Gly Lys Lys His Gln Lys Lys Lys Val Leu Lys
            100                 105                 110

Val Arg Lys Ser Gln Arg Ser Arg Gln Lys Lys Thr Thr
        115                 120                 125
```

<210> SEQ ID NO 11
<211> LENGTH: 1172
<212> TYPE: DNA
<213> ORGANISM: human
<220> FEATURE:
<221> NAME/KEY: CDS
<222> LOCATION: (67)...(363)

<400> SEQUENCE: 11

```
gagacattcc tcaattgctt agacatattc tgagcctaca gcagaggaac ctccagtctc     60

agcacc atg aat caa act gcg att ctg att tgc tgc ctt atc ttt ctg       108
       Met Asn Gln Thr Ala Ile Leu Ile Cys Cys Leu Ile Phe Leu
        1               5                  10

act cta agt ggc att caa gga gta cct ctc tct aga acc gta cgc tgt      156
Thr Leu Ser Gly Ile Gln Gly Val Pro Leu Ser Arg Thr Val Arg Cys
```

-continued

```
 15                  20                  25                  30

acc tgc atc agc att agt aat caa cct gtt aat cca agg tct tta gaa      204
Thr Cys Ile Ser Ile Ser Asn Gln Pro Val Asn Pro Arg Ser Leu Glu
                 35                  40                  45

aaa ctt gaa att att cct gca agc caa ttt tgt cca cgt gtt gag atc      252
Lys Leu Glu Ile Ile Pro Ala Ser Gln Phe Cys Pro Arg Val Glu Ile
             50                  55                  60

att gct aca atg aaa aag aag ggt gag aag aga tgt ctg aat cca gaa      300
Ile Ala Thr Met Lys Lys Lys Gly Glu Lys Arg Cys Leu Asn Pro Glu
         65                  70                  75

tcg aag gcc atc aag aat tta ctg aaa gca gtt agc aag gaa atg tct      348
Ser Lys Ala Ile Lys Asn Leu Leu Lys Ala Val Ser Lys Glu Met Ser
     80                  85                  90

aaa aga tct cct taa aaccagaggg gagcaaaatc gatgcagtgc ttccaaggat      403
Lys Arg Ser Pro  *
 95

ggaccacaca gaggctgcct ctcccatcac ttccctacat ggagtatatg tcaagccata    463

attgttctta gtttgcagtt acactaaaag gtgaccaatg atggtcacca aatcagctgc    523

tactactcct gtaggaaggt taatgttcat catcctaagc tattcagtaa taactctacc    583

ctggcactat aatgtaagct ctactgaggt gctatgttct tagtggatgt tctgaccctg    643

cttcaaatat ttccctcacc tttcccatct tccaagggta ctaaggaatc tttctgcttt    703

ggggtttatc agaattctca gaatctcaaa taactaaaag gtatgcaatc aaatctgctt    763

tttaaagaat gctctttact tcatggactt ccactgccat cctcccaagg ggcccaaatt    823

ctttcagtgg ctacctacat acaattccaa acacatacag gaaggtagaa atatctgaaa    883

atgtatgtgt aagtattctt atttaatgaa agactgtaca aagtataagt cttagatgta    943

tatatttcct atattgtttt cagtgtacat ggaataacat gtaattaagt actatgtatc   1003

aatgagtaac aggaaaattt taaaaataca gatagatata tgctctgcat gttacataag   1063

ataaatgtgc tgaatggttt tcaaataaaa atgaggtact ctcctggaaa tattaagaaa   1123

gactatctaa atgttgaaag atcaaaaggt taataaagta attataact               1172


<210> SEQ ID NO 12
<211> LENGTH: 98
<212> TYPE: PRT
<213> ORGANISM: human

<400> SEQUENCE: 12

Met Asn Gln Thr Ala Ile Leu Ile Cys Cys Leu Ile Phe Leu Thr Leu
 1               5                  10                  15

Ser Gly Ile Gln Gly Val Pro Leu Ser Arg Thr Val Arg Cys Thr Cys
             20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Met Ser Lys Arg
                85                  90                  95

Ser Pro


<210> SEQ ID NO 13
<211> LENGTH: 1261
```

-continued

```
<212> TYPE: DNA
<213> ORGANISM: human
<220> FEATURE:
<221> NAME/KEY: CDS
<222> LOCATION: (244)...(1152)

<400> SEQUENCE: 13

ggcgagggtc ttcggaacgt agcgctggct gcggccccgc ccgcctaccc acccgcccgt      60

ccggcagccg gctcccgccg cctccgcgct ctgtctgggg ccagccacct ggcgggccgc     120

tccggtgcgc ctgcccgcgc ttttcactga caggcgctgt tccccacagc cagcgccgcc     180

cgccacgtcc cagctctcgg ccaacggagc tgcgcggcgg gtgacctttc cgagcccagc     240

gcg atg acg gct cct tgc tcc cag ccg gcg cag ctt cct gga cgc cgc      288
    Met Thr Ala Pro Cys Ser Gln Pro Ala Gln Leu Pro Gly Arg Arg
     1               5                  10                  15

cag ctc ggg ctg gtg ccg ttc ccg ccg ccg ccg ccg cgg acg ccg ctg      336
Gln Leu Gly Leu Val Pro Phe Pro Pro Pro Pro Pro Arg Thr Pro Leu
                20                  25                  30

ctg tgg ctg ctg ctg ctg ctg ctg gcc gcc gtg gcg ccg gcg cgc ggc      384
Leu Trp Leu Leu Leu Leu Leu Leu Ala Ala Val Ala Pro Ala Arg Gly
            35                  40                  45

tgg gag agc gga gac ctg gag ttg ttt gac tta gtg gag gag gtg cag      432
Trp Glu Ser Gly Asp Leu Glu Leu Phe Asp Leu Val Glu Glu Val Gln
        50                  55                  60

ctc aac ttc tac cag ttc ctc ggg gtg cag cag gca cct gaa tgg aca      480
Leu Asn Phe Tyr Gln Phe Leu Gly Val Gln Gln Ala Pro Glu Trp Thr
     65                  70                  75

gaa gag gac ctc agc caa ctg aca aga agt atg gtt aag ttc cca gga      528
Glu Glu Asp Leu Ser Gln Leu Thr Arg Ser Met Val Lys Phe Pro Gly
 80                  85                  90                  95

ggg act cca ggt cga tgg gaa aag att gcc cac gaa ttg ggt cga tct      576
Gly Thr Pro Gly Arg Trp Glu Lys Ile Ala His Glu Leu Gly Arg Ser
                100                 105                 110

gtg aca gat gtg aca acc aaa gcc aag caa ctg aag gat tca gtg acc      624
Val Thr Asp Val Thr Thr Lys Ala Lys Gln Leu Lys Asp Ser Val Thr
            115                 120                 125

tgc tcc cca gga atg gtt aga ctc tcc gaa ctc aaa tcg aca gtt cag      672
Cys Ser Pro Gly Met Val Arg Leu Ser Glu Leu Lys Ser Thr Val Gln
        130                 135                 140

aat tcc agg ccc atc aaa acg gcc acc acc ttg ccc gat gac atg atc      720
Asn Ser Arg Pro Ile Lys Thr Ala Thr Thr Leu Pro Asp Asp Met Ile
    145                 150                 155

acc cag cga gag gac gca gag ggg gtg gca gcg gag gag gag cag gag      768
Thr Gln Arg Glu Asp Ala Glu Gly Val Ala Ala Glu Glu Glu Gln Glu
160                 165                 170                 175

gga gac tcc ggt gag cag gag acc ggg gcc act gat gcc cgg cct cgg      816
Gly Asp Ser Gly Glu Gln Glu Thr Gly Ala Thr Asp Ala Arg Pro Arg
                180                 185                 190

agg cgg aag cca gcc agg ctg ctg gag gct aca gcg aag ccg gag cca      864
Arg Arg Lys Pro Ala Arg Leu Leu Glu Ala Thr Ala Lys Pro Glu Pro
            195                 200                 205

gag gag aag tcc aga gcc aag cgg cag aag gac ttt gac ata gca gaa      912
Glu Glu Lys Ser Arg Ala Lys Arg Gln Lys Asp Phe Asp Ile Ala Glu
        210                 215                 220

caa aac gag tcc agc gac gag gag agc ctg aga aaa gag aga gct cgg      960
Gln Asn Glu Ser Ser Asp Glu Glu Ser Leu Arg Lys Glu Arg Ala Arg
    225                 230                 235

tct gca gag gag ccg tgg act caa aat caa cag aaa ctt ctg gaa ctg     1008
Ser Ala Glu Glu Pro Trp Thr Gln Asn Gln Gln Lys Leu Leu Glu Leu
240                 245                 250                 255
```

-continued

```
gcg ttg cag cag tac cca agg gga tcc tct gac cgc tgg gac aaa ata     1056
Ala Leu Gln Gln Tyr Pro Arg Gly Ser Ser Asp Arg Trp Asp Lys Ile
            260                 265                 270

gcc aga tgt gtc ccg tcc aag agc aag gaa gac tgt atc gct agg tac     1104
Ala Arg Cys Val Pro Ser Lys Ser Lys Glu Asp Cys Ile Ala Arg Tyr
        275                 280                 285

aag ttg ctg gtt gaa ctg gtc caa aag aaa aaa caa gct aaa agc tga     1152
Lys Leu Leu Val Glu Leu Val Gln Lys Lys Lys Gln Ala Lys Ser  *
    290                 295                 300

atattctggg agatgatgtt caccttcatt ttccaaaatg aatatcttaa aaatcttatg   1212

cagaaatttg cattttgtac ctcaatattt ctacgtcatg tgccttagt              1261


<210> SEQ ID NO 14
<211> LENGTH: 302
<212> TYPE: PRT
<213> ORGANISM: human

<400> SEQUENCE: 14

Met Thr Ala Pro Cys Ser Gln Pro Ala Gln Leu Pro Gly Arg Arg Gln
 1               5                  10                  15

Leu Gly Leu Val Pro Phe Pro Pro Pro Pro Pro Arg Thr Pro Leu Leu
            20                  25                  30

Trp Leu Leu Leu Leu Leu Leu Ala Ala Val Ala Pro Ala Arg Gly Trp
        35                  40                  45

Glu Ser Gly Asp Leu Glu Leu Phe Asp Leu Val Glu Glu Val Gln Leu
    50                  55                  60

Asn Phe Tyr Gln Phe Leu Gly Val Gln Gln Ala Pro Glu Trp Thr Glu
65                  70                  75                  80

Glu Asp Leu Ser Gln Leu Thr Arg Ser Met Val Lys Phe Pro Gly Gly
                85                  90                  95

Thr Pro Gly Arg Trp Glu Lys Ile Ala His Glu Leu Gly Arg Ser Val
            100                 105                 110

Thr Asp Val Thr Thr Lys Ala Lys Gln Leu Lys Asp Ser Val Thr Cys
        115                 120                 125

Ser Pro Gly Met Val Arg Leu Ser Glu Leu Lys Ser Thr Val Gln Asn
    130                 135                 140

Ser Arg Pro Ile Lys Thr Ala Thr Thr Leu Pro Asp Asp Met Ile Thr
145                 150                 155                 160

Gln Arg Glu Asp Ala Glu Gly Val Ala Ala Glu Glu Glu Gln Glu Gly
                165                 170                 175

Asp Ser Gly Glu Gln Glu Thr Gly Ala Thr Asp Ala Arg Pro Arg Arg
            180                 185                 190

Arg Lys Pro Ala Arg Leu Leu Glu Ala Thr Ala Lys Pro Glu Pro Glu
        195                 200                 205

Glu Lys Ser Arg Ala Lys Arg Gln Lys Asp Phe Asp Ile Ala Glu Gln
    210                 215                 220

Asn Glu Ser Ser Asp Glu Glu Ser Leu Arg Lys Glu Arg Ala Arg Ser
225                 230                 235                 240

Ala Glu Glu Pro Trp Thr Gln Asn Gln Gln Lys Leu Leu Glu Leu Ala
                245                 250                 255

Leu Gln Gln Tyr Pro Arg Gly Ser Ser Asp Arg Trp Asp Lys Ile Ala
            260                 265                 270

Arg Cys Val Pro Ser Lys Ser Lys Glu Asp Cys Ile Ala Arg Tyr Lys
        275                 280                 285
```

-continued

```
Leu Leu Val Glu Leu Val Gln Lys Lys Lys Gln Ala Lys Ser
    290                 295                 300


<210> SEQ ID NO 15
<211> LENGTH: 1243
<212> TYPE: DNA
<213> ORGANISM: human
<220> FEATURE:
<221> NAME/KEY: CDS
<222> LOCATION: (244)...(1134)

<400> SEQUENCE: 15

ggcgagggtc ttcggaacgt agcgctggct gcggccccgc ccgcctaccc acccgcccgt      60

ccggcagccg gctcccgccg cctccgcgct ctgtctgggg ccagccacct ggcgggccgc     120

tccggtgcgc ctgcccgcgc ttttcactga caggcgctgt tccccacagc cagcgccgcc     180

cgccacgtcc cagctctcgg ccaacggagc tgcgcggcgg gtgacctttc cgagcccagc     240

gcg atg acg gct cct tgc tcc cag ccg gcg cag ctt cct gga cgc cgc       288
    Met Thr Ala Pro Cys Ser Gln Pro Ala Gln Leu Pro Gly Arg Arg
     1               5                  10                  15

cag ctc ggg ctg gtg ccg ttc ccg ccg ccg ccg ccg cgg acg ccg ctg       336
Gln Leu Gly Leu Val Pro Phe Pro Pro Pro Pro Pro Arg Thr Pro Leu
                20                  25                  30

ctg tgg ctg ctg ctg ctg ctg ctg gcc gcc gtg gcg ccg gcg cgc ggc       384
Leu Trp Leu Leu Leu Leu Leu Leu Ala Ala Val Ala Pro Ala Arg Gly
            35                  40                  45

tgg gag agc gga gac ctg gag ttg ttt gac tta gtg gag gag gtg cag       432
Trp Glu Ser Gly Asp Leu Glu Leu Phe Asp Leu Val Glu Glu Val Gln
        50                  55                  60

ctc aac ttc tac cag ttc ctc ggg gtg cag cag gat gca tca tct gca       480
Leu Asn Phe Tyr Gln Phe Leu Gly Val Gln Gln Asp Ala Ser Ser Ala
     65                  70                  75

gac atc aga aaa gca tat cgt aag ctt tca cta act tta cat cca gac       528
Asp Ile Arg Lys Ala Tyr Arg Lys Leu Ser Leu Thr Leu His Pro Asp
 80                  85                  90                  95

aag aat aaa gat gaa aat gca gaa act cag ttt aga caa gtg aca acc       576
Lys Asn Lys Asp Glu Asn Ala Glu Thr Gln Phe Arg Gln Val Thr Thr
                100                 105                 110

aaa gcc aag caa ctg aag gat tca gtg acc tgc tcc cca gga atg gtt       624
Lys Ala Lys Gln Leu Lys Asp Ser Val Thr Cys Ser Pro Gly Met Val
            115                 120                 125

aga ctc tcc gaa ctc aaa tcg aca gtt cag aat tcc agg ccc atc aaa       672
Arg Leu Ser Glu Leu Lys Ser Thr Val Gln Asn Ser Arg Pro Ile Lys
        130                 135                 140

acg gcc acc acc ttg ccc gat gac atg atc acc cag cga gag gac gca       720
Thr Ala Thr Thr Leu Pro Asp Asp Met Ile Thr Gln Arg Glu Asp Ala
    145                 150                 155

gag ggg gtg gca gcg gag gag gag cag gag gga gac tcc ggt gag cag       768
Glu Gly Val Ala Ala Glu Glu Glu Gln Glu Gly Asp Ser Gly Glu Gln
160                 165                 170                 175

gag acc ggg gcc act gat gcc cgg cct cgg agg cgg aag cca gcc agg       816
Glu Thr Gly Ala Thr Asp Ala Arg Pro Arg Arg Arg Lys Pro Ala Arg
                180                 185                 190

ctg ctg gag gct aca gcg aag ccg gag cca gag gag aag tcc aga gcc       864
Leu Leu Glu Ala Thr Ala Lys Pro Glu Pro Glu Glu Lys Ser Arg Ala
            195                 200                 205

aag cgg cag aag gac ttt gac ata gca gaa caa aac gag tcc agc gac       912
Lys Arg Gln Lys Asp Phe Asp Ile Ala Glu Gln Asn Glu Ser Ser Asp
        210                 215                 220

gag gag agc ctg aga aaa gag aga gct cgg tct gca gag gag ccg tgg       960
```

-continued

```
Glu Glu Ser Leu Arg Lys Glu Arg Ala Arg Ser Ala Glu Glu Pro Trp
    225                 230                 235

act caa aat caa cag aaa ctt ctg gaa ctg gcg ttg cag cag tac cca     1008
Thr Gln Asn Gln Gln Lys Leu Leu Glu Leu Ala Leu Gln Gln Tyr Pro
240                 245                 250                 255

agg gga tcc tct gac cgc tgg gac aaa ata gcc aga tgt gtc ccg tcc     1056
Arg Gly Ser Ser Asp Arg Trp Asp Lys Ile Ala Arg Cys Val Pro Ser
                260                 265                 270

aag agc aag gaa gac tgt atc gct agg tac aag ttg ctg gtt gaa ctg     1104
Lys Ser Lys Glu Asp Cys Ile Ala Arg Tyr Lys Leu Leu Val Glu Leu
            275                 280                 285

gtc caa aag aaa aaa caa gct aaa agc tga atattctggg agatgatgtt       1154
Val Gln Lys Lys Lys Gln Ala Lys Ser  *
        290                 295

caccttcatt ttccaaaatg aatatcttaa aaatcttatg cagaaatttg cattttgtac   1214

ctcaatattt ctacgtcatg tgccttagt                                     1243


<210> SEQ ID NO 16
<211> LENGTH: 296
<212> TYPE: PRT
<213> ORGANISM: human

<400> SEQUENCE: 16

Met Thr Ala Pro Cys Ser Gln Pro Ala Gln Leu Pro Gly Arg Arg Gln
 1               5                  10                  15

Leu Gly Leu Val Pro Phe Pro Pro Pro Pro Pro Arg Thr Pro Leu Leu
            20                  25                  30

Trp Leu Leu Leu Leu Leu Leu Ala Ala Val Ala Pro Ala Arg Gly Trp
        35                  40                  45

Glu Ser Gly Asp Leu Glu Leu Phe Asp Leu Val Glu Glu Val Gln Leu
    50                  55                  60

Asn Phe Tyr Gln Phe Leu Gly Val Gln Gln Asp Ala Ser Ser Ala Asp
65                  70                  75                  80

Ile Arg Lys Ala Tyr Arg Lys Leu Ser Leu Thr Leu His Pro Asp Lys
                85                  90                  95

Asn Lys Asp Glu Asn Ala Glu Thr Gln Phe Arg Gln Val Thr Thr Lys
            100                 105                 110

Ala Lys Gln Leu Lys Asp Ser Val Thr Cys Ser Pro Gly Met Val Arg
        115                 120                 125

Leu Ser Glu Leu Lys Ser Thr Val Gln Asn Ser Arg Pro Ile Lys Thr
    130                 135                 140

Ala Thr Thr Leu Pro Asp Asp Met Ile Thr Gln Arg Glu Asp Ala Glu
145                 150                 155                 160

Gly Val Ala Ala Glu Glu Glu Gln Glu Gly Asp Ser Gly Glu Gln Glu
                165                 170                 175

Thr Gly Ala Thr Asp Ala Arg Pro Arg Arg Arg Lys Pro Ala Arg Leu
            180                 185                 190

Leu Glu Ala Thr Ala Lys Pro Glu Pro Glu Glu Lys Ser Arg Ala Lys
        195                 200                 205

Arg Gln Lys Asp Phe Asp Ile Ala Glu Gln Asn Glu Ser Ser Asp Glu
    210                 215                 220

Glu Ser Leu Arg Lys Glu Arg Ala Arg Ser Ala Glu Glu Pro Trp Thr
225                 230                 235                 240

Gln Asn Gln Gln Lys Leu Leu Glu Leu Ala Leu Gln Gln Tyr Pro Arg
                245                 250                 255
```

-continued

```
Gly Ser Ser Asp Arg Trp Asp Lys Ile Ala Arg Cys Val Pro Ser Lys
            260                 265                 270

Ser Lys Glu Asp Cys Ile Ala Arg Tyr Lys Leu Leu Val Glu Leu Val
        275                 280                 285

Gln Lys Lys Lys Gln Ala Lys Ser
    290                 295


<210> SEQ ID NO 17
<211> LENGTH: 1881
<212> TYPE: DNA
<213> ORGANISM: human
<220> FEATURE:
<221> NAME/KEY: CDS
<222> LOCATION: (108)...(1772)

<400> SEQUENCE: 17

gcgcttttca ctgacaggcg ctgttcccca cagccagcgc cgcccgccac gtcccagctc      60

tcggccaacg gagctgcgcg gcgggtgacc tttccgagcc cagcgcg atg acg gct      116
                                                    Met Thr Ala
                                                     1

cct tgc tcc cag ccg gcg cag ctt cct gga cgc cgc cag ctc ggg ctg      164
Pro Cys Ser Gln Pro Ala Gln Leu Pro Gly Arg Arg Gln Leu Gly Leu
     5                  10                  15

gtg ccg ttc ccg ccg ccg ccg ccg cgg acg ccg ctg ctg tgg ctg ctg      212
Val Pro Phe Pro Pro Pro Pro Pro Arg Thr Pro Leu Leu Trp Leu Leu
 20                  25                  30                  35

ctg ctg ctg ctg gcc gcc gtg gcg ccg gcg cgc ggc tgg gag agc gga      260
Leu Leu Leu Leu Ala Ala Val Ala Pro Ala Arg Gly Trp Glu Ser Gly
                 40                  45                  50

gac ctg gag ttg ttt gac tta gtg gag gag gtg cag ctc aac ttc tac      308
Asp Leu Glu Leu Phe Asp Leu Val Glu Glu Val Gln Leu Asn Phe Tyr
             55                  60                  65

cag ttc ctc ggg gtg cag cag gat gca tca tct gca gac atc aga aaa      356
Gln Phe Leu Gly Val Gln Gln Asp Ala Ser Ser Ala Asp Ile Arg Lys
         70                  75                  80

gca tat cgt aag ctt tca cta act tta cat cca gac aag aat aaa gat      404
Ala Tyr Arg Lys Leu Ser Leu Thr Leu His Pro Asp Lys Asn Lys Asp
     85                  90                  95

gaa aat gca gaa act cag ttt aga caa ttg gtg gcc att tat gaa gtt      452
Glu Asn Ala Glu Thr Gln Phe Arg Gln Leu Val Ala Ile Tyr Glu Val
100                 105                 110                 115

tta aag gat gat gaa cga agg cag agg tat gat gat att ctg atc aat      500
Leu Lys Asp Asp Glu Arg Arg Gln Arg Tyr Asp Asp Ile Leu Ile Asn
                120                 125                 130

gga ctt cca gat tgg cga cag cct gta ttc tac tac agg cgg gtg aga      548
Gly Leu Pro Asp Trp Arg Gln Pro Val Phe Tyr Tyr Arg Arg Val Arg
            135                 140                 145

aaa atg agc aat gct gag ctg gca tta ctc ttg ttc att att ctc aca      596
Lys Met Ser Asn Ala Glu Leu Ala Leu Leu Leu Phe Ile Ile Leu Thr
        150                 155                 160

gtg ggt cat tat gct gtg gtt tgg tca atc tac ctg gaa aaa caa ctg      644
Val Gly His Tyr Ala Val Val Trp Ser Ile Tyr Leu Glu Lys Gln Leu
    165                 170                 175

gat gaa cta cta agt aga aaa aag aga gaa aag aaa aaa aag act ggc      692
Asp Glu Leu Leu Ser Arg Lys Lys Arg Glu Lys Lys Lys Lys Thr Gly
180                 185                 190                 195

agc aag agt gtg gat gta tca aaa ctc ggt gct tca gaa aaa aat gaa      740
Ser Lys Ser Val Asp Val Ser Lys Leu Gly Ala Ser Glu Lys Asn Glu
                200                 205                 210

aga ttg ctg atg aaa cca cag tgg cat gat ttg ctt cca tgc aaa ctg      788
```

-continued

```
Arg Leu Leu Met Lys Pro Gln Trp His Asp Leu Leu Pro Cys Lys Leu
            215                 220                 225

ggg att tgg ttt tgc ctt aca cta aaa gca tta cct cac ctc atc cag      836
Gly Ile Trp Phe Cys Leu Thr Leu Lys Ala Leu Pro His Leu Ile Gln
        230                 235                 240

gat gct ggg cag ttt tat gct aaa tat aaa gaa aca aga ttg aag gaa      884
Asp Ala Gly Gln Phe Tyr Ala Lys Tyr Lys Glu Thr Arg Leu Lys Glu
    245                 250                 255

aag gaa gat gca ctg act aga act gaa ctt gaa aca ctt caa aaa cag      932
Lys Glu Asp Ala Leu Thr Arg Thr Glu Leu Glu Thr Leu Gln Lys Gln
260                 265                 270                 275

aag aaa gtt aaa aaa cca aaa cct gaa ttt cct gta tac aca cct tta      980
Lys Lys Val Lys Lys Pro Lys Pro Glu Phe Pro Val Tyr Thr Pro Leu
                280                 285                 290

gaa act aca tat att cag tct tat gat cat gga act tcc ata gaa gaa     1028
Glu Thr Thr Tyr Ile Gln Ser Tyr Asp His Gly Thr Ser Ile Glu Glu
            295                 300                 305

att gag gaa caa atg gat gat tgg ttg gaa aac agg aac cga aca cag     1076
Ile Glu Glu Gln Met Asp Asp Trp Leu Glu Asn Arg Asn Arg Thr Gln
        310                 315                 320

aaa aaa cag gca cct gaa tgg aca gaa gag gac ctc agc caa ctg aca     1124
Lys Lys Gln Ala Pro Glu Trp Thr Glu Glu Asp Leu Ser Gln Leu Thr
    325                 330                 335

aga agt atg gtt aag ttc cca gga ggg act cca ggt cga tgg gaa aag     1172
Arg Ser Met Val Lys Phe Pro Gly Gly Thr Pro Gly Arg Trp Glu Lys
340                 345                 350                 355

att gcc cac gaa ttg ggt cga tct gtg aca gat gtg aca acc aaa gcc     1220
Ile Ala His Glu Leu Gly Arg Ser Val Thr Asp Val Thr Thr Lys Ala
                360                 365                 370

aag caa ctg aag gat tca gtg acc tgc tcc cca gga atg gtt aga ctc     1268
Lys Gln Leu Lys Asp Ser Val Thr Cys Ser Pro Gly Met Val Arg Leu
            375                 380                 385

tcc gaa ctc aaa tcg aca gtt cag aat tcc agg ccc atc aaa acg gcc     1316
Ser Glu Leu Lys Ser Thr Val Gln Asn Ser Arg Pro Ile Lys Thr Ala
        390                 395                 400

acc acc ttg ccc gat gac atg atc acc cag cga gag gac gca gag ggg     1364
Thr Thr Leu Pro Asp Asp Met Ile Thr Gln Arg Glu Asp Ala Glu Gly
    405                 410                 415

gtg gca gcg gag gag gag cag gag gga gac tcc ggt gag cag gag acc     1412
Val Ala Ala Glu Glu Glu Gln Glu Gly Asp Ser Gly Glu Gln Glu Thr
420                 425                 430                 435

ggg gcc act gat gcc cgg cct cgg agg cgg aag cca gcc agg ctg ctg     1460
Gly Ala Thr Asp Ala Arg Pro Arg Arg Arg Lys Pro Ala Arg Leu Leu
                440                 445                 450

gag gct aca gcg aag ccg gag cca gag gag aag tcc aga gcc aag cgg     1508
Glu Ala Thr Ala Lys Pro Glu Pro Glu Glu Lys Ser Arg Ala Lys Arg
            455                 460                 465

cag aag gac ttt gac ata gca gaa caa aac gag tcc agc gac gag gag     1556
Gln Lys Asp Phe Asp Ile Ala Glu Gln Asn Glu Ser Ser Asp Glu Glu
        470                 475                 480

agc ctg aga aaa gag aga gct cgg tct gca gag gag ccg tgg act caa     1604
Ser Leu Arg Lys Glu Arg Ala Arg Ser Ala Glu Glu Pro Trp Thr Gln
    485                 490                 495

aat caa cag aaa ctt ctg gaa ctg gcg ttg cag cag tac cca agg gga     1652
Asn Gln Gln Lys Leu Leu Glu Leu Ala Leu Gln Gln Tyr Pro Arg Gly
500                 505                 510                 515

tcc tct gac cgc tgg gac aaa ata gcc aga tgt gtc ccg tcc aag agc     1700
Ser Ser Asp Arg Trp Asp Lys Ile Ala Arg Cys Val Pro Ser Lys Ser
                520                 525                 530
```

-continued

```
aag gaa gac tgt atc gct agg tac aag ttg ctg gtt gaa ctg gtc caa      1748
Lys Glu Asp Cys Ile Ala Arg Tyr Lys Leu Leu Val Glu Leu Val Gln
            535                 540                 545

aag aaa aaa caa gct aaa agc tga atattctggg agatgatgtt caccttcatt    1802
Lys Lys Lys Gln Ala Lys Ser  *
        550

ttccaaaatg aatatcttaa aaatcttatg cagaaatttg cattttgtac ctcaatattt   1862

ctacgtcatg tgccttagt                                                 1881


<210> SEQ ID NO 18
<211> LENGTH: 554
<212> TYPE: PRT
<213> ORGANISM: human

<400> SEQUENCE: 18

Met Thr Ala Pro Cys Ser Gln Pro Ala Gln Leu Pro Gly Arg Arg Gln
 1               5                  10                  15

Leu Gly Leu Val Pro Phe Pro Pro Pro Pro Pro Arg Thr Pro Leu Leu
            20                  25                  30

Trp Leu Leu Leu Leu Leu Leu Ala Ala Val Ala Pro Ala Arg Gly Trp
        35                  40                  45

Glu Ser Gly Asp Leu Glu Leu Phe Asp Leu Val Glu Glu Val Gln Leu
    50                  55                  60

Asn Phe Tyr Gln Phe Leu Gly Val Gln Gln Asp Ala Ser Ser Ala Asp
65                  70                  75                  80

Ile Arg Lys Ala Tyr Arg Lys Leu Ser Leu Thr Leu His Pro Asp Lys
                85                  90                  95

Asn Lys Asp Glu Asn Ala Glu Thr Gln Phe Arg Gln Leu Val Ala Ile
            100                 105                 110

Tyr Glu Val Leu Lys Asp Asp Glu Arg Arg Gln Arg Tyr Asp Asp Ile
        115                 120                 125

Leu Ile Asn Gly Leu Pro Asp Trp Arg Gln Pro Val Phe Tyr Tyr Arg
    130                 135                 140

Arg Val Arg Lys Met Ser Asn Ala Glu Leu Ala Leu Leu Leu Phe Ile
145                 150                 155                 160

Ile Leu Thr Val Gly His Tyr Ala Val Val Trp Ser Ile Tyr Leu Glu
                165                 170                 175

Lys Gln Leu Asp Glu Leu Leu Ser Arg Lys Lys Arg Glu Lys Lys Lys
            180                 185                 190

Lys Thr Gly Ser Lys Ser Val Asp Val Ser Lys Leu Gly Ala Ser Glu
        195                 200                 205

Lys Asn Glu Arg Leu Leu Met Lys Pro Gln Trp His Asp Leu Leu Pro
    210                 215                 220

Cys Lys Leu Gly Ile Trp Phe Cys Leu Thr Leu Lys Ala Leu Pro His
225                 230                 235                 240

Leu Ile Gln Asp Ala Gly Gln Phe Tyr Ala Lys Tyr Lys Glu Thr Arg
                245                 250                 255

Leu Lys Glu Lys Glu Asp Ala Leu Thr Arg Thr Glu Leu Glu Thr Leu
            260                 265                 270

Gln Lys Gln Lys Lys Val Lys Lys Pro Lys Pro Glu Phe Pro Val Tyr
        275                 280                 285

Thr Pro Leu Glu Thr Thr Tyr Ile Gln Ser Tyr Asp His Gly Thr Ser
    290                 295                 300

Ile Glu Glu Ile Glu Glu Gln Met Asp Asp Trp Leu Glu Asn Arg Asn
305                 310                 315                 320
```

-continued

```
Arg Thr Gln Lys Lys Gln Ala Pro Glu Trp Thr Glu Glu Asp Leu Ser
                325                 330                 335

Gln Leu Thr Arg Ser Met Val Lys Phe Pro Gly Gly Thr Pro Gly Arg
            340                 345                 350

Trp Glu Lys Ile Ala His Glu Leu Gly Arg Ser Val Thr Asp Val Thr
        355                 360                 365

Thr Lys Ala Lys Gln Leu Lys Asp Ser Val Thr Cys Ser Pro Gly Met
    370                 375                 380

Val Arg Leu Ser Glu Leu Lys Ser Thr Val Gln Asn Ser Arg Pro Ile
385                 390                 395                 400

Lys Thr Ala Thr Thr Leu Pro Asp Asp Met Ile Thr Gln Arg Glu Asp
                405                 410                 415

Ala Glu Gly Val Ala Ala Glu Glu Glu Gln Glu Gly Asp Ser Gly Glu
            420                 425                 430

Gln Glu Thr Gly Ala Thr Asp Ala Arg Pro Arg Arg Arg Lys Pro Ala
        435                 440                 445

Arg Leu Leu Glu Ala Thr Ala Lys Pro Glu Pro Glu Glu Lys Ser Arg
    450                 455                 460

Ala Lys Arg Gln Lys Asp Phe Asp Ile Ala Glu Gln Asn Glu Ser Ser
465                 470                 475                 480

Asp Glu Glu Ser Leu Arg Lys Glu Arg Ala Arg Ser Ala Glu Glu Pro
                485                 490                 495

Trp Thr Gln Asn Gln Gln Lys Leu Leu Glu Leu Ala Leu Gln Gln Tyr
            500                 505                 510

Pro Arg Gly Ser Ser Asp Arg Trp Asp Lys Ile Ala Arg Cys Val Pro
        515                 520                 525

Ser Lys Ser Lys Glu Asp Cys Ile Ala Arg Tyr Lys Leu Leu Val Glu
    530                 535                 540

Leu Val Gln Lys Lys Lys Gln Ala Lys Ser
545                 550
```

<210> SEQ ID NO 19
<211> LENGTH: 4252
<212> TYPE: DNA
<213> ORGANISM: human
<220> FEATURE:
<221> NAME/KEY: CDS
<222> LOCATION: (528)...(3053)

<400> SEQUENCE: 19

```
tttatttacg cctacctccc agcccttggc aatctgacta ataacaaact gagctaacaa     60

gaaatactag aaaaggagga aggagaacat tgctgtagct tggatctaca acctaagaaa    120

gcaagagtga tcaatctcag ctctgttaaa catcttgttt acttactgca ttcagcagct    180

tgcaaatggt taactatatg caaaaaagtc agcatagctg tgaagtatgc cgtgaatttt    240

aattgaggga aaaagggaca attgcttcag gatgctctag tatgcactct gcttgaaata    300

ttttcaatga aatgctcagt attctatctt tgaccagagg ttttaacttt atgaagctat    360

gggacttgac aaaaagtgat atttgagaag aaagtacgca gtggttggtg ttttcttttt    420

tttaataaag gaattgaatt actttgaaca cctcttccag ctgtgcatta cagataacgt    480

caggaagagt ctctgcttta cagaatcgga tttcatcaca tgacaac atg aag ctg      536
                                                    Met Lys Leu
                                                     1

tgg att cat ctc ttt tat tca tct ctc ctt gcc tgt ata tct tta cac      584
Trp Ile His Leu Phe Tyr Ser Ser Leu Leu Ala Cys Ile Ser Leu His
```

-continued

```
     5                   10                  15

tcc caa act cca gtg ctc tca tcc aga ggc tct tgt gat tct ctt tgc      632
Ser Gln Thr Pro Val Leu Ser Ser Arg Gly Ser Cys Asp Ser Leu Cys
 20                  25                  30                  35

aat tgt gag gaa aaa gat ggc aca atg cta ata aat tgt gaa gca aaa      680
Asn Cys Glu Glu Lys Asp Gly Thr Met Leu Ile Asn Cys Glu Ala Lys
                 40                  45                  50

ggt atc aag atg gta tct gaa ata agt gtg cca cca tca cga cct ttc      728
Gly Ile Lys Met Val Ser Glu Ile Ser Val Pro Pro Ser Arg Pro Phe
             55                  60                  65

caa cta agc tta tta aat aac ggc ttg acg atg ctt cac aca aat gac      776
Gln Leu Ser Leu Leu Asn Asn Gly Leu Thr Met Leu His Thr Asn Asp
         70                  75                  80

ttt tct ggg ctt acc aat gct att tca ata cac ctt gga ttt aac aat      824
Phe Ser Gly Leu Thr Asn Ala Ile Ser Ile His Leu Gly Phe Asn Asn
     85                  90                  95

att gca gat att gag ata ggt gca ttt aat ggc ctt ggc ctc ctg aaa      872
Ile Ala Asp Ile Glu Ile Gly Ala Phe Asn Gly Leu Gly Leu Leu Lys
100                 105                 110                 115

caa ctt cat atc aat cac aat tct tta gaa att ctt aaa gag gat act      920
Gln Leu His Ile Asn His Asn Ser Leu Glu Ile Leu Lys Glu Asp Thr
                120                 125                 130

ttc cat gga ctg gaa aac ctg gaa ttc ctg caa gca gat aac aat ttt      968
Phe His Gly Leu Glu Asn Leu Glu Phe Leu Gln Ala Asp Asn Asn Phe
            135                 140                 145

atc aca gtg att gaa cca agt gcc ttt agc aag ctc aac aga ctc aaa     1016
Ile Thr Val Ile Glu Pro Ser Ala Phe Ser Lys Leu Asn Arg Leu Lys
        150                 155                 160

gtg tta att tta aat gac aat gct att gag agt ctt cct cca aac atc     1064
Val Leu Ile Leu Asn Asp Asn Ala Ile Glu Ser Leu Pro Pro Asn Ile
    165                 170                 175

ttc cga ttt gtt cct tta acc cat cta gat ctt cgt gga aat caa tta     1112
Phe Arg Phe Val Pro Leu Thr His Leu Asp Leu Arg Gly Asn Gln Leu
180                 185                 190                 195

caa aca ttg cct tat gtt ggt ttt ctc gaa cac att ggc cga ata ttg     1160
Gln Thr Leu Pro Tyr Val Gly Phe Leu Glu His Ile Gly Arg Ile Leu
                200                 205                 210

gat ctt cag ttg gag gac aac aaa tgg gcc tgc aat tgt gac tta ttg     1208
Asp Leu Gln Leu Glu Asp Asn Lys Trp Ala Cys Asn Cys Asp Leu Leu
            215                 220                 225

cag tta aaa act tgg ttg gag aac atg cct cca cag tct ata att ggt     1256
Gln Leu Lys Thr Trp Leu Glu Asn Met Pro Pro Gln Ser Ile Ile Gly
        230                 235                 240

gat gtt gtc tgc aac agc cct cca ttt ttt aaa gga agt ata ctc agt     1304
Asp Val Val Cys Asn Ser Pro Pro Phe Phe Lys Gly Ser Ile Leu Ser
    245                 250                 255

aga cta aag aag gaa tct att tgc cct act cca cca gtg tat gaa gaa     1352
Arg Leu Lys Lys Glu Ser Ile Cys Pro Thr Pro Pro Val Tyr Glu Glu
260                 265                 270                 275

cat gag gat cct tca gga tca tta cat ctg gca gca aca tct tca ata     1400
His Glu Asp Pro Ser Gly Ser Leu His Leu Ala Ala Thr Ser Ser Ile
                280                 285                 290

aat gat agt cgc atg tca act aag acc acg tcc att cta aaa cta ccc     1448
Asn Asp Ser Arg Met Ser Thr Lys Thr Thr Ser Ile Leu Lys Leu Pro
            295                 300                 305

acc aaa gca cca ggt ttg ata cct tat att aca aag cca tcc act caa     1496
Thr Lys Ala Pro Gly Leu Ile Pro Tyr Ile Thr Lys Pro Ser Thr Gln
        310                 315                 320

ctt cca gga cct tac tgc cct att cct tgt aac tgc aaa gtc cta tcc     1544
```

-continued

```
Leu Pro Gly Pro Tyr Cys Pro Ile Pro Cys Asn Cys Lys Val Leu Ser
    325                 330                 335

cca tca gga ctt cta ata cat tgt cag gag cgc aac att gaa agc tta     1592
Pro Ser Gly Leu Leu Ile His Cys Gln Glu Arg Asn Ile Glu Ser Leu
340                 345                 350                 355

tca gat ctg aga cct cct ccg caa aat cct aga aag ctc att cta gcg     1640
Ser Asp Leu Arg Pro Pro Pro Gln Asn Pro Arg Lys Leu Ile Leu Ala
                360                 365                 370

gga aat att att cac agt tta atg aag tct gat cta gtg gaa tat ttc     1688
Gly Asn Ile Ile His Ser Leu Met Lys Ser Asp Leu Val Glu Tyr Phe
            375                 380                 385

act ttg gaa atg ctt cac ttg gga aac aat cgt att gaa gtt ctt gaa     1736
Thr Leu Glu Met Leu His Leu Gly Asn Asn Arg Ile Glu Val Leu Glu
        390                 395                 400

gaa gga tcg ttt atg aac cta acg aga tta caa aaa ctc tat cta aat     1784
Glu Gly Ser Phe Met Asn Leu Thr Arg Leu Gln Lys Leu Tyr Leu Asn
    405                 410                 415

ggt aac cac ctg acc aaa tta agt aaa ggc atg ttc ctt ggt ctc cat     1832
Gly Asn His Leu Thr Lys Leu Ser Lys Gly Met Phe Leu Gly Leu His
420                 425                 430                 435

aat ctt gaa tac tta tat ctt gaa tac aat gcc att aag gaa ata ctg     1880
Asn Leu Glu Tyr Leu Tyr Leu Glu Tyr Asn Ala Ile Lys Glu Ile Leu
                440                 445                 450

cca gga acc ttt aat cca atg cct aaa ctt aaa gtc ctg tat tta aat     1928
Pro Gly Thr Phe Asn Pro Met Pro Lys Leu Lys Val Leu Tyr Leu Asn
            455                 460                 465

aac aac ctc ctc caa gtt tta cca cca cat att ttt tca ggg gtt cct     1976
Asn Asn Leu Leu Gln Val Leu Pro Pro His Ile Phe Ser Gly Val Pro
        470                 475                 480

cta act aag gta aat ctt aaa aca aac cag ttt acc cat cta cct gta     2024
Leu Thr Lys Val Asn Leu Lys Thr Asn Gln Phe Thr His Leu Pro Val
    485                 490                 495

agt aat att ttg gat gat ctt gat tta cta acc cag att gac ctt gag     2072
Ser Asn Ile Leu Asp Asp Leu Asp Leu Leu Thr Gln Ile Asp Leu Glu
500                 505                 510                 515

gat aac ccc tgg gac tgc tcc tgt gac ctg gtt gga ctg cag caa tgg     2120
Asp Asn Pro Trp Asp Cys Ser Cys Asp Leu Val Gly Leu Gln Gln Trp
                520                 525                 530

ata caa aag tta agc aag aac aca gtg aca gat gac atc ctc tgc act     2168
Ile Gln Lys Leu Ser Lys Asn Thr Val Thr Asp Asp Ile Leu Cys Thr
            535                 540                 545

tcc ccc ggg cat ctc gac aaa aag gaa ttg aaa gcc cta aat agt gaa     2216
Ser Pro Gly His Leu Asp Lys Lys Glu Leu Lys Ala Leu Asn Ser Glu
        550                 555                 560

att ctc tgt cca ggt tta gta aat aac cca tcc atg cca aca cag act     2264
Ile Leu Cys Pro Gly Leu Val Asn Asn Pro Ser Met Pro Thr Gln Thr
    565                 570                 575

agt tac ctt atg gtc acc act cct gca aca aca aca aat acg gct gat     2312
Ser Tyr Leu Met Val Thr Thr Pro Ala Thr Thr Thr Asn Thr Ala Asp
580                 585                 590                 595

act att tta cga tct ctt acg gac gct gtg cca ctg tct gtt cta ata     2360
Thr Ile Leu Arg Ser Leu Thr Asp Ala Val Pro Leu Ser Val Leu Ile
                600                 605                 610

ttg gga ctt ctg att atg ttc atc act att gtt ttc tgt gct gca ggg     2408
Leu Gly Leu Leu Ile Met Phe Ile Thr Ile Val Phe Cys Ala Ala Gly
            615                 620                 625

ata gtg gtt ctt gtt ctt cac cgc agg aga aga tac aaa aag aaa caa     2456
Ile Val Val Leu Val Leu His Arg Arg Arg Arg Tyr Lys Lys Lys Gln
        630                 635                 640
```

-continued

```
gta gat gag caa atg aga gac aac agt cct gtg cat ctt cag tac agc     2504
Val Asp Glu Gln Met Arg Asp Asn Ser Pro Val His Leu Gln Tyr Ser
    645                 650                 655

atg tat ggc cat aaa acc act cat cac act act gaa aga ccc tct gcc     2552
Met Tyr Gly His Lys Thr Thr His His Thr Thr Glu Arg Pro Ser Ala
660                 665                 670                 675

tca ctc tat gaa cag cac atg gtg agc ccc atg gtt cat gtc tat aga     2600
Ser Leu Tyr Glu Gln His Met Val Ser Pro Met Val His Val Tyr Arg
                680                 685                 690

agt cca tcc ttt ggt cca aag cat ctg gaa gag gaa gaa gag agg aat     2648
Ser Pro Ser Phe Gly Pro Lys His Leu Glu Glu Glu Glu Glu Arg Asn
            695                 700                 705

gag aaa gaa gga agt gat gca aaa cat ctc caa aga agt ctt ttg gaa     2696
Glu Lys Glu Gly Ser Asp Ala Lys His Leu Gln Arg Ser Leu Leu Glu
        710                 715                 720

cag gaa aat cat tca cca ctc aca ggg tca aat atg aaa tac aaa acc     2744
Gln Glu Asn His Ser Pro Leu Thr Gly Ser Asn Met Lys Tyr Lys Thr
    725                 730                 735

acg aac caa tca aca gaa ttt tta tcc ttc caa gat gcc agc tca ttg     2792
Thr Asn Gln Ser Thr Glu Phe Leu Ser Phe Gln Asp Ala Ser Ser Leu
740                 745                 750                 755

tac aga aac att tta gaa aaa gaa agg gaa ctt cag caa ctg gga atc     2840
Tyr Arg Asn Ile Leu Glu Lys Glu Arg Glu Leu Gln Gln Leu Gly Ile
                760                 765                 770

aca gaa tac cta agg aaa aac att gct cag ctc cag cct gat atg gag     2888
Thr Glu Tyr Leu Arg Lys Asn Ile Ala Gln Leu Gln Pro Asp Met Glu
            775                 780                 785

gca cat tat cct gga gcc cac gaa gag ctg aag tta atg gaa aca tta     2936
Ala His Tyr Pro Gly Ala His Glu Glu Leu Lys Leu Met Glu Thr Leu
        790                 795                 800

atg tac tca cgt cca agg aag gta tta gtg gaa cag aca aaa aat gag     2984
Met Tyr Ser Arg Pro Arg Lys Val Leu Val Glu Gln Thr Lys Asn Glu
    805                 810                 815

tat ttt gaa ctt aaa gct aat tta cat gct gaa cct gac tat tta gaa     3032
Tyr Phe Glu Leu Lys Ala Asn Leu His Ala Glu Pro Asp Tyr Leu Glu
820                 825                 830                 835

gtc ctg gag cag caa aca tag atggagagtt tgagggcttt cgcagaaatg        3083
Val Leu Glu Gln Gln Thr  *
                840

ctgtgattct gttttaagtc cataccttgt aaataagtgc cttacgtgag tgtgtcatca   3143

atcagaacct aagcacagca gtaaactatg gggaaaaaaa aagaagaaga aaaagaaact   3203

cagggatcac tgggagaagc catggcatta tcttcaggca atttagtctg tcccaaataa   3263

aataaatcct tgcatgtaaa tcattcaagg attatagtaa tatttcatat actgaaaagt   3323

gtctcatagg agtcctcttg cacatctaaa aaggctgaac atttaagtat cccgaatttt   3383

cttgaattgc tttccctata gattaattac aattggattt catcatttaa aaaccatact   3443

tgtatatgta gttataaatat gtaaggaata cattgtttat aaccagtatg tacttcaaaa   3503

atgtgtattg tcaaacatac ctaactttct tgcaataaat gcaaaagaaa ctggaacttg   3563

acaattataa atagtaatag tgaagaaaaa atagaaaggt tgcaattata taggccatgg   3623

gtggctcaaa actttgaaca tttgagctta aacaaatgcc actctcatgc attctaaatt   3683

aaaaagttaa aatgattaat agttcaggtg gaagaaataa gcatactttt tgggttttct   3743

acacattttg tgtagacaat tttaatgtca gtgctgctgt gaactaaagt atgtcattta   3803

tgctcaaagt ttaattcttc ttcttgggat attttaaaaa tgctactgag attctgctgt   3863

aaatatgact agagaatata ttgggtttgc tttatttcat aggcttaatt ctttgtaaat   3923
```

```
ctgaatgacc ataatagaaa tacatttctt gtggcaagta attcacagtt gtaaagtaaa   3983

taggaaaaat tattttattt ttattgatgt acattgatag atgccataaa tcagtagcaa   4043

aaggcacttc taaaggtaag tggtttaagt tgcctcaaga gagggacaat gtagctttat   4103

tttacaagaa ggcatagtta gatttctatg aaatatttat tctgtacagt tttatatagt   4163

tttggttcac aaaagtaatt attcttgggt gcctttcaag aaaattaaaa atactactca   4223

ctacaataaa actaaaatga aaactcttt                                     4252
```

<210> SEQ ID NO 20
<211> LENGTH: 841
<212> TYPE: PRT
<213> ORGANISM: human

<400> SEQUENCE: 20

```
Met Lys Leu Trp Ile His Leu Phe Tyr Ser Ser Leu Leu Ala Cys Ile
 1               5                  10                  15

Ser Leu His Ser Gln Thr Pro Val Leu Ser Ser Arg Gly Ser Cys Asp
            20                  25                  30

Ser Leu Cys Asn Cys Glu Glu Lys Asp Gly Thr Met Leu Ile Asn Cys
        35                  40                  45

Glu Ala Lys Gly Ile Lys Met Val Ser Glu Ile Ser Val Pro Pro Ser
    50                  55                  60

Arg Pro Phe Gln Leu Ser Leu Leu Asn Asn Gly Leu Thr Met Leu His
65                  70                  75                  80

Thr Asn Asp Phe Ser Gly Leu Thr Asn Ala Ile Ser Ile His Leu Gly
                85                  90                  95

Phe Asn Asn Ile Ala Asp Ile Glu Ile Gly Ala Phe Asn Gly Leu Gly
            100                 105                 110

Leu Leu Lys Gln Leu His Ile Asn His Asn Ser Leu Glu Ile Leu Lys
        115                 120                 125

Glu Asp Thr Phe His Gly Leu Glu Asn Leu Glu Phe Leu Gln Ala Asp
    130                 135                 140

Asn Asn Phe Ile Thr Val Ile Glu Pro Ser Ala Phe Ser Lys Leu Asn
145                 150                 155                 160

Arg Leu Lys Val Leu Ile Leu Asn Asp Asn Ala Ile Glu Ser Leu Pro
                165                 170                 175

Pro Asn Ile Phe Arg Phe Val Pro Leu Thr His Leu Asp Leu Arg Gly
            180                 185                 190

Asn Gln Leu Gln Thr Leu Pro Tyr Val Gly Phe Leu Glu His Ile Gly
        195                 200                 205

Arg Ile Leu Asp Leu Gln Leu Glu Asp Asn Lys Trp Ala Cys Asn Cys
    210                 215                 220

Asp Leu Leu Gln Leu Lys Thr Trp Leu Glu Asn Met Pro Pro Gln Ser
225                 230                 235                 240

Ile Ile Gly Asp Val Val Cys Asn Ser Pro Pro Phe Phe Lys Gly Ser
                245                 250                 255

Ile Leu Ser Arg Leu Lys Lys Glu Ser Ile Cys Pro Thr Pro Pro Val
            260                 265                 270

Tyr Glu Glu His Glu Asp Pro Ser Gly Ser Leu His Leu Ala Ala Thr
        275                 280                 285

Ser Ser Ile Asn Asp Ser Arg Met Ser Thr Lys Thr Thr Ser Ile Leu
    290                 295                 300

Lys Leu Pro Thr Lys Ala Pro Gly Leu Ile Pro Tyr Ile Thr Lys Pro
```

-continued

```
305                 310                 315                 320

Ser Thr Gln Leu Pro Gly Pro Tyr Cys Pro Ile Pro Cys Asn Cys Lys
                325                 330                 335

Val Leu Ser Pro Ser Gly Leu Leu Ile His Cys Gln Glu Arg Asn Ile
            340                 345                 350

Glu Ser Leu Ser Asp Leu Arg Pro Pro Pro Gln Asn Pro Arg Lys Leu
        355                 360                 365

Ile Leu Ala Gly Asn Ile Ile His Ser Leu Met Lys Ser Asp Leu Val
    370                 375                 380

Glu Tyr Phe Thr Leu Glu Met Leu His Leu Gly Asn Asn Arg Ile Glu
385                 390                 395                 400

Val Leu Glu Glu Gly Ser Phe Met Asn Leu Thr Arg Leu Gln Lys Leu
                405                 410                 415

Tyr Leu Asn Gly Asn His Leu Thr Lys Leu Ser Lys Gly Met Phe Leu
            420                 425                 430

Gly Leu His Asn Leu Glu Tyr Leu Tyr Leu Glu Tyr Asn Ala Ile Lys
        435                 440                 445

Glu Ile Leu Pro Gly Thr Phe Asn Pro Met Pro Lys Leu Lys Val Leu
    450                 455                 460

Tyr Leu Asn Asn Asn Leu Leu Gln Val Leu Pro Pro His Ile Phe Ser
465                 470                 475                 480

Gly Val Pro Leu Thr Lys Val Asn Leu Lys Thr Asn Gln Phe Thr His
                485                 490                 495

Leu Pro Val Ser Asn Ile Leu Asp Asp Leu Asp Leu Leu Thr Gln Ile
            500                 505                 510

Asp Leu Glu Asp Asn Pro Trp Asp Cys Ser Cys Asp Leu Val Gly Leu
        515                 520                 525

Gln Gln Trp Ile Gln Lys Leu Ser Lys Asn Thr Val Thr Asp Asp Ile
    530                 535                 540

Leu Cys Thr Ser Pro Gly His Leu Asp Lys Lys Glu Leu Lys Ala Leu
545                 550                 555                 560

Asn Ser Glu Ile Leu Cys Pro Gly Leu Val Asn Asn Pro Ser Met Pro
                565                 570                 575

Thr Gln Thr Ser Tyr Leu Met Val Thr Thr Pro Ala Thr Thr Thr Asn
            580                 585                 590

Thr Ala Asp Thr Ile Leu Arg Ser Leu Thr Asp Ala Val Pro Leu Ser
        595                 600                 605

Val Leu Ile Leu Gly Leu Leu Ile Met Phe Ile Thr Ile Val Phe Cys
    610                 615                 620

Ala Ala Gly Ile Val Val Leu Val Leu His Arg Arg Arg Arg Tyr Lys
625                 630                 635                 640

Lys Lys Gln Val Asp Glu Gln Met Arg Asp Asn Ser Pro Val His Leu
                645                 650                 655

Gln Tyr Ser Met Tyr Gly His Lys Thr Thr His His Thr Thr Glu Arg
            660                 665                 670

Pro Ser Ala Ser Leu Tyr Glu Gln His Met Val Ser Pro Met Val His
        675                 680                 685

Val Tyr Arg Ser Pro Ser Phe Gly Pro Lys His Leu Glu Glu Glu Glu
    690                 695                 700

Glu Arg Asn Glu Lys Glu Gly Ser Asp Ala Lys His Leu Gln Arg Ser
705                 710                 715                 720

Leu Leu Glu Gln Glu Asn His Ser Pro Leu Thr Gly Ser Asn Met Lys
                725                 730                 735
```

```
Tyr Lys Thr Thr Asn Gln Ser Thr Glu Phe Leu Ser Phe Gln Asp Ala
            740                 745                 750

Ser Ser Leu Tyr Arg Asn Ile Leu Glu Lys Glu Arg Glu Leu Gln Gln
        755                 760                 765

Leu Gly Ile Thr Glu Tyr Leu Arg Lys Asn Ile Ala Gln Leu Gln Pro
    770                 775                 780

Asp Met Glu Ala His Tyr Pro Gly Ala His Glu Glu Leu Lys Leu Met
785                 790                 795                 800

Glu Thr Leu Met Tyr Ser Arg Pro Arg Lys Val Leu Val Glu Gln Thr
                805                 810                 815

Lys Asn Glu Tyr Phe Glu Leu Lys Ala Asn Leu His Ala Glu Pro Asp
            820                 825                 830

Tyr Leu Glu Val Leu Glu Gln Gln Thr
        835                 840


<210> SEQ ID NO 21
<211> LENGTH: 3609
<212> TYPE: DNA
<213> ORGANISM: human
<220> FEATURE:
<221> NAME/KEY: CDS
<222> LOCATION: (282)...(2549)

<400> SEQUENCE: 21

cgaagggggc ggtggttccc cgcggcgctg cgcgcggcgg taattagtga ttgtcttcca      60

gcttcgcgaa ggctaggggc gcggctgccg ggtggctgcg cggcgctgcc cccggaccga     120

ggggcagcca atccaatgaa accaccgcgt gttcgcgcct ggtagagatt tctcgaagac     180

accagtgggc ccgttccgag ccctctggac cgcccgtgtg gaaccaaacc tgcgcgcgtg     240

gccgggccgt gggacaacga ggccgcggag acgaaggcgc a atg gcg agg aag tta     296
                                              Met Ala Arg Lys Leu
                                               1               5

tct gta atc ttg atc ctg acc ttt gcc ctc tct gtc aca aat ccc ctt       344
Ser Val Ile Leu Ile Leu Thr Phe Ala Leu Ser Val Thr Asn Pro Leu
                 10                  15                  20

cat gaa cta aaa gca gct gct ttc ccc cag acc act gag aaa att agt       392
His Glu Leu Lys Ala Ala Ala Phe Pro Gln Thr Thr Glu Lys Ile Ser
             25                  30                  35

ccg aat tgg gaa tct ggc att aat gtt gac ttg gca att tcc aca cgg       440
Pro Asn Trp Glu Ser Gly Ile Asn Val Asp Leu Ala Ile Ser Thr Arg
         40                  45                  50

caa tat cat cta caa cag ctt ttc tac cgc tat gga gaa aat aat tct       488
Gln Tyr His Leu Gln Gln Leu Phe Tyr Arg Tyr Gly Glu Asn Asn Ser
     55                  60                  65

ttg tca gtt gaa ggg ttc aga aaa tta ctt caa aat ata ggc ata gat       536
Leu Ser Val Glu Gly Phe Arg Lys Leu Leu Gln Asn Ile Gly Ile Asp
 70                  75                  80                  85

aag att aaa aga atc cat ata cac cat gac cac gac cat cac tca gac       584
Lys Ile Lys Arg Ile His Ile His His Asp His Asp His His Ser Asp
                 90                  95                 100

cac gag cat cac tca gac cat gag cgt cac tca gac cat gag cat cac       632
His Glu His His Ser Asp His Glu Arg His Ser Asp His Glu His His
            105                 110                 115

tca gac cac gag cat cac tct gac cat gat cat cac tct cac cat aat       680
Ser Asp His Glu His His Ser Asp His Asp His His Ser His His Asn
        120                 125                 130

cat gct gct tct ggt aaa aat aag cga aaa gct ctt tgc cca gac cat       728
His Ala Ala Ser Gly Lys Asn Lys Arg Lys Ala Leu Cys Pro Asp His
```

-continued

```
    135                 140                 145

gac tca gat agt tca ggt aaa gat cct aga aac agc cag ggg aaa gga      776
Asp Ser Asp Ser Ser Gly Lys Asp Pro Arg Asn Ser Gln Gly Lys Gly
150                 155                 160                 165

gct cac cga cca gaa cat gcc agt ggt aga agg aat gtc aag gac agt      824
Ala His Arg Pro Glu His Ala Ser Gly Arg Arg Asn Val Lys Asp Ser
                170                 175                 180

gtt agt gct agt gaa gtg acc tca act gtg tac aac act gtc tct gaa      872
Val Ser Ala Ser Glu Val Thr Ser Thr Val Tyr Asn Thr Val Ser Glu
            185                 190                 195

gga act cac ttt cta gag aca ata gag act cca aga cct gga aaa ctc      920
Gly Thr His Phe Leu Glu Thr Ile Glu Thr Pro Arg Pro Gly Lys Leu
        200                 205                 210

ttc ccc aaa gat gta agc agc tcc act cca ccc agt gtc aca tca aag      968
Phe Pro Lys Asp Val Ser Ser Ser Thr Pro Pro Ser Val Thr Ser Lys
    215                 220                 225

agc cgg gtg agc cgg ctg gct ggt agg aaa aca aat gaa tct gtg agt     1016
Ser Arg Val Ser Arg Leu Ala Gly Arg Lys Thr Asn Glu Ser Val Ser
230                 235                 240                 245

gag ccc cga aaa ggc ttt atg tat tcc aga aac aca aat gaa aat cct     1064
Glu Pro Arg Lys Gly Phe Met Tyr Ser Arg Asn Thr Asn Glu Asn Pro
                250                 255                 260

cag gag tgt ttc aat gca tca aag cta ctg aca tct cat ggc atg ggc     1112
Gln Glu Cys Phe Asn Ala Ser Lys Leu Leu Thr Ser His Gly Met Gly
            265                 270                 275

atc cag gtt ccg ctg aat gca aca gag ttc aac tat ctc tgt cca gcc     1160
Ile Gln Val Pro Leu Asn Ala Thr Glu Phe Asn Tyr Leu Cys Pro Ala
        280                 285                 290

atc atc aac caa att gat gct aga tct tgt ctg att cat aca agt gaa     1208
Ile Ile Asn Gln Ile Asp Ala Arg Ser Cys Leu Ile His Thr Ser Glu
    295                 300                 305

aag aag gct gaa atc cct cca aag acc tat tca tta caa ata gcc tgg     1256
Lys Lys Ala Glu Ile Pro Pro Lys Thr Tyr Ser Leu Gln Ile Ala Trp
310                 315                 320                 325

gtt ggt ggt ttt ata gcc att tcc atc atc agt ttc ctg tct ctg ctg     1304
Val Gly Gly Phe Ile Ala Ile Ser Ile Ile Ser Phe Leu Ser Leu Leu
                330                 335                 340

ggg gtt atc tta gtg cct ctc atg aat cgg gtg ttt ttc aaa ttt ctc     1352
Gly Val Ile Leu Val Pro Leu Met Asn Arg Val Phe Phe Lys Phe Leu
            345                 350                 355

ctg agt ttc ctt gtg gca ctg gcc gtt ggg act ttg agt ggt gat gct     1400
Leu Ser Phe Leu Val Ala Leu Ala Val Gly Thr Leu Ser Gly Asp Ala
        360                 365                 370

ttt tta cac ctt ctt cca cat tct cat gca agt cac cac cat agt cat     1448
Phe Leu His Leu Leu Pro His Ser His Ala Ser His His His Ser His
    375                 380                 385

agc cat gaa gaa cca gca atg gaa atg aaa aga gga cca ctt ttc agt     1496
Ser His Glu Glu Pro Ala Met Glu Met Lys Arg Gly Pro Leu Phe Ser
390                 395                 400                 405

cat ctg tct tct caa aac ata gaa gaa agt gcc tat ttt gat tcc acg     1544
His Leu Ser Ser Gln Asn Ile Glu Glu Ser Ala Tyr Phe Asp Ser Thr
                410                 415                 420

tgg aag ggt cta aca gct cta gga ggc ctg tat ttc atg ttt ctt gtt     1592
Trp Lys Gly Leu Thr Ala Leu Gly Gly Leu Tyr Phe Met Phe Leu Val
            425                 430                 435

gaa cat gtc ctc aca ttg atc aaa caa ttt aaa gat aag aag aaa aag     1640
Glu His Val Leu Thr Leu Ile Lys Gln Phe Lys Asp Lys Lys Lys Lys
        440                 445                 450

aat cag aag aaa cct gaa aat gat gat gat gtg gag att aag aag cag     1688
```

-continued

```
Asn Gln Lys Lys Pro Glu Asn Asp Asp Asp Val Glu Ile Lys Lys Gln
    455                 460                 465

ttg tcc aag tat gaa tct caa ctt tca aca aat gag gag aaa gta gat      1736
Leu Ser Lys Tyr Glu Ser Gln Leu Ser Thr Asn Glu Glu Lys Val Asp
470                 475                 480                 485

aca gat gat cga act gaa ggc tat tta cga gca gac tca caa gag ccc      1784
Thr Asp Asp Arg Thr Glu Gly Tyr Leu Arg Ala Asp Ser Gln Glu Pro
                490                 495                 500

tcc cac ttt gat tct cag cag cct gca gtc ttg gaa gaa gaa gag gtc      1832
Ser His Phe Asp Ser Gln Gln Pro Ala Val Leu Glu Glu Glu Glu Val
            505                 510                 515

atg ata gct cat gct cat cca cag gaa gtc tac aat gaa tat gta ccc      1880
Met Ile Ala His Ala His Pro Gln Glu Val Tyr Asn Glu Tyr Val Pro
        520                 525                 530

aga ggg tgc aag aat aaa tgc cat tca cat ttc cac gat aca ctc ggc      1928
Arg Gly Cys Lys Asn Lys Cys His Ser His Phe His Asp Thr Leu Gly
    535                 540                 545

cag tca gac gat ctc att cac cac cat cat gac tac cat cat att ctc      1976
Gln Ser Asp Asp Leu Ile His His His His Asp Tyr His His Ile Leu
550                 555                 560                 565

cat cat cac cac cac caa aac cac cat cct cac agt cac agc cag cgc      2024
His His His His His Gln Asn His His Pro His Ser His Ser Gln Arg
                570                 575                 580

tac tct cgg gag gag ctg aaa gat gcc ggc gtc gcc act ctg gcc tgg      2072
Tyr Ser Arg Glu Glu Leu Lys Asp Ala Gly Val Ala Thr Leu Ala Trp
            585                 590                 595

atg gtg ata atg ggt gat ggc ctg cac aat ttc agc gat ggc cta gca      2120
Met Val Ile Met Gly Asp Gly Leu His Asn Phe Ser Asp Gly Leu Ala
        600                 605                 610

att ggt gct gct ttt act gaa ggc tta tca agt ggt tta agt act tct      2168
Ile Gly Ala Ala Phe Thr Glu Gly Leu Ser Ser Gly Leu Ser Thr Ser
    615                 620                 625

gtt gct gtg ttc tgt cat gag ttg cct cat gaa tta ggt gac ttt gct      2216
Val Ala Val Phe Cys His Glu Leu Pro His Glu Leu Gly Asp Phe Ala
630                 635                 640                 645

gtt cta cta aag gct ggc atg acc gtt aag cag gct gtc ctt tat aat      2264
Val Leu Leu Lys Ala Gly Met Thr Val Lys Gln Ala Val Leu Tyr Asn
                650                 655                 660

gca ttg tca gcc atg ctg gcg tat ctt gga atg gca aca gga att ttc      2312
Ala Leu Ser Ala Met Leu Ala Tyr Leu Gly Met Ala Thr Gly Ile Phe
            665                 670                 675

att ggt cat tat gct gaa aat gtt tct atg tgg ata ttt gca ctt act      2360
Ile Gly His Tyr Ala Glu Asn Val Ser Met Trp Ile Phe Ala Leu Thr
        680                 685                 690

gct ggc tta ttc atg tat gtt gct ctg gtt gat atg gta cct gaa atg      2408
Ala Gly Leu Phe Met Tyr Val Ala Leu Val Asp Met Val Pro Glu Met
    695                 700                 705

ctg cac aat gat gct agt gac cat gga tgt agc cgc tgg ggg tat ttc      2456
Leu His Asn Asp Ala Ser Asp His Gly Cys Ser Arg Trp Gly Tyr Phe
710                 715                 720                 725

ttt tta cag aat gct ggg atg ctt ttg ggt ttt gga att atg tta ctt      2504
Phe Leu Gln Asn Ala Gly Met Leu Leu Gly Phe Gly Ile Met Leu Leu
                730                 735                 740

att tcc ata ttt gaa cat aaa atc gtg ttt cgt ata aat ttc tag          2549
Ile Ser Ile Phe Glu His Lys Ile Val Phe Arg Ile Asn Phe  *
            745                 750                 755

ttaaggttta aatgctagag tagcttaaaa agttgtcata gtttcagtag gtcataggga   2609

gatgagtttg tatgctgtac tatgcagcgt ttaaagttag tgggttttgt gatttttat    2669
```

-continued

```
tgaatattgc tgtctgttac aaagtcagtt aaaggtacgt tttaatattt aagttattct   2729

atcttggaga taaaatctgt atgtgcaatt caccggtatt accagtttat tatgtaaaca   2789

agagatttgg catgacatgt tctgtatgtt tcagggaaaa atgtctttaa tgctttttca   2849

agaactaaca cagttattcc tatactggat tttaggtctc tgaagaactg ctggtgttta   2909

ggaataagaa tgtgcatgaa gcctaaaata ccaagaaagc ttatactgaa tttaagcaaa   2969

gaaataaagg agaaaagaga agaatctgag aattggggag gcatagattc ttataaaaat   3029

cacaaaattt gttgtaaatt agaggggaga aatttagaat taagtataaa aaggcagaat   3089

tagtatagag tacattcatt aaacattttt gtcaggatta tttcccgtaa aaacgtagtg   3149

agcacttttc atatactaat ttagttgtac atttaacttt gtataataca gaaatctaaa   3209

tatatttaat gaattcaagc aatatatcac ttgaccaaga aattggaatt tcaaaatgtt   3269

cgtgcgggta tataccagat gagtacagtg agtagtttta tgtatcacca gactgggtta   3329

ttgccaagtt atatatcacc aaaagctgta tgactggatg ttctggttac ctggtttaca   3389

aaattatcag agtagtaaaa ctttgatata tatgaggata ttaaaactac actaagtatc   3449

atttgattcg attcagaaag tactttgata tctctcagtg cttcagtgct atcattgtga   3509

gcaattgtct tttatatacg gtactgtagc catactaggc ctgtctgtgg cattctctag   3569

atgtttcttt tttacacaat aaattcctta tatcagcttg                         3609
```

<210> SEQ ID NO 22
<211> LENGTH: 755
<212> TYPE: PRT
<213> ORGANISM: human

<400> SEQUENCE: 22

```
Met Ala Arg Lys Leu Ser Val Ile Leu Ile Leu Thr Phe Ala Leu Ser
 1               5                  10                  15

Val Thr Asn Pro Leu His Glu Leu Lys Ala Ala Ala Phe Pro Gln Thr
            20                  25                  30

Thr Glu Lys Ile Ser Pro Asn Trp Glu Ser Gly Ile Asn Val Asp Leu
        35                  40                  45

Ala Ile Ser Thr Arg Gln Tyr His Leu Gln Gln Leu Phe Tyr Arg Tyr
    50                  55                  60

Gly Glu Asn Asn Ser Leu Ser Val Glu Gly Phe Arg Lys Leu Leu Gln
65                  70                  75                  80

Asn Ile Gly Ile Asp Lys Ile Lys Arg Ile His Ile His His Asp His
                85                  90                  95

Asp His His Ser Asp His Glu His His Ser Asp His Glu Arg His Ser
            100                 105                 110

Asp His Glu His His Ser Asp His Glu His His Ser Asp His Asp His
        115                 120                 125

His Ser His His Asn His Ala Ala Ser Gly Lys Asn Lys Arg Lys Ala
    130                 135                 140

Leu Cys Pro Asp His Asp Ser Asp Ser Ser Gly Lys Asp Pro Arg Asn
145                 150                 155                 160

Ser Gln Gly Lys Gly Ala His Arg Pro Glu His Ala Ser Gly Arg Arg
                165                 170                 175

Asn Val Lys Asp Ser Val Ser Ala Ser Glu Val Thr Ser Thr Val Tyr
            180                 185                 190

Asn Thr Val Ser Glu Gly Thr His Phe Leu Glu Thr Ile Glu Thr Pro
        195                 200                 205
```

-continued

```
Arg Pro Gly Lys Leu Phe Pro Lys Asp Val Ser Ser Ser Thr Pro Pro
    210                 215                 220

Ser Val Thr Ser Lys Ser Arg Val Ser Arg Leu Ala Gly Arg Lys Thr
225                 230                 235                 240

Asn Glu Ser Val Ser Glu Pro Arg Lys Gly Phe Met Tyr Ser Arg Asn
                245                 250                 255

Thr Asn Glu Asn Pro Gln Glu Cys Phe Asn Ala Ser Lys Leu Leu Thr
            260                 265                 270

Ser His Gly Met Gly Ile Gln Val Pro Leu Asn Ala Thr Glu Phe Asn
        275                 280                 285

Tyr Leu Cys Pro Ala Ile Ile Asn Gln Ile Asp Ala Arg Ser Cys Leu
    290                 295                 300

Ile His Thr Ser Glu Lys Lys Ala Glu Ile Pro Pro Lys Thr Tyr Ser
305                 310                 315                 320

Leu Gln Ile Ala Trp Val Gly Gly Phe Ile Ala Ile Ser Ile Ile Ser
                325                 330                 335

Phe Leu Ser Leu Leu Gly Val Ile Leu Val Pro Leu Met Asn Arg Val
            340                 345                 350

Phe Phe Lys Phe Leu Leu Ser Phe Leu Val Ala Leu Ala Val Gly Thr
        355                 360                 365

Leu Ser Gly Asp Ala Phe Leu His Leu Leu Pro His Ser His Ala Ser
    370                 375                 380

His His His Ser His Ser His Glu Glu Pro Ala Met Glu Met Lys Arg
385                 390                 395                 400

Gly Pro Leu Phe Ser His Leu Ser Ser Gln Asn Ile Glu Glu Ser Ala
                405                 410                 415

Tyr Phe Asp Ser Thr Trp Lys Gly Leu Thr Ala Leu Gly Gly Leu Tyr
            420                 425                 430

Phe Met Phe Leu Val Glu His Val Leu Thr Leu Ile Lys Gln Phe Lys
        435                 440                 445

Asp Lys Lys Lys Lys Asn Gln Lys Lys Pro Glu Asn Asp Asp Asp Val
    450                 455                 460

Glu Ile Lys Lys Gln Leu Ser Lys Tyr Glu Ser Gln Leu Ser Thr Asn
465                 470                 475                 480

Glu Glu Lys Val Asp Thr Asp Asp Arg Thr Glu Gly Tyr Leu Arg Ala
                485                 490                 495

Asp Ser Gln Glu Pro Ser His Phe Asp Ser Gln Gln Pro Ala Val Leu
            500                 505                 510

Glu Glu Glu Glu Val Met Ile Ala His Ala His Pro Gln Glu Val Tyr
        515                 520                 525

Asn Glu Tyr Val Pro Arg Gly Cys Lys Asn Lys Cys His Ser His Phe
    530                 535                 540

His Asp Thr Leu Gly Gln Ser Asp Asp Leu Ile His His His His Asp
545                 550                 555                 560

Tyr His His Ile Leu His His His His His Gln Asn His His Pro His
                565                 570                 575

Ser His Ser Gln Arg Tyr Ser Arg Glu Glu Leu Lys Asp Ala Gly Val
            580                 585                 590

Ala Thr Leu Ala Trp Met Val Ile Met Gly Asp Gly Leu His Asn Phe
        595                 600                 605

Ser Asp Gly Leu Ala Ile Gly Ala Ala Phe Thr Glu Gly Leu Ser Ser
    610                 615                 620

Gly Leu Ser Thr Ser Val Ala Val Phe Cys His Glu Leu Pro His Glu
```

-continued

```
625                 630                 635                 640

Leu Gly Asp Phe Ala Val Leu Leu Lys Ala Gly Met Thr Val Lys Gln
                645                 650                 655

Ala Val Leu Tyr Asn Ala Leu Ser Ala Met Leu Ala Tyr Leu Gly Met
            660                 665                 670

Ala Thr Gly Ile Phe Ile Gly His Tyr Ala Glu Asn Val Ser Met Trp
        675                 680                 685

Ile Phe Ala Leu Thr Ala Gly Leu Phe Met Tyr Val Ala Leu Val Asp
    690                 695                 700

Met Val Pro Glu Met Leu His Asn Asp Ala Ser Asp His Gly Cys Ser
705                 710                 715                 720

Arg Trp Gly Tyr Phe Phe Leu Gln Asn Ala Gly Met Leu Leu Gly Phe
                725                 730                 735

Gly Ile Met Leu Leu Ile Ser Ile Phe Glu His Lys Ile Val Phe Arg
            740                 745                 750

Ile Asn Phe
        755


<210> SEQ ID NO 23
<211> LENGTH: 2811
<212> TYPE: DNA
<213> ORGANISM: human
<220> FEATURE:
<221> NAME/KEY: CDS
<222> LOCATION: (309)...(1751)

<400> SEQUENCE: 23

cgaaggggc ggtggttccc cgcggcgctg cgcgcggcgg taattagtga ttgtcttcca     60

gcttcgcgaa ggctaggggc gcggctgccg ggtggctgcg cggcgctgcc cccggaccga    120

ggggcagcca atccaatgaa accaccgcgt gttcgcgcct ggtagagatt tctcgaagac    180

accagtgggc ccgttccgag ccctctggac cgcccgtgtg gaaccaaacc tgcgcgcgtg    240

gccgggccgt gggacaacga ggccgcggag actgtttcaa tgcatcaaag ctactgacat    300

ctcatggc atg ggc atc cag gtt ccg ctg aat gca aca gag ttc aac tat     350
         Met Gly Ile Gln Val Pro Leu Asn Ala Thr Glu Phe Asn Tyr
          1               5                  10

ctc tgt cca gcc atc atc aac caa att gat gct aga tct tgt ctg att      398
Leu Cys Pro Ala Ile Ile Asn Gln Ile Asp Ala Arg Ser Cys Leu Ile
 15                  20                  25                  30

cat aca agt gaa aag aag gct gaa atc cct cca aag acc tat tca tta      446
His Thr Ser Glu Lys Lys Ala Glu Ile Pro Pro Lys Thr Tyr Ser Leu
                 35                  40                  45

caa ata gcc tgg gtt ggt ggt ttt ata gcc att tcc atc atc agt ttc      494
Gln Ile Ala Trp Val Gly Gly Phe Ile Ala Ile Ser Ile Ile Ser Phe
             50                  55                  60

ctg tct ctg ctg ggg gtt atc tta gtg cct ctc atg aat cgg gtg ttt      542
Leu Ser Leu Leu Gly Val Ile Leu Val Pro Leu Met Asn Arg Val Phe
         65                  70                  75

ttc aaa ttt ctc ctg agt ttc ctt gtg gca ctg gcc gtt ggg act ttg      590
Phe Lys Phe Leu Leu Ser Phe Leu Val Ala Leu Ala Val Gly Thr Leu
     80                  85                  90

agt ggt gat gct ttt tta cac ctt ctt cca cat tct cat gca agt cac      638
Ser Gly Asp Ala Phe Leu His Leu Leu Pro His Ser His Ala Ser His
 95                 100                 105                 110

cac cat agt cat agc cat gaa gaa cca gca atg gaa atg aaa aga gga      686
His His Ser His Ser His Glu Glu Pro Ala Met Glu Met Lys Arg Gly
                115                 120                 125
```

-continued

```
cca ctt ttc agt cat ctg tct tct caa aac ata gaa gaa agt gcc tat      734
Pro Leu Phe Ser His Leu Ser Ser Gln Asn Ile Glu Glu Ser Ala Tyr
            130                 135                 140

ttt gat tcc acg tgg aag ggt cta aca gct cta gga ggc ctg tat ttc      782
Phe Asp Ser Thr Trp Lys Gly Leu Thr Ala Leu Gly Gly Leu Tyr Phe
        145                 150                 155

atg ttt ctt gtt gaa cat gtc ctc aca ttg atc aaa caa ttt aaa gat      830
Met Phe Leu Val Glu His Val Leu Thr Leu Ile Lys Gln Phe Lys Asp
    160                 165                 170

aag aag aaa aag aat cag aag aaa cct gaa aat gat gat gat gtg gag      878
Lys Lys Lys Lys Asn Gln Lys Lys Pro Glu Asn Asp Asp Asp Val Glu
175                 180                 185                 190

att aag aag cag ttg tcc aag tat gaa tct caa ctt tca aca aat gag      926
Ile Lys Lys Gln Leu Ser Lys Tyr Glu Ser Gln Leu Ser Thr Asn Glu
                195                 200                 205

gag aaa gta gat aca gat gat cga act gaa ggc tat tta cga gca gac      974
Glu Lys Val Asp Thr Asp Asp Arg Thr Glu Gly Tyr Leu Arg Ala Asp
            210                 215                 220

tca caa gag ccc tcc cac ttt gat tct cag cag cct gca gtc ttg gaa     1022
Ser Gln Glu Pro Ser His Phe Asp Ser Gln Gln Pro Ala Val Leu Glu
        225                 230                 235

gaa gaa gag gtc atg ata gct cat gct cat cca cag gaa gtc tac aat     1070
Glu Glu Glu Val Met Ile Ala His Ala His Pro Gln Glu Val Tyr Asn
    240                 245                 250

gaa tat gta ccc aga ggg tgc aag aat aaa tgc cat tca cat ttc cac     1118
Glu Tyr Val Pro Arg Gly Cys Lys Asn Lys Cys His Ser His Phe His
255                 260                 265                 270

gat aca ctc ggc cag tca gac gat ctc att cac cac cat cat gac tac     1166
Asp Thr Leu Gly Gln Ser Asp Asp Leu Ile His His His His Asp Tyr
                275                 280                 285

cat cat att ctc cat cat cac cac cac caa aac cac cat cct cac agt     1214
His His Ile Leu His His His His His Gln Asn His His Pro His Ser
            290                 295                 300

cac agc cag cgc tac tct cgg gag gag ctg aaa gat gcc ggc gtc gcc     1262
His Ser Gln Arg Tyr Ser Arg Glu Glu Leu Lys Asp Ala Gly Val Ala
        305                 310                 315

act ctg gcc tgg atg gtg ata atg ggt gat ggc ctg cac aat ttc agc     1310
Thr Leu Ala Trp Met Val Ile Met Gly Asp Gly Leu His Asn Phe Ser
    320                 325                 330

gat ggc cta gca att ggt gct gct ttt act gaa ggc tta tca agt ggt     1358
Asp Gly Leu Ala Ile Gly Ala Ala Phe Thr Glu Gly Leu Ser Ser Gly
335                 340                 345                 350

tta agt act tct gtt gct gtg ttc tgt cat gag ttg cct cat gaa tta     1406
Leu Ser Thr Ser Val Ala Val Phe Cys His Glu Leu Pro His Glu Leu
                355                 360                 365

ggt gac ttt gct gtt cta cta aag gct ggc atg acc gtt aag cag gct     1454
Gly Asp Phe Ala Val Leu Leu Lys Ala Gly Met Thr Val Lys Gln Ala
            370                 375                 380

gtc ctt tat aat gca ttg tca gcc atg ctg gcg tat ctt gga atg gca     1502
Val Leu Tyr Asn Ala Leu Ser Ala Met Leu Ala Tyr Leu Gly Met Ala
        385                 390                 395

aca gga att ttc att ggt cat tat gct gaa aat gtt tct atg tgg ata     1550
Thr Gly Ile Phe Ile Gly His Tyr Ala Glu Asn Val Ser Met Trp Ile
    400                 405                 410

ttt gca ctt act gct ggc tta ttc atg tat gtt gct ctg gtt gat atg     1598
Phe Ala Leu Thr Ala Gly Leu Phe Met Tyr Val Ala Leu Val Asp Met
415                 420                 425                 430

gta cct gaa atg ctg cac aat gat gct agt gac cat gga tgt agc cgc     1646
Val Pro Glu Met Leu His Asn Asp Ala Ser Asp His Gly Cys Ser Arg
                435                 440                 445
```

-continued

```
tgg ggg tat ttc ttt tta cag aat gct ggg atg ctt ttg ggt ttt gga     1694
Trp Gly Tyr Phe Phe Leu Gln Asn Ala Gly Met Leu Leu Gly Phe Gly
            450                 455                 460

att atg tta ctt att tcc ata ttt gaa cat aaa atc gtg ttt cgt ata     1742
Ile Met Leu Leu Ile Ser Ile Phe Glu His Lys Ile Val Phe Arg Ile
        465                 470                 475

aat ttc tag ttaaggttta aatgctagag tagcttaaaa agttgtcata             1791
Asn Phe  *
    480

gtttcagtag gtcataggga gatgagtttg tatgctgtac tatgcagcgt ttaaagttag   1851

tgggttttgt gattttttat tgaatattgc tgtctgttac aaagtcagtt aaaggtacgt   1911

tttaatattt aagttattct atcttggaga taaaatctgt atgtgcaatt caccggtatt   1971

accagtttat tatgtaaaca agagatttgg catgacatgt tctgtatgtt tcagggaaaa   2031

atgtctttaa tgctttttca agaactaaca cagttattcc tatactggat tttaggtctc   2091

tgaagaactg ctggtgttta ggaataagaa tgtgcatgaa gcctaaaata ccaagaaagc   2151

ttatactgaa tttaagcaaa gaaataaagg agaaaagaga agaatctgag aattggggag   2211

gcatagattc ttataaaaat cacaaaattt gttgtaaatt agaggggaga aatttagaat   2271

taagtataaa aaggcagaat tagtatagag tacattcatt aaacattttt gtcaggatta   2331

tttcccgtaa aaacgtagtg agcacttttc atatactaat ttagttgtac atttaacttt   2391

gtataataca gaaatctaaa tatatttaat gaattcaagc aatatatcac ttgaccaaga   2451

aattggaatt tcaaaatgtt cgtgcgggta tataccagat gagtacagtg agtagtttta   2511

tgtatcacca gactgggtta ttgccaagtt atatatcacc aaaagctgta tgactggatg   2571

ttctggttac ctggtttaca aaattatcag agtagtaaaa ctttgatata tatgaggata   2631

ttaaaactac actaagtatc atttgattcg attcagaaag tactttgata tctctcagtg   2691

cttcagtgct atcattgtga gcaattgtct tttatatacg gtactgtagc catactaggc   2751

ctgtctgtgg cattctctag atgtttcttt tttacacaat aaattcctta tatcagcttg   2811


<210> SEQ ID NO 24
<211> LENGTH: 480
<212> TYPE: PRT
<213> ORGANISM: human

<400> SEQUENCE: 24

Met Gly Ile Gln Val Pro Leu Asn Ala Thr Glu Phe Asn Tyr Leu Cys
 1               5                  10                  15

Pro Ala Ile Ile Asn Gln Ile Asp Ala Arg Ser Cys Leu Ile His Thr
            20                  25                  30

Ser Glu Lys Lys Ala Glu Ile Pro Pro Lys Thr Tyr Ser Leu Gln Ile
        35                  40                  45

Ala Trp Val Gly Gly Phe Ile Ala Ile Ser Ile Ile Ser Phe Leu Ser
    50                  55                  60

Leu Leu Gly Val Ile Leu Val Pro Leu Met Asn Arg Val Phe Phe Lys
65                  70                  75                  80

Phe Leu Leu Ser Phe Leu Val Ala Leu Ala Val Gly Thr Leu Ser Gly
                85                  90                  95

Asp Ala Phe Leu His Leu Leu Pro His Ser His Ala Ser His His His
            100                 105                 110

Ser His Ser His Glu Glu Pro Ala Met Glu Met Lys Arg Gly Pro Leu
        115                 120                 125
```

-continued

```
Phe Ser His Leu Ser Ser Gln Asn Ile Glu Glu Ser Ala Tyr Phe Asp
    130                 135                 140

Ser Thr Trp Lys Gly Leu Thr Ala Leu Gly Gly Leu Tyr Phe Met Phe
145                 150                 155                 160

Leu Val Glu His Val Leu Thr Leu Ile Lys Gln Phe Lys Asp Lys Lys
                165                 170                 175

Lys Lys Asn Gln Lys Lys Pro Glu Asn Asp Asp Asp Val Glu Ile Lys
            180                 185                 190

Lys Gln Leu Ser Lys Tyr Glu Ser Gln Leu Ser Thr Asn Glu Glu Lys
        195                 200                 205

Val Asp Thr Asp Asp Arg Thr Glu Gly Tyr Leu Arg Ala Asp Ser Gln
    210                 215                 220

Glu Pro Ser His Phe Asp Ser Gln Gln Pro Ala Val Leu Glu Glu Glu
225                 230                 235                 240

Glu Val Met Ile Ala His Ala His Pro Gln Glu Val Tyr Asn Glu Tyr
                245                 250                 255

Val Pro Arg Gly Cys Lys Asn Lys Cys His Ser His Phe His Asp Thr
            260                 265                 270

Leu Gly Gln Ser Asp Asp Leu Ile His His His His Asp Tyr His His
        275                 280                 285

Ile Leu His His His His His Gln Asn His His Pro His Ser His Ser
    290                 295                 300

Gln Arg Tyr Ser Arg Glu Glu Leu Lys Asp Ala Gly Val Ala Thr Leu
305                 310                 315                 320

Ala Trp Met Val Ile Met Gly Asp Gly Leu His Asn Phe Ser Asp Gly
                325                 330                 335

Leu Ala Ile Gly Ala Ala Phe Thr Glu Gly Leu Ser Ser Gly Leu Ser
            340                 345                 350

Thr Ser Val Ala Val Phe Cys His Glu Leu Pro His Glu Leu Gly Asp
        355                 360                 365

Phe Ala Val Leu Leu Lys Ala Gly Met Thr Val Lys Gln Ala Val Leu
    370                 375                 380

Tyr Asn Ala Leu Ser Ala Met Leu Ala Tyr Leu Gly Met Ala Thr Gly
385                 390                 395                 400

Ile Phe Ile Gly His Tyr Ala Glu Asn Val Ser Met Trp Ile Phe Ala
                405                 410                 415

Leu Thr Ala Gly Leu Phe Met Tyr Val Ala Leu Val Asp Met Val Pro
            420                 425                 430

Glu Met Leu His Asn Asp Ala Ser Asp His Gly Cys Ser Arg Trp Gly
        435                 440                 445

Tyr Phe Phe Leu Gln Asn Ala Gly Met Leu Leu Gly Phe Gly Ile Met
    450                 455                 460

Leu Leu Ile Ser Ile Phe Glu His Lys Ile Val Phe Arg Ile Asn Phe
465                 470                 475                 480
```

```
<210> SEQ ID NO 25
<211> LENGTH: 2260
<212> TYPE: DNA
<213> ORGANISM: human
<220> FEATURE:
<221> NAME/KEY: CDS
<222> LOCATION: (23)...(1489)

<400> SEQUENCE: 25

aagcccagca gccccggggc gg atg gct cca gca gca tgg cta cga agt gca      52
                         Met Ala Pro Ala Ala Trp Leu Arg Ser Ala
```

-continued

```
                                 1               5                  10

gct gct cga gca cta cta cca cct atg ctg ctg ctg ctg ctc cag ccg        100
Ala Ala Arg Ala Leu Leu Pro Pro Met Leu Leu Leu Leu Leu Gln Pro
                 15                  20                  25

ccg ccg ctg ctg gcc cgg gct ctg ccg ccg gac gtc cac cac ctc cat        148
Pro Pro Leu Leu Ala Arg Ala Leu Pro Pro Asp Val His His Leu His
             30                  35                  40

gcc gag agg agg ggg cca cag ccc tgg cat gca gcc ctg ccc agt agc        196
Ala Glu Arg Arg Gly Pro Gln Pro Trp His Ala Ala Leu Pro Ser Ser
         45                  50                  55

ccg gca cct gcc cct gcc acg cag gaa gcc ccc cgg cct gcc agc agc        244
Pro Ala Pro Ala Pro Ala Thr Gln Glu Ala Pro Arg Pro Ala Ser Ser
     60                  65                  70

ctc agg cct ccc cgc tgt ggc gtg ccc gac cca tct gat ggg ctg agt        292
Leu Arg Pro Pro Arg Cys Gly Val Pro Asp Pro Ser Asp Gly Leu Ser
 75                  80                  85                  90

gcc cgc aac cga cag aag agg ttc gtg ctt tct ggc ggg cgc tgg gag        340
Ala Arg Asn Arg Gln Lys Arg Phe Val Leu Ser Gly Gly Arg Trp Glu
                 95                 100                 105

aag acg gac ctc acc tac agg atc ctt cgg ttc cca tgg cag ttg gtg        388
Lys Thr Asp Leu Thr Tyr Arg Ile Leu Arg Phe Pro Trp Gln Leu Val
            110                 115                 120

cag gag cag gtg cgg cag acg atg gca gag gcc cta aag gta tgg agc        436
Gln Glu Gln Val Arg Gln Thr Met Ala Glu Ala Leu Lys Val Trp Ser
        125                 130                 135

gat gtg acg cca ctc acc ttt act gag gtg cac gag ggc cgt gct gac        484
Asp Val Thr Pro Leu Thr Phe Thr Glu Val His Glu Gly Arg Ala Asp
    140                 145                 150

atc atg atc gac ttc gcc agg tac tgg cat ggg gac gac ctg ccg ttt        532
Ile Met Ile Asp Phe Ala Arg Tyr Trp His Gly Asp Asp Leu Pro Phe
155                 160                 165                 170

gat ggg cct ggg ggc atc ctg gcc cat gcc ttc ttc ccc aag act cac        580
Asp Gly Pro Gly Gly Ile Leu Ala His Ala Phe Phe Pro Lys Thr His
                175                 180                 185

cga gaa ggg gat gtc cac ttc gac tat gat gag acc tgg act atc ggg        628
Arg Glu Gly Asp Val His Phe Asp Tyr Asp Glu Thr Trp Thr Ile Gly
            190                 195                 200

gat gac cag ggc aca gac ctg ctg cag gtg gca gcc cat gaa ttt ggc        676
Asp Asp Gln Gly Thr Asp Leu Leu Gln Val Ala Ala His Glu Phe Gly
        205                 210                 215

cac gtg ctg ggg ctg cag cac aca aca gca gcc aag gcc ctg atg tcc        724
His Val Leu Gly Leu Gln His Thr Thr Ala Ala Lys Ala Leu Met Ser
    220                 225                 230

gcc ttc tac acc ttt cgc tac cca ctg agt ctc agc cca gat gac tgc        772
Ala Phe Tyr Thr Phe Arg Tyr Pro Leu Ser Leu Ser Pro Asp Asp Cys
235                 240                 245                 250

agg ggc gtt caa cac cta tat ggc cag ccc tgg ccc act gtc acc tcc        820
Arg Gly Val Gln His Leu Tyr Gly Gln Pro Trp Pro Thr Val Thr Ser
                255                 260                 265

agg acc cca gcc ctg ggc ccc cag gct ggg ata gac acc aat gag att        868
Arg Thr Pro Ala Leu Gly Pro Gln Ala Gly Ile Asp Thr Asn Glu Ile
            270                 275                 280

gca ccg ctg gag cca gac gcc ccg cca gat gcc tgt gag gcc tcc ttt        916
Ala Pro Leu Glu Pro Asp Ala Pro Pro Asp Ala Cys Glu Ala Ser Phe
        285                 290                 295

gac gcg gtc tcc acc atc cga ggc gag ctc ttt ttc ttc aaa gcg ggc        964
Asp Ala Val Ser Thr Ile Arg Gly Glu Leu Phe Phe Phe Lys Ala Gly
    300                 305                 310

ttt gtg tgg cgc ctc cgt ggg ggc cag ctg cag ccc ggc tac cca gca       1012
```

-continued

```
Phe Val Trp Arg Leu Arg Gly Gly Gln Leu Gln Pro Gly Tyr Pro Ala
315                 320                 325                 330

ttg gcc tct cgc cac tgg cag gga ctg ccc agc cct gtg gac gct gcc     1060
Leu Ala Ser Arg His Trp Gln Gly Leu Pro Ser Pro Val Asp Ala Ala
                335                 340                 345

ttc gag gat gcc cag ggc cac att tgg ttc ttc caa ggt gct cag tac     1108
Phe Glu Asp Ala Gln Gly His Ile Trp Phe Phe Gln Gly Ala Gln Tyr
            350                 355                 360

tgg gtg tac gac ggt gaa aag cca gtc ctg ggc ccc gca ccc ctc acc     1156
Trp Val Tyr Asp Gly Glu Lys Pro Val Leu Gly Pro Ala Pro Leu Thr
        365                 370                 375

gag ctg ggc ctg gtg agg ttc ccg gtc cat gct gcc ttg gtc tgg ggt     1204
Glu Leu Gly Leu Val Arg Phe Pro Val His Ala Ala Leu Val Trp Gly
    380                 385                 390

ccc gag aag aac aag atc tac ttc ttc cga ggc agg gac tac tgg cgt     1252
Pro Glu Lys Asn Lys Ile Tyr Phe Phe Arg Gly Arg Asp Tyr Trp Arg
395                 400                 405                 410

ttc cac ccc agc acc cgg cgt gta gac agt ccc gtg ccc cgc agg gcc     1300
Phe His Pro Ser Thr Arg Arg Val Asp Ser Pro Val Pro Arg Arg Ala
                415                 420                 425

act gac tgg aga ggg gtg ccc tct gag atc gac gct gcc ttc cag gat     1348
Thr Asp Trp Arg Gly Val Pro Ser Glu Ile Asp Ala Ala Phe Gln Asp
            430                 435                 440

gct gat ggc tat gcc tac ttc ctg cgc ggc cgc ctc tac tgg aag ttt     1396
Ala Asp Gly Tyr Ala Tyr Phe Leu Arg Gly Arg Leu Tyr Trp Lys Phe
        445                 450                 455

gac cct gtg aag gtg aag gct ctg gaa ggc ttc ccc cgt ctc gtg ggt     1444
Asp Pro Val Lys Val Lys Ala Leu Glu Gly Phe Pro Arg Leu Val Gly
    460                 465                 470

cct gac ttc ttt ggc tgt gcc gag cct gcc aac act ttc ctc tga         1489
Pro Asp Phe Phe Gly Cys Ala Glu Pro Ala Asn Thr Phe Leu  *
475                 480                 485

ccatggcttg gatgccctca ggggtgctga cccctgccag gccacgaata tcaggctaga   1549

gacccatggc catctttgtg gctgtgggca ccaggcatgg gactgagccc atgtctcctg   1609

caggggggatg gggtggggta caaccaccat gacaactgcc gggagggcca cgcaggtcgt   1669

ggtcacctgc cagcgactgt ctcagactgg gcagggaggc tttggcatga cttaagagga   1729

agggcagtct tgggacccgc tatgcaggtc ctggcaaacc tggctgccct gtctcatccc   1789

tgtccctcag ggtagcacca tggcaggact gggggaactg gagtgtcctt gctgtatccc   1849

tgttgtgagg ttccttccag ggctggcac tgaagcaagg gtgctggggc cccatggcct   1909

tcagccctgg ctgagcaact gggctgtagg gcagggccac ttcctgaggt caggtcttgg   1969

taggtgcctg catctgtctg ccttctggct gacaatcctg gaaatctgtt ctccagaatc   2029

caggccaaaa agttcacagt caaatgggga ggggtattct tcatgcagga gaccccaggc   2089

cctggaggct gcaacatacc tcaatcctgt cccaggccgg atcctcctga agccctttc    2149

gcagcactgc tatcctccaa agccattgta aatgtgtgta cagtgtgtat aaaccttctt   2209

cttcttttt ttttttaaac tgaggattgt cattaaacac agttgttttc t             2260


<210> SEQ ID NO 26
<211> LENGTH: 488
<212> TYPE: PRT
<213> ORGANISM: human

<400> SEQUENCE: 26

Met Ala Pro Ala Ala Trp Leu Arg Ser Ala Ala Ala Arg Ala Leu Leu
 1               5                  10                  15
```

-continued

```
Pro Pro Met Leu Leu Leu Leu Leu Gln Pro Pro Pro Leu Leu Ala Arg
            20                  25                  30

Ala Leu Pro Pro Asp Val His His Leu His Ala Glu Arg Arg Gly Pro
        35                  40                  45

Gln Pro Trp His Ala Ala Leu Pro Ser Ser Pro Ala Pro Ala Pro Ala
    50                  55                  60

Thr Gln Glu Ala Pro Arg Pro Ala Ser Ser Leu Arg Pro Pro Arg Cys
65                  70                  75                  80

Gly Val Pro Asp Pro Ser Asp Gly Leu Ser Ala Arg Asn Arg Gln Lys
                85                  90                  95

Arg Phe Val Leu Ser Gly Gly Arg Trp Glu Lys Thr Asp Leu Thr Tyr
            100                 105                 110

Arg Ile Leu Arg Phe Pro Trp Gln Leu Val Gln Glu Gln Val Arg Gln
        115                 120                 125

Thr Met Ala Glu Ala Leu Lys Val Trp Ser Asp Val Thr Pro Leu Thr
    130                 135                 140

Phe Thr Glu Val His Glu Gly Arg Ala Asp Ile Met Ile Asp Phe Ala
145                 150                 155                 160

Arg Tyr Trp His Gly Asp Asp Leu Pro Phe Asp Gly Pro Gly Gly Ile
                165                 170                 175

Leu Ala His Ala Phe Phe Pro Lys Thr His Arg Glu Gly Asp Val His
            180                 185                 190

Phe Asp Tyr Asp Glu Thr Trp Thr Ile Gly Asp Asp Gln Gly Thr Asp
        195                 200                 205

Leu Leu Gln Val Ala Ala His Glu Phe Gly His Val Leu Gly Leu Gln
    210                 215                 220

His Thr Thr Ala Ala Lys Ala Leu Met Ser Ala Phe Tyr Thr Phe Arg
225                 230                 235                 240

Tyr Pro Leu Ser Leu Ser Pro Asp Asp Cys Arg Gly Val Gln His Leu
                245                 250                 255

Tyr Gly Gln Pro Trp Pro Thr Val Thr Ser Arg Thr Pro Ala Leu Gly
            260                 265                 270

Pro Gln Ala Gly Ile Asp Thr Asn Glu Ile Ala Pro Leu Glu Pro Asp
        275                 280                 285

Ala Pro Pro Asp Ala Cys Glu Ala Ser Phe Asp Ala Val Ser Thr Ile
    290                 295                 300

Arg Gly Glu Leu Phe Phe Phe Lys Ala Gly Phe Val Trp Arg Leu Arg
305                 310                 315                 320

Gly Gly Gln Leu Gln Pro Gly Tyr Pro Ala Leu Ala Ser Arg His Trp
                325                 330                 335

Gln Gly Leu Pro Ser Pro Val Asp Ala Ala Phe Glu Asp Ala Gln Gly
            340                 345                 350

His Ile Trp Phe Phe Gln Gly Ala Gln Tyr Trp Val Tyr Asp Gly Glu
        355                 360                 365

Lys Pro Val Leu Gly Pro Ala Pro Leu Thr Glu Leu Gly Leu Val Arg
    370                 375                 380

Phe Pro Val His Ala Ala Leu Val Trp Gly Pro Glu Lys Asn Lys Ile
385                 390                 395                 400

Tyr Phe Phe Arg Gly Arg Asp Tyr Trp Arg Phe His Pro Ser Thr Arg
                405                 410                 415

Arg Val Asp Ser Pro Val Pro Arg Arg Ala Thr Asp Trp Arg Gly Val
            420                 425                 430
```

-continued

```
Pro Ser Glu Ile Asp Ala Ala Phe Gln Asp Ala Asp Gly Tyr Ala Tyr
        435                 440                 445

Phe Leu Arg Gly Arg Leu Tyr Trp Lys Phe Asp Pro Val Lys Val Lys
    450                 455                 460

Ala Leu Glu Gly Phe Pro Arg Leu Val Gly Pro Asp Phe Phe Gly Cys
465                 470                 475                 480

Ala Glu Pro Ala Asn Thr Phe Leu
                485


<210> SEQ ID NO 27
<211> LENGTH: 2778
<212> TYPE: DNA
<213> ORGANISM: human
<220> FEATURE:
<221> NAME/KEY: CDS
<222> LOCATION: (272)...(1426)

<400> SEQUENCE: 27

agcggaatct ttaggatctg agcaggagaa ataccagcgg atcttcccca ctctgctccc      60

ttccattccc acccttcctt ctttaataag caggagcgaa aaagacaaat tccaaagagg     120

attgttcagt tcaagggaat gaagaattca gaataatttt ggtaaatgga ttccaatatg     180

gggaataaga ataagctgaa cagttgacct gctttgaaga aacatactgt ccatttgtct     240

aaaataatct ataacaacca aaccaatcaa a atg aat tca aca tta ttt tcc        292
                                   Met Asn Ser Thr Leu Phe Ser
                                    1               5

cag gtt gaa aat cat tca gtc cac tct aat ttc tca gag aag aat gcc       340
Gln Val Glu Asn His Ser Val His Ser Asn Phe Ser Glu Lys Asn Ala
        10                  15                  20

cag ctt ctg gct ttt gaa aat gat gat tgt cat ctg ccc ttg gcc atg       388
Gln Leu Leu Ala Phe Glu Asn Asp Asp Cys His Leu Pro Leu Ala Met
    25                  30                  35

ata ttt acc tta gct ctt gct tat gga gct gtg atc att ctt ggt gtc       436
Ile Phe Thr Leu Ala Leu Ala Tyr Gly Ala Val Ile Ile Leu Gly Val
 40                  45                  50                  55

tct gga aac ctg gcc ttg atc ata atc atc ttg aaa caa aag gag atg       484
Ser Gly Asn Leu Ala Leu Ile Ile Ile Ile Leu Lys Gln Lys Glu Met
                60                  65                  70

aga aat gtt acc aac atc ctg att gtg aac ctt tcc ttc tca gac ttg       532
Arg Asn Val Thr Asn Ile Leu Ile Val Asn Leu Ser Phe Ser Asp Leu
            75                  80                  85

ctt gtt gcc atc atg tgt ctc ccc ttt aca ttt gtc tac aca tta atg       580
Leu Val Ala Ile Met Cys Leu Pro Phe Thr Phe Val Tyr Thr Leu Met
        90                  95                  100

gac cac tgg gtc ttt ggt gag gcg atg tgt aag ttg aat cct ttt gtg       628
Asp His Trp Val Phe Gly Glu Ala Met Cys Lys Leu Asn Pro Phe Val
    105                 110                 115

caa tgt gtt tca atc act gtg tcc att ttc tct ctg gtt ctc att gct       676
Gln Cys Val Ser Ile Thr Val Ser Ile Phe Ser Leu Val Leu Ile Ala
120                 125                 130                 135

gtg gaa cga cat cag ctg ata atc aac cct cga ggg tgg aga cca aat       724
Val Glu Arg His Gln Leu Ile Ile Asn Pro Arg Gly Trp Arg Pro Asn
                140                 145                 150

aat aga cat gct tat gta ggt att gct gtg att tgg gtc ctt gct gtg       772
Asn Arg His Ala Tyr Val Gly Ile Ala Val Ile Trp Val Leu Ala Val
            155                 160                 165

gct tct tct ttg cct ttc ctg atc tac caa gta atg act gat gag ccg       820
Ala Ser Ser Leu Pro Phe Leu Ile Tyr Gln Val Met Thr Asp Glu Pro
        170                 175                 180
```

-continued

```
ttc caa aat gta aca ctt gat gcg tac aaa gac aaa tac gtg tgc ttt      868
Phe Gln Asn Val Thr Leu Asp Ala Tyr Lys Asp Lys Tyr Val Cys Phe
    185                 190                 195

gat caa ttt cca tcg gac tct cat agg ttg tct tat acc act ctc ctc      916
Asp Gln Phe Pro Ser Asp Ser His Arg Leu Ser Tyr Thr Thr Leu Leu
200                 205                 210                 215

ttg gtg ctg cag tat ttt ggt cca ctt tgt ttt ata ttt att tgc tac      964
Leu Val Leu Gln Tyr Phe Gly Pro Leu Cys Phe Ile Phe Ile Cys Tyr
                220                 225                 230

ttc aag ata tat ata cgc cta aaa agg aga aac aac atg atg gac aag     1012
Phe Lys Ile Tyr Ile Arg Leu Lys Arg Arg Asn Asn Met Met Asp Lys
            235                 240                 245

atg aga gac aat aag tac agg tcc agt gaa acc aaa aga atc aat atc     1060
Met Arg Asp Asn Lys Tyr Arg Ser Ser Glu Thr Lys Arg Ile Asn Ile
        250                 255                 260

atg ctg ctc tcc att gtg gta gca ttt gca gtc tgc tgg ctc cct ctt     1108
Met Leu Leu Ser Ile Val Val Ala Phe Ala Val Cys Trp Leu Pro Leu
    265                 270                 275

acc atc ttt aac act gtg ttt gat tgg aat cat cag atc att gct acc     1156
Thr Ile Phe Asn Thr Val Phe Asp Trp Asn His Gln Ile Ile Ala Thr
280                 285                 290                 295

tgc aac cac aat ctg tta ttc ctg ctc tgc cac ctc aca gca atg ata     1204
Cys Asn His Asn Leu Leu Phe Leu Leu Cys His Leu Thr Ala Met Ile
                300                 305                 310

tcc act tgt gtc aac ccc ata ttt tat ggg ttc ctg aac aaa aac ttc     1252
Ser Thr Cys Val Asn Pro Ile Phe Tyr Gly Phe Leu Asn Lys Asn Phe
            315                 320                 325

cag aga gac ttg cag ttc ttc ttc aac ttt tgt gat ttc cgg tct cgg     1300
Gln Arg Asp Leu Gln Phe Phe Phe Asn Phe Cys Asp Phe Arg Ser Arg
        330                 335                 340

gat gat gat tat gaa aca ata gcc atg tcc acg atg cac aca gat gtt     1348
Asp Asp Asp Tyr Glu Thr Ile Ala Met Ser Thr Met His Thr Asp Val
    345                 350                 355

tcc aaa act tct ttg aag caa gca agc cca gtc gca ttt aaa aaa atc     1396
Ser Lys Thr Ser Leu Lys Gln Ala Ser Pro Val Ala Phe Lys Lys Ile
360                 365                 370                 375

aac aac aat gat gat aat gaa aaa atc tga aactacttat agcctatggt       1446
Asn Asn Asn Asp Asp Asn Glu Lys Ile  *
                380

cccggatgac atctgtttaa aaacaagcac aacctgcaac atactttgat tacctgttct   1506

cccaaggaat ggggttgaaa tcatttgaaa atgactaaga ttttcttgtc ttgcttttta   1566

ctgcttttgt tgtagttgtc ataattacat ttggaacaaa aggtgtgggc tttggggtct   1626

tctggaaata gttttgacca gacatctttg aagtgctttt tgtgaattta tgcatataat   1686

ataaagactt ttatactgta cttattggaa tgaaatttct ttaaagtatt actattaact   1746

gacttcagaa gtacctgcca tccaatacgg tcattagatt gggtcatctt gattagatta   1806

gattagatta gattgtcaac agattgggcc atccttactt tatgataggc atcattttag   1866

tgtgttacaa tagtaacagt atgcaaaagc agcattcagg agccgaaaga tagtctgaag   1926

tcattcagaa gtggtttgag gtttctgttt tttggtggtt tttgtttgtt ttttttttt    1986

caccttaagg gaggatttaa tttgctccca actgattgtc acttaaatga aaatttaaaa   2046

atgaataaaa agacatactt ctcagctgca aatattatgg agaattgggg cacccacagg   2106

aatgaagaga gaaagcagct ccctaacttc aaaaccattt tggtacctga caacaagagc   2166

attttagagt aattaattta ataaagtaaa ttagtattgc tgcaaatagc taaattatat   2226

ttatttgaat tgatggtcaa gagattttcc attttttta cagactgttc agtgtttgtc    2286
```

-continued

```
aagctttctg gcataaatat gtactcaaaa ggcatttccg cttacaattt gtagaaacac   2346

aaaatgcgtt ttccatacag cagtgcctat atagtgactg atttttaact ttcaatgtcc   2406

atctttcaaa ggaagtaaca ccaaggtaca atgttaaagg aatattcact ttacctagca   2466

gggaaaaata cacaaaaact gcagatactt catatagccc attttaactt gtataaactg   2526

tgtgacttgt ggcgtcttat aaataatgca ctgtaaagat tactgaatag ttgtgtcatg   2586

ttaatgtgcc taatttcatg tatcttgtaa tcatgattga gcctcagaat catttggaga   2646

aactatattt taaagaacaa gacatacttc aatgtattat acagataaag tattacatgt   2706

gtttgatttt aaaagggcgg acattttatt aaaatcaata ttgtttttgc tttttcaaaa   2766

aaaaaaaaaa aa                                                        2778


<210> SEQ ID NO 28
<211> LENGTH: 384
<212> TYPE: PRT
<213> ORGANISM: human

<400> SEQUENCE: 28

Met Asn Ser Thr Leu Phe Ser Gln Val Glu Asn His Ser Val His Ser
 1               5                  10                  15

Asn Phe Ser Glu Lys Asn Ala Gln Leu Leu Ala Phe Glu Asn Asp Asp
            20                  25                  30

Cys His Leu Pro Leu Ala Met Ile Phe Thr Leu Ala Leu Ala Tyr Gly
        35                  40                  45

Ala Val Ile Ile Leu Gly Val Ser Gly Asn Leu Ala Leu Ile Ile Ile
    50                  55                  60

Ile Leu Lys Gln Lys Glu Met Arg Asn Val Thr Asn Ile Leu Ile Val
65                  70                  75                  80

Asn Leu Ser Phe Ser Asp Leu Leu Val Ala Ile Met Cys Leu Pro Phe
                85                  90                  95

Thr Phe Val Tyr Thr Leu Met Asp His Trp Val Phe Gly Glu Ala Met
            100                 105                 110

Cys Lys Leu Asn Pro Phe Val Gln Cys Val Ser Ile Thr Val Ser Ile
        115                 120                 125

Phe Ser Leu Val Leu Ile Ala Val Glu Arg His Gln Leu Ile Ile Asn
    130                 135                 140

Pro Arg Gly Trp Arg Pro Asn Asn Arg His Ala Tyr Val Gly Ile Ala
145                 150                 155                 160

Val Ile Trp Val Leu Ala Val Ala Ser Ser Leu Pro Phe Leu Ile Tyr
                165                 170                 175

Gln Val Met Thr Asp Glu Pro Phe Gln Asn Val Thr Leu Asp Ala Tyr
            180                 185                 190

Lys Asp Lys Tyr Val Cys Phe Asp Gln Phe Pro Ser Asp Ser His Arg
        195                 200                 205

Leu Ser Tyr Thr Thr Leu Leu Leu Val Leu Gln Tyr Phe Gly Pro Leu
    210                 215                 220

Cys Phe Ile Phe Ile Cys Tyr Phe Lys Ile Tyr Ile Arg Leu Lys Arg
225                 230                 235                 240

Arg Asn Asn Met Met Asp Lys Met Arg Asp Asn Lys Tyr Arg Ser Ser
                245                 250                 255

Glu Thr Lys Arg Ile Asn Ile Met Leu Leu Ser Ile Val Val Ala Phe
            260                 265                 270

Ala Val Cys Trp Leu Pro Leu Thr Ile Phe Asn Thr Val Phe Asp Trp
```

-continued

```
        275                 280                 285

Asn His Gln Ile Ile Ala Thr Cys Asn His Asn Leu Leu Phe Leu Leu
    290                 295                 300

Cys His Leu Thr Ala Met Ile Ser Thr Cys Val Asn Pro Ile Phe Tyr
305                 310                 315                 320

Gly Phe Leu Asn Lys Asn Phe Gln Arg Asp Leu Gln Phe Phe Phe Asn
                325                 330                 335

Phe Cys Asp Phe Arg Ser Arg Asp Asp Asp Tyr Glu Thr Ile Ala Met
            340                 345                 350

Ser Thr Met His Thr Asp Val Ser Lys Thr Ser Leu Lys Gln Ala Ser
        355                 360                 365

Pro Val Ala Phe Lys Lys Ile Asn Asn Asn Asp Asp Asn Glu Lys Ile
    370                 375                 380


<210> SEQ ID NO 29
<211> LENGTH: 2881
<212> TYPE: DNA
<213> ORGANISM: human
<220> FEATURE:
<221> NAME/KEY: CDS
<222> LOCATION: (241)...(1005)

<400> SEQUENCE: 29

ttttcacttt aaagagttct gtgagtcaga agtcattttg actgccctca ataaaattag      60

taatgcaatt ggtcattttc tctttacaga ttgttcagtt caagggaatg aagaattcag     120

aataattttg gtaaatggat tccaatatcg ggaataagaa taagctgaac agttgacctg     180

ctttgaagaa acatactgtc catttgtcta aaataatcta taacaaccaa accaatcaaa     240

atg aat tca aca tta ttt tcc cag gtt gaa aat cat tca gtc cac tct       288
Met Asn Ser Thr Leu Phe Ser Gln Val Glu Asn His Ser Val His Ser
 1               5                  10                  15

aat ttc tca gag aag aat gcc cag ctt ctg gct ttt gaa aat gat gat       336
Asn Phe Ser Glu Lys Asn Ala Gln Leu Leu Ala Phe Glu Asn Asp Asp
            20                  25                  30

tgt cat ctg ccc ttg gcc atg ata ttt acc tta gct ctt gct tat gga       384
Cys His Leu Pro Leu Ala Met Ile Phe Thr Leu Ala Leu Ala Tyr Gly
        35                  40                  45

gct gtg atc att ctt ggt gtc tct gga aac ctg gcc ttg atc ata atc       432
Ala Val Ile Ile Leu Gly Val Ser Gly Asn Leu Ala Leu Ile Ile Ile
    50                  55                  60

atc ttg aaa caa aag gag atg aga aat gtt acc aac atc ctg att gtg       480
Ile Leu Lys Gln Lys Glu Met Arg Asn Val Thr Asn Ile Leu Ile Val
 65                  70                  75                  80

aac ctt tcc ttc tca gac ttg ctt gtt gcc atc atg tgt ctc ccc ttt       528
Asn Leu Ser Phe Ser Asp Leu Leu Val Ala Ile Met Cys Leu Pro Phe
                85                  90                  95

aca ttt gtc tac aca tta atg gac cac tgg gtc ttt ggt gag gcg atg       576
Thr Phe Val Tyr Thr Leu Met Asp His Trp Val Phe Gly Glu Ala Met
            100                 105                 110

tgt aag ttg aat cct ttt gtg caa tgt gtt tca atc act gtg tcc att       624
Cys Lys Leu Asn Pro Phe Val Gln Cys Val Ser Ile Thr Val Ser Ile
        115                 120                 125

ttc tct ctg gtt ctc att gct gtg gaa cga cat cag ctg ata atc aac       672
Phe Ser Leu Val Leu Ile Ala Val Glu Arg His Gln Leu Ile Ile Asn
    130                 135                 140

cct cga ggg tgg aga cca aat aat aga cat gct tat gta ggt att gct       720
Pro Arg Gly Trp Arg Pro Asn Asn Arg His Ala Tyr Val Gly Ile Ala
145                 150                 155                 160
```

-continued

```
gtg att tgg gtc ctt gct gtg gct tct tct ttg cct ttc ctg atc tac      768
Val Ile Trp Val Leu Ala Val Ala Ser Ser Leu Pro Phe Leu Ile Tyr
                165                 170                 175

caa gta atg act gat gag ccg ttc caa aat gta aca ctt gat gcg tac      816
Gln Val Met Thr Asp Glu Pro Phe Gln Asn Val Thr Leu Asp Ala Tyr
            180                 185                 190

aaa gac aaa tac gtg tgc ttt gat caa ttt cca tcg gac tct cat agg      864
Lys Asp Lys Tyr Val Cys Phe Asp Gln Phe Pro Ser Asp Ser His Arg
        195                 200                 205

ttg tct tat acc act ctc ctc ttg gtg ctg cag tat ttt ggt cca ctt      912
Leu Ser Tyr Thr Thr Leu Leu Leu Val Leu Gln Tyr Phe Gly Pro Leu
    210                 215                 220

tgt ttt ata ttt att tgc tac ttc aag gta aga aaa ctt ttt ttc tat      960
Cys Phe Ile Phe Ile Cys Tyr Phe Lys Val Arg Lys Leu Phe Phe Tyr
225                 230                 235                 240

cat ttc cat ttt tac ctt ctt tac aca gaa ttc ctc atc aaa tga         1005
His Phe His Phe Tyr Leu Leu Tyr Thr Glu Phe Leu Ile Lys  *
                245                 250

gtgtttctat ttaaactttt ttcttccata gatatatata cgcctaaaaa ggagaaacaa   1065

catgatggac aagatgagag acaataagta caggtccagt gaaaccaaaa gaatcaatat   1125

catgctgctc tccattgtgg tagcatttgc agtctgctgg ctccctctta ccatctttaa   1185

cactgtgttt gattggaatc atcagatcat tgctacctgc aaccacaatc tgttattcct   1245

gctctgccac ctcacagcaa tgatatccac ttgtgtcaac cccatatttt atgggttcct   1305

gaacaaaaac ttccagagag acttgcagtt cttcttcaac ttttgtgatt tccggtctcg   1365

ggatgatgat tatgaaacaa tagccatgtc cacgatgcac acagatgttt ccaaaacttc   1425

tttgaagcaa gcaagcccag tcgcatttaa aaaaatcaac aacaatgatg ataatgaaaa   1485

aatctgaaac tacttatagc ctatggtccc ggatgacatc tgtttaaaaa caagcacaac   1545

ctgcaacata ctttgattac ctgttctccc aaggaatggg gttgaaatca tttgaaaatg   1605

actaagattt tcttgtcttg ctttttactg cttttgttgt agttgtcata attacatttg   1665

gaacaaaagg tgtgggcttt ggggtcttct ggaaatagtt ttgaccagac atctttgaag   1725

tgctttttgt gaatttatgc atataatata aagactttta tactgtactt attggaatga   1785

aatttcttta aagtattacg atgcgctgac ttcagaagta cctgccatcc aatacggtca   1845

ttagattggg tcatcttgat tagattagat tagattagat tgtcaacaga ttgggccatc   1905

cttactttat gataggcatc attttagtgt gttacaatag taacagtatg caaaagcagc   1965

attcaggagc cgaaagatag tcttgaagtc attcagaagt ggtttgaggt ttctgttttt   2025

tggtggtttt tgtttgtttt tttttttttt caccttaagg gaggctttca tttcctcccg   2085

actgattgtc acttaaatca aaatttaaaa atgaataaaa agacatactt ctcagctgca   2145

aatattatgg agaattgggc acccacagga atgaagagag aaagcagctc cccaacttca   2205

aaaccatttt ggtacctgac aacaagagca ttttagagta attaatttaa taaagtaaat   2265

tagtattgct gcaaatagct aaattatatt tatttgaatt gatggtcaag agattttcca   2325

ttttttttac agactgttca gtgtttgtca agcttctggt ctaatatgta ctcgaaagac   2385

tttccgctta caatttgtag aaacacaaat atcgttttcc atacagcagt gcctatatag   2445

tgactgattt taactttcaa tgtccatctt tcaaaggaag taacaccaag gtacaatgtt   2505

aaaggaatat tcactttacc tagcagggaa aaatacacaa aaactgcaga tacttcatat   2565

agcccatttt aacttgtata aactgtgtga cttgtggcgt cttataaata atgcactgta   2625

aagattactg aatagttgtg tcatgttaat gtgcctaatt tcatgtatct tgtaatcatg   2685
```

-continued

```
attgagcctc agaatcattt ggagaaacta tattttaaag aacaagacat acttcaatgt   2745

attatacaga taaagtatta catgtgtttg attttaaaag ggcggacatt ttattaaaat   2805

caatattgtt tttgcttttt ctgaggagtc tctttcagtt tcatttttttc tcatcccatg   2865

acttccctcc gatggt                                                   2881


<210> SEQ ID NO 30
<211> LENGTH: 254
<212> TYPE: PRT
<213> ORGANISM: human

<400> SEQUENCE: 30

Met Asn Ser Thr Leu Phe Ser Gln Val Glu Asn His Ser Val His Ser
 1               5                  10                  15

Asn Phe Ser Glu Lys Asn Ala Gln Leu Leu Ala Phe Glu Asn Asp Asp
            20                  25                  30

Cys His Leu Pro Leu Ala Met Ile Phe Thr Leu Ala Leu Ala Tyr Gly
        35                  40                  45

Ala Val Ile Ile Leu Gly Val Ser Gly Asn Leu Ala Leu Ile Ile Ile
    50                  55                  60

Ile Leu Lys Gln Lys Glu Met Arg Asn Val Thr Asn Ile Leu Ile Val
65                  70                  75                  80

Asn Leu Ser Phe Ser Asp Leu Leu Val Ala Ile Met Cys Leu Pro Phe
                85                  90                  95

Thr Phe Val Tyr Thr Leu Met Asp His Trp Val Phe Gly Glu Ala Met
            100                 105                 110

Cys Lys Leu Asn Pro Phe Val Gln Cys Val Ser Ile Thr Val Ser Ile
        115                 120                 125

Phe Ser Leu Val Leu Ile Ala Val Glu Arg His Gln Leu Ile Ile Asn
    130                 135                 140

Pro Arg Gly Trp Arg Pro Asn Asn Arg His Ala Tyr Val Gly Ile Ala
145                 150                 155                 160

Val Ile Trp Val Leu Ala Val Ala Ser Ser Leu Pro Phe Leu Ile Tyr
                165                 170                 175

Gln Val Met Thr Asp Glu Pro Phe Gln Asn Val Thr Leu Asp Ala Tyr
            180                 185                 190

Lys Asp Lys Tyr Val Cys Phe Asp Gln Phe Pro Ser Asp Ser His Arg
        195                 200                 205

Leu Ser Tyr Thr Thr Leu Leu Leu Val Leu Gln Tyr Phe Gly Pro Leu
    210                 215                 220

Cys Phe Ile Phe Ile Cys Tyr Phe Lys Val Arg Lys Leu Phe Phe Tyr
225                 230                 235                 240

His Phe His Phe Tyr Leu Leu Tyr Thr Glu Phe Leu Ile Lys
                245                 250


<210> SEQ ID NO 31
<211> LENGTH: 2492
<212> TYPE: DNA
<213> ORGANISM: human
<220> FEATURE:
<221> NAME/KEY: CDS
<222> LOCATION: (272)...(700)

<400> SEQUENCE: 31

agcggaatct ttaggatctg agcaggagaa ataccagcgg atcttcccca ctctgctccc     60

ttccattccc acccttcctt ctttaataag caggagcgaa aaagacaaat tccaaagagg    120
```

-continued

```
attgttcagt tcaagggaat gaagaattca gaataatttt ggtaaatgga ttccaatatg    180

gggaataaga ataagctgaa cagttgacct gctttgaaga aacatactgt ccatttgtct    240

aaaataatct ataacaacca aaccaatcaa a atg aat tca aca tta ttt tcc       292
                                   Met Asn Ser Thr Leu Phe Ser
                                    1               5

cag gtt gaa aat cat tca gtc cac tct aat ttc tca gag aag aat gcc      340
Gln Val Glu Asn His Ser Val His Ser Asn Phe Ser Glu Lys Asn Ala
        10                  15                  20

cag ctt ctg gct ttt gaa aat gat gat tgt cat ctg ccc ttg gcc atg      388
Gln Leu Leu Ala Phe Glu Asn Asp Asp Cys His Leu Pro Leu Ala Met
    25                  30                  35

ata ttt acc tta gct ctt gct tat gga gct gtg atc att ctt ggt gtc      436
Ile Phe Thr Leu Ala Leu Ala Tyr Gly Ala Val Ile Ile Leu Gly Val
 40                  45                  50                  55

tct gga aac ctg gcc ttg atc ata atc atc ttg aaa caa aag gag atg      484
Ser Gly Asn Leu Ala Leu Ile Ile Ile Ile Leu Lys Gln Lys Glu Met
                60                  65                  70

aga aat gtt acc aac atc ctg att gtg aac ctt tcc ttc tca gac ttg      532
Arg Asn Val Thr Asn Ile Leu Ile Val Asn Leu Ser Phe Ser Asp Leu
            75                  80                  85

ctt gtt gcc atc atg tgt ctc ccc ttt aca ttt gtc tac aca tta atg      580
Leu Val Ala Ile Met Cys Leu Pro Phe Thr Phe Val Tyr Thr Leu Met
        90                  95                  100

gac cac tgg gtc ttt ggt gag gcg atg tgt tgt ctt ata cca ctc tcc      628
Asp His Trp Val Phe Gly Glu Ala Met Cys Cys Leu Ile Pro Leu Ser
    105                 110                 115

tct tgg tgc tgc agt att ttg gtc cac ttt gtt tta tat tta ttt gct      676
Ser Trp Cys Cys Ser Ile Leu Val His Phe Val Leu Tyr Leu Phe Ala
120                 125                 130                 135

act tca aga tat ata tac gcc taa aaaggagaaa caacatgatg gacaagatga     730
Thr Ser Arg Tyr Ile Tyr Ala  *
                140

gagacaataa gtacaggtcc agtgaaacca aaagaatcaa tatcatgctg ctctccattg    790

tggtagcatt tgcagtctgc tggctccctc ttaccatctt taacactgtg tttgattgga    850

atcatcagat cattgctacc tgcaaccaca atctgttatt cctgctctgc cacctcacag    910

caatgatatc cacttgtgtc aaccccatat tttatgggtt cctgaacaaa aacttccaga    970

gagacttgca gttcttcttc aacttttgtg atttccggtc tcgggatgat gattatgaaa   1030

caatagccat gtccacgatg cacacagatg tttccaaaac ttctttgaag caagcaagcc   1090

cagtcgcatt taaaaaaatc aacaacaatg atgataatga aaaaatctga aactacttat   1150

agcctatggt cccggatgac atctgtttaa aaacaagcac aacctgcaac atactttgat   1210

tacctgttct cccaaggaat ggggttgaaa tcatttgaaa atgactaaga ttttcttgtc   1270

ttgcttttta ctgcttttgt tgtagttgtc ataattacat ttggaacaaa aggtgtgggc   1330

tttggggtct tctggaaata gttttgacca gacatctttg aagtgctttt tgtgaattta   1390

tgcatataat ataaagactt ttatactgta cttattggaa tgaaatttct ttaaagtatt   1450

actattaact gacttcagaa gtacctgcca tccaatacgg tcattagatt gggtcatctt   1510

gattagatta gattagatta gattgtcaac agattgggcc atccttactt tatgataggc   1570

atcattttag tgtgttacaa tagtaacagt atgcaaaagc agcattcagg agccgaaaga   1630

tagtctgaag tcattcagaa gtggtttgag gtttctgttt tttggtggtt tttgtttgtt   1690

tttttttttt caccttaagg gaggatttaa tttgctccca actgattgtc acttaaatga   1750
```

-continued

```
aaatttaaaa atgaataaaa agacatactt ctcagctgca aatattatgg agaattgggg   1810

cacccacagg aatgaagaga gaaagcagct ccctaacttc aaaaccattt tggtacctga   1870

caacaagagc attttagagt aattaattta ataaagtaaa ttagtattgc tgcaaatagc   1930

taaattatat ttatttgaat tgatggtcaa gagattttcc atttttttta cagactgttc   1990

agtgtttgtc aagctttctg gcataaatat gtactcaaaa ggcatttccg cttacaattt   2050

gtagaaacac aaaatgcgtt ttccatacag cagtgcctat atagtgactg atttttaact   2110

ttcaatgtcc atctttcaaa ggaagtaaca ccaaggtaca atgttaaagg aatattcact   2170

ttacctagca gggaaaaata cacaaaaact gcagatactt catatagccc attttaactt   2230

gtataaactg tgtgacttgt ggcgtcttat aaataatgca ctgtaaagat tactgaatag   2290

ttgtgtcatg ttaatgtgcc taatttcatg tatcttgtaa tcatgattga gcctcagaat   2350

catttggaga aactatattt taaagaacaa gacatacttc aatgtattat acagataaag   2410

tattacatgt gtttgatttt aaaagggcgg acattttatt aaaatcaata ttgtttttgc   2470

tttttcaaaa aaaaaaaaaa aa                                             2492


<210> SEQ ID NO 32
<211> LENGTH: 142
<212> TYPE: PRT
<213> ORGANISM: human

<400> SEQUENCE: 32

Met Asn Ser Thr Leu Phe Ser Gln Val Glu Asn His Ser Val His Ser
 1               5                  10                  15

Asn Phe Ser Glu Lys Asn Ala Gln Leu Leu Ala Phe Glu Asn Asp Asp
            20                  25                  30

Cys His Leu Pro Leu Ala Met Ile Phe Thr Leu Ala Leu Ala Tyr Gly
        35                  40                  45

Ala Val Ile Ile Leu Gly Val Ser Gly Asn Leu Ala Leu Ile Ile Ile
    50                  55                  60

Ile Leu Lys Gln Lys Glu Met Arg Asn Val Thr Asn Ile Leu Ile Val
65                  70                  75                  80

Asn Leu Ser Phe Ser Asp Leu Leu Val Ala Ile Met Cys Leu Pro Phe
                85                  90                  95

Thr Phe Val Tyr Thr Leu Met Asp His Trp Val Phe Gly Glu Ala Met
            100                 105                 110

Cys Cys Leu Ile Pro Leu Ser Ser Trp Cys Cys Ser Ile Leu Val His
        115                 120                 125

Phe Val Leu Tyr Leu Phe Ala Thr Ser Arg Tyr Ile Tyr Ala
    130                 135                 140


<210> SEQ ID NO 33
<211> LENGTH: 4458
<212> TYPE: DNA
<213> ORGANISM: human
<220> FEATURE:
<221> NAME/KEY: CDS
<222> LOCATION: (100)...(4125)

<400> SEQUENCE: 33

ctagtctata ccagcaacga ctcctacatc gtccactctg gggatcttag aaagatccat     60

aaagctgcct cccggggaca agtccggaag ctggagaag atg aca aag agg aag       114
                                           Met Thr Lys Arg Lys
                                            1               5

aag acc atc aac ctt aat ata caa gac gcc cag aag agg act gct cta      162
```

-continued

```
Lys Thr Ile Asn Leu Asn Ile Gln Asp Ala Gln Lys Arg Thr Ala Leu
                10                  15                  20

cac tgg gcc tgt gtc aat ggc cat gag gaa gta gta aca ttt ctg gta      210
His Trp Ala Cys Val Asn Gly His Glu Glu Val Val Thr Phe Leu Val
            25                  30                  35

gac aga aag tgc cag ctt gac gtc ctt gat ggc gaa cac agg aca cct      258
Asp Arg Lys Cys Gln Leu Asp Val Leu Asp Gly Glu His Arg Thr Pro
        40                  45                  50

ctg atg aag gct cta caa tgc cat cag gag gct tgt gca aat att ctg      306
Leu Met Lys Ala Leu Gln Cys His Gln Glu Ala Cys Ala Asn Ile Leu
    55                  60                  65

ata gat tct ggt gcc gat ata aat ctc gta gat gtg tat ggc aac atg      354
Ile Asp Ser Gly Ala Asp Ile Asn Leu Val Asp Val Tyr Gly Asn Met
 70                  75                  80                  85

gct ctc cat tat gct gtt tat agt gag att ttg tca gtg gtg gca aaa      402
Ala Leu His Tyr Ala Val Tyr Ser Glu Ile Leu Ser Val Val Ala Lys
                90                  95                  100

ctg ctg tcc cat ggt gca gtc atc gaa gtg cac aac aag gct agc ctc      450
Leu Leu Ser His Gly Ala Val Ile Glu Val His Asn Lys Ala Ser Leu
            105                 110                 115

aca cca ctt tta cta tcc ata acg aaa aga agt gag caa att gtg gaa      498
Thr Pro Leu Leu Leu Ser Ile Thr Lys Arg Ser Glu Gln Ile Val Glu
        120                 125                 130

ttt ttg ctg ata aaa aat gca aat gcg aat gca gtt aat aag tat aaa      546
Phe Leu Leu Ile Lys Asn Ala Asn Ala Asn Ala Val Asn Lys Tyr Lys
    135                 140                 145

tgc aca gcc ctc atg ctt gct gta tgt cat gga tca tca gag ata gtt      594
Cys Thr Ala Leu Met Leu Ala Val Cys His Gly Ser Ser Glu Ile Val
150                 155                 160                 165

ggc atg ctt ctt cag caa aat gtt gac gtc ttt gct gca gat ata tgt      642
Gly Met Leu Leu Gln Gln Asn Val Asp Val Phe Ala Ala Asp Ile Cys
                170                 175                 180

gga gta act gca gaa cat tat gct gtt act tgt gga ttt cat cac att      690
Gly Val Thr Ala Glu His Tyr Ala Val Thr Cys Gly Phe His His Ile
            185                 190                 195

cat gaa caa att atg gaa tat ata cga aaa tta tct aaa aat cat caa      738
His Glu Gln Ile Met Glu Tyr Ile Arg Lys Leu Ser Lys Asn His Gln
        200                 205                 210

aat acc aat cca gaa gga aca tct gca gga aca cct gat gag gct gca      786
Asn Thr Asn Pro Glu Gly Thr Ser Ala Gly Thr Pro Asp Glu Ala Ala
    215                 220                 225

ccc ttg gcg gaa aga aca cct gac aca gct gaa agc ttg gtg gaa aaa      834
Pro Leu Ala Glu Arg Thr Pro Asp Thr Ala Glu Ser Leu Val Glu Lys
230                 235                 240                 245

aca cct gat gag gct gca ccc ttg gtg gaa aga aca cct gac acg gct      882
Thr Pro Asp Glu Ala Ala Pro Leu Val Glu Arg Thr Pro Asp Thr Ala
                250                 255                 260

gaa agc ttg gtg gaa aaa aca cct gat gag gct gca tcc ttg gtg gag      930
Glu Ser Leu Val Glu Lys Thr Pro Asp Glu Ala Ala Ser Leu Val Glu
            265                 270                 275

gga aca tct gac aaa att caa tgt ttg gag aaa gcg aca tct gga aag      978
Gly Thr Ser Asp Lys Ile Gln Cys Leu Glu Lys Ala Thr Ser Gly Lys
        280                 285                 290

ttc gaa cag tca gca gaa gaa aca cct agg gaa att acg agt cct gca     1026
Phe Glu Gln Ser Ala Glu Glu Thr Pro Arg Glu Ile Thr Ser Pro Ala
    295                 300                 305

aaa gaa aca tct gag aaa ttt acg tgg cca gca aaa gga aga cct agg     1074
Lys Glu Thr Ser Glu Lys Phe Thr Trp Pro Ala Lys Gly Arg Pro Arg
310                 315                 320                 325
```

-continued

```
aag atc gca tgg gag aaa aaa gaa gac aca cct agg gaa att atg agt      1122
Lys Ile Ala Trp Glu Lys Lys Glu Asp Thr Pro Arg Glu Ile Met Ser
                330                 335                 340

ccc gca aaa gaa aca tct gag aaa ttt acg tgg gca gca aaa gga aga      1170
Pro Ala Lys Glu Thr Ser Glu Lys Phe Thr Trp Ala Ala Lys Gly Arg
            345                 350                 355

cct agg aag atc gca tgg gag aaa aaa gaa aca cct gta aag act gga      1218
Pro Arg Lys Ile Ala Trp Glu Lys Lys Glu Thr Pro Val Lys Thr Gly
        360                 365                 370

tgc gtg gca aga gta aca tct aat aaa act aaa gtt ttg gaa aaa gga      1266
Cys Val Ala Arg Val Thr Ser Asn Lys Thr Lys Val Leu Glu Lys Gly
    375                 380                 385

aga tct aag atg att gca tgt cct aca aaa gaa tca tct aca aaa gca      1314
Arg Ser Lys Met Ile Ala Cys Pro Thr Lys Glu Ser Ser Thr Lys Ala
390                 395                 400                 405

agt gcc aat gat cag agg ttc cca tca gaa tcc aaa caa gag gaa gat      1362
Ser Ala Asn Asp Gln Arg Phe Pro Ser Glu Ser Lys Gln Glu Glu Asp
                410                 415                 420

gaa gaa tat tct tgt gat tct cgg agt ctc ttt gag agt tct gca aag      1410
Glu Glu Tyr Ser Cys Asp Ser Arg Ser Leu Phe Glu Ser Ser Ala Lys
            425                 430                 435

att caa gtg tgt ata cct gag tct ata tat caa aaa gta atg gag ata      1458
Ile Gln Val Cys Ile Pro Glu Ser Ile Tyr Gln Lys Val Met Glu Ile
        440                 445                 450

aat aga gaa gta gaa gag cct cct aag aag cca tct gcc ttc aag cct      1506
Asn Arg Glu Val Glu Glu Pro Pro Lys Lys Pro Ser Ala Phe Lys Pro
    455                 460                 465

gcc att gaa atg caa aac tct gtt cca aat aaa gcc ttt gaa ttg aag      1554
Ala Ile Glu Met Gln Asn Ser Val Pro Asn Lys Ala Phe Glu Leu Lys
470                 475                 480                 485

aat gaa caa aca ttg aga gca gat ccg atg ttc cca cca gaa tcc aaa      1602
Asn Glu Gln Thr Leu Arg Ala Asp Pro Met Phe Pro Pro Glu Ser Lys
                490                 495                 500

caa aag gac tat gaa gaa aat tct tgg gat tct gag agt ctc tgt gag      1650
Gln Lys Asp Tyr Glu Glu Asn Ser Trp Asp Ser Glu Ser Leu Cys Glu
            505                 510                 515

act gtt tca cag aag gat gtg tgt tta ccc aag gct aca cat caa aaa      1698
Thr Val Ser Gln Lys Asp Val Cys Leu Pro Lys Ala Thr His Gln Lys
        520                 525                 530

gaa ata gat aaa ata aat gga aaa tta gaa gag tct cct aat aaa gat      1746
Glu Ile Asp Lys Ile Asn Gly Lys Leu Glu Glu Ser Pro Asn Lys Asp
    535                 540                 545

ggt ctt ctg aag gct acc tgc gga atg aaa gtt tct att cca act aaa      1794
Gly Leu Leu Lys Ala Thr Cys Gly Met Lys Val Ser Ile Pro Thr Lys
550                 555                 560                 565

gcc tta gaa ttg aag gac atg caa act ttc aaa gcg gag cct ccg ggg      1842
Ala Leu Glu Leu Lys Asp Met Gln Thr Phe Lys Ala Glu Pro Pro Gly
                570                 575                 580

aag cca tct gcc ttc gag cct gcc act gaa atg caa aag tct gtc cca      1890
Lys Pro Ser Ala Phe Glu Pro Ala Thr Glu Met Gln Lys Ser Val Pro
            585                 590                 595

aat aaa gcc ttg gaa ttg aaa aat gaa caa aca tgg aga gca gat gag      1938
Asn Lys Ala Leu Glu Leu Lys Asn Glu Gln Thr Trp Arg Ala Asp Glu
        600                 605                 610

ata ctc cca tca gaa tcc aaa caa aag gac tat gaa gaa aat tct tgg      1986
Ile Leu Pro Ser Glu Ser Lys Gln Lys Asp Tyr Glu Glu Asn Ser Trp
    615                 620                 625

gat act gag agt ctc tgt gag act gtt tca cag aag gat gtg tgt tta      2034
Asp Thr Glu Ser Leu Cys Glu Thr Val Ser Gln Lys Asp Val Cys Leu
630                 635                 640                 645
```

-continued

```
ccc aag gct gcg cat caa aaa gaa ata gat aaa ata aat gga aaa tta     2082
Pro Lys Ala Ala His Gln Lys Glu Ile Asp Lys Ile Asn Gly Lys Leu
                650                 655                 660

gaa ggg tct cct gtt aaa gat ggt ctt ctg aag gct aac tgc gga atg     2130
Glu Gly Ser Pro Val Lys Asp Gly Leu Leu Lys Ala Asn Cys Gly Met
            665                 670                 675

aaa gtt tct att cca act aaa gcc tta gaa ttg atg gac atg caa act     2178
Lys Val Ser Ile Pro Thr Lys Ala Leu Glu Leu Met Asp Met Gln Thr
        680                 685                 690

ttc aaa gca gag cct ccc gag aag cca tct gcc ttc gag cct gcc att     2226
Phe Lys Ala Glu Pro Pro Glu Lys Pro Ser Ala Phe Glu Pro Ala Ile
    695                 700                 705

gaa atg caa aag tct gtt cca aat aaa gcc ttg gaa ttg aag aat gaa     2274
Glu Met Gln Lys Ser Val Pro Asn Lys Ala Leu Glu Leu Lys Asn Glu
710                 715                 720                 725

caa aca ttg aga gca gat gag ata ctc cca tca gaa tcc aaa caa aag     2322
Gln Thr Leu Arg Ala Asp Glu Ile Leu Pro Ser Glu Ser Lys Gln Lys
                730                 735                 740

gac tat gaa gaa agt tct tgg gat tct gag agt ctc tgt gag act gtt     2370
Asp Tyr Glu Glu Ser Ser Trp Asp Ser Glu Ser Leu Cys Glu Thr Val
            745                 750                 755

tca cag aag gat gtg tgt tta ccc aag gct aca cat caa aaa gaa ata     2418
Ser Gln Lys Asp Val Cys Leu Pro Lys Ala Thr His Gln Lys Glu Ile
        760                 765                 770

gat aaa ata aat gga aaa tta gaa gag tct cct gat aat gat ggt ttt     2466
Asp Lys Ile Asn Gly Lys Leu Glu Glu Ser Pro Asp Asn Asp Gly Phe
    775                 780                 785

ctg aag gct ccc tgc aga atg aaa gtt tct att cca act aaa gcc tta     2514
Leu Lys Ala Pro Cys Arg Met Lys Val Ser Ile Pro Thr Lys Ala Leu
790                 795                 800                 805

gaa ttg atg gac atg caa act ttc aaa gca gag cct ccc gag aag cca     2562
Glu Leu Met Asp Met Gln Thr Phe Lys Ala Glu Pro Pro Glu Lys Pro
                810                 815                 820

tct gcc ttc gag cct gcc att gaa atg caa aag tct gtt cca aat aaa     2610
Ser Ala Phe Glu Pro Ala Ile Glu Met Gln Lys Ser Val Pro Asn Lys
            825                 830                 835

gcc ttg gaa ttg aag aat gaa caa aca ttg aga gca gat cag atg ttc     2658
Ala Leu Glu Leu Lys Asn Glu Gln Thr Leu Arg Ala Asp Gln Met Phe
        840                 845                 850

cct tca gaa tca aaa caa aag aag gtt gaa gaa aat tct tgg gat tct     2706
Pro Ser Glu Ser Lys Gln Lys Lys Val Glu Glu Asn Ser Trp Asp Ser
    855                 860                 865

gag agt ctc cgt gag act gtt tca cag aag gat gtg tgt gta ccc aag     2754
Glu Ser Leu Arg Glu Thr Val Ser Gln Lys Asp Val Cys Val Pro Lys
870                 875                 880                 885

gct aca cat caa aaa gaa atg gat aaa ata agt gga aaa tta gaa gat     2802
Ala Thr His Gln Lys Glu Met Asp Lys Ile Ser Gly Lys Leu Glu Asp
                890                 895                 900

tca act agc cta tca aaa atc ttg gat aca gtt cat tct tgt gaa aga     2850
Ser Thr Ser Leu Ser Lys Ile Leu Asp Thr Val His Ser Cys Glu Arg
            905                 910                 915

gca agg gaa ctt caa aaa gat cac tgt gaa caa cgt aca gga aaa atg     2898
Ala Arg Glu Leu Gln Lys Asp His Cys Glu Gln Arg Thr Gly Lys Met
        920                 925                 930

gaa caa atg aaa aag aag ttt tgt gta ctg aaa aag aaa ctg tca gaa     2946
Glu Gln Met Lys Lys Lys Phe Cys Val Leu Lys Lys Lys Leu Ser Glu
    935                 940                 945

gca aaa gaa ata aaa tca cag tta gag aac caa aaa gtt aaa tgg gaa     2994
Ala Lys Glu Ile Lys Ser Gln Leu Glu Asn Gln Lys Val Lys Trp Glu
```

-continued

```
950                 955                 960                 965

caa gag ctc tgc agt gtg aga ttg act tta aac caa gaa gaa gag aag     3042
Gln Glu Leu Cys Ser Val Arg Leu Thr Leu Asn Gln Glu Glu Glu Lys
                970                 975                 980

aga aga aat gcc gat ata tta aat gaa aaa att agg gaa gaa tta gga     3090
Arg Arg Asn Ala Asp Ile Leu Asn Glu Lys Ile Arg Glu Glu Leu Gly
            985                 990                 995

aga atc gaa gag cag cat agg aaa gag tta gaa gtg aaa caa caa ctt     3138
Arg Ile Glu Glu Gln His Arg Lys Glu Leu Glu Val Lys Gln Gln Leu
        1000                1005                1010

gaa cag gct ctc aga ata caa gat ata gaa ttg aag agt gta gaa agt     3186
Glu Gln Ala Leu Arg Ile Gln Asp Ile Glu Leu Lys Ser Val Glu Ser
    1015                1020                1025

aat ttg aat cag gtt tct cac act cat gaa aat gaa aat tat ctc tta     3234
Asn Leu Asn Gln Val Ser His Thr His Glu Asn Glu Asn Tyr Leu Leu
1030                1035                1040                1045

cat gaa aat tgc atg ttg aaa aag gaa att gcc atg cta aaa ctg gaa     3282
His Glu Asn Cys Met Leu Lys Lys Glu Ile Ala Met Leu Lys Leu Glu
                1050                1055                1060

ata gcc aca ctg aaa cac caa tac cag gaa aag gaa aat aaa tac ttt     3330
Ile Ala Thr Leu Lys His Gln Tyr Gln Glu Lys Glu Asn Lys Tyr Phe
            1065                1070                1075

gag gac att aag att tta aaa gaa aag aat gct gaa ctt cag atg acc     3378
Glu Asp Ile Lys Ile Leu Lys Glu Lys Asn Ala Glu Leu Gln Met Thr
        1080                1085                1090

cta aaa ctg aaa gag gaa tca tta act aaa agg gca tct caa tat agt     3426
Leu Lys Leu Lys Glu Glu Ser Leu Thr Lys Arg Ala Ser Gln Tyr Ser
    1095                1100                1105

ggg cag ctt aaa gtt ctg ata gct gag aac aca atg ctc act tct aaa     3474
Gly Gln Leu Lys Val Leu Ile Ala Glu Asn Thr Met Leu Thr Ser Lys
1110                1115                1120                1125

ttg aag gaa aaa caa gac aaa gaa ata cta gag gca gaa att gaa tca     3522
Leu Lys Glu Lys Gln Asp Lys Glu Ile Leu Glu Ala Glu Ile Glu Ser
                1130                1135                1140

cac cat cct aga ctg gct tct gct gta caa gac cat gat caa att gtg     3570
His His Pro Arg Leu Ala Ser Ala Val Gln Asp His Asp Gln Ile Val
            1145                1150                1155

aca tca aga aaa agt caa gaa cct gct ttc cac att gca gga gat gct     3618
Thr Ser Arg Lys Ser Gln Glu Pro Ala Phe His Ile Ala Gly Asp Ala
        1160                1165                1170

tgt ttg caa aga aaa atg aat gtt gat gtg agt agt acg ata tat aac     3666
Cys Leu Gln Arg Lys Met Asn Val Asp Val Ser Ser Thr Ile Tyr Asn
    1175                1180                1185

aat gag gtg ctc cat caa cca ctt tct gaa gct caa agg aaa tcc aaa     3714
Asn Glu Val Leu His Gln Pro Leu Ser Glu Ala Gln Arg Lys Ser Lys
1190                1195                1200                1205

agc cta aaa att aat ctc aat tat gca gga gat gct cta aga gaa aat     3762
Ser Leu Lys Ile Asn Leu Asn Tyr Ala Gly Asp Ala Leu Arg Glu Asn
                1210                1215                1220

aca ttg gtt tca gaa cat gca caa aga gac caa cgt gaa aca cag tgt     3810
Thr Leu Val Ser Glu His Ala Gln Arg Asp Gln Arg Glu Thr Gln Cys
            1225                1230                1235

caa atg aag gaa gct gaa cac atg tat caa aac gaa caa gat aat gtg     3858
Gln Met Lys Glu Ala Glu His Met Tyr Gln Asn Glu Gln Asp Asn Val
        1240                1245                1250

aac aaa cac act gaa cag cag gag tct cta gat cag aaa tta ttt caa     3906
Asn Lys His Thr Glu Gln Gln Glu Ser Leu Asp Gln Lys Leu Phe Gln
    1255                1260                1265

cta caa agc aaa aat atg tgg ctt caa cag caa tta gtt cat gca cat     3954
```

-continued

```
Leu Gln Ser Lys Asn Met Trp Leu Gln Gln Gln Leu Val His Ala His
1270                1275                1280                1285

aag aaa gct gac aac aaa agc aag ata aca att gat att cat ttt ctt     4002
Lys Lys Ala Asp Asn Lys Ser Lys Ile Thr Ile Asp Ile His Phe Leu
                1290                1295                1300

gag agg aaa atg caa cat cat ctc cta aaa gag aaa aat gag gag ata     4050
Glu Arg Lys Met Gln His His Leu Leu Lys Glu Lys Asn Glu Glu Ile
            1305                1310                1315

ttt aat tac aat aac cat tta aaa aac cgt ata tat caa tat gaa aaa     4098
Phe Asn Tyr Asn Asn His Leu Lys Asn Arg Ile Tyr Gln Tyr Glu Lys
        1320                1325                1330

gag aaa gca gaa aca gaa aac tca tga gagacaagca gtaagaaact           4145
Glu Lys Ala Glu Thr Glu Asn Ser  *
    1335                1340

tcttttggag aaacaacaga ccagatcttt actcacaact catgctagga ggccagtcct   4205

agcatcacct tatgttgaaa atcttaccaa tagtctgtgt caacagaata cttattttag   4265

aagaaaaatt catgatttct tcctgaagcc tacagacata aaataacagt gtgaagaatt   4325

acttgttcac gaattgcata aagctgcaca ggattcccat ctaccctgat gatgcagcag   4385

acatcattca atccaaccag aatctcgctc tgcactccag cctaggtgac agagtgagac   4445

tccacctcgg aaa                                                      4458


<210> SEQ ID NO 34
<211> LENGTH: 1341
<212> TYPE: PRT
<213> ORGANISM: human

<400> SEQUENCE: 34

Met Thr Lys Arg Lys Lys Thr Ile Asn Leu Asn Ile Gln Asp Ala Gln
 1               5                  10                  15

Lys Arg Thr Ala Leu His Trp Ala Cys Val Asn Gly His Glu Glu Val
            20                  25                  30

Val Thr Phe Leu Val Asp Arg Lys Cys Gln Leu Asp Val Leu Asp Gly
        35                  40                  45

Glu His Arg Thr Pro Leu Met Lys Ala Leu Gln Cys His Gln Glu Ala
    50                  55                  60

Cys Ala Asn Ile Leu Ile Asp Ser Gly Ala Asp Ile Asn Leu Val Asp
65                  70                  75                  80

Val Tyr Gly Asn Met Ala Leu His Tyr Ala Val Tyr Ser Glu Ile Leu
                85                  90                  95

Ser Val Val Ala Lys Leu Leu Ser His Gly Ala Val Ile Glu Val His
            100                 105                 110

Asn Lys Ala Ser Leu Thr Pro Leu Leu Leu Ser Ile Thr Lys Arg Ser
        115                 120                 125

Glu Gln Ile Val Glu Phe Leu Leu Ile Lys Asn Ala Asn Ala Asn Ala
    130                 135                 140

Val Asn Lys Tyr Lys Cys Thr Ala Leu Met Leu Ala Val Cys His Gly
145                 150                 155                 160

Ser Ser Glu Ile Val Gly Met Leu Leu Gln Gln Asn Val Asp Val Phe
                165                 170                 175

Ala Ala Asp Ile Cys Gly Val Thr Ala Glu His Tyr Ala Val Thr Cys
            180                 185                 190

Gly Phe His His Ile His Glu Gln Ile Met Glu Tyr Ile Arg Lys Leu
        195                 200                 205

Ser Lys Asn His Gln Asn Thr Asn Pro Glu Gly Thr Ser Ala Gly Thr
```

-continued

```
    210                 215                 220

Pro Asp Glu Ala Ala Pro Leu Ala Glu Arg Thr Pro Asp Thr Ala Glu
225                 230                 235                 240

Ser Leu Val Glu Lys Thr Pro Asp Glu Ala Ala Pro Leu Val Glu Arg
                245                 250                 255

Thr Pro Asp Thr Ala Glu Ser Leu Val Glu Lys Thr Pro Asp Glu Ala
            260                 265                 270

Ala Ser Leu Val Glu Gly Thr Ser Asp Lys Ile Gln Cys Leu Glu Lys
        275                 280                 285

Ala Thr Ser Gly Lys Phe Glu Gln Ser Ala Glu Glu Thr Pro Arg Glu
    290                 295                 300

Ile Thr Ser Pro Ala Lys Glu Thr Ser Glu Lys Phe Thr Trp Pro Ala
305                 310                 315                 320

Lys Gly Arg Pro Arg Lys Ile Ala Trp Glu Lys Lys Glu Asp Thr Pro
                325                 330                 335

Arg Glu Ile Met Ser Pro Ala Lys Glu Thr Ser Glu Lys Phe Thr Trp
            340                 345                 350

Ala Ala Lys Gly Arg Pro Arg Lys Ile Ala Trp Glu Lys Lys Glu Thr
        355                 360                 365

Pro Val Lys Thr Gly Cys Val Ala Arg Val Thr Ser Asn Lys Thr Lys
    370                 375                 380

Val Leu Glu Lys Gly Arg Ser Lys Met Ile Ala Cys Pro Thr Lys Glu
385                 390                 395                 400

Ser Ser Thr Lys Ala Ser Ala Asn Asp Gln Arg Phe Pro Ser Glu Ser
                405                 410                 415

Lys Gln Glu Glu Asp Glu Glu Tyr Ser Cys Asp Ser Arg Ser Leu Phe
            420                 425                 430

Glu Ser Ser Ala Lys Ile Gln Val Cys Ile Pro Glu Ser Ile Tyr Gln
        435                 440                 445

Lys Val Met Glu Ile Asn Arg Glu Val Glu Glu Pro Pro Lys Lys Pro
    450                 455                 460

Ser Ala Phe Lys Pro Ala Ile Glu Met Gln Asn Ser Val Pro Asn Lys
465                 470                 475                 480

Ala Phe Glu Leu Lys Asn Glu Gln Thr Leu Arg Ala Asp Pro Met Phe
                485                 490                 495

Pro Pro Glu Ser Lys Gln Lys Asp Tyr Glu Glu Asn Ser Trp Asp Ser
            500                 505                 510

Glu Ser Leu Cys Glu Thr Val Ser Gln Lys Asp Val Cys Leu Pro Lys
        515                 520                 525

Ala Thr His Gln Lys Glu Ile Asp Lys Ile Asn Gly Lys Leu Glu Glu
    530                 535                 540

Ser Pro Asn Lys Asp Gly Leu Leu Lys Ala Thr Cys Gly Met Lys Val
545                 550                 555                 560

Ser Ile Pro Thr Lys Ala Leu Glu Leu Lys Asp Met Gln Thr Phe Lys
                565                 570                 575

Ala Glu Pro Pro Gly Lys Pro Ser Ala Phe Glu Pro Ala Thr Glu Met
            580                 585                 590

Gln Lys Ser Val Pro Asn Lys Ala Leu Glu Leu Lys Asn Glu Gln Thr
        595                 600                 605

Trp Arg Ala Asp Glu Ile Leu Pro Ser Glu Ser Lys Gln Lys Asp Tyr
    610                 615                 620

Glu Glu Asn Ser Trp Asp Thr Glu Ser Leu Cys Glu Thr Val Ser Gln
625                 630                 635                 640
```

-continued

```
Lys Asp Val Cys Leu Pro Lys Ala Ala His Gln Lys Glu Ile Asp Lys
                645                 650                 655

Ile Asn Gly Lys Leu Glu Gly Ser Pro Val Lys Asp Gly Leu Leu Lys
            660                 665                 670

Ala Asn Cys Gly Met Lys Val Ser Ile Pro Thr Lys Ala Leu Glu Leu
        675                 680                 685

Met Asp Met Gln Thr Phe Lys Ala Glu Pro Pro Glu Lys Pro Ser Ala
    690                 695                 700

Phe Glu Pro Ala Ile Glu Met Gln Lys Ser Val Pro Asn Lys Ala Leu
705                 710                 715                 720

Glu Leu Lys Asn Glu Gln Thr Leu Arg Ala Asp Glu Ile Leu Pro Ser
                725                 730                 735

Glu Ser Lys Gln Lys Asp Tyr Glu Glu Ser Ser Trp Asp Ser Glu Ser
            740                 745                 750

Leu Cys Glu Thr Val Ser Gln Lys Asp Val Cys Leu Pro Lys Ala Thr
        755                 760                 765

His Gln Lys Glu Ile Asp Lys Ile Asn Gly Lys Leu Glu Glu Ser Pro
    770                 775                 780

Asp Asn Asp Gly Phe Leu Lys Ala Pro Cys Arg Met Lys Val Ser Ile
785                 790                 795                 800

Pro Thr Lys Ala Leu Glu Leu Met Asp Met Gln Thr Phe Lys Ala Glu
                805                 810                 815

Pro Pro Glu Lys Pro Ser Ala Phe Glu Pro Ala Ile Glu Met Gln Lys
            820                 825                 830

Ser Val Pro Asn Lys Ala Leu Glu Leu Lys Asn Glu Gln Thr Leu Arg
        835                 840                 845

Ala Asp Gln Met Phe Pro Ser Glu Ser Lys Gln Lys Lys Val Glu Glu
    850                 855                 860

Asn Ser Trp Asp Ser Glu Ser Leu Arg Glu Thr Val Ser Gln Lys Asp
865                 870                 875                 880

Val Cys Val Pro Lys Ala Thr His Gln Lys Glu Met Asp Lys Ile Ser
                885                 890                 895

Gly Lys Leu Glu Asp Ser Thr Ser Leu Ser Lys Ile Leu Asp Thr Val
            900                 905                 910

His Ser Cys Glu Arg Ala Arg Glu Leu Gln Lys Asp His Cys Glu Gln
        915                 920                 925

Arg Thr Gly Lys Met Glu Gln Met Lys Lys Lys Phe Cys Val Leu Lys
    930                 935                 940

Lys Lys Leu Ser Glu Ala Lys Glu Ile Lys Ser Gln Leu Glu Asn Gln
945                 950                 955                 960

Lys Val Lys Trp Glu Gln Glu Leu Cys Ser Val Arg Leu Thr Leu Asn
                965                 970                 975

Gln Glu Glu Glu Lys Arg Arg Asn Ala Asp Ile Leu Asn Glu Lys Ile
            980                 985                 990

Arg Glu Glu Leu Gly Arg Ile Glu Glu Gln His Arg Lys Glu Leu Glu
        995                 1000                1005

Val Lys Gln Gln Leu Glu Gln Ala Leu Arg Ile Gln Asp Ile Glu Leu
    1010                1015                1020

Lys Ser Val Glu Ser Asn Leu Asn Gln Val Ser His Thr His Glu Asn
1025                1030                1035                1040

Glu Asn Tyr Leu Leu His Glu Asn Cys Met Leu Lys Lys Glu Ile Ala
                1045                1050                1055
```

-continued

```
Met Leu Lys Leu Glu Ile Ala Thr Leu Lys His Gln Tyr Gln Glu Lys
            1060                1065                1070

Glu Asn Lys Tyr Phe Glu Asp Ile Lys Ile Leu Lys Glu Lys Asn Ala
        1075                1080                1085

Glu Leu Gln Met Thr Leu Lys Leu Lys Glu Glu Ser Leu Thr Lys Arg
    1090                1095                1100

Ala Ser Gln Tyr Ser Gly Gln Leu Lys Val Leu Ile Ala Glu Asn Thr
1105                1110                1115                1120

Met Leu Thr Ser Lys Leu Lys Glu Lys Gln Asp Lys Glu Ile Leu Glu
                1125                1130                1135

Ala Glu Ile Glu Ser His His Pro Arg Leu Ala Ser Ala Val Gln Asp
            1140                1145                1150

His Asp Gln Ile Val Thr Ser Arg Lys Ser Gln Glu Pro Ala Phe His
        1155                1160                1165

Ile Ala Gly Asp Ala Cys Leu Gln Arg Lys Met Asn Val Asp Val Ser
    1170                1175                1180

Ser Thr Ile Tyr Asn Asn Glu Val Leu His Gln Pro Leu Ser Glu Ala
1185                1190                1195                1200

Gln Arg Lys Ser Lys Ser Leu Lys Ile Asn Leu Asn Tyr Ala Gly Asp
                1205                1210                1215

Ala Leu Arg Glu Asn Thr Leu Val Ser Glu His Ala Gln Arg Asp Gln
            1220                1225                1230

Arg Glu Thr Gln Cys Gln Met Lys Glu Ala Glu His Met Tyr Gln Asn
        1235                1240                1245

Glu Gln Asp Asn Val Asn Lys His Thr Glu Gln Gln Glu Ser Leu Asp
    1250                1255                1260

Gln Lys Leu Phe Gln Leu Gln Ser Lys Asn Met Trp Leu Gln Gln Gln
1265                1270                1275                1280

Leu Val His Ala His Lys Lys Ala Asp Asn Lys Ser Lys Ile Thr Ile
                1285                1290                1295

Asp Ile His Phe Leu Glu Arg Lys Met Gln His His Leu Leu Lys Glu
            1300                1305                1310

Lys Asn Glu Glu Ile Phe Asn Tyr Asn Asn His Leu Lys Asn Arg Ile
        1315                1320                1325

Tyr Gln Tyr Glu Lys Glu Lys Ala Glu Thr Glu Asn Ser
    1330                1335                1340


<210> SEQ ID NO 35
<211> LENGTH: 3213
<212> TYPE: DNA
<213> ORGANISM: human
<220> FEATURE:
<221> NAME/KEY: CDS
<222> LOCATION: (12)...(2522)

<400> SEQUENCE: 35

agagactcaa g atg att ccc ttt tta ccc atg ttt tct cta cta ttg ctg      50
             Met Ile Pro Phe Leu Pro Met Phe Ser Leu Leu Leu Leu
               1               5                  10

ctt att gtt aac cct ata aac gcc aac aat cat tat gac aag atc ttg       98
Leu Ile Val Asn Pro Ile Asn Ala Asn Asn His Tyr Asp Lys Ile Leu
     15                  20                  25

gct cat agt cgt atc agg ggt cgg gac caa ggc cca aat gtc tgt gcc      146
Ala His Ser Arg Ile Arg Gly Arg Asp Gln Gly Pro Asn Val Cys Ala
 30                  35                  40                  45

ctt caa cag att ttg ggc acc aaa aag aaa tac ttc agc act tgt aag      194
Leu Gln Gln Ile Leu Gly Thr Lys Lys Lys Tyr Phe Ser Thr Cys Lys
```

-continued

```
                50                  55                  60

aac tgg tat aaa aag tcc atc tgt gga cag aaa acg act gtg tta tat      242
Asn Trp Tyr Lys Lys Ser Ile Cys Gly Gln Lys Thr Thr Val Leu Tyr
            65                  70                  75

gaa tgt tgc cct ggt tat atg aga atg gaa gga atg aaa ggc tgc cca      290
Glu Cys Cys Pro Gly Tyr Met Arg Met Glu Gly Met Lys Gly Cys Pro
        80                  85                  90

gca gtt ttg ccc att gac cat gtt tat ggc act ctg ggc atc gtg gga      338
Ala Val Leu Pro Ile Asp His Val Tyr Gly Thr Leu Gly Ile Val Gly
    95                  100                 105

gcc acc aca acg cag cgc tat tct gac gcc tca aaa ctg agg gag gag      386
Ala Thr Thr Thr Gln Arg Tyr Ser Asp Ala Ser Lys Leu Arg Glu Glu
110                 115                 120                 125

atc gag gga aag gga tcc ttc act tac ttt gca ccg agt aat gag gct      434
Ile Glu Gly Lys Gly Ser Phe Thr Tyr Phe Ala Pro Ser Asn Glu Ala
                130                 135                 140

tgg gac aac ttg gat tct gat atc cgt aga ggt ttg gag agc aac gtg      482
Trp Asp Asn Leu Asp Ser Asp Ile Arg Arg Gly Leu Glu Ser Asn Val
            145                 150                 155

aat gtt gaa tta ctg aat gct tta cat agt cac atg att aat aag aga      530
Asn Val Glu Leu Leu Asn Ala Leu His Ser His Met Ile Asn Lys Arg
        160                 165                 170

atg ttg acc aag gac tta aaa aat ggc atg att att cct tca atg tat      578
Met Leu Thr Lys Asp Leu Lys Asn Gly Met Ile Ile Pro Ser Met Tyr
    175                 180                 185

aac aat ttg ggg ctt ttc att aac cat tat cct aat ggg gtt gtc act      626
Asn Asn Leu Gly Leu Phe Ile Asn His Tyr Pro Asn Gly Val Val Thr
190                 195                 200                 205

gtt aat tgt gct cga atc atc cat ggg aac cag att gca aca aat ggt      674
Val Asn Cys Ala Arg Ile Ile His Gly Asn Gln Ile Ala Thr Asn Gly
                210                 215                 220

gtt gtc cat gtc att gac cgt gtg ctt aca caa att ggt acc tca att      722
Val Val His Val Ile Asp Arg Val Leu Thr Gln Ile Gly Thr Ser Ile
            225                 230                 235

caa gac ttc att gaa gca gaa gat gac ctt tca tct ttt aga gca gct      770
Gln Asp Phe Ile Glu Ala Glu Asp Asp Leu Ser Ser Phe Arg Ala Ala
        240                 245                 250

gcc atc aca tcg gac ata ttg gag gcc ctt gga aga gac ggt cac ttc      818
Ala Ile Thr Ser Asp Ile Leu Glu Ala Leu Gly Arg Asp Gly His Phe
    255                 260                 265

aca ctc ttt gct ccc acc aat gag gct ttt gag aaa ctt cca cga ggt      866
Thr Leu Phe Ala Pro Thr Asn Glu Ala Phe Glu Lys Leu Pro Arg Gly
270                 275                 280                 285

gtc cta gaa agg atc atg gga gac aaa gtg gct tcc gaa gct ctt atg      914
Val Leu Glu Arg Ile Met Gly Asp Lys Val Ala Ser Glu Ala Leu Met
                290                 295                 300

aag tac cac atc tta aat act ctc cag tgt tct gag tct att atg gga      962
Lys Tyr His Ile Leu Asn Thr Leu Gln Cys Ser Glu Ser Ile Met Gly
            305                 310                 315

gga gca gtc ttt gag acg ctg gaa gga aat aca att gag ata gga tgt     1010
Gly Ala Val Phe Glu Thr Leu Glu Gly Asn Thr Ile Glu Ile Gly Cys
        320                 325                 330

gac ggt gac agt ata aca gta aat gga atc aaa atg gtg aac aaa aag     1058
Asp Gly Asp Ser Ile Thr Val Asn Gly Ile Lys Met Val Asn Lys Lys
    335                 340                 345

gat att gtg aca aat aat ggt gtg atc cat ttg att gat cag gtc cta     1106
Asp Ile Val Thr Asn Asn Gly Val Ile His Leu Ile Asp Gln Val Leu
350                 355                 360                 365

att cct gat tct gcc aaa caa gtt att gag ctg gct gga aaa cag caa     1154
```

-continued

```
Ile Pro Asp Ser Ala Lys Gln Val Ile Glu Leu Ala Gly Lys Gln Gln
                370                 375                 380

acc acc ttc acg gat ctt gtg gcc caa tta ggc ttg gca tct gct ctg      1202
Thr Thr Phe Thr Asp Leu Val Ala Gln Leu Gly Leu Ala Ser Ala Leu
            385                 390                 395

agg cca gat gga gaa tac act ttg ctg gca cct gtg aat aat gca ttt      1250
Arg Pro Asp Gly Glu Tyr Thr Leu Leu Ala Pro Val Asn Asn Ala Phe
        400                 405                 410

tct gat gat act ctc agc atg gat cag cgc ctc ctt aaa tta att ctg      1298
Ser Asp Asp Thr Leu Ser Met Asp Gln Arg Leu Leu Lys Leu Ile Leu
    415                 420                 425

cag aat cac ata ttg aaa gta aaa gtt ggc ctt aat gag ctt tac aac      1346
Gln Asn His Ile Leu Lys Val Lys Val Gly Leu Asn Glu Leu Tyr Asn
430                 435                 440                 445

ggg caa ata ctg gaa acc atc gga ggc aaa cag ctc aga gtc ttc gta      1394
Gly Gln Ile Leu Glu Thr Ile Gly Gly Lys Gln Leu Arg Val Phe Val
                450                 455                 460

tat cgt aca gct gtc tgc att gaa aat tca tgc atg gag aaa ggg agt      1442
Tyr Arg Thr Ala Val Cys Ile Glu Asn Ser Cys Met Glu Lys Gly Ser
            465                 470                 475

aag caa ggg aga aac ggt gcg att cac ata ttc cgc gag atc atc aag      1490
Lys Gln Gly Arg Asn Gly Ala Ile His Ile Phe Arg Glu Ile Ile Lys
        480                 485                 490

cca gca gag aaa tcc ctc cat gaa aag tta aaa caa gat aag cgc ttt      1538
Pro Ala Glu Lys Ser Leu His Glu Lys Leu Lys Gln Asp Lys Arg Phe
    495                 500                 505

agc acc ttc ctc agc cta ctt gaa gct gca gac ttg aaa gag ctc ctg      1586
Ser Thr Phe Leu Ser Leu Leu Glu Ala Ala Asp Leu Lys Glu Leu Leu
510                 515                 520                 525

aca caa cct gga gac tgg aca tta ttt gtg cca acc aat gat gct ttt      1634
Thr Gln Pro Gly Asp Trp Thr Leu Phe Val Pro Thr Asn Asp Ala Phe
                530                 535                 540

aag gga atg act agt gaa gaa aaa gaa att ctg ata cgg gac aaa aat      1682
Lys Gly Met Thr Ser Glu Glu Lys Glu Ile Leu Ile Arg Asp Lys Asn
            545                 550                 555

gct ctt caa aac atc att ctt tat cac ctg aca cca gga gtt ttc att      1730
Ala Leu Gln Asn Ile Ile Leu Tyr His Leu Thr Pro Gly Val Phe Ile
        560                 565                 570

gga aaa gga ttt gaa cct ggt gtt act aac att tta aag acc aca caa      1778
Gly Lys Gly Phe Glu Pro Gly Val Thr Asn Ile Leu Lys Thr Thr Gln
    575                 580                 585

gga agc aaa atc ttt ctg aaa gaa gta aat gat aca ctt ctg gtg aat      1826
Gly Ser Lys Ile Phe Leu Lys Glu Val Asn Asp Thr Leu Leu Val Asn
590                 595                 600                 605

gaa ttg aaa tca aaa gaa tct gac atc atg aca aca aat ggt gta att      1874
Glu Leu Lys Ser Lys Glu Ser Asp Ile Met Thr Thr Asn Gly Val Ile
                610                 615                 620

cat gtt gta gat aaa ctc ctc tat cca gca gac aca cct gtt gga aat      1922
His Val Val Asp Lys Leu Leu Tyr Pro Ala Asp Thr Pro Val Gly Asn
            625                 630                 635

gat caa ctg ctg gaa ata ctt aat aaa tta atc aaa tac atc caa att      1970
Asp Gln Leu Leu Glu Ile Leu Asn Lys Leu Ile Lys Tyr Ile Gln Ile
        640                 645                 650

aag ttt gtt cgt ggt agc acc ttc aaa gaa atc ccc gtg act gtc tat      2018
Lys Phe Val Arg Gly Ser Thr Phe Lys Glu Ile Pro Val Thr Val Tyr
    655                 660                 665

aca act aaa att ata acc aaa gtt gtg gaa cca aaa att aaa gtg att      2066
Thr Thr Lys Ile Ile Thr Lys Val Val Glu Pro Lys Ile Lys Val Ile
670                 675                 680                 685
```

-continued

```
gaa ggc agt ctt cag cct att atc aaa act gaa gga ccc aca cta aca      2114
Glu Gly Ser Leu Gln Pro Ile Ile Lys Thr Glu Gly Pro Thr Leu Thr
                690                 695                 700

aaa gtc aaa att gaa ggt gaa cct gaa ttc aga ctg att aaa gaa ggt      2162
Lys Val Lys Ile Glu Gly Glu Pro Glu Phe Arg Leu Ile Lys Glu Gly
            705                 710                 715

gaa aca ata act gaa gtg atc cat gga gag cca att att aaa aaa tac      2210
Glu Thr Ile Thr Glu Val Ile His Gly Glu Pro Ile Ile Lys Lys Tyr
        720                 725                 730

acc aaa atc att gat gga gtg cct gtg gaa ata act gaa aaa gag aca      2258
Thr Lys Ile Ile Asp Gly Val Pro Val Glu Ile Thr Glu Lys Glu Thr
    735                 740                 745

cga gaa gaa cga atc att aca ggt cct gaa ata aaa tac act agg att      2306
Arg Glu Glu Arg Ile Ile Thr Gly Pro Glu Ile Lys Tyr Thr Arg Ile
750                 755                 760                 765

tct act gga ggt gga gaa aca gaa gaa act ctg aag aaa ttg tta caa      2354
Ser Thr Gly Gly Gly Glu Thr Glu Glu Thr Leu Lys Lys Leu Leu Gln
                770                 775                 780

gaa gag gtc acc aag gtc acc aaa ttc att gaa ggt ggt gat ggt cat      2402
Glu Glu Val Thr Lys Val Thr Lys Phe Ile Glu Gly Gly Asp Gly His
            785                 790                 795

tta ttt gaa gat gaa gaa att aaa aga ctg ctt cag gga gac aca ccc      2450
Leu Phe Glu Asp Glu Glu Ile Lys Arg Leu Leu Gln Gly Asp Thr Pro
        800                 805                 810

gtg agg aag ttg caa gcc aac aaa aaa gtt caa gga tct aga aga cga      2498
Val Arg Lys Leu Gln Ala Asn Lys Lys Val Gln Gly Ser Arg Arg Arg
    815                 820                 825

tta agg gaa ggt cgt tct cag tga aaatccaaaa accagaaaaa aatgtttata     2552
Leu Arg Glu Gly Arg Ser Gln  *
830                 835

caaccctaag tcaataacct gaccttagaa aattgtgaga gccaagttga cttcaggaac   2612

tgaaacatca gcacaaagaa gcaatcatca aataattctg aacacaaatt taatattttt   2672

ttttctgaat gagaaacatg agggaaattg tggagttagc ctcctgtggt aaaggaattg   2732

aagaaaatat aacaccttac accctttttc atcttgacat taaaagttct ggctaacttt   2792

ggaatccatt agagaaaaat ccttgtcacc agattcatta caattcaaat cgaagagttg   2852

tgaactgtta tcccattgaa aagaccgagc cttgtatgta tgttatggat acataaaatg   2912

cacgcaagcc attatctctc catgggaagc taagttataa aaataggtgc ttggtgtaca   2972

aaacttttta tatcaaaagg ctttgcacat ttctatatga gtgggtttac tggtaaatta   3032

tgttattttt tacaactaat tttgtactct cagaatgttt gtcatatgct tcttgcaatg   3092

catatttttt aatctcaaac gtttcaataa aaccattttt cagatataaa gagaattact   3152

tcaaattgag taattcagaa aaactcaaga tttaagttaa aaagtggttt ggacttggga   3212

a                                                                   3213


<210> SEQ ID NO 36
<211> LENGTH: 836
<212> TYPE: PRT
<213> ORGANISM: human

<400> SEQUENCE: 36

Met Ile Pro Phe Leu Pro Met Phe Ser Leu Leu Leu Leu Leu Ile Val
 1               5                  10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
```

-continued

```
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
    450                 455                 460
```

-continued

```
Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Thr Thr Lys
            660                 665                 670

Ile Ile Thr Lys Val Val Glu Pro Lys Ile Lys Val Ile Glu Gly Ser
        675                 680                 685

Leu Gln Pro Ile Ile Lys Thr Glu Gly Pro Thr Leu Thr Lys Val Lys
    690                 695                 700

Ile Glu Gly Glu Pro Glu Phe Arg Leu Ile Lys Glu Gly Glu Thr Ile
705                 710                 715                 720

Thr Glu Val Ile His Gly Glu Pro Ile Ile Lys Lys Tyr Thr Lys Ile
                725                 730                 735

Ile Asp Gly Val Pro Val Glu Ile Thr Glu Lys Glu Thr Arg Glu Glu
            740                 745                 750

Arg Ile Ile Thr Gly Pro Glu Ile Lys Tyr Thr Arg Ile Ser Thr Gly
        755                 760                 765

Gly Gly Glu Thr Glu Glu Thr Leu Lys Lys Leu Leu Gln Glu Glu Val
    770                 775                 780

Thr Lys Val Thr Lys Phe Ile Glu Gly Gly Asp Gly His Leu Phe Glu
785                 790                 795                 800

Asp Glu Glu Ile Lys Arg Leu Leu Gln Gly Asp Thr Pro Val Arg Lys
                805                 810                 815

Leu Gln Ala Asn Lys Lys Val Gln Gly Ser Arg Arg Arg Leu Arg Glu
            820                 825                 830

Gly Arg Ser Gln
        835
```

<210> SEQ ID NO 37
<211> LENGTH: 3129
<212> TYPE: DNA
<213> ORGANISM: human
<220> FEATURE:

-continued

<221> NAME/KEY: CDS
<222> LOCATION: (12)...(2438)

<400> SEQUENCE: 37
agagactcaa g atg att ccc ttt tta ccc atg ttt tct cta cta ttg ctg 50
Met Ile Pro Phe Leu Pro Met Phe Ser Leu Leu Leu Leu
1 5 10 ctt att gtt aac cct ata aac gcc aac aat cat tat gac aag atc ttg 98
Leu Ile Val Asn Pro Ile Asn Ala Asn Asn His Tyr Asp Lys Ile Leu
15 20 25 gct cat agt cgt atc agg ggt cgg gac caa ggc cca aat gtc tgt gcc 146
Ala His Ser Arg Ile Arg Gly Arg Asp Gln Gly Pro Asn Val Cys Ala
30 35 40 45 ctt caa cag att ttg ggc acc aaa aag aaa tac ttc agc act tgt aag 194
Leu Gln Gln Ile Leu Gly Thr Lys Lys Lys Tyr Phe Ser Thr Cys Lys
50 55 60 aac tgg tat aaa aag tcc atc tgt gga cag aaa acg act gtg tta tat 242
Asn Trp Tyr Lys Lys Ser Ile Cys Gly Gln Lys Thr Thr Val Leu Tyr
65 70 75 gaa tgt tgc cct ggt tat atg aga atg gaa gga atg aaa ggc tgc cca 290
Glu Cys Cys Pro Gly Tyr Met Arg Met Glu Gly Met Lys Gly Cys Pro
80 85 90 gca gtt ttg ccc att gac cat gtt tat ggc act ctg ggc atc gtg gga 338
Ala Val Leu Pro Ile Asp His Val Tyr Gly Thr Leu Gly Ile Val Gly
95 100 105 gcc acc aca acg cag cgc tat tct gac gcc tca aaa ctg agg gag gag 386
Ala Thr Thr Thr Gln Arg Tyr Ser Asp Ala Ser Lys Leu Arg Glu Glu
110 115 120 125 atc gag gga aag gga tcc ttc act tac ttt gca ccg agt aat gag gct 434
Ile Glu Gly Lys Gly Ser Phe Thr Tyr Phe Ala Pro Ser Asn Glu Ala
130 135 140 tgg gac aac ttg gat tct gat atc cgt aga ggt ttg gag agc aac gtg 482
Trp Asp Asn Leu Asp Ser Asp Ile Arg Arg Gly Leu Glu Ser Asn Val
145 150 155 aat gtt gaa tta ctg aat gct tta cat agt cac atg att aat aag aga 530
Asn Val Glu Leu Leu Asn Ala Leu His Ser His Met Ile Asn Lys Arg
160 165 170 atg ttg acc aag gac tta aaa aat ggc atg att att cct tca atg tat 578
Met Leu Thr Lys Asp Leu Lys Asn Gly Met Ile Ile Pro Ser Met Tyr
175 180 185 aac aat ttg ggg ctt ttc att aac cat tat cct aat ggg gtt gtc act 626
Asn Asn Leu Gly Leu Phe Ile Asn His Tyr Pro Asn Gly Val Val Thr
190 195 200 205 gtt aat tgt gct cga atc atc cat ggg aac cag att gca aca aat ggt 674
Val Asn Cys Ala Arg Ile Ile His Gly Asn Gln Ile Ala Thr Asn Gly
210 215 220 gtt gtc cat gtc att gac cgt gtg ctt aca caa att ggt acc tca att 722
Val Val His Val Ile Asp Arg Val Leu Thr Gln Ile Gly Thr Ser Ile
225 230 235 caa gac ttc att gaa gca gaa gat gac ctt tca tct ttt aga gca gct 770
Gln Asp Phe Ile Glu Ala Glu Asp Asp Leu Ser Ser Phe Arg Ala Ala
240 245 250 gcc atc aca tcg gac ata ttg gag gcc ctt gga aga gac ggt cac ttc 818
Ala Ile Thr Ser Asp Ile Leu Glu Ala Leu Gly Arg Asp Gly His Phe
255 260 265 aca ctc ttt gct ccc acc aat gag gct ttt gag aaa ctt cca cga ggt 866
Thr Leu Phe Ala Pro Thr Asn Glu Ala Phe Glu Lys Leu Pro Arg Gly
270 275 280 285 gtc cta gaa agg atc atg gga gac aaa gtg gct tcc gaa gct ctt atg 914
Val Leu Glu Arg Ile Met Gly Asp Lys Val Ala Ser Glu Ala Leu Met -continued

```
                290                 295                 300

aag tac cac atc tta aat act ctc cag tgt tct gag tct att atg gga      962
Lys Tyr His Ile Leu Asn Thr Leu Gln Cys Ser Glu Ser Ile Met Gly
            305                 310                 315

gga gca gtc ttt gag acg ctg gaa gga aat aca att gag ata gga tgt     1010
Gly Ala Val Phe Glu Thr Leu Glu Gly Asn Thr Ile Glu Ile Gly Cys
        320                 325                 330

gac ggt gac agt ata aca gta aat gga atc aaa atg gtg aac aaa aag     1058
Asp Gly Asp Ser Ile Thr Val Asn Gly Ile Lys Met Val Asn Lys Lys
    335                 340                 345

gat att gtg aca aat aat ggt gtg atc cat ttg att gat cag gtc cta     1106
Asp Ile Val Thr Asn Asn Gly Val Ile His Leu Ile Asp Gln Val Leu
350                 355                 360                 365

att cct gat tct gcc aaa caa gtt att gag ctg gct gga aaa cag caa     1154
Ile Pro Asp Ser Ala Lys Gln Val Ile Glu Leu Ala Gly Lys Gln Gln
            370                 375                 380

acc acc ttc acg gat ctt gtg gcc caa tta ggc ttg gca tct gct ctg     1202
Thr Thr Phe Thr Asp Leu Val Ala Gln Leu Gly Leu Ala Ser Ala Leu
            385                 390                 395

agg cca gat gga gaa tac act ttg ctg gca cct gtg aat aat gca ttt     1250
Arg Pro Asp Gly Glu Tyr Thr Leu Leu Ala Pro Val Asn Asn Ala Phe
        400                 405                 410

tct gat gat act ctc agc atg gat cag cgc ctc ctt aaa tta att ctg     1298
Ser Asp Asp Thr Leu Ser Met Asp Gln Arg Leu Leu Lys Leu Ile Leu
    415                 420                 425

cag aat cac ata ttg aaa gta aaa gtt ggc ctt aat gag ctt tac aac     1346
Gln Asn His Ile Leu Lys Val Lys Val Gly Leu Asn Glu Leu Tyr Asn
430                 435                 440                 445

ggg caa ata ctg gaa acc atc gga ggc aaa cag ctc aga gtc ttc gta     1394
Gly Gln Ile Leu Glu Thr Ile Gly Gly Lys Gln Leu Arg Val Phe Val
                450                 455                 460

tat cgt aca gct gtc tgc att gaa aat tca tgc atg gag aaa ggg agt     1442
Tyr Arg Thr Ala Val Cys Ile Glu Asn Ser Cys Met Glu Lys Gly Ser
            465                 470                 475

aag caa ggg aga aac ggt gcg att cac ata ttc cgc gag atc atc aag     1490
Lys Gln Gly Arg Asn Gly Ala Ile His Ile Phe Arg Glu Ile Ile Lys
        480                 485                 490

cca gca gag aaa tcc ctc cat gaa aag tta aaa caa gat aag cgc ttt     1538
Pro Ala Glu Lys Ser Leu His Glu Lys Leu Lys Gln Asp Lys Arg Phe
    495                 500                 505

agc acc ttc ctc agc cta ctt gaa gct gca gac ttg aaa gag ctc ctg     1586
Ser Thr Phe Leu Ser Leu Leu Glu Ala Ala Asp Leu Lys Glu Leu Leu
510                 515                 520                 525

aca caa cct gga gac tgg aca tta ttt gtg cca acc aat gat gct ttt     1634
Thr Gln Pro Gly Asp Trp Thr Leu Phe Val Pro Thr Asn Asp Ala Phe
                530                 535                 540

aag gga atg act agt gaa gaa aaa gaa att ctg ata cgg gac aaa aat     1682
Lys Gly Met Thr Ser Glu Glu Lys Glu Ile Leu Ile Arg Asp Lys Asn
            545                 550                 555

gct ctt caa aac atc att ctt tat cac ctg aca cca gga gtt ttc att     1730
Ala Leu Gln Asn Ile Ile Leu Tyr His Leu Thr Pro Gly Val Phe Ile
        560                 565                 570

gga aaa gga ttt gaa cct ggt gtt act aac att tta aag acc aca caa     1778
Gly Lys Gly Phe Glu Pro Gly Val Thr Asn Ile Leu Lys Thr Thr Gln
    575                 580                 585

gga agc aaa atc ttt ctg aaa gaa gta aat gat aca ctt ctg gtg aat     1826
Gly Ser Lys Ile Phe Leu Lys Glu Val Asn Asp Thr Leu Leu Val Asn
590                 595                 600                 605

gaa ttg aaa tca aaa gaa tct gac atc atg aca aca aat ggt gta att     1874
```

-continued

```
Glu Leu Lys Ser Lys Glu Ser Asp Ile Met Thr Thr Asn Gly Val Ile
                610                 615                 620

cat gtt gta gat aaa ctc ctc tat cca gca gac aca cct gtt gga aat     1922
His Val Val Asp Lys Leu Leu Tyr Pro Ala Asp Thr Pro Val Gly Asn
            625                 630                 635

gat caa ctg ctg gaa ata ctt aat aaa tta atc aaa tac atc caa att     1970
Asp Gln Leu Leu Glu Ile Leu Asn Lys Leu Ile Lys Tyr Ile Gln Ile
        640                 645                 650

aag ttt gtt cgt ggt agc acc ttc aaa gaa atc ccc gtg act gtc tat     2018
Lys Phe Val Arg Gly Ser Thr Phe Lys Glu Ile Pro Val Thr Val Tyr
    655                 660                 665

aca act aaa att ata acc aaa gtt gtg gaa cca aaa att aaa gtg att     2066
Thr Thr Lys Ile Ile Thr Lys Val Val Glu Pro Lys Ile Lys Val Ile
670                 675                 680                 685

gaa ggc agt ctt cag cct att atc aaa act gaa gga ccc aca cta aca     2114
Glu Gly Ser Leu Gln Pro Ile Ile Lys Thr Glu Gly Pro Thr Leu Thr
                690                 695                 700

aaa gtc aaa att gaa ggt gaa cct gaa ttc aga ctg att aaa gaa ggt     2162
Lys Val Lys Ile Glu Gly Glu Pro Glu Phe Arg Leu Ile Lys Glu Gly
            705                 710                 715

gaa aca ata act gaa gtg atc cat gga gag cca att att aaa aaa tac     2210
Glu Thr Ile Thr Glu Val Ile His Gly Glu Pro Ile Ile Lys Lys Tyr
        720                 725                 730

acc aaa atc att gat gga gtg cct gtg gaa ata act gaa aaa gag aca     2258
Thr Lys Ile Ile Asp Gly Val Pro Val Glu Ile Thr Glu Lys Glu Thr
    735                 740                 745

cga gaa gaa cga atc att aca ggt cct gaa ata aaa tac act agg att     2306
Arg Glu Glu Arg Ile Ile Thr Gly Pro Glu Ile Lys Tyr Thr Arg Ile
750                 755                 760                 765

tct act gga ggt gga gaa aca gaa gaa act ctg aag aaa ttg tta caa     2354
Ser Thr Gly Gly Gly Glu Thr Glu Glu Thr Leu Lys Lys Leu Leu Gln
                770                 775                 780

gaa gac aca ccc gtg agg aag ttg caa gcc aac aaa aaa gtt caa gga     2402
Glu Asp Thr Pro Val Arg Lys Leu Gln Ala Asn Lys Lys Val Gln Gly
            785                 790                 795

tct aga aga cga tta agg gaa ggt cgt tct cag tga aaatccaaaa          2448
Ser Arg Arg Arg Leu Arg Glu Gly Arg Ser Gln  *
        800                 805

accagaaaaa aatgtttata caaccctaag tcaataacct gaccttagaa aattgtgaga   2508

gccaagttga cttcaggaac tgaaacatca gcacaaagaa gcaatcatca aataattctg   2568

aacacaaatt taatattttt ttttctgaat gagaaacatg agggaaattg tggagttagc   2628

ctcctgtggt aaaggaattg aagaaaatat aacaccttac accctttttc atcttgacat   2688

taaaagttct ggctaacttt ggaatccatt agagaaaaat ccttgtcacc agattcatta   2748

caattcaaat cgaagagttg tgaactgtta tcccattgaa aagaccgagc cttgtatgta   2808

tgttatggat acataaaatg cacgcaagcc attatctctc catgggaagc taagttataa   2868

aaataggtgc ttggtgtaca aaacttttta tatcaaaagg ctttgcacat ttctatatga   2928

gtgggtttac tggtaaatta tgttattttt tacaactaat tttgtactct cagaatgttt   2988

gtcatatgct tcttgcaatg catatttttt aatctcaaac gtttcaataa aaccattttt   3048

cagatataaa gagaattact tcaaattgag taattcagaa aaactcaaga tttaagttaa   3108

aaagtggttt ggacttggga a                                             3129
```

<210> SEQ ID NO 38
<211> LENGTH: 808
<212> TYPE: PRT

-continued

<213> ORGANISM: human

<400> SEQUENCE: 38

```
Met Ile Pro Phe Leu Pro Met Phe Ser Leu Leu Leu Leu Leu Ile Val
 1               5                  10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400
```

-continued

```
Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Thr Thr Lys
            660                 665                 670

Ile Ile Thr Lys Val Val Glu Pro Lys Ile Lys Val Ile Glu Gly Ser
        675                 680                 685

Leu Gln Pro Ile Ile Lys Thr Glu Gly Pro Thr Leu Thr Lys Val Lys
    690                 695                 700

Ile Glu Gly Glu Pro Glu Phe Arg Leu Ile Lys Glu Gly Glu Thr Ile
705                 710                 715                 720

Thr Glu Val Ile His Gly Glu Pro Ile Ile Lys Lys Tyr Thr Lys Ile
                725                 730                 735

Ile Asp Gly Val Pro Val Glu Ile Thr Glu Lys Glu Thr Arg Glu Glu
            740                 745                 750

Arg Ile Ile Thr Gly Pro Glu Ile Lys Tyr Thr Arg Ile Ser Thr Gly
        755                 760                 765

Gly Gly Glu Thr Glu Glu Thr Leu Lys Lys Leu Leu Gln Glu Asp Thr
    770                 775                 780

Pro Val Arg Lys Leu Gln Ala Asn Lys Lys Val Gln Gly Ser Arg Arg
785                 790                 795                 800

Arg Leu Arg Glu Gly Arg Ser Gln
                805
```

-continued

```
<210> SEQ ID NO 39
<211> LENGTH: 3132
<212> TYPE: DNA
<213> ORGANISM: human
<220> FEATURE:
<221> NAME/KEY: CDS
<222> LOCATION: (12)...(2441)

<400> SEQUENCE: 39

agagactcaa g atg att ccc ttt tta ccc atg ttt tct cta cta ttg ctg      50
             Met Ile Pro Phe Leu Pro Met Phe Ser Leu Leu Leu Leu
              1               5                  10

ctt att gtt aac cct ata aac gcc aac aat cat tat gac aag atc ttg       98
Leu Ile Val Asn Pro Ile Asn Ala Asn Asn His Tyr Asp Lys Ile Leu
     15                  20                  25

gct cat agt cgt atc agg ggt cgg gac caa ggc cca aat gtc tgt gcc      146
Ala His Ser Arg Ile Arg Gly Arg Asp Gln Gly Pro Asn Val Cys Ala
 30                  35                  40                  45

ctt caa cag att ttg ggc acc aaa aag aaa tac ttc agc act tgt aag      194
Leu Gln Gln Ile Leu Gly Thr Lys Lys Lys Tyr Phe Ser Thr Cys Lys
                 50                  55                  60

aac tgg tat aaa aag tcc atc tgt gga cag aaa acg act gtg tta tat      242
Asn Trp Tyr Lys Lys Ser Ile Cys Gly Gln Lys Thr Thr Val Leu Tyr
             65                  70                  75

gaa tgt tgc cct ggt tat atg aga atg gaa gga atg aaa ggc tgc cca      290
Glu Cys Cys Pro Gly Tyr Met Arg Met Glu Gly Met Lys Gly Cys Pro
         80                  85                  90

gca gtt ttg ccc att gac cat gtt tat ggc act ctg ggc atc gtg gga      338
Ala Val Leu Pro Ile Asp His Val Tyr Gly Thr Leu Gly Ile Val Gly
     95                 100                 105

gcc acc aca acg cag cgc tat tct gac gcc tca aaa ctg agg gag gag      386
Ala Thr Thr Thr Gln Arg Tyr Ser Asp Ala Ser Lys Leu Arg Glu Glu
110                 115                 120                 125

atc gag gga aag gga tcc ttc act tac ttt gca ccg agt aat gag gct      434
Ile Glu Gly Lys Gly Ser Phe Thr Tyr Phe Ala Pro Ser Asn Glu Ala
                130                 135                 140

tgg gac aac ttg gat tct gat atc cgt aga ggt ttg gag agc aac gtg      482
Trp Asp Asn Leu Asp Ser Asp Ile Arg Arg Gly Leu Glu Ser Asn Val
            145                 150                 155

aat gtt gaa tta ctg aat gct tta cat agt cac atg att aat aag aga      530
Asn Val Glu Leu Leu Asn Ala Leu His Ser His Met Ile Asn Lys Arg
        160                 165                 170

atg ttg acc aag gac tta aaa aat ggc atg att att cct tca atg tat      578
Met Leu Thr Lys Asp Leu Lys Asn Gly Met Ile Ile Pro Ser Met Tyr
    175                 180                 185

aac aat ttg ggg ctt ttc att aac cat tat cct aat ggg gtt gtc act      626
Asn Asn Leu Gly Leu Phe Ile Asn His Tyr Pro Asn Gly Val Val Thr
190                 195                 200                 205

gtt aat tgt gct cga atc atc cat ggg aac cag att gca aca aat ggt      674
Val Asn Cys Ala Arg Ile Ile His Gly Asn Gln Ile Ala Thr Asn Gly
                210                 215                 220

gtt gtc cat gtc att gac cgt gtg ctt aca caa att ggt acc tca att      722
Val Val His Val Ile Asp Arg Val Leu Thr Gln Ile Gly Thr Ser Ile
            225                 230                 235

caa gac ttc att gaa gca gaa gat gac ctt tca tct ttt aga gca gct      770
Gln Asp Phe Ile Glu Ala Glu Asp Asp Leu Ser Ser Phe Arg Ala Ala
        240                 245                 250

gcc atc aca tcg gac ata ttg gag gcc ctt gga aga gac ggt cac ttc      818
Ala Ile Thr Ser Asp Ile Leu Glu Ala Leu Gly Arg Asp Gly His Phe
    255                 260                 265

aca ctc ttt gct ccc acc aat gag gct ttt gag aaa ctt cca cga ggt      866
```

-continued

```
Thr Leu Phe Ala Pro Thr Asn Glu Ala Phe Glu Lys Leu Pro Arg Gly
270                 275                 280                 285

gtc cta gaa agg atc atg gga gac aaa gtg gct tcc gaa gct ctt atg      914
Val Leu Glu Arg Ile Met Gly Asp Lys Val Ala Ser Glu Ala Leu Met
                290                 295                 300

aag tac cac atc tta aat act ctc cag tgt tct gag tct att atg gga      962
Lys Tyr His Ile Leu Asn Thr Leu Gln Cys Ser Glu Ser Ile Met Gly
            305                 310                 315

gga gca gtc ttt gag acg ctg gaa gga aat aca att gag ata gga tgt     1010
Gly Ala Val Phe Glu Thr Leu Glu Gly Asn Thr Ile Glu Ile Gly Cys
        320                 325                 330

gac ggt gac agt ata aca gta aat gga atc aaa atg gtg aac aaa aag     1058
Asp Gly Asp Ser Ile Thr Val Asn Gly Ile Lys Met Val Asn Lys Lys
    335                 340                 345

gat att gtg aca aat aat ggt gtg atc cat ttg att gat cag gtc cta     1106
Asp Ile Val Thr Asn Asn Gly Val Ile His Leu Ile Asp Gln Val Leu
350                 355                 360                 365

att cct gat tct gcc aaa caa gtt att gag ctg gct gga aaa cag caa     1154
Ile Pro Asp Ser Ala Lys Gln Val Ile Glu Leu Ala Gly Lys Gln Gln
                370                 375                 380

acc acc ttc acg gat ctt gtg gcc caa tta ggc ttg gca tct gct ctg     1202
Thr Thr Phe Thr Asp Leu Val Ala Gln Leu Gly Leu Ala Ser Ala Leu
            385                 390                 395

agg cca gat gga gaa tac act ttg ctg gca cct gtg aat aat gca ttt     1250
Arg Pro Asp Gly Glu Tyr Thr Leu Leu Ala Pro Val Asn Asn Ala Phe
        400                 405                 410

tct gat gat act ctc agc atg gat cag cgc ctc ctt aaa tta att ctg     1298
Ser Asp Asp Thr Leu Ser Met Asp Gln Arg Leu Leu Lys Leu Ile Leu
    415                 420                 425

cag aat cac ata ttg aaa gta aaa gtt ggc ctt aat gag ctt tac aac     1346
Gln Asn His Ile Leu Lys Val Lys Val Gly Leu Asn Glu Leu Tyr Asn
430                 435                 440                 445

ggg caa ata ctg gaa acc atc gga ggc aaa cag ctc aga gtc ttc gta     1394
Gly Gln Ile Leu Glu Thr Ile Gly Gly Lys Gln Leu Arg Val Phe Val
                450                 455                 460

tat cgt aca gct gtc tgc att gaa aat tca tgc atg gag aaa ggg agt     1442
Tyr Arg Thr Ala Val Cys Ile Glu Asn Ser Cys Met Glu Lys Gly Ser
            465                 470                 475

aag caa ggg aga aac ggt gcg att cac ata ttc cgc gag atc atc aag     1490
Lys Gln Gly Arg Asn Gly Ala Ile His Ile Phe Arg Glu Ile Ile Lys
        480                 485                 490

cca gca gag aaa tcc ctc cat gaa aag tta aaa caa gat aag cgc ttt     1538
Pro Ala Glu Lys Ser Leu His Glu Lys Leu Lys Gln Asp Lys Arg Phe
    495                 500                 505

agc acc ttc ctc agc cta ctt gaa gct gca gac ttg aaa gag ctc ctg     1586
Ser Thr Phe Leu Ser Leu Leu Glu Ala Ala Asp Leu Lys Glu Leu Leu
510                 515                 520                 525

aca caa cct gga gac tgg aca tta ttt gtg cca acc aat gat gct ttt     1634
Thr Gln Pro Gly Asp Trp Thr Leu Phe Val Pro Thr Asn Asp Ala Phe
                530                 535                 540

aag gga atg act agt gaa gaa aaa gaa att ctg ata cgg gac aaa aat     1682
Lys Gly Met Thr Ser Glu Glu Lys Glu Ile Leu Ile Arg Asp Lys Asn
            545                 550                 555

gct ctt caa aac atc att ctt tat cac ctg aca cca gga gtt ttc att     1730
Ala Leu Gln Asn Ile Ile Leu Tyr His Leu Thr Pro Gly Val Phe Ile
        560                 565                 570

gga aaa gga ttt gaa cct ggt gtt act aac att tta aag acc aca caa     1778
Gly Lys Gly Phe Glu Pro Gly Val Thr Asn Ile Leu Lys Thr Thr Gln
    575                 580                 585
```

-continued

```
gga agc aaa atc ttt ctg aaa gaa gta aat gat aca ctt ctg gtg aat      1826
Gly Ser Lys Ile Phe Leu Lys Glu Val Asn Asp Thr Leu Leu Val Asn
590                 595                 600                 605

gaa ttg aaa tca aaa gaa tct gac atc atg aca aca aat ggt gta att      1874
Glu Leu Lys Ser Lys Glu Ser Asp Ile Met Thr Thr Asn Gly Val Ile
                610                 615                 620

cat gtt gta gat aaa ctc ctc tat cca gca gac aca cct gtt gga aat      1922
His Val Val Asp Lys Leu Leu Tyr Pro Ala Asp Thr Pro Val Gly Asn
            625                 630                 635

gat caa ctg ctg gaa ata ctt aat aaa tta atc aaa tac atc caa att      1970
Asp Gln Leu Leu Glu Ile Leu Asn Lys Leu Ile Lys Tyr Ile Gln Ile
        640                 645                 650

aag ttt gtt cgt ggt agc acc ttc aaa gaa atc ccc gtg act gtc tat      2018
Lys Phe Val Arg Gly Ser Thr Phe Lys Glu Ile Pro Val Thr Val Tyr
    655                 660                 665

aga ccc aca cta aca aaa gtc aaa att gaa ggt gaa cct gaa ttc aga      2066
Arg Pro Thr Leu Thr Lys Val Lys Ile Glu Gly Glu Pro Glu Phe Arg
670                 675                 680                 685

ctg att aaa gaa ggt gaa aca ata act gaa gtg atc cat gga gag cca      2114
Leu Ile Lys Glu Gly Glu Thr Ile Thr Glu Val Ile His Gly Glu Pro
                690                 695                 700

att att aaa aaa tac acc aaa atc att gat gga gtg cct gtg gaa ata      2162
Ile Ile Lys Lys Tyr Thr Lys Ile Ile Asp Gly Val Pro Val Glu Ile
            705                 710                 715

act gaa aaa gag aca cga gaa gaa cga atc att aca ggt cct gaa ata      2210
Thr Glu Lys Glu Thr Arg Glu Glu Arg Ile Ile Thr Gly Pro Glu Ile
        720                 725                 730

aaa tac act agg att tct act gga ggt gga gaa aca gaa gaa act ctg      2258
Lys Tyr Thr Arg Ile Ser Thr Gly Gly Gly Glu Thr Glu Glu Thr Leu
    735                 740                 745

aag aaa ttg tta caa gaa gag gtc acc aag gtc acc aaa ttc att gaa      2306
Lys Lys Leu Leu Gln Glu Glu Val Thr Lys Val Thr Lys Phe Ile Glu
750                 755                 760                 765

ggt ggt gat ggt cat tta ttt gaa gat gaa gaa att aaa aga ctg ctt      2354
Gly Gly Asp Gly His Leu Phe Glu Asp Glu Glu Ile Lys Arg Leu Leu
                770                 775                 780

cag gga gac aca ccc gtg agg aag ttg caa gcc aac aaa aaa gtt caa      2402
Gln Gly Asp Thr Pro Val Arg Lys Leu Gln Ala Asn Lys Lys Val Gln
            785                 790                 795

gga tct aga aga cga tta agg gaa ggt cgt tct cag tga aaatccaaaa      2451
Gly Ser Arg Arg Arg Leu Arg Glu Gly Arg Ser Gln  *
        800                 805

accagaaaaa aatgtttata caaccctaag tcaataacct gaccttagaa aattgtgaga   2511

gccaagttga cttcaggaac tgaaacatca gcacaaagaa gcaatcatca aataattctg   2571

aacacaaatt taatattttt ttttctgaat gagaaacatg agggaaattg tggagttagc   2631

ctcctgtggt aaaggaattg aagaaaatat aacaccttac accctttttc atcttgacat   2691

taaaagttct ggctaacttt ggaatccatt agagaaaaat ccttgtcacc agattcatta   2751

caattcaaat cgaagagttg tgaactgtta tcccattgaa aagaccgagc cttgtatgta   2811

tgttatggat acataaaatg cacgcaagcc attatctctc catgggaagc taagttataa   2871

aaataggtgc ttggtgtaca aaacttttta tatcaaaagg ctttgcacat ttctatatga   2931

gtgggtttac tggtaaatta tgttattttt tacaactaat tttgtactct cagaatgttt   2991

gtcatatgct tcttgcaatg catatttttt aatctcaaac gtttcaataa aaccattttt   3051

cagatataaa gagaattact tcaaattgag taattcagaa aaactcaaga tttaagttaa   3111

aaagtggttt ggacttggga a                                             3132
```

-continued

<210> SEQ ID NO 40
<211> LENGTH: 809
<212> TYPE: PRT
<213> ORGANISM: human

<400> SEQUENCE: 40

```
Met Ile Pro Phe Leu Pro Met Phe Ser Leu Leu Leu Leu Leu Ile Val
 1               5                  10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
```

-continued

```
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Arg Pro Thr
            660                 665                 670

Leu Thr Lys Val Lys Ile Glu Gly Glu Pro Glu Phe Arg Leu Ile Lys
        675                 680                 685

Glu Gly Glu Thr Ile Thr Glu Val Ile His Gly Glu Pro Ile Ile Lys
    690                 695                 700

Lys Tyr Thr Lys Ile Ile Asp Gly Val Pro Val Glu Ile Thr Glu Lys
705                 710                 715                 720

Glu Thr Arg Glu Glu Arg Ile Ile Thr Gly Pro Glu Ile Lys Tyr Thr
                725                 730                 735

Arg Ile Ser Thr Gly Gly Gly Glu Thr Glu Glu Thr Leu Lys Lys Leu
            740                 745                 750

Leu Gln Glu Glu Val Thr Lys Val Thr Lys Phe Ile Glu Gly Gly Asp
        755                 760                 765

Gly His Leu Phe Glu Asp Glu Glu Ile Lys Arg Leu Leu Gln Gly Asp
    770                 775                 780

Thr Pro Val Arg Lys Leu Gln Ala Asn Lys Lys Val Gln Gly Ser Arg
785                 790                 795                 800
```

-continued

```
Arg Arg Leu Arg Glu Gly Arg Ser Gln
                805


<210> SEQ ID NO 41
<211> LENGTH: 3048
<212> TYPE: DNA
<213> ORGANISM: human
<220> FEATURE:
<221> NAME/KEY: CDS
<222> LOCATION: (12)...(2357)

<400> SEQUENCE: 41

agagactcaa g atg att ccc ttt tta ccc atg ttt tct cta cta ttg ctg      50
             Met Ile Pro Phe Leu Pro Met Phe Ser Leu Leu Leu Leu
              1               5                  10

ctt att gtt aac cct ata aac gcc aac aat cat tat gac aag atc ttg       98
Leu Ile Val Asn Pro Ile Asn Ala Asn Asn His Tyr Asp Lys Ile Leu
     15                  20                  25

gct cat agt cgt atc agg ggt cgg gac caa ggc cca aat gtc tgt gcc      146
Ala His Ser Arg Ile Arg Gly Arg Asp Gln Gly Pro Asn Val Cys Ala
 30                  35                  40                  45

ctt caa cag att ttg ggc acc aaa aag aaa tac ttc agc act tgt aag      194
Leu Gln Gln Ile Leu Gly Thr Lys Lys Lys Tyr Phe Ser Thr Cys Lys
                 50                  55                  60

aac tgg tat aaa aag tcc atc tgt gga cag aaa acg act gtg tta tat      242
Asn Trp Tyr Lys Lys Ser Ile Cys Gly Gln Lys Thr Thr Val Leu Tyr
             65                  70                  75

gaa tgt tgc cct ggt tat atg aga atg gaa gga atg aaa ggc tgc cca      290
Glu Cys Cys Pro Gly Tyr Met Arg Met Glu Gly Met Lys Gly Cys Pro
         80                  85                  90

gca gtt ttg ccc att gac cat gtt tat ggc act ctg ggc atc gtg gga      338
Ala Val Leu Pro Ile Asp His Val Tyr Gly Thr Leu Gly Ile Val Gly
     95                 100                 105

gcc acc aca acg cag cgc tat tct gac gcc tca aaa ctg agg gag gag      386
Ala Thr Thr Thr Gln Arg Tyr Ser Asp Ala Ser Lys Leu Arg Glu Glu
110                 115                 120                 125

atc gag gga aag gga tcc ttc act tac ttt gca ccg agt aat gag gct      434
Ile Glu Gly Lys Gly Ser Phe Thr Tyr Phe Ala Pro Ser Asn Glu Ala
                130                 135                 140

tgg gac aac ttg gat tct gat atc cgt aga ggt ttg gag agc aac gtg      482
Trp Asp Asn Leu Asp Ser Asp Ile Arg Arg Gly Leu Glu Ser Asn Val
            145                 150                 155

aat gtt gaa tta ctg aat gct tta cat agt cac atg att aat aag aga      530
Asn Val Glu Leu Leu Asn Ala Leu His Ser His Met Ile Asn Lys Arg
        160                 165                 170

atg ttg acc aag gac tta aaa aat ggc atg att att cct tca atg tat      578
Met Leu Thr Lys Asp Leu Lys Asn Gly Met Ile Ile Pro Ser Met Tyr
    175                 180                 185

aac aat ttg ggg ctt ttc att aac cat tat cct aat ggg gtt gtc act      626
Asn Asn Leu Gly Leu Phe Ile Asn His Tyr Pro Asn Gly Val Val Thr
190                 195                 200                 205

gtt aat tgt gct cga atc atc cat ggg aac cag att gca aca aat ggt      674
Val Asn Cys Ala Arg Ile Ile His Gly Asn Gln Ile Ala Thr Asn Gly
                210                 215                 220

gtt gtc cat gtc att gac cgt gtg ctt aca caa att ggt acc tca att      722
Val Val His Val Ile Asp Arg Val Leu Thr Gln Ile Gly Thr Ser Ile
            225                 230                 235

caa gac ttc att gaa gca gaa gat gac ctt tca tct ttt aga gca gct      770
Gln Asp Phe Ile Glu Ala Glu Asp Asp Leu Ser Ser Phe Arg Ala Ala
        240                 245                 250
```

-continued

```
gcc atc aca tcg gac ata ttg gag gcc ctt gga aga gac ggt cac ttc      818
Ala Ile Thr Ser Asp Ile Leu Glu Ala Leu Gly Arg Asp Gly His Phe
    255                 260                 265

aca ctc ttt gct ccc acc aat gag gct ttt gag aaa ctt cca cga ggt      866
Thr Leu Phe Ala Pro Thr Asn Glu Ala Phe Glu Lys Leu Pro Arg Gly
270                 275                 280                 285

gtc cta gaa agg atc atg gga gac aaa gtg gct tcc gaa gct ctt atg      914
Val Leu Glu Arg Ile Met Gly Asp Lys Val Ala Ser Glu Ala Leu Met
                290                 295                 300

aag tac cac atc tta aat act ctc cag tgt tct gag tct att atg gga      962
Lys Tyr His Ile Leu Asn Thr Leu Gln Cys Ser Glu Ser Ile Met Gly
            305                 310                 315

gga gca gtc ttt gag acg ctg gaa gga aat aca att gag ata gga tgt     1010
Gly Ala Val Phe Glu Thr Leu Glu Gly Asn Thr Ile Glu Ile Gly Cys
        320                 325                 330

gac ggt gac agt ata aca gta aat gga atc aaa atg gtg aac aaa aag     1058
Asp Gly Asp Ser Ile Thr Val Asn Gly Ile Lys Met Val Asn Lys Lys
    335                 340                 345

gat att gtg aca aat aat ggt gtg atc cat ttg att gat cag gtc cta     1106
Asp Ile Val Thr Asn Asn Gly Val Ile His Leu Ile Asp Gln Val Leu
350                 355                 360                 365

att cct gat tct gcc aaa caa gtt att gag ctg gct gga aaa cag caa     1154
Ile Pro Asp Ser Ala Lys Gln Val Ile Glu Leu Ala Gly Lys Gln Gln
                370                 375                 380

acc acc ttc acg gat ctt gtg gcc caa tta ggc ttg gca tct gct ctg     1202
Thr Thr Phe Thr Asp Leu Val Ala Gln Leu Gly Leu Ala Ser Ala Leu
            385                 390                 395

agg cca gat gga gaa tac act ttg ctg gca cct gtg aat aat gca ttt     1250
Arg Pro Asp Gly Glu Tyr Thr Leu Leu Ala Pro Val Asn Asn Ala Phe
        400                 405                 410

tct gat gat act ctc agc atg gat cag cgc ctc ctt aaa tta att ctg     1298
Ser Asp Asp Thr Leu Ser Met Asp Gln Arg Leu Leu Lys Leu Ile Leu
    415                 420                 425

cag aat cac ata ttg aaa gta aaa gtt ggc ctt aat gag ctt tac aac     1346
Gln Asn His Ile Leu Lys Val Lys Val Gly Leu Asn Glu Leu Tyr Asn
430                 435                 440                 445

ggg caa ata ctg gaa acc atc gga ggc aaa cag ctc aga gtc ttc gta     1394
Gly Gln Ile Leu Glu Thr Ile Gly Gly Lys Gln Leu Arg Val Phe Val
                450                 455                 460

tat cgt aca gct gtc tgc att gaa aat tca tgc atg gag aaa ggg agt     1442
Tyr Arg Thr Ala Val Cys Ile Glu Asn Ser Cys Met Glu Lys Gly Ser
            465                 470                 475

aag caa ggg aga aac ggt gcg att cac ata ttc cgc gag atc atc aag     1490
Lys Gln Gly Arg Asn Gly Ala Ile His Ile Phe Arg Glu Ile Ile Lys
        480                 485                 490

cca gca gag aaa tcc ctc cat gaa aag tta aaa caa gat aag cgc ttt     1538
Pro Ala Glu Lys Ser Leu His Glu Lys Leu Lys Gln Asp Lys Arg Phe
    495                 500                 505

agc acc ttc ctc agc cta ctt gaa gct gca gac ttg aaa gag ctc ctg     1586
Ser Thr Phe Leu Ser Leu Leu Glu Ala Ala Asp Leu Lys Glu Leu Leu
510                 515                 520                 525

aca caa cct gga gac tgg aca tta ttt gtg cca acc aat gat gct ttt     1634
Thr Gln Pro Gly Asp Trp Thr Leu Phe Val Pro Thr Asn Asp Ala Phe
                530                 535                 540

aag gga atg act agt gaa gaa aaa gaa att ctg ata cgg gac aaa aat     1682
Lys Gly Met Thr Ser Glu Glu Lys Glu Ile Leu Ile Arg Asp Lys Asn
            545                 550                 555

gct ctt caa aac atc att ctt tat cac ctg aca cca gga gtt ttc att     1730
Ala Leu Gln Asn Ile Ile Leu Tyr His Leu Thr Pro Gly Val Phe Ile
        560                 565                 570
```

-continued

```
gga aaa gga ttt gaa cct ggt gtt act aac att tta aag acc aca caa     1778
Gly Lys Gly Phe Glu Pro Gly Val Thr Asn Ile Leu Lys Thr Thr Gln
    575                 580                 585

gga agc aaa atc ttt ctg aaa gaa gta aat gat aca ctt ctg gtg aat     1826
Gly Ser Lys Ile Phe Leu Lys Glu Val Asn Asp Thr Leu Leu Val Asn
590                 595                 600                 605

gaa ttg aaa tca aaa gaa tct gac atc atg aca aca aat ggt gta att     1874
Glu Leu Lys Ser Lys Glu Ser Asp Ile Met Thr Thr Asn Gly Val Ile
                610                 615                 620

cat gtt gta gat aaa ctc ctc tat cca gca gac aca cct gtt gga aat     1922
His Val Val Asp Lys Leu Leu Tyr Pro Ala Asp Thr Pro Val Gly Asn
            625                 630                 635

gat caa ctg ctg gaa ata ctt aat aaa tta atc aaa tac atc caa att     1970
Asp Gln Leu Leu Glu Ile Leu Asn Lys Leu Ile Lys Tyr Ile Gln Ile
        640                 645                 650

aag ttt gtt cgt ggt agc acc ttc aaa gaa atc ccc gtg act gtc tat     2018
Lys Phe Val Arg Gly Ser Thr Phe Lys Glu Ile Pro Val Thr Val Tyr
    655                 660                 665

aga ccc aca cta aca aaa gtc aaa att gaa ggt gaa cct gaa ttc aga     2066
Arg Pro Thr Leu Thr Lys Val Lys Ile Glu Gly Glu Pro Glu Phe Arg
670                 675                 680                 685

ctg att aaa gaa ggt gaa aca ata act gaa gtg atc cat gga gag cca     2114
Leu Ile Lys Glu Gly Glu Thr Ile Thr Glu Val Ile His Gly Glu Pro
                690                 695                 700

att att aaa aaa tac acc aaa atc att gat gga gtg cct gtg gaa ata     2162
Ile Ile Lys Lys Tyr Thr Lys Ile Ile Asp Gly Val Pro Val Glu Ile
            705                 710                 715

act gaa aaa gag aca cga gaa gaa cga atc att aca ggt cct gaa ata     2210
Thr Glu Lys Glu Thr Arg Glu Glu Arg Ile Ile Thr Gly Pro Glu Ile
        720                 725                 730

aaa tac act agg att tct act gga ggt gga gaa aca gaa gaa act ctg     2258
Lys Tyr Thr Arg Ile Ser Thr Gly Gly Gly Glu Thr Glu Glu Thr Leu
    735                 740                 745

aag aaa ttg tta caa gaa gac aca ccc gtg agg aag ttg caa gcc aac     2306
Lys Lys Leu Leu Gln Glu Asp Thr Pro Val Arg Lys Leu Gln Ala Asn
750                 755                 760                 765

aaa aaa gtt caa ggt tct aga aga cga tta agg gaa ggt cgt tct cag     2354
Lys Lys Val Gln Gly Ser Arg Arg Arg Leu Arg Glu Gly Arg Ser Gln
                770                 775                 780

tga aaatccaaaa accagaaaaa aatgtttata caaccctaag tcaataacct         2407
 *

gaccttagaa aattgtgaga gccaagttga cttcaggaac tgaaacatca gcacaaagaa   2467

gcaatcatca aataattctg aacacaaatt taatattttt ttttctgaat gagaaacatg   2527

agggaaattg tggagttagc ctcctgtggt aaaggaattg aagaaaatat aacaccttac   2587

accctttttc atcttgacat taaaagttct ggctaacttt ggaatccatt agagaaaaat   2647

ccttgtcacc agattcatta caattcaaat cgaagagttg tgaactgtta tcccattgaa   2707

aagaccgagc cttgtatgta tgttatggat acataaaatg cacgcaagcc attatctctc   2767

catgggaagc taagttataa aaataggtgc ttggtgtaca aaacttttta tatcaaaagg   2827

ctttgcacat ttctatatga gtgggtttac tggtaaatta tgttattttt tacaactaat   2887

tttgtactct cagaatgttt gtcatatgct tcttgcaatg catatttttt aatctcaaac   2947

gtttcaataa aaccattttt cagatataaa gagaattact tcaaattgag taattcagaa   3007

aaactcaaga tttaagttaa aaagtggttt ggacttggga a                      3048
```

-continued

<210> SEQ ID NO 42
<211> LENGTH: 781
<212> TYPE: PRT
<213> ORGANISM: human

<400> SEQUENCE: 42

```
Met Ile Pro Phe Leu Pro Met Phe Ser Leu Leu Leu Leu Leu Ile Val
 1               5                  10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380
```

-continued

```
Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Arg Pro Thr
            660                 665                 670

Leu Thr Lys Val Lys Ile Glu Gly Glu Pro Glu Phe Arg Leu Ile Lys
        675                 680                 685

Glu Gly Glu Thr Ile Thr Glu Val Ile His Gly Glu Pro Ile Ile Lys
    690                 695                 700

Lys Tyr Thr Lys Ile Ile Asp Gly Val Pro Val Glu Ile Thr Glu Lys
705                 710                 715                 720

Glu Thr Arg Glu Glu Arg Ile Ile Thr Gly Pro Glu Ile Lys Tyr Thr
                725                 730                 735

Arg Ile Ser Thr Gly Gly Gly Glu Thr Glu Glu Thr Leu Lys Lys Leu
            740                 745                 750

Leu Gln Glu Asp Thr Pro Val Arg Lys Leu Gln Ala Asn Lys Lys Val
        755                 760                 765

Gln Gly Ser Arg Arg Arg Leu Arg Glu Gly Arg Ser Gln
    770                 775                 780
```

<210> SEQ ID NO 43
<211> LENGTH: 3042
<212> TYPE: DNA

-continued

```
<213> ORGANISM: human
<220> FEATURE:
<221> NAME/KEY: CDS
<222> LOCATION: (12)...(2351)

<400> SEQUENCE: 43

agagactcaa g atg att ccc ttt tta ccc atg ttt tct cta cta ttg ctg      50
             Met Ile Pro Phe Leu Pro Met Phe Ser Leu Leu Leu Leu
              1               5                  10

ctt att gtt aac cct ata aac gcc aac aat cat tat gac aag atc ttg       98
Leu Ile Val Asn Pro Ile Asn Ala Asn Asn His Tyr Asp Lys Ile Leu
     15                  20                  25

gct cat agt cgt atc agg ggt cgg gac caa ggc cca aat gtc tgt gcc      146
Ala His Ser Arg Ile Arg Gly Arg Asp Gln Gly Pro Asn Val Cys Ala
 30                  35                  40                  45

ctt caa cag att ttg ggc acc aaa aag aaa tac ttc agc act tgt aag      194
Leu Gln Gln Ile Leu Gly Thr Lys Lys Lys Tyr Phe Ser Thr Cys Lys
                 50                  55                  60

aac tgg tat aaa aag tcc atc tgt gga cag aaa acg act gtg tta tat      242
Asn Trp Tyr Lys Lys Ser Ile Cys Gly Gln Lys Thr Thr Val Leu Tyr
             65                  70                  75

gaa tgt tgc cct ggt tat atg aga atg gaa gga atg aaa ggc tgc cca      290
Glu Cys Cys Pro Gly Tyr Met Arg Met Glu Gly Met Lys Gly Cys Pro
         80                  85                  90

gca gtt ttg ccc att gac cat gtt tat ggc act ctg ggc atc gtg gga      338
Ala Val Leu Pro Ile Asp His Val Tyr Gly Thr Leu Gly Ile Val Gly
     95                 100                 105

gcc acc aca acg cag cgc tat tct gac gcc tca aaa ctg agg gag gag      386
Ala Thr Thr Thr Gln Arg Tyr Ser Asp Ala Ser Lys Leu Arg Glu Glu
110                 115                 120                 125

atc gag gga aag gga tcc ttc act tac ttt gca ccg agt aat gag gct      434
Ile Glu Gly Lys Gly Ser Phe Thr Tyr Phe Ala Pro Ser Asn Glu Ala
                130                 135                 140

tgg gac aac ttg gat tct gat atc cgt aga ggt ttg gag agc aac gtg      482
Trp Asp Asn Leu Asp Ser Asp Ile Arg Arg Gly Leu Glu Ser Asn Val
            145                 150                 155

aat gtt gaa tta ctg aat gct tta cat agt cac atg att aat aag aga      530
Asn Val Glu Leu Leu Asn Ala Leu His Ser His Met Ile Asn Lys Arg
        160                 165                 170

atg ttg acc aag gac tta aaa aat ggc atg att att cct tca atg tat      578
Met Leu Thr Lys Asp Leu Lys Asn Gly Met Ile Ile Pro Ser Met Tyr
    175                 180                 185

aac aat ttg ggg ctt ttc att aac cat tat cct aat ggg gtt gtc act      626
Asn Asn Leu Gly Leu Phe Ile Asn His Tyr Pro Asn Gly Val Val Thr
190                 195                 200                 205

gtt aat tgt gct cga atc atc cat ggg aac cag att gca aca aat ggt      674
Val Asn Cys Ala Arg Ile Ile His Gly Asn Gln Ile Ala Thr Asn Gly
                210                 215                 220

gtt gtc cat gtc att gac cgt gtg ctt aca caa att ggt acc tca att      722
Val Val His Val Ile Asp Arg Val Leu Thr Gln Ile Gly Thr Ser Ile
            225                 230                 235

caa gac ttc att gaa gca gaa gat gac ctt tca tct ttt aga gca gct      770
Gln Asp Phe Ile Glu Ala Glu Asp Asp Leu Ser Ser Phe Arg Ala Ala
        240                 245                 250

gcc atc aca tcg gac ata ttg gag gcc ctt gga aga gac ggt cac ttc      818
Ala Ile Thr Ser Asp Ile Leu Glu Ala Leu Gly Arg Asp Gly His Phe
    255                 260                 265

aca ctc ttt gct ccc acc aat gag gct ttt gag aaa ctt cca cga ggt      866
Thr Leu Phe Ala Pro Thr Asn Glu Ala Phe Glu Lys Leu Pro Arg Gly
270                 275                 280                 285
```

-continued

```
gtc cta gaa agg atc atg gga gac aaa gtg gct tcc gaa gct ctt atg      914
Val Leu Glu Arg Ile Met Gly Asp Lys Val Ala Ser Glu Ala Leu Met
            290                 295                 300

aag tac cac atc tta aat act ctc cag tgt tct gag tct att atg gga      962
Lys Tyr His Ile Leu Asn Thr Leu Gln Cys Ser Glu Ser Ile Met Gly
            305                 310                 315

gga gca gtc ttt gag acg ctg gaa gga aat aca att gag ata gga tgt     1010
Gly Ala Val Phe Glu Thr Leu Glu Gly Asn Thr Ile Glu Ile Gly Cys
        320                 325                 330

gac ggt gac agt ata aca gta aat gga atc aaa atg gtg aac aaa aag     1058
Asp Gly Asp Ser Ile Thr Val Asn Gly Ile Lys Met Val Asn Lys Lys
    335                 340                 345

gat att gtg aca aat aat ggt gtg atc cat ttg att gat cag gtc cta     1106
Asp Ile Val Thr Asn Asn Gly Val Ile His Leu Ile Asp Gln Val Leu
350                 355                 360                 365

att cct gat tct gcc aaa caa gtt att gag ctg gct gga aaa cag caa     1154
Ile Pro Asp Ser Ala Lys Gln Val Ile Glu Leu Ala Gly Lys Gln Gln
            370                 375                 380

acc acc ttc acg gat ctt gtg gcc caa tta ggc ttg gca tct gct ctg     1202
Thr Thr Phe Thr Asp Leu Val Ala Gln Leu Gly Leu Ala Ser Ala Leu
            385                 390                 395

agg cca gat gga gaa tac act ttg ctg gca cct gtg aat aat gca ttt     1250
Arg Pro Asp Gly Glu Tyr Thr Leu Leu Ala Pro Val Asn Asn Ala Phe
        400                 405                 410

tct gat gat act ctc agc atg gat cag cgc ctc ctt aaa tta att ctg     1298
Ser Asp Asp Thr Leu Ser Met Asp Gln Arg Leu Leu Lys Leu Ile Leu
    415                 420                 425

cag aat cac ata ttg aaa gta aaa gtt ggc ctt aat gag ctt tac aac     1346
Gln Asn His Ile Leu Lys Val Lys Val Gly Leu Asn Glu Leu Tyr Asn
430                 435                 440                 445

ggg caa ata ctg gaa acc atc gga ggc aaa cag ctc aga gtc ttc gta     1394
Gly Gln Ile Leu Glu Thr Ile Gly Gly Lys Gln Leu Arg Val Phe Val
            450                 455                 460

tat cgt aca gct gtc tgc att gaa aat tca tgc atg gag aaa ggg agt     1442
Tyr Arg Thr Ala Val Cys Ile Glu Asn Ser Cys Met Glu Lys Gly Ser
            465                 470                 475

aag caa ggg aga aac ggt gcg att cac ata ttc cgc gag atc atc aag     1490
Lys Gln Gly Arg Asn Gly Ala Ile His Ile Phe Arg Glu Ile Ile Lys
        480                 485                 490

cca gca gag aaa tcc ctc cat gaa aag tta aaa caa gat aag cgc ttt     1538
Pro Ala Glu Lys Ser Leu His Glu Lys Leu Lys Gln Asp Lys Arg Phe
    495                 500                 505

agc acc ttc ctc agc cta ctt gaa gct gca gac ttg aaa gag ctc ctg     1586
Ser Thr Phe Leu Ser Leu Leu Glu Ala Ala Asp Leu Lys Glu Leu Leu
510                 515                 520                 525

aca caa cct gga gac tgg aca tta ttt gtg cca acc aat gat gct ttt     1634
Thr Gln Pro Gly Asp Trp Thr Leu Phe Val Pro Thr Asn Asp Ala Phe
            530                 535                 540

aag gga atg act agt gaa gaa aaa gaa att ctg ata cgg gac aaa aat     1682
Lys Gly Met Thr Ser Glu Glu Lys Glu Ile Leu Ile Arg Asp Lys Asn
            545                 550                 555

gct ctt caa aac atc att ctt tat cac ctg aca cca gga gtt ttc att     1730
Ala Leu Gln Asn Ile Ile Leu Tyr His Leu Thr Pro Gly Val Phe Ile
        560                 565                 570

gga aaa gga ttt gaa cct ggt gtt act aac att tta aag acc aca caa     1778
Gly Lys Gly Phe Glu Pro Gly Val Thr Asn Ile Leu Lys Thr Thr Gln
    575                 580                 585

gga agc aaa atc ttt ctg aaa gaa gta aat gat aca ctt ctg gtg aat     1826
Gly Ser Lys Ile Phe Leu Lys Glu Val Asn Asp Thr Leu Leu Val Asn
590                 595                 600                 605
```

-continued

```
gaa ttg aaa tca aaa gaa tct gac atc atg aca aca aat ggt gta att     1874
Glu Leu Lys Ser Lys Glu Ser Asp Ile Met Thr Thr Asn Gly Val Ile
                610                 615                 620

cat gtt gta gat aaa ctc ctc tat cca gca gac aca cct gtt gga aat     1922
His Val Val Asp Lys Leu Leu Tyr Pro Ala Asp Thr Pro Val Gly Asn
            625                 630                 635

gat caa ctg ctg gaa ata ctt aat aaa tta atc aaa tac atc caa att     1970
Asp Gln Leu Leu Glu Ile Leu Asn Lys Leu Ile Lys Tyr Ile Gln Ile
        640                 645                 650

aag ttt gtt cgt ggt agc acc ttc aaa gaa atc ccc gtg act gtc tat     2018
Lys Phe Val Arg Gly Ser Thr Phe Lys Glu Ile Pro Val Thr Val Tyr
    655                 660                 665

aag cca att att aaa aaa tac acc aaa atc att gat gga gtg cct gtg     2066
Lys Pro Ile Ile Lys Lys Tyr Thr Lys Ile Ile Asp Gly Val Pro Val
670                 675                 680                 685

gaa ata act gaa aaa gag aca cga gaa gaa cga atc att aca ggt cct     2114
Glu Ile Thr Glu Lys Glu Thr Arg Glu Glu Arg Ile Ile Thr Gly Pro
                690                 695                 700

gaa ata aaa tac act agg att tct act gga ggt gga gaa aca gaa gaa     2162
Glu Ile Lys Tyr Thr Arg Ile Ser Thr Gly Gly Gly Glu Thr Glu Glu
            705                 710                 715

act ctg aag aaa ttg tta caa gaa gag gtc acc aag gtc acc aaa ttc     2210
Thr Leu Lys Lys Leu Leu Gln Glu Glu Val Thr Lys Val Thr Lys Phe
        720                 725                 730

att gaa ggt ggt gat ggt cat tta ttt gaa gat gaa gaa att aaa aga     2258
Ile Glu Gly Gly Asp Gly His Leu Phe Glu Asp Glu Glu Ile Lys Arg
    735                 740                 745

ctg ctt cag gga gac aca ccc gtg agg aag ttg caa gcc aac aaa aaa     2306
Leu Leu Gln Gly Asp Thr Pro Val Arg Lys Leu Gln Ala Asn Lys Lys
750                 755                 760                 765

gtt caa ggt tct aga aga cga tta agg gaa ggt cgt tct cag tga         2351
Val Gln Gly Ser Arg Arg Arg Leu Arg Glu Gly Arg Ser Gln  *
                770                 775

aaatccaaaa accagaaaaa aatgtttata caaccctaag tcaataacct gaccttagaa   2411

aattgtgaga gccaagttga cttcaggaac tgaaacatca gcacaaagaa gcaatcatca   2471

aataattctg aacacaaatt taatattttt ttttctgaat gagaaacatg agggaaattg   2531

tggagttagc ctcctgtggt aaaggaattg aagaaaatat aacaccttac accctttttc   2591

atcttgacat taaaagttct ggctaacttt ggaatccatt agagaaaaat ccttgtcacc   2651

agattcatta caattcaaat cgaagagttg tgaactgtta tcccattgaa aagaccgagc   2711

cttgtatgta tgttatggat acataaaatg cacgcaagcc attatctctc catgggaagc   2771

taagttataa aaataggtgc ttggtgtaca aaacttttta tatcaaaagg ctttgcacat   2831

ttctatatga gtgggtttac tggtaaatta tgttattttt tacaactaat tttgtactct   2891

cagaatgttt gtcatatgct tcttgcaatg catatttttt aatctcaaac gtttcaataa   2951

aaccattttt cagatataaa gagaattact tcaaattgag taattcagaa aaactcaaga   3011

tttaagttaa aaagtggttt ggacttggga a                                  3042


<210> SEQ ID NO 44
<211> LENGTH: 779
<212> TYPE: PRT
<213> ORGANISM: human

<400> SEQUENCE: 44

Met Ile Pro Phe Leu Pro Met Phe Ser Leu Leu Leu Leu Leu Ile Val
 1               5                  10                  15
```

-continued

```
Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430
```

-continued

```
Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Lys Pro Ile
            660                 665                 670

Ile Lys Lys Tyr Thr Lys Ile Ile Asp Gly Val Pro Val Glu Ile Thr
        675                 680                 685

Glu Lys Glu Thr Arg Glu Glu Arg Ile Ile Thr Gly Pro Glu Ile Lys
    690                 695                 700

Tyr Thr Arg Ile Ser Thr Gly Gly Gly Glu Thr Glu Glu Thr Leu Lys
705                 710                 715                 720

Lys Leu Leu Gln Glu Glu Val Thr Lys Val Thr Lys Phe Ile Glu Gly
                725                 730                 735

Gly Asp Gly His Leu Phe Glu Asp Glu Glu Ile Lys Arg Leu Leu Gln
            740                 745                 750

Gly Asp Thr Pro Val Arg Lys Leu Gln Ala Asn Lys Lys Val Gln Gly
        755                 760                 765

Ser Arg Arg Arg Leu Arg Glu Gly Arg Ser Gln
    770                 775
```

<210> SEQ ID NO 45
<211> LENGTH: 2958
<212> TYPE: DNA
<213> ORGANISM: human
<220> FEATURE:
<221> NAME/KEY: CDS
<222> LOCATION: (12)...(2267)

<400> SEQUENCE: 45

```
agagactcaa g atg att ccc ttt tta ccc atg ttt tct cta cta ttg ctg      50
             Met Ile Pro Phe Leu Pro Met Phe Ser Leu Leu Leu Leu
```

-continued

```
                  1               5                  10

ctt att gtt aac cct ata aac gcc aac aat cat tat gac aag atc ttg        98
Leu Ile Val Asn Pro Ile Asn Ala Asn Asn His Tyr Asp Lys Ile Leu
     15                  20                  25

gct cat agt cgt atc agg ggt cgg gac caa ggc cca aat gtc tgt gcc       146
Ala His Ser Arg Ile Arg Gly Arg Asp Gln Gly Pro Asn Val Cys Ala
 30                  35                  40                  45

ctt caa cag att ttg ggc acc aaa aag aaa tac ttc agc act tgt aag       194
Leu Gln Gln Ile Leu Gly Thr Lys Lys Lys Tyr Phe Ser Thr Cys Lys
                 50                  55                  60

aac tgg tat aaa aag tcc atc tgt gga cag aaa acg act gtg tta tat       242
Asn Trp Tyr Lys Lys Ser Ile Cys Gly Gln Lys Thr Thr Val Leu Tyr
             65                  70                  75

gaa tgt tgc cct ggt tat atg aga atg gaa gga atg aaa ggc tgc cca       290
Glu Cys Cys Pro Gly Tyr Met Arg Met Glu Gly Met Lys Gly Cys Pro
         80                  85                  90

gca gtt ttg ccc att gac cat gtt tat ggc act ctg ggc atc gtg gga       338
Ala Val Leu Pro Ile Asp His Val Tyr Gly Thr Leu Gly Ile Val Gly
     95                 100                 105

gcc acc aca acg cag cgc tat tct gac gcc tca aaa ctg agg gag gag       386
Ala Thr Thr Thr Gln Arg Tyr Ser Asp Ala Ser Lys Leu Arg Glu Glu
110                 115                 120                 125

atc gag gga aag gga tcc ttc act tac ttt gca ccg agt aat gag gct       434
Ile Glu Gly Lys Gly Ser Phe Thr Tyr Phe Ala Pro Ser Asn Glu Ala
                130                 135                 140

tgg gac aac ttg gat tct gat atc cgt aga ggt ttg gag agc aac gtg       482
Trp Asp Asn Leu Asp Ser Asp Ile Arg Arg Gly Leu Glu Ser Asn Val
            145                 150                 155

aat gtt gaa tta ctg aat gct tta cat agt cac atg att aat aag aga       530
Asn Val Glu Leu Leu Asn Ala Leu His Ser His Met Ile Asn Lys Arg
        160                 165                 170

atg ttg acc aag gac tta aaa aat ggc atg att att cct tca atg tat       578
Met Leu Thr Lys Asp Leu Lys Asn Gly Met Ile Ile Pro Ser Met Tyr
    175                 180                 185

aac aat ttg ggg ctt ttc att aac cat tat cct aat ggg gtt gtc act       626
Asn Asn Leu Gly Leu Phe Ile Asn His Tyr Pro Asn Gly Val Val Thr
190                 195                 200                 205

gtt aat tgt gct cga atc atc cat ggg aac cag att gca aca aat ggt       674
Val Asn Cys Ala Arg Ile Ile His Gly Asn Gln Ile Ala Thr Asn Gly
                210                 215                 220

gtt gtc cat gtc att gac cgt gtg ctt aca caa att ggt acc tca att       722
Val Val His Val Ile Asp Arg Val Leu Thr Gln Ile Gly Thr Ser Ile
            225                 230                 235

caa gac ttc att gaa gca gaa gat gac ctt tca tct ttt aga gca gct       770
Gln Asp Phe Ile Glu Ala Glu Asp Asp Leu Ser Ser Phe Arg Ala Ala
        240                 245                 250

gcc atc aca tcg gac ata ttg gag gcc ctt gga aga gac ggt cac ttc       818
Ala Ile Thr Ser Asp Ile Leu Glu Ala Leu Gly Arg Asp Gly His Phe
    255                 260                 265

aca ctc ttt gct ccc acc aat gag gct ttt gag aaa ctt cca cga ggt       866
Thr Leu Phe Ala Pro Thr Asn Glu Ala Phe Glu Lys Leu Pro Arg Gly
270                 275                 280                 285

gtc cta gaa agg atc atg gga gac aaa gtg gct tcc gaa gct ctt atg       914
Val Leu Glu Arg Ile Met Gly Asp Lys Val Ala Ser Glu Ala Leu Met
                290                 295                 300

aag tac cac atc tta aat act ctc cag tgt tct gag tct att atg gga       962
Lys Tyr His Ile Leu Asn Thr Leu Gln Cys Ser Glu Ser Ile Met Gly
            305                 310                 315

gga gca gtc ttt gag acg ctg gaa gga aat aca att gag ata gga tgt      1010
```

-continued

```
Gly Ala Val Phe Glu Thr Leu Glu Gly Asn Thr Ile Glu Ile Gly Cys
        320                 325                 330

gac ggt gac agt ata aca gta aat gga atc aaa atg gtg aac aaa aag      1058
Asp Gly Asp Ser Ile Thr Val Asn Gly Ile Lys Met Val Asn Lys Lys
    335                 340                 345

gat att gtg aca aat aat ggt gtg atc cat ttg att gat cag gtc cta      1106
Asp Ile Val Thr Asn Asn Gly Val Ile His Leu Ile Asp Gln Val Leu
350                 355                 360                 365

att cct gat tct gcc aaa caa gtt att gag ctg gct gga aaa cag caa      1154
Ile Pro Asp Ser Ala Lys Gln Val Ile Glu Leu Ala Gly Lys Gln Gln
                370                 375                 380

acc acc ttc acg gat ctt gtg gcc caa tta ggc ttg gca tct gct ctg      1202
Thr Thr Phe Thr Asp Leu Val Ala Gln Leu Gly Leu Ala Ser Ala Leu
            385                 390                 395

agg cca gat gga gaa tac act ttg ctg gca cct gtg aat aat gca ttt      1250
Arg Pro Asp Gly Glu Tyr Thr Leu Leu Ala Pro Val Asn Asn Ala Phe
        400                 405                 410

tct gat gat act ctc agc atg gat cag cgc ctc ctt aaa tta att ctg      1298
Ser Asp Asp Thr Leu Ser Met Asp Gln Arg Leu Leu Lys Leu Ile Leu
    415                 420                 425

cag aat cac ata ttg aaa gta aaa gtt ggc ctt aat gag ctt tac aac      1346
Gln Asn His Ile Leu Lys Val Lys Val Gly Leu Asn Glu Leu Tyr Asn
430                 435                 440                 445

ggg caa ata ctg gaa acc atc gga ggc aaa cag ctc aga gtc ttc gta      1394
Gly Gln Ile Leu Glu Thr Ile Gly Gly Lys Gln Leu Arg Val Phe Val
                450                 455                 460

tat cgt aca gct gtc tgc att gaa aat tca tgc atg gag aaa ggg agt      1442
Tyr Arg Thr Ala Val Cys Ile Glu Asn Ser Cys Met Glu Lys Gly Ser
            465                 470                 475

aag caa ggg aga aac ggt gcg att cac ata ttc cgc gag atc atc aag      1490
Lys Gln Gly Arg Asn Gly Ala Ile His Ile Phe Arg Glu Ile Ile Lys
        480                 485                 490

cca gca gag aaa tcc ctc cat gaa aag tta aaa caa gat aag cgc ttt      1538
Pro Ala Glu Lys Ser Leu His Glu Lys Leu Lys Gln Asp Lys Arg Phe
    495                 500                 505

agc acc ttc ctc agc cta ctt gaa gct gca gac ttg aaa gag ctc ctg      1586
Ser Thr Phe Leu Ser Leu Leu Glu Ala Ala Asp Leu Lys Glu Leu Leu
510                 515                 520                 525

aca caa cct gga gac tgg aca tta ttt gtg cca acc aat gat gct ttt      1634
Thr Gln Pro Gly Asp Trp Thr Leu Phe Val Pro Thr Asn Asp Ala Phe
                530                 535                 540

aag gga atg act agt gaa gaa aaa gaa att ctg ata cgg gac aaa aat      1682
Lys Gly Met Thr Ser Glu Glu Lys Glu Ile Leu Ile Arg Asp Lys Asn
            545                 550                 555

gct ctt caa aac atc att ctt tat cac ctg aca cca gga gtt ttc att      1730
Ala Leu Gln Asn Ile Ile Leu Tyr His Leu Thr Pro Gly Val Phe Ile
        560                 565                 570

gga aaa gga ttt gaa cct ggt gtt act aac att tta aag acc aca caa      1778
Gly Lys Gly Phe Glu Pro Gly Val Thr Asn Ile Leu Lys Thr Thr Gln
    575                 580                 585

gga agc aaa atc ttt ctg aaa gaa gta aat gat aca ctt ctg gtg aat      1826
Gly Ser Lys Ile Phe Leu Lys Glu Val Asn Asp Thr Leu Leu Val Asn
590                 595                 600                 605

gaa ttg aaa tca aaa gaa tct gac atc atg aca aca aat ggt gta att      1874
Glu Leu Lys Ser Lys Glu Ser Asp Ile Met Thr Thr Asn Gly Val Ile
                610                 615                 620

cat gtt gta gat aaa ctc ctc tat cca gca gac aca cct gtt gga aat      1922
His Val Val Asp Lys Leu Leu Tyr Pro Ala Asp Thr Pro Val Gly Asn
            625                 630                 635
```

-continued

```
gat caa ctg ctg gaa ata ctt aat aaa tta atc aaa tac atc caa att     1970
Asp Gln Leu Leu Glu Ile Leu Asn Lys Leu Ile Lys Tyr Ile Gln Ile
        640                 645                 650

aag ttt gtt cgt ggt agc acc ttc aaa gaa atc ccc gtg act gtc tat     2018
Lys Phe Val Arg Gly Ser Thr Phe Lys Glu Ile Pro Val Thr Val Tyr
    655                 660                 665

aag cca att att aaa aaa tac acc aaa atc att gat gga gtg cct gtg     2066
Lys Pro Ile Ile Lys Lys Tyr Thr Lys Ile Ile Asp Gly Val Pro Val
670                 675                 680                 685

gaa ata act gaa aaa gag aca cga gaa gaa cga atc att aca ggt cct     2114
Glu Ile Thr Glu Lys Glu Thr Arg Glu Glu Arg Ile Ile Thr Gly Pro
                690                 695                 700

gaa ata aaa tac act agg att tct act gga ggt gga gaa aca gaa gaa     2162
Glu Ile Lys Tyr Thr Arg Ile Ser Thr Gly Gly Gly Glu Thr Glu Glu
            705                 710                 715

act ctg aag aaa ttg tta caa gaa gac aca ccc gtg agg aag ttg caa     2210
Thr Leu Lys Lys Leu Leu Gln Glu Asp Thr Pro Val Arg Lys Leu Gln
        720                 725                 730

gcc aac aaa aaa gtt caa ggt tct aga aga cga tta agg gaa ggt cgt     2258
Ala Asn Lys Lys Val Gln Gly Ser Arg Arg Arg Leu Arg Glu Gly Arg
    735                 740                 745

tct cag tga aaatccaaaa accagaaaaa aatgtttata caaccctaag             2307
Ser Gln  *
750

tcaataacct gaccttagaa aattgtgaga gccaagttga cttcaggaac tgaaacatca   2367

gcacaaagaa gcaatcatca aataattctg aacacaaatt taatattttt ttttctgaat   2427

gagaaacatg agggaaattg tggagttagc ctcctgtggt aaaggaattg aagaaaatat   2487

aacaccttac acccttttc atcttgacat taaaagttct ggctaacttt ggaatccatt   2547

agagaaaaat ccttgtcacc agattcatta caattcaaat cgaagagttg tgaactgtta   2607

tcccattgaa aagaccgagc cttgtatgta tgttatggat acataaaatg cacgcaagcc   2667

attatctctc catgggaagc taagttataa aaataggtgc ttggtgtaca aaacttttta   2727

tatcaaaagg ctttgcacat ttctatatga gtgggtttac tggtaaatta tgttattttt   2787

tacaactaat tttgtactct cagaatgttt gtcatatgct tcttgcaatg catatttttt   2847

aatctcaaac gtttcaataa aaccattttt cagatataaa gagaattact tcaaattgag   2907

taattcagaa aaactcaaga tttaagttaa aaagtggttt ggacttggga a            2958


<210> SEQ ID NO 46
<211> LENGTH: 751
<212> TYPE: PRT
<213> ORGANISM: human

<400> SEQUENCE: 46

Met Ile Pro Phe Leu Pro Met Phe Ser Leu Leu Leu Leu Leu Ile Val
 1               5                  10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95
```

-continued

```
Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510
```

-continued

```
Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Lys Pro Ile
            660                 665                 670

Ile Lys Lys Tyr Thr Lys Ile Ile Asp Gly Val Pro Val Glu Ile Thr
        675                 680                 685

Glu Lys Glu Thr Arg Glu Glu Arg Ile Ile Thr Gly Pro Glu Ile Lys
    690                 695                 700

Tyr Thr Arg Ile Ser Thr Gly Gly Gly Glu Thr Glu Glu Thr Leu Lys
705                 710                 715                 720

Lys Leu Leu Gln Glu Asp Thr Pro Val Arg Lys Leu Gln Ala Asn Lys
                725                 730                 735

Lys Val Gln Gly Ser Arg Arg Arg Leu Arg Glu Gly Arg Ser Gln
            740                 745                 750


<210> SEQ ID NO 47
<211> LENGTH: 2952
<212> TYPE: DNA
<213> ORGANISM: human
<220> FEATURE:
<221> NAME/KEY: CDS
<222> LOCATION: (12)...(2261)

<400> SEQUENCE: 47

agagactcaa g atg att ccc ttt tta ccc atg ttt tct cta cta ttg ctg       50
             Met Ile Pro Phe Leu Pro Met Phe Ser Leu Leu Leu Leu
               1               5                  10

ctt att gtt aac cct ata aac gcc aac aat cat tat gac aag atc ttg        98
Leu Ile Val Asn Pro Ile Asn Ala Asn Asn His Tyr Asp Lys Ile Leu
     15                  20                  25

gct cat agt cgt atc agg ggt cgg gac caa ggc cca aat gtc tgt gcc       146
Ala His Ser Arg Ile Arg Gly Arg Asp Gln Gly Pro Asn Val Cys Ala
 30                  35                  40                  45

ctt caa cag att ttg ggc acc aaa aag aaa tac ttc agc act tgt aag       194
Leu Gln Gln Ile Leu Gly Thr Lys Lys Lys Tyr Phe Ser Thr Cys Lys
                 50                  55                  60

aac tgg tat aaa aag tcc atc tgt gga cag aaa acg act gtg tta tat       242
Asn Trp Tyr Lys Lys Ser Ile Cys Gly Gln Lys Thr Thr Val Leu Tyr
             65                  70                  75

gaa tgt tgc cct ggt tat atg aga atg gaa gga atg aaa ggc tgc cca       290
Glu Cys Cys Pro Gly Tyr Met Arg Met Glu Gly Met Lys Gly Cys Pro
         80                  85                  90
```

-continued

```
gca gtt ttg ccc att gac cat gtt tat ggc act ctg ggc atc gtg gga      338
Ala Val Leu Pro Ile Asp His Val Tyr Gly Thr Leu Gly Ile Val Gly
     95                 100                 105

gcc acc aca acg cag cgc tat tct gac gcc tca aaa ctg agg gag gag      386
Ala Thr Thr Thr Gln Arg Tyr Ser Asp Ala Ser Lys Leu Arg Glu Glu
110                 115                 120                 125

atc gag gga aag gga tcc ttc act tac ttt gca ccg agt aat gag gct      434
Ile Glu Gly Lys Gly Ser Phe Thr Tyr Phe Ala Pro Ser Asn Glu Ala
                130                 135                 140

tgg gac aac ttg gat tct gat atc cgt aga ggt ttg gag agc aac gtg      482
Trp Asp Asn Leu Asp Ser Asp Ile Arg Arg Gly Leu Glu Ser Asn Val
            145                 150                 155

aat gtt gaa tta ctg aat gct tta cat agt cac atg att aat aag aga      530
Asn Val Glu Leu Leu Asn Ala Leu His Ser His Met Ile Asn Lys Arg
        160                 165                 170

atg ttg acc aag gac tta aaa aat ggc atg att att cct tca atg tat      578
Met Leu Thr Lys Asp Leu Lys Asn Gly Met Ile Ile Pro Ser Met Tyr
    175                 180                 185

aac aat ttg ggg ctt ttc att aac cat tat cct aat ggg gtt gtc act      626
Asn Asn Leu Gly Leu Phe Ile Asn His Tyr Pro Asn Gly Val Val Thr
190                 195                 200                 205

gtt aat tgt gct cga atc atc cat ggg aac cag att gca aca aat ggt      674
Val Asn Cys Ala Arg Ile Ile His Gly Asn Gln Ile Ala Thr Asn Gly
                210                 215                 220

gtt gtc cat gtc att gac cgt gtg ctt aca caa att ggt acc tca att      722
Val Val His Val Ile Asp Arg Val Leu Thr Gln Ile Gly Thr Ser Ile
            225                 230                 235

caa gac ttc att gaa gca gaa gat gac ctt tca tct ttt aga gca gct      770
Gln Asp Phe Ile Glu Ala Glu Asp Asp Leu Ser Ser Phe Arg Ala Ala
        240                 245                 250

gcc atc aca tcg gac ata ttg gag gcc ctt gga aga gac ggt cac ttc      818
Ala Ile Thr Ser Asp Ile Leu Glu Ala Leu Gly Arg Asp Gly His Phe
    255                 260                 265

aca ctc ttt gct ccc acc aat gag gct ttt gag aaa ctt cca cga ggt      866
Thr Leu Phe Ala Pro Thr Asn Glu Ala Phe Glu Lys Leu Pro Arg Gly
270                 275                 280                 285

gtc cta gaa agg atc atg gga gac aaa gtg gct tcc gaa gct ctt atg      914
Val Leu Glu Arg Ile Met Gly Asp Lys Val Ala Ser Glu Ala Leu Met
                290                 295                 300

aag tac cac atc tta aat act ctc cag tgt tct gag tct att atg gga      962
Lys Tyr His Ile Leu Asn Thr Leu Gln Cys Ser Glu Ser Ile Met Gly
            305                 310                 315

gga gca gtc ttt gag acg ctg gaa gga aat aca att gag ata gga tgt     1010
Gly Ala Val Phe Glu Thr Leu Glu Gly Asn Thr Ile Glu Ile Gly Cys
        320                 325                 330

gac ggt gac agt ata aca gta aat gga atc aaa atg gtg aac aaa aag     1058
Asp Gly Asp Ser Ile Thr Val Asn Gly Ile Lys Met Val Asn Lys Lys
    335                 340                 345

gat att gtg aca aat aat ggt gtg atc cat ttg att gat cag gtc cta     1106
Asp Ile Val Thr Asn Asn Gly Val Ile His Leu Ile Asp Gln Val Leu
350                 355                 360                 365

att cct gat tct gcc aaa caa gtt att gag ctg gct gga aaa cag caa     1154
Ile Pro Asp Ser Ala Lys Gln Val Ile Glu Leu Ala Gly Lys Gln Gln
                370                 375                 380

acc acc ttc acg gat ctt gtg gcc caa tta ggc ttg gca tct gct ctg     1202
Thr Thr Phe Thr Asp Leu Val Ala Gln Leu Gly Leu Ala Ser Ala Leu
            385                 390                 395

agg cca gat gga gaa tac act ttg ctg gca cct gtg aat aat gca ttt     1250
Arg Pro Asp Gly Glu Tyr Thr Leu Leu Ala Pro Val Asn Asn Ala Phe
```

-continued

```
        400                 405                 410

tct gat gat act ctc agc atg gat cag cgc ctc ctt aaa tta att ctg     1298
Ser Asp Asp Thr Leu Ser Met Asp Gln Arg Leu Leu Lys Leu Ile Leu
    415                 420                 425

cag aat cac ata ttg aaa gta aaa gtt ggc ctt aat gag ctt tac aac     1346
Gln Asn His Ile Leu Lys Val Lys Val Gly Leu Asn Glu Leu Tyr Asn
430                 435                 440                 445

ggg caa ata ctg gaa acc atc gga ggc aaa cag ctc aga gtc ttc gta     1394
Gly Gln Ile Leu Glu Thr Ile Gly Gly Lys Gln Leu Arg Val Phe Val
                450                 455                 460

tat cgt aca gct gtc tgc att gaa aat tca tgc atg gag aaa ggg agt     1442
Tyr Arg Thr Ala Val Cys Ile Glu Asn Ser Cys Met Glu Lys Gly Ser
            465                 470                 475

aag caa ggg aga aac ggt gcg att cac ata ttc cgc gag atc atc aag     1490
Lys Gln Gly Arg Asn Gly Ala Ile His Ile Phe Arg Glu Ile Ile Lys
        480                 485                 490

cca gca gag aaa tcc ctc cat gaa aag tta aaa caa gat aag cgc ttt     1538
Pro Ala Glu Lys Ser Leu His Glu Lys Leu Lys Gln Asp Lys Arg Phe
    495                 500                 505

agc acc ttc ctc agc cta ctt gaa gct gca gac ttg aaa gag ctc ctg     1586
Ser Thr Phe Leu Ser Leu Leu Glu Ala Ala Asp Leu Lys Glu Leu Leu
510                 515                 520                 525

aca caa cct gga gac tgg aca tta ttt gtg cca acc aat gat gct ttt     1634
Thr Gln Pro Gly Asp Trp Thr Leu Phe Val Pro Thr Asn Asp Ala Phe
                530                 535                 540

aag gga atg act agt gaa gaa aaa gaa att ctg ata cgg gac aaa aat     1682
Lys Gly Met Thr Ser Glu Glu Lys Glu Ile Leu Ile Arg Asp Lys Asn
            545                 550                 555

gct ctt caa aac atc att ctt tat cac ctg aca cca gga gtt ttc att     1730
Ala Leu Gln Asn Ile Ile Leu Tyr His Leu Thr Pro Gly Val Phe Ile
        560                 565                 570

gga aaa gga ttt gaa cct ggt gtt act aac att tta aag acc aca caa     1778
Gly Lys Gly Phe Glu Pro Gly Val Thr Asn Ile Leu Lys Thr Thr Gln
    575                 580                 585

gga agc aaa atc ttt ctg aaa gaa gta aat gat aca ctt ctg gtg aat     1826
Gly Ser Lys Ile Phe Leu Lys Glu Val Asn Asp Thr Leu Leu Val Asn
590                 595                 600                 605

gaa ttg aaa tca aaa gaa tct gac atc atg aca aca aat ggt gta att     1874
Glu Leu Lys Ser Lys Glu Ser Asp Ile Met Thr Thr Asn Gly Val Ile
                610                 615                 620

cat gtt gta gat aaa ctc ctc tat cca gca gac aca cct gtt gga aat     1922
His Val Val Asp Lys Leu Leu Tyr Pro Ala Asp Thr Pro Val Gly Asn
            625                 630                 635

gat caa ctg ctg gaa ata ctt aat aaa tta atc aaa tac atc caa att     1970
Asp Gln Leu Leu Glu Ile Leu Asn Lys Leu Ile Lys Tyr Ile Gln Ile
        640                 645                 650

aag ttt gtt cgt ggt agc acc ttc aaa gaa atc ccc gtg act gtc tat     2018
Lys Phe Val Arg Gly Ser Thr Phe Lys Glu Ile Pro Val Thr Val Tyr
    655                 660                 665

agt cct gaa ata aaa tac act agg att tct act gga ggt gga gaa aca     2066
Ser Pro Glu Ile Lys Tyr Thr Arg Ile Ser Thr Gly Gly Gly Glu Thr
670                 675                 680                 685

gaa gaa act ctg aag aaa ttg tta caa gaa gag gtc acc aag gtc acc     2114
Glu Glu Thr Leu Lys Lys Leu Leu Gln Glu Glu Val Thr Lys Val Thr
                690                 695                 700

aaa ttc att gaa ggt ggt gat ggt cat tta ttt gaa gat gaa gaa att     2162
Lys Phe Ile Glu Gly Gly Asp Gly His Leu Phe Glu Asp Glu Glu Ile
            705                 710                 715

aaa aga ctg ctt cag gga gac aca ccc gtg agg aag ttg caa gcc aac     2210
```

-continued

```
Lys Arg Leu Leu Gln Gly Asp Thr Pro Val Arg Lys Leu Gln Ala Asn
        720                 725                 730

aaa aaa gtt caa ggt tct aga aga cga tta agg gaa ggt cgt tct cag     2258
Lys Lys Val Gln Gly Ser Arg Arg Arg Leu Arg Glu Gly Arg Ser Gln
    735                 740                 745

tga aaatccaaaa accagaaaaa aatgtttata caaccctaag tcaataacct          2311
 *

gaccttagaa aattgtgaga gccaagttga cttcaggaac tgaaacatca gcacaaagaa   2371

gcaatcatca aataattctg aacacaaatt taatattttt ttttctgaat gagaaacatg   2431

agggaaattg tggagttagc ctcctgtggt aaaggaattg aagaaaatat aacaccttac   2491

acccttttc atcttgacat taaaagttct ggctaacttt ggaatccatt agagaaaaat    2551

ccttgtcacc agattcatta caattcaaat cgaagagttg tgaactgtta tcccattgaa   2611

aagaccgagc cttgtatgta tgttatggat acataaaatg cacgcaagcc attatctctc   2671

catgggaagc taagttataa aaataggtgc ttggtgtaca aaacttttta tatcaaaagg   2731

ctttgcacat ttctatatga gtgggtttac tggtaaatta tgttattttt tacaactaat   2791

tttgtactct cagaatgttt gtcatatgct tcttgcaatg catatttttt aatctcaaac   2851

gtttcaataa aaccattttt cagatataaa gagaattact tcaaattgag taattcagaa   2911

aaactcaaga tttaagttaa aaagtggttt ggacttggga a                       2952


<210> SEQ ID NO 48
<211> LENGTH: 749
<212> TYPE: PRT
<213> ORGANISM: human

<400> SEQUENCE: 48

Met Ile Pro Phe Leu Pro Met Phe Ser Leu Leu Leu Leu Leu Ile Val
 1               5                  10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205
```

-continued

```
Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
```

-continued

```
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Ser Pro Glu
            660                 665                 670

Ile Lys Tyr Thr Arg Ile Ser Thr Gly Gly Gly Glu Thr Glu Glu Thr
        675                 680                 685

Leu Lys Lys Leu Leu Gln Glu Glu Val Thr Lys Val Thr Lys Phe Ile
    690                 695                 700

Glu Gly Gly Asp Gly His Leu Phe Glu Asp Glu Glu Ile Lys Arg Leu
705                 710                 715                 720

Leu Gln Gly Asp Thr Pro Val Arg Lys Leu Gln Ala Asn Lys Lys Val
                725                 730                 735

Gln Gly Ser Arg Arg Arg Leu Arg Glu Gly Arg Ser Gln
            740                 745


<210> SEQ ID NO 49
<211> LENGTH: 2868
<212> TYPE: DNA
<213> ORGANISM: human
<220> FEATURE:
<221> NAME/KEY: CDS
<222> LOCATION: (12)...(2177)

<400> SEQUENCE: 49

agagactcaa g atg att ccc ttt tta ccc atg ttt tct cta cta ttg ctg      50
             Met Ile Pro Phe Leu Pro Met Phe Ser Leu Leu Leu Leu
              1               5                  10

ctt att gtt aac cct ata aac gcc aac aat cat tat gac aag atc ttg       98
Leu Ile Val Asn Pro Ile Asn Ala Asn Asn His Tyr Asp Lys Ile Leu
     15                  20                  25

gct cat agt cgt atc agg ggt cgg gac caa ggc cca aat gtc tgt gcc      146
Ala His Ser Arg Ile Arg Gly Arg Asp Gln Gly Pro Asn Val Cys Ala
 30                  35                  40                  45

ctt caa cag att ttg ggc acc aaa aag aaa tac ttc agc act tgt aag      194
Leu Gln Gln Ile Leu Gly Thr Lys Lys Lys Tyr Phe Ser Thr Cys Lys
                 50                  55                  60

aac tgg tat aaa aag tcc atc tgt gga cag aaa acg act gtg tta tat      242
Asn Trp Tyr Lys Lys Ser Ile Cys Gly Gln Lys Thr Thr Val Leu Tyr
             65                  70                  75

gaa tgt tgc cct ggt tat atg aga atg gaa gga atg aaa ggc tgc cca      290
Glu Cys Cys Pro Gly Tyr Met Arg Met Glu Gly Met Lys Gly Cys Pro
         80                  85                  90

gca gtt ttg ccc att gac cat gtt tat ggc act ctg ggc atc gtg gga      338
Ala Val Leu Pro Ile Asp His Val Tyr Gly Thr Leu Gly Ile Val Gly
     95                 100                 105

gcc acc aca acg cag cgc tat tct gac gcc tca aaa ctg agg gag gag      386
Ala Thr Thr Thr Gln Arg Tyr Ser Asp Ala Ser Lys Leu Arg Glu Glu
110                 115                 120                 125

atc gag gga aag gga tcc ttc act tac ttt gca ccg agt aat gag gct      434
Ile Glu Gly Lys Gly Ser Phe Thr Tyr Phe Ala Pro Ser Asn Glu Ala
                130                 135                 140

tgg gac aac ttg gat tct gat atc cgt aga ggt ttg gag agc aac gtg      482
Trp Asp Asn Leu Asp Ser Asp Ile Arg Arg Gly Leu Glu Ser Asn Val
            145                 150                 155

aat gtt gaa tta ctg aat gct tta cat agt cac atg att aat aag aga      530
Asn Val Glu Leu Leu Asn Ala Leu His Ser His Met Ile Asn Lys Arg
        160                 165                 170

atg ttg acc aag gac tta aaa aat ggc atg att att cct tca atg tat      578
```

-continued

```
Met Leu Thr Lys Asp Leu Lys Asn Gly Met Ile Ile Pro Ser Met Tyr
    175                 180                 185

aac aat ttg ggg ctt ttc att aac cat tat cct aat ggg gtt gtc act      626
Asn Asn Leu Gly Leu Phe Ile Asn His Tyr Pro Asn Gly Val Val Thr
190                 195                 200                 205

gtt aat tgt gct cga atc atc cat ggg aac cag att gca aca aat ggt      674
Val Asn Cys Ala Arg Ile Ile His Gly Asn Gln Ile Ala Thr Asn Gly
                210                 215                 220

gtt gtc cat gtc att gac cgt gtg ctt aca caa att ggt acc tca att      722
Val Val His Val Ile Asp Arg Val Leu Thr Gln Ile Gly Thr Ser Ile
            225                 230                 235

caa gac ttc att gaa gca gaa gat gac ctt tca tct ttt aga gca gct      770
Gln Asp Phe Ile Glu Ala Glu Asp Asp Leu Ser Ser Phe Arg Ala Ala
        240                 245                 250

gcc atc aca tcg gac ata ttg gag gcc ctt gga aga gac ggt cac ttc      818
Ala Ile Thr Ser Asp Ile Leu Glu Ala Leu Gly Arg Asp Gly His Phe
    255                 260                 265

aca ctc ttt gct ccc acc aat gag gct ttt gag aaa ctt cca cga ggt      866
Thr Leu Phe Ala Pro Thr Asn Glu Ala Phe Glu Lys Leu Pro Arg Gly
270                 275                 280                 285

gtc cta gaa agg atc atg gga gac aaa gtg gct tcc gaa gct ctt atg      914
Val Leu Glu Arg Ile Met Gly Asp Lys Val Ala Ser Glu Ala Leu Met
                290                 295                 300

aag tac cac atc tta aat act ctc cag tgt tct gag tct att atg gga      962
Lys Tyr His Ile Leu Asn Thr Leu Gln Cys Ser Glu Ser Ile Met Gly
            305                 310                 315

gga gca gtc ttt gag acg ctg gaa gga aat aca att gag ata gga tgt     1010
Gly Ala Val Phe Glu Thr Leu Glu Gly Asn Thr Ile Glu Ile Gly Cys
        320                 325                 330

gac ggt gac agt ata aca gta aat gga atc aaa atg gtg aac aaa aag     1058
Asp Gly Asp Ser Ile Thr Val Asn Gly Ile Lys Met Val Asn Lys Lys
    335                 340                 345

gat att gtg aca aat aat ggt gtg atc cat ttg att gat cag gtc cta     1106
Asp Ile Val Thr Asn Asn Gly Val Ile His Leu Ile Asp Gln Val Leu
350                 355                 360                 365

att cct gat tct gcc aaa caa gtt att gag ctg gct gga aaa cag caa     1154
Ile Pro Asp Ser Ala Lys Gln Val Ile Glu Leu Ala Gly Lys Gln Gln
                370                 375                 380

acc acc ttc acg gat ctt gtg gcc caa tta ggc ttg gca tct gct ctg     1202
Thr Thr Phe Thr Asp Leu Val Ala Gln Leu Gly Leu Ala Ser Ala Leu
            385                 390                 395

agg cca gat gga gaa tac act ttg ctg gca cct gtg aat aat gca ttt     1250
Arg Pro Asp Gly Glu Tyr Thr Leu Leu Ala Pro Val Asn Asn Ala Phe
        400                 405                 410

tct gat gat act ctc agc atg gat cag cgc ctc ctt aaa tta att ctg     1298
Ser Asp Asp Thr Leu Ser Met Asp Gln Arg Leu Leu Lys Leu Ile Leu
    415                 420                 425

cag aat cac ata ttg aaa gta aaa gtt ggc ctt aat gag ctt tac aac     1346
Gln Asn His Ile Leu Lys Val Lys Val Gly Leu Asn Glu Leu Tyr Asn
430                 435                 440                 445

ggg caa ata ctg gaa acc atc gga ggc aaa cag ctc aga gtc ttc gta     1394
Gly Gln Ile Leu Glu Thr Ile Gly Gly Lys Gln Leu Arg Val Phe Val
                450                 455                 460

tat cgt aca gct gtc tgc att gaa aat tca tgc atg gag aaa ggg agt     1442
Tyr Arg Thr Ala Val Cys Ile Glu Asn Ser Cys Met Glu Lys Gly Ser
            465                 470                 475

aag caa ggg aga aac ggt gcg att cac ata ttc cgc gag atc atc aag     1490
Lys Gln Gly Arg Asn Gly Ala Ile His Ile Phe Arg Glu Ile Ile Lys
        480                 485                 490
```

-continued

```
cca gca gag aaa tcc ctc cat gaa aag tta aaa caa gat aag cgc ttt     1538
Pro Ala Glu Lys Ser Leu His Glu Lys Leu Lys Gln Asp Lys Arg Phe
    495                 500                 505

agc acc ttc ctc agc cta ctt gaa gct gca gac ttg aaa gag ctc ctg     1586
Ser Thr Phe Leu Ser Leu Leu Glu Ala Ala Asp Leu Lys Glu Leu Leu
510                 515                 520                 525

aca caa cct gga gac tgg aca tta ttt gtg cca acc aat gat gct ttt     1634
Thr Gln Pro Gly Asp Trp Thr Leu Phe Val Pro Thr Asn Asp Ala Phe
                530                 535                 540

aag gga atg act agt gaa gaa aaa gaa att ctg ata cgg gac aaa aat     1682
Lys Gly Met Thr Ser Glu Glu Lys Glu Ile Leu Ile Arg Asp Lys Asn
            545                 550                 555

gct ctt caa aac atc att ctt tat cac ctg aca cca gga gtt ttc att     1730
Ala Leu Gln Asn Ile Ile Leu Tyr His Leu Thr Pro Gly Val Phe Ile
        560                 565                 570

gga aaa gga ttt gaa cct ggt gtt act aac att tta aag acc aca caa     1778
Gly Lys Gly Phe Glu Pro Gly Val Thr Asn Ile Leu Lys Thr Thr Gln
    575                 580                 585

gga agc aaa atc ttt ctg aaa gaa gta aat gat aca ctt ctg gtg aat     1826
Gly Ser Lys Ile Phe Leu Lys Glu Val Asn Asp Thr Leu Leu Val Asn
590                 595                 600                 605

gaa ttg aaa tca aaa gaa tct gac atc atg aca aca aat ggt gta att     1874
Glu Leu Lys Ser Lys Glu Ser Asp Ile Met Thr Thr Asn Gly Val Ile
                610                 615                 620

cat gtt gta gat aaa ctc ctc tat cca gca gac aca cct gtt gga aat     1922
His Val Val Asp Lys Leu Leu Tyr Pro Ala Asp Thr Pro Val Gly Asn
            625                 630                 635

gat caa ctg ctg gaa ata ctt aat aaa tta atc aaa tac atc caa att     1970
Asp Gln Leu Leu Glu Ile Leu Asn Lys Leu Ile Lys Tyr Ile Gln Ile
        640                 645                 650

aag ttt gtt cgt ggt agc acc ttc aaa gaa atc ccc gtg act gtc tat     2018
Lys Phe Val Arg Gly Ser Thr Phe Lys Glu Ile Pro Val Thr Val Tyr
    655                 660                 665

agt cct gaa ata aaa tac act agg att tct act gga ggt gga gaa aca     2066
Ser Pro Glu Ile Lys Tyr Thr Arg Ile Ser Thr Gly Gly Gly Glu Thr
670                 675                 680                 685

gaa gaa act ctg aag aaa ttg tta caa gaa gac aca ccc gtg agg aag     2114
Glu Glu Thr Leu Lys Lys Leu Leu Gln Glu Asp Thr Pro Val Arg Lys
                690                 695                 700

ttg caa gcc aac aaa aaa gtt caa ggt tct aga aga cga tta agg gaa     2162
Leu Gln Ala Asn Lys Lys Val Gln Gly Ser Arg Arg Arg Leu Arg Glu
            705                 710                 715

ggt cgt tct cag tga aaatccaaaa accagaaaaa aatgtttata caaccctaag     2217
Gly Arg Ser Gln  *
        720

tcaataacct gaccttagaa aattgtgaga gccaagttga cttcaggaac tgaaacatca   2277

gcacaaagaa gcaatcatca aataattctg aacacaaatt taatattttt ttttctgaat   2337

gagaaacatg agggaaattg tggagttagc ctcctgtggt aaaggaattg aagaaaatat   2397

aacaccttac acccttttttc atcttgacat taaaagttct ggctaacttt ggaatccatt  2457

agagaaaaat ccttgtcacc agattcatta caattcaaat cgaagagttg tgaactgtta   2517

tcccattgaa aagaccgagc cttgtatgta tgttatggat acataaaatg cacgcaagcc   2577

attatctctc catgggaagc taagttataa aaataggtgc ttggtgtaca aaacttttta   2637

tatcaaaagg ctttgcacat ttctatatga gtgggtttac tggtaaatta tgttattttt   2697

tacaactaat tttgtactct cagaatgttt gtcatatgct tcttgcaatg catatttttt   2757

aatctcaaac gtttcaataa aaccattttt cagatataaa gagaattact tcaaattgag   2817
```

-continued

```
taattcagaa aaactcaaga tttaagttaa aaagtggttt ggacttggga a           2868


<210> SEQ ID NO 50
<211> LENGTH: 721
<212> TYPE: PRT
<213> ORGANISM: human

<400> SEQUENCE: 50

Met Ile Pro Phe Leu Pro Met Phe Ser Leu Leu Leu Leu Leu Ile Val
 1               5                  10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365
```

```
Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Ser Pro Glu
            660                 665                 670

Ile Lys Tyr Thr Arg Ile Ser Thr Gly Gly Gly Glu Thr Glu Glu Thr
        675                 680                 685

Leu Lys Lys Leu Leu Gln Glu Asp Thr Pro Val Arg Lys Leu Gln Ala
    690                 695                 700

Asn Lys Lys Val Gln Gly Ser Arg Arg Arg Leu Arg Glu Gly Arg Ser
705                 710                 715                 720

Gln
```

<210> SEQ ID NO 51
<211> LENGTH: 576
<212> TYPE: DNA
<213> ORGANISM: human
<220> FEATURE:
<221> NAME/KEY: CDS
<222> LOCATION: (37)...(477)

<400> SEQUENCE: 51

```
cttctctggg acacattgcc ttctgttttc tccagc atg cgc ttg ctc cag ctc       54
                                        Met Arg Leu Leu Gln Leu
                                         1               5

ctg ttc agg gcc agc cct gcc acc ctg ctc ctg gtt ctc tgc ctg cag      102
Leu Phe Arg Ala Ser Pro Ala Thr Leu Leu Leu Val Leu Cys Leu Gln
             10                  15                  20

ttg ggg gcc aac aaa gct cag gac aac act cgg aag atc ata ata aag      150
Leu Gly Ala Asn Lys Ala Gln Asp Asn Thr Arg Lys Ile Ile Ile Lys
         25                  30                  35

aat ttt gac att ccc aag tca gta cgt cca aat gac gaa gtc act gca      198
Asn Phe Asp Ile Pro Lys Ser Val Arg Pro Asn Asp Glu Val Thr Ala
     40                  45                  50

gtg ctt gca gtt caa aca gaa ttg aaa gaa tgc atg gtg gtt aaa act      246
Val Leu Ala Val Gln Thr Glu Leu Lys Glu Cys Met Val Val Lys Thr
 55                  60                  65                  70

tac ctc att agc agc atc cct cta caa ggt gca ttt aac tat aag tat      294
Tyr Leu Ile Ser Ser Ile Pro Leu Gln Gly Ala Phe Asn Tyr Lys Tyr
                 75                  80                  85

act gcc tgc cta tgt gac gac aat cca aaa acc ttc tac tgg gac ttt      342
Thr Ala Cys Leu Cys Asp Asp Asn Pro Lys Thr Phe Tyr Trp Asp Phe
             90                  95                 100

tac acc aac aga act gtg caa att gca gcc gtc gtt gat gtt att cgg      390
Tyr Thr Asn Arg Thr Val Gln Ile Ala Ala Val Val Asp Val Ile Arg
        105                 110                 115

gaa tta ggc atc tgc cct gat gat gct gct gta atc ccc atc aaa aac      438
Glu Leu Gly Ile Cys Pro Asp Asp Ala Ala Val Ile Pro Ile Lys Asn
    120                 125                 130

aac cgg ttt tat act att gaa atc cta aag gta gaa taa tggaagccct       487
Asn Arg Phe Tyr Thr Ile Glu Ile Leu Lys Val Glu  *
135                 140                 145

gtctgtttgc cacacccagg tgatttcctc taaagaaact tggctggaat ttctgctgtg    547

gtctataaaa taaacttctt aacatgctt                                      576


<210> SEQ ID NO 52
<211> LENGTH: 146
<212> TYPE: PRT
<213> ORGANISM: human

<400> SEQUENCE: 52

Met Arg Leu Leu Gln Leu Leu Phe Arg Ala Ser Pro Ala Thr Leu Leu
 1               5                  10                  15

Leu Val Leu Cys Leu Gln Leu Gly Ala Asn Lys Ala Gln Asp Asn Thr
             20                  25                  30

Arg Lys Ile Ile Ile Lys Asn Phe Asp Ile Pro Lys Ser Val Arg Pro
        35                  40                  45

Asn Asp Glu Val Thr Ala Val Leu Ala Val Gln Thr Glu Leu Lys Glu
    50                  55                  60

Cys Met Val Val Lys Thr Tyr Leu Ile Ser Ser Ile Pro Leu Gln Gly
65                  70                  75                  80

Ala Phe Asn Tyr Lys Tyr Thr Ala Cys Leu Cys Asp Asp Asn Pro Lys
                85                  90                  95

Thr Phe Tyr Trp Asp Phe Tyr Thr Asn Arg Thr Val Gln Ile Ala Ala
            100                 105                 110

Val Val Asp Val Ile Arg Glu Leu Gly Ile Cys Pro Asp Asp Ala Ala
        115                 120                 125

Val Ile Pro Ile Lys Asn Asn Arg Phe Tyr Thr Ile Glu Ile Leu Lys
    130                 135                 140
```

-continued

```
Val Glu
145


<210> SEQ ID NO 53
<211> LENGTH: 3734
<212> TYPE: DNA
<213> ORGANISM: human
<220> FEATURE:
<221> NAME/KEY: CDS
<222> LOCATION: (81)...(3077)

<400> SEQUENCE: 53

ggcgtccgcg cacacctccc cgcgccgccg ccgccaccgc ccgcactccg ccgcctctgc     60

ccgcaaccgc tgagccatcc atg ggg gtc gcg ggc cgc aac cgt ccc ggg gcg    113
                      Met Gly Val Ala Gly Arg Asn Arg Pro Gly Ala
                        1               5                   10

gcc tgg gcg gtg ctg ctg ctg ctg ctg ctg cta cca ctg ctg ctg ctg      161
Ala Trp Ala Val Leu Leu Leu Leu Leu Leu Leu Pro Leu Leu Leu Leu
             15                  20                  25

gtg ggg gcc gtc ccg ccg ggt cgg ggc cgt gcc gcg ggg ccg cag gag      209
Val Gly Ala Val Pro Pro Gly Arg Gly Arg Ala Ala Gly Pro Gln Glu
         30                  35                  40

gat gta gat gag tgt gcc caa ggg cta gat gac tgc cat gcc gac gcc      257
Asp Val Asp Glu Cys Ala Gln Gly Leu Asp Asp Cys His Ala Asp Ala
     45                  50                  55

ctg tgt cag aac aca ccc acc tcc tac aag tgc tcc tgc aag cct ggc      305
Leu Cys Gln Asn Thr Pro Thr Ser Tyr Lys Cys Ser Cys Lys Pro Gly
 60                  65                  70                  75

tac caa ggg gaa ggc agg cag tgt gag gac atc gat gaa tgt gga aat      353
Tyr Gln Gly Glu Gly Arg Gln Cys Glu Asp Ile Asp Glu Cys Gly Asn
                 80                  85                  90

gag ctc aat gga ggc tgt gtc cat gac tgt ttg aat att cca ggc aat      401
Glu Leu Asn Gly Gly Cys Val His Asp Cys Leu Asn Ile Pro Gly Asn
             95                 100                 105

tat cgt tgc act tgt ttt gat ggc ttc atg ttg gct cat gac ggt cat      449
Tyr Arg Cys Thr Cys Phe Asp Gly Phe Met Leu Ala His Asp Gly His
        110                 115                 120

aat tgt ctt gat gtg gac gag tgc ctg gag aac aat ggc ggc tgc cag      497
Asn Cys Leu Asp Val Asp Glu Cys Leu Glu Asn Asn Gly Gly Cys Gln
    125                 130                 135

cat acc tgt gtc aac gtc atg ggg agc tat gag tgc tgc tgc aag gag      545
His Thr Cys Val Asn Val Met Gly Ser Tyr Glu Cys Cys Cys Lys Glu
140                 145                 150                 155

ggg ttt ttc ctg agt gac aat cag cac acc tgc att cac cgc tcg gaa      593
Gly Phe Phe Leu Ser Asp Asn Gln His Thr Cys Ile His Arg Ser Glu
                160                 165                 170

gag ggc ctg agc tgc atg aat aag gat cac ggc tgt agt cac atc tgc      641
Glu Gly Leu Ser Cys Met Asn Lys Asp His Gly Cys Ser His Ile Cys
            175                 180                 185

aag gag gcc cca agg ggc agc gtc gcc tgt gag tgc agg cct ggt ttt      689
Lys Glu Ala Pro Arg Gly Ser Val Ala Cys Glu Cys Arg Pro Gly Phe
        190                 195                 200

gag ctg gcc aag aac cag aga gac tgc atc ttg acc tgt aac cat ggg      737
Glu Leu Ala Lys Asn Gln Arg Asp Cys Ile Leu Thr Cys Asn His Gly
    205                 210                 215

aac ggt ggg tgc cag cac tcc tgt gac gat aca gcc gat ggc cca gag      785
Asn Gly Gly Cys Gln His Ser Cys Asp Asp Thr Ala Asp Gly Pro Glu
220                 225                 230                 235

tgc agc tgc cat cca cag tac aag atg cac aca gat ggg agg agc tgc      833
Cys Ser Cys His Pro Gln Tyr Lys Met His Thr Asp Gly Arg Ser Cys
```

-continued

```
                240                 245                 250

ctt gag cga gag gac act gtc ctg gag gtg aca gag agc aac acc aca      881
Leu Glu Arg Glu Asp Thr Val Leu Glu Val Thr Glu Ser Asn Thr Thr
            255                 260                 265

tca gtg gtg gat ggg gat aaa cgg gtg aaa cgg cgg ctg ctc atg gaa      929
Ser Val Val Asp Gly Asp Lys Arg Val Lys Arg Arg Leu Leu Met Glu
        270                 275                 280

acg tgt gct gtc aac aat gga ggc tgt gac cgc acc tgt aag gat act      977
Thr Cys Ala Val Asn Asn Gly Gly Cys Asp Arg Thr Cys Lys Asp Thr
    285                 290                 295

tcg aca ggt gtc cac tgc agt tgt cct gtt gga ttc act ctc cag ttg     1025
Ser Thr Gly Val His Cys Ser Cys Pro Val Gly Phe Thr Leu Gln Leu
300                 305                 310                 315

gat ggg aag aca tgt aaa gat att gat gag tgc cag acc cgc aat gga     1073
Asp Gly Lys Thr Cys Lys Asp Ile Asp Glu Cys Gln Thr Arg Asn Gly
                320                 325                 330

ggt tgt gat cat ttc tgc aaa aac atc gtg ggc agt ttt gac tgc ggc     1121
Gly Cys Asp His Phe Cys Lys Asn Ile Val Gly Ser Phe Asp Cys Gly
            335                 340                 345

tgc aag aaa gga ttt aaa tta tta aca gat gag aag tct tgc caa gat     1169
Cys Lys Lys Gly Phe Lys Leu Leu Thr Asp Glu Lys Ser Cys Gln Asp
        350                 355                 360

gtg gat gag tgc tct ttg gat agg acc tgt gac cac agc tgc atc aac     1217
Val Asp Glu Cys Ser Leu Asp Arg Thr Cys Asp His Ser Cys Ile Asn
    365                 370                 375

cac cct ggc aca ttt gct tgt gct tgc aac cga ggg tac acc ctg tat     1265
His Pro Gly Thr Phe Ala Cys Ala Cys Asn Arg Gly Tyr Thr Leu Tyr
380                 385                 390                 395

ggc ttc acc cac tgt gga gac acc aat gag tgc agc atc aac aac gga     1313
Gly Phe Thr His Cys Gly Asp Thr Asn Glu Cys Ser Ile Asn Asn Gly
                400                 405                 410

ggc tgt cag cag gtc tgt gtg aac aca gtg ggc agc tat gaa tgc cag     1361
Gly Cys Gln Gln Val Cys Val Asn Thr Val Gly Ser Tyr Glu Cys Gln
            415                 420                 425

tgc cac cct ggg tac aag ctc cac tgg aat aaa aaa gac tgt gtg gaa     1409
Cys His Pro Gly Tyr Lys Leu His Trp Asn Lys Lys Asp Cys Val Glu
        430                 435                 440

gtg aag ggg ctc ctg ccc aca agt gtg tca ccc cgt gtg tcc ctg cac     1457
Val Lys Gly Leu Leu Pro Thr Ser Val Ser Pro Arg Val Ser Leu His
    445                 450                 455

tgc ggt aag agt ggt gga gga gac ggg tgc ttc ctc aga tgt cac tct     1505
Cys Gly Lys Ser Gly Gly Gly Asp Gly Cys Phe Leu Arg Cys His Ser
460                 465                 470                 475

ggc att cac ctc tct tca gat gtc acc acc atc agg aca agt gta acc     1553
Gly Ile His Leu Ser Ser Asp Val Thr Thr Ile Arg Thr Ser Val Thr
                480                 485                 490

ttt aag cta aat gaa ggc aag tgt agt ttg aaa aat gct gag ctg ttt     1601
Phe Lys Leu Asn Glu Gly Lys Cys Ser Leu Lys Asn Ala Glu Leu Phe
            495                 500                 505

ccc gag ggt ctg cga cca gca cta cca gag aag cac agc tca gta aaa     1649
Pro Glu Gly Leu Arg Pro Ala Leu Pro Glu Lys His Ser Ser Val Lys
        510                 515                 520

gag agc ttc cgc tac gta aac ctt aca tgc agc tct ggc aag caa gtc     1697
Glu Ser Phe Arg Tyr Val Asn Leu Thr Cys Ser Ser Gly Lys Gln Val
    525                 530                 535

cca gga gcc cct ggc cga cca agc acc cct aag gaa atg ttt atc act     1745
Pro Gly Ala Pro Gly Arg Pro Ser Thr Pro Lys Glu Met Phe Ile Thr
540                 545                 550                 555

gtt gag ttt gag ctt gaa act aac caa aag gag gtg aca gct tct tgt     1793
```

-continued

```
Val Glu Phe Glu Leu Glu Thr Asn Gln Lys Glu Val Thr Ala Ser Cys
                560                 565                 570

gac ctg agc tgc atc gta aag cga acc gag aag cgg ctc cgt aaa gcc      1841
Asp Leu Ser Cys Ile Val Lys Arg Thr Glu Lys Arg Leu Arg Lys Ala
            575                 580                 585

atc cgc acg ctc aga aag gcc gtc cac agg gag cag ttt cac ctc cag      1889
Ile Arg Thr Leu Arg Lys Ala Val His Arg Glu Gln Phe His Leu Gln
        590                 595                 600

ctc tca ggc atg aac ctc gac gtg gct aaa aag cct ccc aga aca tct      1937
Leu Ser Gly Met Asn Leu Asp Val Ala Lys Lys Pro Pro Arg Thr Ser
    605                 610                 615

gaa cgc cag gca gag tcc tgt gga gtg ggc cag ggt cat gca gaa aac      1985
Glu Arg Gln Ala Glu Ser Cys Gly Val Gly Gln Gly His Ala Glu Asn
620                 625                 630                 635

caa tgt gtc agt tgc agg gct ggg acc tat tat gat gga gca cga gaa      2033
Gln Cys Val Ser Cys Arg Ala Gly Thr Tyr Tyr Asp Gly Ala Arg Glu
                640                 645                 650

cgc tgc att tta tgt cca aat gga acc ttc caa aat gag gaa gga caa      2081
Arg Cys Ile Leu Cys Pro Asn Gly Thr Phe Gln Asn Glu Glu Gly Gln
            655                 660                 665

atg act tgt gaa cca tgc cca aga cca gga aat tct ggg gcc ctg aag      2129
Met Thr Cys Glu Pro Cys Pro Arg Pro Gly Asn Ser Gly Ala Leu Lys
        670                 675                 680

acc cca gaa gct tgg aat atg tct gaa tgt gga ggt ctg tgt caa cct      2177
Thr Pro Glu Ala Trp Asn Met Ser Glu Cys Gly Gly Leu Cys Gln Pro
    685                 690                 695

ggt gaa tat tct gca gat ggc ttt gca cct tgc cag ctc tgt gcc ctg      2225
Gly Glu Tyr Ser Ala Asp Gly Phe Ala Pro Cys Gln Leu Cys Ala Leu
700                 705                 710                 715

ggc acg ttc cag cct gaa gct ggt cga act tcc tgc ttc ccc tgt gga      2273
Gly Thr Phe Gln Pro Glu Ala Gly Arg Thr Ser Cys Phe Pro Cys Gly
                720                 725                 730

gga ggc ctt gcc acc aaa cat cag gga gct act tcc ttt cag gac tgt      2321
Gly Gly Leu Ala Thr Lys His Gln Gly Ala Thr Ser Phe Gln Asp Cys
            735                 740                 745

gaa acc aga gtt caa tgt tca cct gga cat ttc tac aac acc acc act      2369
Glu Thr Arg Val Gln Cys Ser Pro Gly His Phe Tyr Asn Thr Thr Thr
        750                 755                 760

cac cga tgt att cgt tgc cca gtg gga aca tac cag cct gaa ttt gga      2417
His Arg Cys Ile Arg Cys Pro Val Gly Thr Tyr Gln Pro Glu Phe Gly
    765                 770                 775

aaa aat aat tgt gtt tct tgc cca gga aat act acg act gac ttt gat      2465
Lys Asn Asn Cys Val Ser Cys Pro Gly Asn Thr Thr Thr Asp Phe Asp
780                 785                 790                 795

ggc tcc aca aac ata acc cag tgt aaa aac aga aga tgt gga ggg gag      2513
Gly Ser Thr Asn Ile Thr Gln Cys Lys Asn Arg Arg Cys Gly Gly Glu
                800                 805                 810

ctg gga gat ttc act ggg tac att gaa tcc cca aac tac cca ggc aat      2561
Leu Gly Asp Phe Thr Gly Tyr Ile Glu Ser Pro Asn Tyr Pro Gly Asn
            815                 820                 825

tac cca gcc aac acc gag tgt acg tgg acc atc aac cca ccc ccc aag      2609
Tyr Pro Ala Asn Thr Glu Cys Thr Trp Thr Ile Asn Pro Pro Pro Lys
        830                 835                 840

cgc cgc atc ctg atc gtg gtc cct gag atc ttc ctg ccc ata gag gac      2657
Arg Arg Ile Leu Ile Val Val Pro Glu Ile Phe Leu Pro Ile Glu Asp
    845                 850                 855

gac tgt ggg gac tat ctg gtg atg cgg aaa acc tct tca tcc aat tct      2705
Asp Cys Gly Asp Tyr Leu Val Met Arg Lys Thr Ser Ser Ser Asn Ser
860                 865                 870                 875
```

-continued

```
gtg aca aca tat gaa acc tgc cag acc tac gaa cgc ccc atc gcc ttc     2753
Val Thr Thr Tyr Glu Thr Cys Gln Thr Tyr Glu Arg Pro Ile Ala Phe
                880                 885                 890

acc tcc agg tca aag aag ctg tgg att cag ttc aag tcc aat gaa ggg     2801
Thr Ser Arg Ser Lys Lys Leu Trp Ile Gln Phe Lys Ser Asn Glu Gly
            895                 900                 905

aac agc gct aga ggg ttc cag gtc cca tac gtg aca tat gat gag gac     2849
Asn Ser Ala Arg Gly Phe Gln Val Pro Tyr Val Thr Tyr Asp Glu Asp
        910                 915                 920

tac cag gaa ctc att gaa gac ata gtt cga gat ggc agg ctc tat gca     2897
Tyr Gln Glu Leu Ile Glu Asp Ile Val Arg Asp Gly Arg Leu Tyr Ala
    925                 930                 935

tct gag aac cat cag gaa ata ctt aag gat aag aaa ctt atc aag gct     2945
Ser Glu Asn His Gln Glu Ile Leu Lys Asp Lys Lys Leu Ile Lys Ala
940                 945                 950                 955

ctg ttt gat gtc ctg gcc cat ccc cag aac tat ttc aag tac aca gcc     2993
Leu Phe Asp Val Leu Ala His Pro Gln Asn Tyr Phe Lys Tyr Thr Ala
                960                 965                 970

cag gag tcc cga gag atg ttt cca aga tcg ttc atc cga ttg cta cgt     3041
Gln Glu Ser Arg Glu Met Phe Pro Arg Ser Phe Ile Arg Leu Leu Arg
            975                 980                 985

tcc aaa gtg tcc agg ttt ttg aga cct tac aaa tga ctcagcccac          3087
Ser Lys Val Ser Arg Phe Leu Arg Pro Tyr Lys  *
         990                 995

gtgccactca atacaaatgt tctgctatag ggttggtggg acagagctgt cttccttctg   3147

catgtcagca cagtcgggta ttgctgcctc ccgtatcagt gactcattag agttcaattt   3207

ttatagataa tacagatatt ttggtaaatt gaacttggtt tttctttccc agcatcgtgg   3267

atgtagactg agaatggctt tgagtggcat cagcttctca ctgctgtggg cggatgtctt   3327

ggatagatca cgggctggct gagctggact ttggtcagcc taggtgagac tcacctgtcc   3387

ttctggggtc ttactcctcc tcaaggagtc tgtagtggaa aggaggccac agaataagct   3447

gcttattctg aaacttcagc ttcctctagc ccggccctct ctaagggagc cctctgcact   3507

cgtgtgcagg ctctgaccag gcagaacagg caagagggga gggaaggaga cccctgcagg   3567

ctccctccac ccaccttgag acctgggagg actcagtttc tccacagcct tctccagcct   3627

gtgtgataca agtttgatcc caggaacttg agttctaagc agtgctcgtg aaaaaaaaaa   3687

gcagaaagaa ttagaaataa ataaaaacta agcacttctg gagacat                 3734


<210> SEQ ID NO 54
<211> LENGTH: 998
<212> TYPE: PRT
<213> ORGANISM: human

<400> SEQUENCE: 54

Met Gly Val Ala Gly Arg Asn Arg Pro Gly Ala Ala Trp Ala Val Leu
 1               5                  10                  15

Leu Leu Leu Leu Leu Leu Pro Leu Leu Leu Leu Val Gly Ala Val Pro
            20                  25                  30

Pro Gly Arg Gly Arg Ala Ala Gly Pro Gln Glu Asp Val Asp Glu Cys
        35                  40                  45

Ala Gln Gly Leu Asp Asp Cys His Ala Asp Ala Leu Cys Gln Asn Thr
    50                  55                  60

Pro Thr Ser Tyr Lys Cys Ser Cys Lys Pro Gly Tyr Gln Gly Glu Gly
65                  70                  75                  80

Arg Gln Cys Glu Asp Ile Asp Glu Cys Gly Asn Glu Leu Asn Gly Gly
                85                  90                  95
```

-continued

```
Cys Val His Asp Cys Leu Asn Ile Pro Gly Asn Tyr Arg Cys Thr Cys
            100                 105                 110

Phe Asp Gly Phe Met Leu Ala His Asp Gly His Asn Cys Leu Asp Val
        115                 120                 125

Asp Glu Cys Leu Glu Asn Asn Gly Gly Cys Gln His Thr Cys Val Asn
    130                 135                 140

Val Met Gly Ser Tyr Glu Cys Cys Cys Lys Glu Gly Phe Phe Leu Ser
145                 150                 155                 160

Asp Asn Gln His Thr Cys Ile His Arg Ser Glu Glu Gly Leu Ser Cys
                165                 170                 175

Met Asn Lys Asp His Gly Cys Ser His Ile Cys Lys Glu Ala Pro Arg
            180                 185                 190

Gly Ser Val Ala Cys Glu Cys Arg Pro Gly Phe Glu Leu Ala Lys Asn
        195                 200                 205

Gln Arg Asp Cys Ile Leu Thr Cys Asn His Gly Asn Gly Gly Cys Gln
    210                 215                 220

His Ser Cys Asp Asp Thr Ala Asp Gly Pro Glu Cys Ser Cys His Pro
225                 230                 235                 240

Gln Tyr Lys Met His Thr Asp Gly Arg Ser Cys Leu Glu Arg Glu Asp
                245                 250                 255

Thr Val Leu Glu Val Thr Glu Ser Asn Thr Thr Ser Val Val Asp Gly
            260                 265                 270

Asp Lys Arg Val Lys Arg Arg Leu Leu Met Glu Thr Cys Ala Val Asn
        275                 280                 285

Asn Gly Gly Cys Asp Arg Thr Cys Lys Asp Thr Ser Thr Gly Val His
    290                 295                 300

Cys Ser Cys Pro Val Gly Phe Thr Leu Gln Leu Asp Gly Lys Thr Cys
305                 310                 315                 320

Lys Asp Ile Asp Glu Cys Gln Thr Arg Asn Gly Gly Cys Asp His Phe
                325                 330                 335

Cys Lys Asn Ile Val Gly Ser Phe Asp Cys Gly Cys Lys Lys Gly Phe
            340                 345                 350

Lys Leu Leu Thr Asp Glu Lys Ser Cys Gln Asp Val Asp Glu Cys Ser
        355                 360                 365

Leu Asp Arg Thr Cys Asp His Ser Cys Ile Asn His Pro Gly Thr Phe
    370                 375                 380

Ala Cys Ala Cys Asn Arg Gly Tyr Thr Leu Tyr Gly Phe Thr His Cys
385                 390                 395                 400

Gly Asp Thr Asn Glu Cys Ser Ile Asn Asn Gly Gly Cys Gln Gln Val
                405                 410                 415

Cys Val Asn Thr Val Gly Ser Tyr Glu Cys Gln Cys His Pro Gly Tyr
            420                 425                 430

Lys Leu His Trp Asn Lys Lys Asp Cys Val Glu Val Lys Gly Leu Leu
        435                 440                 445

Pro Thr Ser Val Ser Pro Arg Val Ser Leu His Cys Gly Lys Ser Gly
    450                 455                 460

Gly Gly Asp Gly Cys Phe Leu Arg Cys His Ser Gly Ile His Leu Ser
465                 470                 475                 480

Ser Asp Val Thr Thr Ile Arg Thr Ser Val Thr Phe Lys Leu Asn Glu
                485                 490                 495

Gly Lys Cys Ser Leu Lys Asn Ala Glu Leu Phe Pro Glu Gly Leu Arg
            500                 505                 510
```

-continued

```
Pro Ala Leu Pro Glu Lys His Ser Ser Val Lys Glu Ser Phe Arg Tyr
        515                 520                 525

Val Asn Leu Thr Cys Ser Ser Gly Lys Gln Val Pro Gly Ala Pro Gly
    530                 535                 540

Arg Pro Ser Thr Pro Lys Glu Met Phe Ile Thr Val Glu Phe Glu Leu
545                 550                 555                 560

Glu Thr Asn Gln Lys Glu Val Thr Ala Ser Cys Asp Leu Ser Cys Ile
                565                 570                 575

Val Lys Arg Thr Glu Lys Arg Leu Arg Lys Ala Ile Arg Thr Leu Arg
            580                 585                 590

Lys Ala Val His Arg Glu Gln Phe His Leu Gln Leu Ser Gly Met Asn
        595                 600                 605

Leu Asp Val Ala Lys Lys Pro Pro Arg Thr Ser Glu Arg Gln Ala Glu
    610                 615                 620

Ser Cys Gly Val Gly Gln Gly His Ala Glu Asn Gln Cys Val Ser Cys
625                 630                 635                 640

Arg Ala Gly Thr Tyr Tyr Asp Gly Ala Arg Glu Arg Cys Ile Leu Cys
                645                 650                 655

Pro Asn Gly Thr Phe Gln Asn Glu Glu Gly Gln Met Thr Cys Glu Pro
            660                 665                 670

Cys Pro Arg Pro Gly Asn Ser Gly Ala Leu Lys Thr Pro Glu Ala Trp
        675                 680                 685

Asn Met Ser Glu Cys Gly Gly Leu Cys Gln Pro Gly Glu Tyr Ser Ala
    690                 695                 700

Asp Gly Phe Ala Pro Cys Gln Leu Cys Ala Leu Gly Thr Phe Gln Pro
705                 710                 715                 720

Glu Ala Gly Arg Thr Ser Cys Phe Pro Cys Gly Gly Gly Leu Ala Thr
                725                 730                 735

Lys His Gln Gly Ala Thr Ser Phe Gln Asp Cys Glu Thr Arg Val Gln
            740                 745                 750

Cys Ser Pro Gly His Phe Tyr Asn Thr Thr Thr His Arg Cys Ile Arg
        755                 760                 765

Cys Pro Val Gly Thr Tyr Gln Pro Glu Phe Gly Lys Asn Asn Cys Val
    770                 775                 780

Ser Cys Pro Gly Asn Thr Thr Thr Asp Phe Asp Gly Ser Thr Asn Ile
785                 790                 795                 800

Thr Gln Cys Lys Asn Arg Arg Cys Gly Gly Glu Leu Gly Asp Phe Thr
                805                 810                 815

Gly Tyr Ile Glu Ser Pro Asn Tyr Pro Gly Asn Tyr Pro Ala Asn Thr
            820                 825                 830

Glu Cys Thr Trp Thr Ile Asn Pro Pro Pro Lys Arg Arg Ile Leu Ile
        835                 840                 845

Val Val Pro Glu Ile Phe Leu Pro Ile Glu Asp Asp Cys Gly Asp Tyr
    850                 855                 860

Leu Val Met Arg Lys Thr Ser Ser Ser Asn Ser Val Thr Thr Tyr Glu
865                 870                 875                 880

Thr Cys Gln Thr Tyr Glu Arg Pro Ile Ala Phe Thr Ser Arg Ser Lys
                885                 890                 895

Lys Leu Trp Ile Gln Phe Lys Ser Asn Glu Gly Asn Ser Ala Arg Gly
            900                 905                 910

Phe Gln Val Pro Tyr Val Thr Tyr Asp Glu Asp Tyr Gln Glu Leu Ile
        915                 920                 925

Glu Asp Ile Val Arg Asp Gly Arg Leu Tyr Ala Ser Glu Asn His Gln
```

-continued

```
        930                 935                 940

Glu Ile Leu Lys Asp Lys Lys Leu Ile Lys Ala Leu Phe Asp Val Leu
945                 950                 955                 960

Ala His Pro Gln Asn Tyr Phe Lys Tyr Thr Ala Gln Glu Ser Arg Glu
                965                 970                 975

Met Phe Pro Arg Ser Phe Ile Arg Leu Leu Arg Ser Lys Val Ser Arg
            980                 985                 990

Phe Leu Arg Pro Tyr Lys
        995


<210> SEQ ID NO 55
<211> LENGTH: 3494
<212> TYPE: DNA
<213> ORGANISM: human
<220> FEATURE:
<221> NAME/KEY: CDS
<222> LOCATION: (81)...(2837)

<400> SEQUENCE: 55

ggcgtccgcg cacacctccc cgcgccgccg ccgccaccgc ccgcactccg ccgcctctgc     60

ccgcaaccgc tgagccatcc atg ggg gtc gcg ggc cgc aac cgt ccc ggg gcg    113
                      Met Gly Val Ala Gly Arg Asn Arg Pro Gly Ala
                        1               5                  10

gcc tgg gcg gtg ctg ctg ctg ctg ctg ctg cta cca ctg ctg ctg ctg      161
Ala Trp Ala Val Leu Leu Leu Leu Leu Leu Leu Pro Leu Leu Leu Leu
            15                  20                  25

gtg ggg gcc gtc ccg ccg ggt cgg ggc cgt gcc gcg ggg ccg cag gag      209
Val Gly Ala Val Pro Pro Gly Arg Gly Arg Ala Ala Gly Pro Gln Glu
        30                  35                  40

gat gta gat gag tgt gcc caa ggg cta gat gac tgc cat gcc gac gcc      257
Asp Val Asp Glu Cys Ala Gln Gly Leu Asp Asp Cys His Ala Asp Ala
    45                  50                  55

ctg tgt cag aac aca ccc acc tcc tac aag tgc tcc tgc aag cct ggc      305
Leu Cys Gln Asn Thr Pro Thr Ser Tyr Lys Cys Ser Cys Lys Pro Gly
 60                 65                  70                  75

tac caa ggg gaa ggc agg cag tgt gag gac atc gat gaa tgt gga aat      353
Tyr Gln Gly Glu Gly Arg Gln Cys Glu Asp Ile Asp Glu Cys Gly Asn
                80                  85                  90

gag ctc aat gga ggc tgt gtc cat gac tgt ttg aat att cca ggc aat      401
Glu Leu Asn Gly Gly Cys Val His Asp Cys Leu Asn Ile Pro Gly Asn
            95                 100                 105

tat cgt tgc act tgt ttt gat ggc ttc atg ttg gct cat gac ggt cat      449
Tyr Arg Cys Thr Cys Phe Asp Gly Phe Met Leu Ala His Asp Gly His
        110                 115                 120

aat tgt ctt gat gtg gac gag tgc ctg gag aac aat ggc ggc tgc cag      497
Asn Cys Leu Asp Val Asp Glu Cys Leu Glu Asn Asn Gly Gly Cys Gln
    125                 130                 135

cat acc tgt gtc aac gtc atg ggg agc tat gag tgc tgc tgc aag gag      545
His Thr Cys Val Asn Val Met Gly Ser Tyr Glu Cys Cys Cys Lys Glu
140                 145                 150                 155

ggg ttt ttc ctg agt gac aat cag cac acc tgc att cac cgc tcg gaa      593
Gly Phe Phe Leu Ser Asp Asn Gln His Thr Cys Ile His Arg Ser Glu
            160                 165                 170

gag ggc ctg agc tgc atg aat aag gat cac ggc tgt agt cac atc tgc      641
Glu Gly Leu Ser Cys Met Asn Lys Asp His Gly Cys Ser His Ile Cys
            175                 180                 185

aag gag gcc cca agg ggc agc gtc gcc tgt gag tgc agg cct ggt ttt      689
Lys Glu Ala Pro Arg Gly Ser Val Ala Cys Glu Cys Arg Pro Gly Phe
        190                 195                 200
```

-continued

```
gag ctg gcc aag aac cag aga gac tgc atc ttg acc tgt aac cat ggg      737
Glu Leu Ala Lys Asn Gln Arg Asp Cys Ile Leu Thr Cys Asn His Gly
    205                 210                 215

aac ggt ggg tgc cag cac tcc tgt gac gat aca gcc gat ggc cca gag      785
Asn Gly Gly Cys Gln His Ser Cys Asp Asp Thr Ala Asp Gly Pro Glu
220                 225                 230                 235

tgc agc tgc cat cca cag tac aag atg cac aca gat ggg agg agc tgc      833
Cys Ser Cys His Pro Gln Tyr Lys Met His Thr Asp Gly Arg Ser Cys
                240                 245                 250

ctt gag cga gag gac act gtc ctg gag gtg aca gag agc aac acc aca      881
Leu Glu Arg Glu Asp Thr Val Leu Glu Val Thr Glu Ser Asn Thr Thr
            255                 260                 265

tca gtg gtg gat ggg gat aaa cgg gtg aaa cgg cgg ctg ctc atg gaa      929
Ser Val Val Asp Gly Asp Lys Arg Val Lys Arg Arg Leu Leu Met Glu
        270                 275                 280

acg tgt gct gtc aac aat gga ggc tgt gac cgc acc tgt aag gat act      977
Thr Cys Ala Val Asn Asn Gly Gly Cys Asp Arg Thr Cys Lys Asp Thr
    285                 290                 295

tcg aca ggt gtc cac tgc agt tgt cct gtt gga ttc act ctc cag ttg     1025
Ser Thr Gly Val His Cys Ser Cys Pro Val Gly Phe Thr Leu Gln Leu
300                 305                 310                 315

gat ggg aag aca tgt aaa gat att gat gag tgc cag acc cgc aat gga     1073
Asp Gly Lys Thr Cys Lys Asp Ile Asp Glu Cys Gln Thr Arg Asn Gly
                320                 325                 330

ggt tgt gat cat ttc tgc aaa aac atc gtg ggc agt ttt gac tgc ggc     1121
Gly Cys Asp His Phe Cys Lys Asn Ile Val Gly Ser Phe Asp Cys Gly
            335                 340                 345

tgc aag aaa gga ttt aaa tta tta aca gat gag aag tct tgc caa gat     1169
Cys Lys Lys Gly Phe Lys Leu Leu Thr Asp Glu Lys Ser Cys Gln Asp
        350                 355                 360

gtg gat gag tgc tct ttg gat agg acc tgt gac cac agc tgc atc aac     1217
Val Asp Glu Cys Ser Leu Asp Arg Thr Cys Asp His Ser Cys Ile Asn
    365                 370                 375

cac cct ggc aca ttt gct tgt gct tgc aac cga ggg tac acc ctg tat     1265
His Pro Gly Thr Phe Ala Cys Ala Cys Asn Arg Gly Tyr Thr Leu Tyr
380                 385                 390                 395

ggc ttc acc cac tgt gga gat gtc acc acc atc agg aca agt gta acc     1313
Gly Phe Thr His Cys Gly Asp Val Thr Thr Ile Arg Thr Ser Val Thr
                400                 405                 410

ttt aag cta aat gaa ggc aag tgt agt ttg aaa aat gct gag ctg ttt     1361
Phe Lys Leu Asn Glu Gly Lys Cys Ser Leu Lys Asn Ala Glu Leu Phe
            415                 420                 425

ccc gag ggt ctg cga cca gca cta cca gag aag cac agc tca gta aaa     1409
Pro Glu Gly Leu Arg Pro Ala Leu Pro Glu Lys His Ser Ser Val Lys
        430                 435                 440

gag agc ttc cgc tac gta aac ctt aca tgc agc tct ggc aag caa gtc     1457
Glu Ser Phe Arg Tyr Val Asn Leu Thr Cys Ser Ser Gly Lys Gln Val
    445                 450                 455

cca gga gcc cct ggc cga cca agc acc cct aag gaa atg ttt atc act     1505
Pro Gly Ala Pro Gly Arg Pro Ser Thr Pro Lys Glu Met Phe Ile Thr
460                 465                 470                 475

gtt gag ttt gag ctt gaa act aac caa aag gag gtg aca gct tct tgt     1553
Val Glu Phe Glu Leu Glu Thr Asn Gln Lys Glu Val Thr Ala Ser Cys
                480                 485                 490

gac ctg agc tgc atc gta aag cga acc gag aag cgg ctc cgt aaa gcc     1601
Asp Leu Ser Cys Ile Val Lys Arg Thr Glu Lys Arg Leu Arg Lys Ala
            495                 500                 505

atc cgc acg ctc aga aag gcc gtc cac agg gag cag ttt cac ctc cag     1649
Ile Arg Thr Leu Arg Lys Ala Val His Arg Glu Gln Phe His Leu Gln
        510                 515                 520
```

-continued

```
ctc tca ggc atg aac ctc gac gtg gct aaa aag cct ccc aga aca tct      1697
Leu Ser Gly Met Asn Leu Asp Val Ala Lys Lys Pro Pro Arg Thr Ser
    525                 530                 535

gaa cgc cag gca gag tcc tgt gga gtg ggc cag ggt cat gca gaa aac      1745
Glu Arg Gln Ala Glu Ser Cys Gly Val Gly Gln Gly His Ala Glu Asn
540                 545                 550                 555

caa tgt gtc agt tgc agg gct ggg acc tat tat gat gga gca cga gaa      1793
Gln Cys Val Ser Cys Arg Ala Gly Thr Tyr Tyr Asp Gly Ala Arg Glu
                560                 565                 570

cgc tgc att tta tgt cca aat gga acc ttc caa aat gag gaa gga caa      1841
Arg Cys Ile Leu Cys Pro Asn Gly Thr Phe Gln Asn Glu Glu Gly Gln
            575                 580                 585

atg act tgt gaa cca tgc cca aga cca gga aat tct ggg gcc ctg aag      1889
Met Thr Cys Glu Pro Cys Pro Arg Pro Gly Asn Ser Gly Ala Leu Lys
        590                 595                 600

acc cca gaa gct tgg aat atg tct gaa tgt gga ggt ctg tgt caa cct      1937
Thr Pro Glu Ala Trp Asn Met Ser Glu Cys Gly Gly Leu Cys Gln Pro
    605                 610                 615

ggt gaa tat tct gca gat ggc ttt gca cct tgc cag ctc tgt gcc ctg      1985
Gly Glu Tyr Ser Ala Asp Gly Phe Ala Pro Cys Gln Leu Cys Ala Leu
620                 625                 630                 635

ggc acg ttc cag cct gaa gct ggt cga act tcc tgc ttc ccc tgt gga      2033
Gly Thr Phe Gln Pro Glu Ala Gly Arg Thr Ser Cys Phe Pro Cys Gly
                640                 645                 650

gga ggc ctt gcc acc aaa cat cag gga gct act tcc ttt cag gac tgt      2081
Gly Gly Leu Ala Thr Lys His Gln Gly Ala Thr Ser Phe Gln Asp Cys
            655                 660                 665

gaa acc aga gtt caa tgt tca cct gga cat ttc tac aac acc acc act      2129
Glu Thr Arg Val Gln Cys Ser Pro Gly His Phe Tyr Asn Thr Thr Thr
        670                 675                 680

cac cga tgt att cgt tgc cca gtg gga aca tac cag cct gaa ttt gga      2177
His Arg Cys Ile Arg Cys Pro Val Gly Thr Tyr Gln Pro Glu Phe Gly
    685                 690                 695

aaa aat aat tgt gtt tct tgc cca gga aat act acg act gac ttt gat      2225
Lys Asn Asn Cys Val Ser Cys Pro Gly Asn Thr Thr Thr Asp Phe Asp
700                 705                 710                 715

ggc tcc aca aac ata acc cag tgt aaa aac aga aga tgt gga ggg gag      2273
Gly Ser Thr Asn Ile Thr Gln Cys Lys Asn Arg Arg Cys Gly Gly Glu
                720                 725                 730

ctg gga gat ttc act ggg tac att gaa tcc cca aac tac cca ggc aat      2321
Leu Gly Asp Phe Thr Gly Tyr Ile Glu Ser Pro Asn Tyr Pro Gly Asn
            735                 740                 745

tac cca gcc aac acc gag tgt acg tgg acc atc aac cca ccc ccc aag      2369
Tyr Pro Ala Asn Thr Glu Cys Thr Trp Thr Ile Asn Pro Pro Pro Lys
        750                 755                 760

cgc cgc atc ctg atc gtg gtc cct gag atc ttc ctg ccc ata gag gac      2417
Arg Arg Ile Leu Ile Val Val Pro Glu Ile Phe Leu Pro Ile Glu Asp
    765                 770                 775

gac tgt ggg gac tat ctg gtg atg cgg aaa acc tct tca tcc aat tct      2465
Asp Cys Gly Asp Tyr Leu Val Met Arg Lys Thr Ser Ser Ser Asn Ser
780                 785                 790                 795

gtg aca aca tat gaa acc tgc cag acc tac gaa cgc ccc atc gcc ttc      2513
Val Thr Thr Tyr Glu Thr Cys Gln Thr Tyr Glu Arg Pro Ile Ala Phe
                800                 805                 810

acc tcc agg tca aag aag ctg tgg att cag ttc aag tcc aat gaa ggg      2561
Thr Ser Arg Ser Lys Lys Leu Trp Ile Gln Phe Lys Ser Asn Glu Gly
            815                 820                 825

aac agc gct aga ggg ttc cag gtc cca tac gtg aca tat gat gag gac      2609
Asn Ser Ala Arg Gly Phe Gln Val Pro Tyr Val Thr Tyr Asp Glu Asp
```

-continued

```
        830                 835                 840

tac cag gaa ctc att gaa gac ata gtt cga gat ggc agg ctc tat gca      2657
Tyr Gln Glu Leu Ile Glu Asp Ile Val Arg Asp Gly Arg Leu Tyr Ala
    845                 850                 855

tct gag aac cat cag gaa ata ctt aag gat aag aaa ctt atc aag gct      2705
Ser Glu Asn His Gln Glu Ile Leu Lys Asp Lys Lys Leu Ile Lys Ala
860                 865                 870                 875

ctg ttt gat gtc ctg gcc cat ccc cag aac tat ttc aag tac aca gcc      2753
Leu Phe Asp Val Leu Ala His Pro Gln Asn Tyr Phe Lys Tyr Thr Ala
                880                 885                 890

cag gag tcc cga gag atg ttt cca aga tcg ttc atc cga ttg cta cgt      2801
Gln Glu Ser Arg Glu Met Phe Pro Arg Ser Phe Ile Arg Leu Leu Arg
            895                 900                 905

tcc aaa gtg tcc agg ttt ttg aga cct tac aaa tga ctcagcccac          2847
Ser Lys Val Ser Arg Phe Leu Arg Pro Tyr Lys  *
        910                 915

gtgccactca atacaaatgt tctgctatag ggttggtggg acagagctgt cttccttctg   2907

catgtcagca cagtcgggta ttgctgcctc ccgtatcagt gactcattag agttcaattt   2967

ttatagataa tacagatatt ttggtaaatt gaacttggtt tttctttccc agcatcgtgg   3027

atgtagactg agaatggctt tgagtggcat cagcttctca ctgctgtggg cggatgtctt   3087

ggatagatca cgggctggct gagctggact ttggtcagcc taggtgagac tcacctgtcc   3147

ttctggggtc ttactcctcc tcaaggagtc tgtagtggaa aggaggccac agaataagct   3207

gcttattctg aaacttcagc ttcctctagc ccggccctct ctaagggagc cctctgcact   3267

cgtgtgcagg ctctgaccag gcagaacagg caagagggga gggaaggaga cccctgcagg   3327

ctccctccac ccaccttgag acctgggagg actcagtttc tccacagcct tctccagcct   3387

gtgtgataca agtttgatcc caggaacttg agttctaagc agtgctcgtg aaaaaaaaaa   3447

gcagaaagaa ttagaaataa ataaaaacta agcacttctg gagacat                 3494


<210> SEQ ID NO 56
<211> LENGTH: 918
<212> TYPE: PRT
<213> ORGANISM: human

<400> SEQUENCE: 56

Met Gly Val Ala Gly Arg Asn Arg Pro Gly Ala Ala Trp Ala Val Leu
 1               5                  10                  15

Leu Leu Leu Leu Leu Leu Pro Leu Leu Leu Leu Val Gly Ala Val Pro
            20                  25                  30

Pro Gly Arg Gly Arg Ala Ala Gly Pro Gln Glu Asp Val Asp Glu Cys
        35                  40                  45

Ala Gln Gly Leu Asp Asp Cys His Ala Asp Ala Leu Cys Gln Asn Thr
    50                  55                  60

Pro Thr Ser Tyr Lys Cys Ser Cys Lys Pro Gly Tyr Gln Gly Glu Gly
65                  70                  75                  80

Arg Gln Cys Glu Asp Ile Asp Glu Cys Gly Asn Glu Leu Asn Gly Gly
                85                  90                  95

Cys Val His Asp Cys Leu Asn Ile Pro Gly Asn Tyr Arg Cys Thr Cys
            100                 105                 110

Phe Asp Gly Phe Met Leu Ala His Asp Gly His Asn Cys Leu Asp Val
        115                 120                 125

Asp Glu Cys Leu Glu Asn Asn Gly Gly Cys Gln His Thr Cys Val Asn
    130                 135                 140
```

-continued

```
Val Met Gly Ser Tyr Glu Cys Cys Cys Lys Glu Gly Phe Phe Leu Ser
145                 150                 155                 160

Asp Asn Gln His Thr Cys Ile His Arg Ser Glu Glu Gly Leu Ser Cys
                165                 170                 175

Met Asn Lys Asp His Gly Cys Ser His Ile Cys Lys Glu Ala Pro Arg
            180                 185                 190

Gly Ser Val Ala Cys Glu Cys Arg Pro Gly Phe Glu Leu Ala Lys Asn
        195                 200                 205

Gln Arg Asp Cys Ile Leu Thr Cys Asn His Gly Asn Gly Gly Cys Gln
    210                 215                 220

His Ser Cys Asp Asp Thr Ala Asp Gly Pro Glu Cys Ser Cys His Pro
225                 230                 235                 240

Gln Tyr Lys Met His Thr Asp Gly Arg Ser Cys Leu Glu Arg Glu Asp
                245                 250                 255

Thr Val Leu Glu Val Thr Glu Ser Asn Thr Thr Ser Val Val Asp Gly
            260                 265                 270

Asp Lys Arg Val Lys Arg Arg Leu Leu Met Glu Thr Cys Ala Val Asn
        275                 280                 285

Asn Gly Gly Cys Asp Arg Thr Cys Lys Asp Thr Ser Thr Gly Val His
    290                 295                 300

Cys Ser Cys Pro Val Gly Phe Thr Leu Gln Leu Asp Gly Lys Thr Cys
305                 310                 315                 320

Lys Asp Ile Asp Glu Cys Gln Thr Arg Asn Gly Gly Cys Asp His Phe
                325                 330                 335

Cys Lys Asn Ile Val Gly Ser Phe Asp Cys Gly Cys Lys Lys Gly Phe
            340                 345                 350

Lys Leu Leu Thr Asp Glu Lys Ser Cys Gln Asp Val Asp Glu Cys Ser
        355                 360                 365

Leu Asp Arg Thr Cys Asp His Ser Cys Ile Asn His Pro Gly Thr Phe
    370                 375                 380

Ala Cys Ala Cys Asn Arg Gly Tyr Thr Leu Tyr Gly Phe Thr His Cys
385                 390                 395                 400

Gly Asp Val Thr Thr Ile Arg Thr Ser Val Thr Phe Lys Leu Asn Glu
                405                 410                 415

Gly Lys Cys Ser Leu Lys Asn Ala Glu Leu Phe Pro Glu Gly Leu Arg
            420                 425                 430

Pro Ala Leu Pro Glu Lys His Ser Ser Val Lys Glu Ser Phe Arg Tyr
        435                 440                 445

Val Asn Leu Thr Cys Ser Ser Gly Lys Gln Val Pro Gly Ala Pro Gly
    450                 455                 460

Arg Pro Ser Thr Pro Lys Glu Met Phe Ile Thr Val Glu Phe Glu Leu
465                 470                 475                 480

Glu Thr Asn Gln Lys Glu Val Thr Ala Ser Cys Asp Leu Ser Cys Ile
                485                 490                 495

Val Lys Arg Thr Glu Lys Arg Leu Arg Lys Ala Ile Arg Thr Leu Arg
            500                 505                 510

Lys Ala Val His Arg Glu Gln Phe His Leu Gln Leu Ser Gly Met Asn
        515                 520                 525

Leu Asp Val Ala Lys Lys Pro Pro Arg Thr Ser Glu Arg Gln Ala Glu
    530                 535                 540

Ser Cys Gly Val Gly Gln Gly His Ala Glu Asn Gln Cys Val Ser Cys
545                 550                 555                 560

Arg Ala Gly Thr Tyr Tyr Asp Gly Ala Arg Glu Arg Cys Ile Leu Cys
```

-continued

```
                565                 570                 575

Pro Asn Gly Thr Phe Gln Asn Glu Glu Gly Gln Met Thr Cys Glu Pro
            580                 585                 590

Cys Pro Arg Pro Gly Asn Ser Gly Ala Leu Lys Thr Pro Glu Ala Trp
        595                 600                 605

Asn Met Ser Glu Cys Gly Gly Leu Cys Gln Pro Gly Glu Tyr Ser Ala
    610                 615                 620

Asp Gly Phe Ala Pro Cys Gln Leu Cys Ala Leu Gly Thr Phe Gln Pro
625                 630                 635                 640

Glu Ala Gly Arg Thr Ser Cys Phe Pro Cys Gly Gly Gly Leu Ala Thr
                645                 650                 655

Lys His Gln Gly Ala Thr Ser Phe Gln Asp Cys Glu Thr Arg Val Gln
            660                 665                 670

Cys Ser Pro Gly His Phe Tyr Asn Thr Thr Thr His Arg Cys Ile Arg
        675                 680                 685

Cys Pro Val Gly Thr Tyr Gln Pro Glu Phe Gly Lys Asn Asn Cys Val
    690                 695                 700

Ser Cys Pro Gly Asn Thr Thr Thr Asp Phe Asp Gly Ser Thr Asn Ile
705                 710                 715                 720

Thr Gln Cys Lys Asn Arg Arg Cys Gly Gly Glu Leu Gly Asp Phe Thr
                725                 730                 735

Gly Tyr Ile Glu Ser Pro Asn Tyr Pro Gly Asn Tyr Pro Ala Asn Thr
            740                 745                 750

Glu Cys Thr Trp Thr Ile Asn Pro Pro Pro Lys Arg Arg Ile Leu Ile
        755                 760                 765

Val Val Pro Glu Ile Phe Leu Pro Ile Glu Asp Asp Cys Gly Asp Tyr
    770                 775                 780

Leu Val Met Arg Lys Thr Ser Ser Ser Asn Ser Val Thr Thr Tyr Glu
785                 790                 795                 800

Thr Cys Gln Thr Tyr Glu Arg Pro Ile Ala Phe Thr Ser Arg Ser Lys
                805                 810                 815

Lys Leu Trp Ile Gln Phe Lys Ser Asn Glu Gly Asn Ser Ala Arg Gly
            820                 825                 830

Phe Gln Val Pro Tyr Val Thr Tyr Asp Glu Asp Tyr Gln Glu Leu Ile
        835                 840                 845

Glu Asp Ile Val Arg Asp Gly Arg Leu Tyr Ala Ser Glu Asn His Gln
    850                 855                 860

Glu Ile Leu Lys Asp Lys Lys Leu Ile Lys Ala Leu Phe Asp Val Leu
865                 870                 875                 880

Ala His Pro Gln Asn Tyr Phe Lys Tyr Thr Ala Gln Glu Ser Arg Glu
                885                 890                 895

Met Phe Pro Arg Ser Phe Ile Arg Leu Leu Arg Ser Lys Val Ser Arg
            900                 905                 910

Phe Leu Arg Pro Tyr Lys
        915


<210> SEQ ID NO 57
<211> LENGTH: 3356
<212> TYPE: DNA
<213> ORGANISM: human
<220> FEATURE:
<221> NAME/KEY: CDS
<222> LOCATION: (81)...(2699)

<400> SEQUENCE: 57
```

-continued

```
ggcgtccgcg cacacctccc cgcgccgccg ccgccaccgc ccgcactccg ccgcctctgc      60

ccgcaaccgc tgagccatcc atg ggg gtc gcg ggc cgc aac cgt ccc ggg gcg     113
                      Met Gly Val Ala Gly Arg Asn Arg Pro Gly Ala
                      1               5                   10

gcc tgg gcg gtg ctg ctg ctg ctg ctg ctg cta cca ctg ctg ctg ctg       161
Ala Trp Ala Val Leu Leu Leu Leu Leu Leu Leu Pro Leu Leu Leu Leu
            15                  20                  25

gtg ggg gcc gtc ccg ccg ggt cgg ggc cgt gcc gcg ggg ccg cag gag       209
Val Gly Ala Val Pro Pro Gly Arg Gly Arg Ala Ala Gly Pro Gln Glu
        30                  35                  40

gat gta gat gag tgt gcc caa ggg cta gat gac tgc cat gcc gac gcc       257
Asp Val Asp Glu Cys Ala Gln Gly Leu Asp Asp Cys His Ala Asp Ala
    45                  50                  55

ctg tgt cag aac aca ccc acc tcc tac aag tgc tcc tgc aag cct ggc       305
Leu Cys Gln Asn Thr Pro Thr Ser Tyr Lys Cys Ser Cys Lys Pro Gly
60                  65                  70                  75

tac caa ggg gaa ggc agg cag tgt gag gac atc gat gaa tgt gga aat       353
Tyr Gln Gly Glu Gly Arg Gln Cys Glu Asp Ile Asp Glu Cys Gly Asn
                80                  85                  90

gag ctc aat gga ggc tgt gtc cat gac tgt ttg aat att cca ggc aat       401
Glu Leu Asn Gly Gly Cys Val His Asp Cys Leu Asn Ile Pro Gly Asn
            95                  100                 105

tat cgt tgc act tgt ttt gat ggc ttc atg ttg gct cat gac ggt cat       449
Tyr Arg Cys Thr Cys Phe Asp Gly Phe Met Leu Ala His Asp Gly His
        110                 115                 120

aat tgt ctt gat gtg gac gag tgc ctg gag aac aat ggc ggc tgc cag       497
Asn Cys Leu Asp Val Asp Glu Cys Leu Glu Asn Asn Gly Gly Cys Gln
    125                 130                 135

cat acc tgt gtc aac gtc atg ggg agc tat gag tgc tgc tgc aag gag       545
His Thr Cys Val Asn Val Met Gly Ser Tyr Glu Cys Cys Cys Lys Glu
140                 145                 150                 155

ggg ttt ttc ctg agt gac aat cag cac acc tgc att cac cgc tcg gaa       593
Gly Phe Phe Leu Ser Asp Asn Gln His Thr Cys Ile His Arg Ser Glu
                160                 165                 170

gag ggc ctg agc tgc atg aat aag gat cac ggc tgt agt cac atc tgc       641
Glu Gly Leu Ser Cys Met Asn Lys Asp His Gly Cys Ser His Ile Cys
            175                 180                 185

aag gag gcc cca agg ggc agc gtc gcc tgt gag tgc agg cct ggt ttt       689
Lys Glu Ala Pro Arg Gly Ser Val Ala Cys Glu Cys Arg Pro Gly Phe
        190                 195                 200

gag ctg gcc aag aac cag aga gac tgc atc ttg acc tgt aac cat ggg       737
Glu Leu Ala Lys Asn Gln Arg Asp Cys Ile Leu Thr Cys Asn His Gly
    205                 210                 215

aac ggt ggg tgc cag cac tcc tgt gac gat aca gcc gat ggc cca gag       785
Asn Gly Gly Cys Gln His Ser Cys Asp Asp Thr Ala Asp Gly Pro Glu
220                 225                 230                 235

tgc agc tgc cat cca cag tac aag atg cac aca gat ggg agg agc tgc       833
Cys Ser Cys His Pro Gln Tyr Lys Met His Thr Asp Gly Arg Ser Cys
                240                 245                 250

ctt gag cga gag gac act gtc ctg gag gtg aca gag agc aac acc aca       881
Leu Glu Arg Glu Asp Thr Val Leu Glu Val Thr Glu Ser Asn Thr Thr
            255                 260                 265

tca gtg gtg gat ggg gat aaa cgg gtg aaa cgg cgg ctg ctc atg gaa       929
Ser Val Val Asp Gly Asp Lys Arg Val Lys Arg Arg Leu Leu Met Glu
        270                 275                 280

acg tgt gct gtc aac aat gga ggc tgt gac cgc acc tgt aag gat act       977
Thr Cys Ala Val Asn Asn Gly Gly Cys Asp Arg Thr Cys Lys Asp Thr
    285                 290                 295

tcg aca ggt gtc cac tgc agt tgt cct gtt gga ttc act ctc cag ttg      1025
```

-continued

```
Ser Thr Gly Val His Cys Ser Cys Pro Val Gly Phe Thr Leu Gln Leu
300                 305                 310                 315

gat ggg aag aca tgt aaa gat att gat gag tgc cag acc cgc aat gga      1073
Asp Gly Lys Thr Cys Lys Asp Ile Asp Glu Cys Gln Thr Arg Asn Gly
                320                 325                 330

ggt tgt gat cat ttc tgc aaa aac atc gtg ggc agt ttt gac tgc ggc      1121
Gly Cys Asp His Phe Cys Lys Asn Ile Val Gly Ser Phe Asp Cys Gly
            335                 340                 345

tgc aag aaa gga ttt aaa tta tta aca gat gag aag tct tgc caa gat      1169
Cys Lys Lys Gly Phe Lys Leu Leu Thr Asp Glu Lys Ser Cys Gln Asp
        350                 355                 360

gtg gat gag tgc tct ttg gat agg acc tgt gac cac agc tgc atc aac      1217
Val Asp Glu Cys Ser Leu Asp Arg Thr Cys Asp His Ser Cys Ile Asn
    365                 370                 375

cac cct ggc aca ttt gct tgt gct tgc aac cga ggg tac acc ctg tat      1265
His Pro Gly Thr Phe Ala Cys Ala Cys Asn Arg Gly Tyr Thr Leu Tyr
380                 385                 390                 395

ggc ttc acc cac tgt gga gac acc aat gag tgc agc atc aac aac gga      1313
Gly Phe Thr His Cys Gly Asp Thr Asn Glu Cys Ser Ile Asn Asn Gly
                400                 405                 410

ggc tgt cag cag gtc tgt gtg aac aca gtg ggc agc tat gaa tgc cag      1361
Gly Cys Gln Gln Val Cys Val Asn Thr Val Gly Ser Tyr Glu Cys Gln
            415                 420                 425

tgc cac cct ggg tac aag ctc cac tgg aat aaa aaa gac tgt gtg gct      1409
Cys His Pro Gly Tyr Lys Leu His Trp Asn Lys Lys Asp Cys Val Ala
        430                 435                 440

tct tgt gac ctg agc tgc atc gta aag cga acc gag aag cgg ctc cgt      1457
Ser Cys Asp Leu Ser Cys Ile Val Lys Arg Thr Glu Lys Arg Leu Arg
    445                 450                 455

aaa gcc atc cgc acg ctc aga aag gcc gtc cac agg gag cag ttt cac      1505
Lys Ala Ile Arg Thr Leu Arg Lys Ala Val His Arg Glu Gln Phe His
460                 465                 470                 475

ctc cag ctc tca ggc atg aac ctc gac gtg gct aaa aag cct ccc aga      1553
Leu Gln Leu Ser Gly Met Asn Leu Asp Val Ala Lys Lys Pro Pro Arg
                480                 485                 490

aca tct gaa cgc cag gca gag tcc tgt gga gtg ggc cag ggt cat gca      1601
Thr Ser Glu Arg Gln Ala Glu Ser Cys Gly Val Gly Gln Gly His Ala
            495                 500                 505

gaa aac caa tgt gtc agt tgc agg gct ggg acc tat tat gat gga gca      1649
Glu Asn Gln Cys Val Ser Cys Arg Ala Gly Thr Tyr Tyr Asp Gly Ala
        510                 515                 520

cga gaa cgc tgc att tta tgt cca aat gga acc ttc caa aat gag gaa      1697
Arg Glu Arg Cys Ile Leu Cys Pro Asn Gly Thr Phe Gln Asn Glu Glu
    525                 530                 535

gga caa atg act tgt gaa cca tgc cca aga cca gga aat tct ggg gcc      1745
Gly Gln Met Thr Cys Glu Pro Cys Pro Arg Pro Gly Asn Ser Gly Ala
540                 545                 550                 555

ctg aag acc cca gaa gct tgg aat atg tct gaa tgt gga ggt ctg tgt      1793
Leu Lys Thr Pro Glu Ala Trp Asn Met Ser Glu Cys Gly Gly Leu Cys
                560                 565                 570

caa cct ggt gaa tat tct gca gat ggc ttt gca cct tgc cag ctc tgt      1841
Gln Pro Gly Glu Tyr Ser Ala Asp Gly Phe Ala Pro Cys Gln Leu Cys
            575                 580                 585

gcc ctg ggc acg ttc cag cct gaa gct ggt cga act tcc tgc ttc ccc      1889
Ala Leu Gly Thr Phe Gln Pro Glu Ala Gly Arg Thr Ser Cys Phe Pro
        590                 595                 600

tgt gga gga ggc ctt gcc acc aaa cat cag gga gct act tcc ttt cag      1937
Cys Gly Gly Gly Leu Ala Thr Lys His Gln Gly Ala Thr Ser Phe Gln
    605                 610                 615
```

-continued

```
gac tgt gaa acc aga gtt caa tgt tca cct gga cat ttc tac aac acc     1985
Asp Cys Glu Thr Arg Val Gln Cys Ser Pro Gly His Phe Tyr Asn Thr
620                 625                 630                 635

acc act cac cga tgt att cgt tgc cca gtg gga aca tac cag cct gaa     2033
Thr Thr His Arg Cys Ile Arg Cys Pro Val Gly Thr Tyr Gln Pro Glu
                640                 645                 650

ttt gga aaa aat aat tgt gtt tct tgc cca gga aat act acg act gac     2081
Phe Gly Lys Asn Asn Cys Val Ser Cys Pro Gly Asn Thr Thr Thr Asp
            655                 660                 665

ttt gat ggc tcc aca aac ata acc cag tgt aaa aac aga aga tgt gga     2129
Phe Asp Gly Ser Thr Asn Ile Thr Gln Cys Lys Asn Arg Arg Cys Gly
        670                 675                 680

ggg gag ctg gga gat ttc act ggg tac att gaa tcc cca aac tac cca     2177
Gly Glu Leu Gly Asp Phe Thr Gly Tyr Ile Glu Ser Pro Asn Tyr Pro
    685                 690                 695

ggc aat tac cca gcc aac acc gag tgt acg tgg acc atc aac cca ccc     2225
Gly Asn Tyr Pro Ala Asn Thr Glu Cys Thr Trp Thr Ile Asn Pro Pro
700                 705                 710                 715

ccc aag cgc cgc atc ctg atc gtg gtc cct gag atc ttc ctg ccc ata     2273
Pro Lys Arg Arg Ile Leu Ile Val Val Pro Glu Ile Phe Leu Pro Ile
                720                 725                 730

gag gac gac tgt ggg gac tat ctg gtg atg cgg aaa acc tct tca tcc     2321
Glu Asp Asp Cys Gly Asp Tyr Leu Val Met Arg Lys Thr Ser Ser Ser
            735                 740                 745

aat tct gtg aca aca tat gaa acc tgc cag acc tac gaa cgc ccc atc     2369
Asn Ser Val Thr Thr Tyr Glu Thr Cys Gln Thr Tyr Glu Arg Pro Ile
        750                 755                 760

gcc ttc acc tcc agg tca aag aag ctg tgg att cag ttc aag tcc aat     2417
Ala Phe Thr Ser Arg Ser Lys Lys Leu Trp Ile Gln Phe Lys Ser Asn
    765                 770                 775

gaa ggg aac agc gct aga ggg ttc cag gtc cca tac gtg aca tat gat     2465
Glu Gly Asn Ser Ala Arg Gly Phe Gln Val Pro Tyr Val Thr Tyr Asp
780                 785                 790                 795

gag gac tac cag gaa ctc att gaa gac ata gtt cga gat ggc agg ctc     2513
Glu Asp Tyr Gln Glu Leu Ile Glu Asp Ile Val Arg Asp Gly Arg Leu
                800                 805                 810

tat gca tct gag aac cat cag gaa ata ctt aag gat aag aaa ctt atc     2561
Tyr Ala Ser Glu Asn His Gln Glu Ile Leu Lys Asp Lys Lys Leu Ile
            815                 820                 825

aag gct ctg ttt gat gtc ctg gcc cat ccc cag aac tat ttc aag tac     2609
Lys Ala Leu Phe Asp Val Leu Ala His Pro Gln Asn Tyr Phe Lys Tyr
        830                 835                 840

aca gcc cag gag tcc cga gag atg ttt cca aga tcg ttc atc cga ttg     2657
Thr Ala Gln Glu Ser Arg Glu Met Phe Pro Arg Ser Phe Ile Arg Leu
    845                 850                 855

cta cgt tcc aaa gtg tcc agg ttt ttg aga cct tac aaa tga             2699
Leu Arg Ser Lys Val Ser Arg Phe Leu Arg Pro Tyr Lys  *
860                 865                 870

ctcagcccac gtgccactca atacaaatgt tctgctatag ggttggtggg acagagctgt   2759

cttccttctg catgtcagca cagtcgggta ttgctgcctc ccgtatcagt gactcattag   2819

agttcaattt ttatagataa tacagatatt ttggtaaatt gaacttggtt tttctttccc   2879

agcatcgtgg atgtagactg agaatggctt tgagtggcat cagcttctca ctgctgtggg   2939

cggatgtctt ggatagatca cgggctggct gagctggact ttggtcagcc taggtgagac   2999

tcacctgtcc ttctggggtc ttactcctcc tcaaggagtc tgtagtggaa aggaggccac   3059

agaataagct gcttattctg aaacttcagc ttcctctagc ccggccctct ctaagggagc   3119

cctctgcact cgtgtgcagg ctctgaccag gcagaacagg caagagggga gggaaggaga   3179
```

-continued

```
ccccctgcagg ctccctccac ccaccttgag acctgggagg actcagtttc tccacagcct   3239

tctccagcct gtgtgataca agtttgatcc caggaacttg agttctaagc agtgctcgtg   3299

aaaaaaaaaa gcagaaagaa ttagaaataa ataaaaacta agcacttctg gagacat      3356


<210> SEQ ID NO 58
<211> LENGTH: 872
<212> TYPE: PRT
<213> ORGANISM: human

<400> SEQUENCE: 58

Met Gly Val Ala Gly Arg Asn Arg Pro Gly Ala Ala Trp Ala Val Leu
 1               5                  10                  15

Leu Leu Leu Leu Leu Leu Pro Leu Leu Leu Leu Val Gly Ala Val Pro
            20                  25                  30

Pro Gly Arg Gly Arg Ala Ala Gly Pro Gln Glu Asp Val Asp Glu Cys
        35                  40                  45

Ala Gln Gly Leu Asp Asp Cys His Ala Asp Ala Leu Cys Gln Asn Thr
    50                  55                  60

Pro Thr Ser Tyr Lys Cys Ser Cys Lys Pro Gly Tyr Gln Gly Glu Gly
65                  70                  75                  80

Arg Gln Cys Glu Asp Ile Asp Glu Cys Gly Asn Glu Leu Asn Gly Gly
                85                  90                  95

Cys Val His Asp Cys Leu Asn Ile Pro Gly Asn Tyr Arg Cys Thr Cys
            100                 105                 110

Phe Asp Gly Phe Met Leu Ala His Asp Gly His Asn Cys Leu Asp Val
        115                 120                 125

Asp Glu Cys Leu Glu Asn Asn Gly Gly Cys Gln His Thr Cys Val Asn
    130                 135                 140

Val Met Gly Ser Tyr Glu Cys Cys Cys Lys Glu Gly Phe Phe Leu Ser
145                 150                 155                 160

Asp Asn Gln His Thr Cys Ile His Arg Ser Glu Glu Gly Leu Ser Cys
                165                 170                 175

Met Asn Lys Asp His Gly Cys Ser His Ile Cys Lys Glu Ala Pro Arg
            180                 185                 190

Gly Ser Val Ala Cys Glu Cys Arg Pro Gly Phe Glu Leu Ala Lys Asn
        195                 200                 205

Gln Arg Asp Cys Ile Leu Thr Cys Asn His Gly Asn Gly Gly Cys Gln
    210                 215                 220

His Ser Cys Asp Asp Thr Ala Asp Gly Pro Glu Cys Ser Cys His Pro
225                 230                 235                 240

Gln Tyr Lys Met His Thr Asp Gly Arg Ser Cys Leu Glu Arg Glu Asp
                245                 250                 255

Thr Val Leu Glu Val Thr Glu Ser Asn Thr Thr Ser Val Val Asp Gly
            260                 265                 270

Asp Lys Arg Val Lys Arg Arg Leu Leu Met Glu Thr Cys Ala Val Asn
        275                 280                 285

Asn Gly Gly Cys Asp Arg Thr Cys Lys Asp Thr Ser Thr Gly Val His
    290                 295                 300

Cys Ser Cys Pro Val Gly Phe Thr Leu Gln Leu Asp Gly Lys Thr Cys
305                 310                 315                 320

Lys Asp Ile Asp Glu Cys Gln Thr Arg Asn Gly Gly Cys Asp His Phe
                325                 330                 335

Cys Lys Asn Ile Val Gly Ser Phe Asp Cys Gly Cys Lys Lys Gly Phe
```

-continued

```
            340                 345                 350

Lys Leu Leu Thr Asp Glu Lys Ser Cys Gln Asp Val Asp Glu Cys Ser
        355                 360                 365

Leu Asp Arg Thr Cys Asp His Ser Cys Ile Asn His Pro Gly Thr Phe
    370                 375                 380

Ala Cys Ala Cys Asn Arg Gly Tyr Thr Leu Tyr Gly Phe Thr His Cys
385                 390                 395                 400

Gly Asp Thr Asn Glu Cys Ser Ile Asn Asn Gly Gly Cys Gln Gln Val
                405                 410                 415

Cys Val Asn Thr Val Gly Ser Tyr Glu Cys Gln Cys His Pro Gly Tyr
            420                 425                 430

Lys Leu His Trp Asn Lys Lys Asp Cys Val Ala Ser Cys Asp Leu Ser
        435                 440                 445

Cys Ile Val Lys Arg Thr Glu Lys Arg Leu Arg Lys Ala Ile Arg Thr
    450                 455                 460

Leu Arg Lys Ala Val His Arg Glu Gln Phe His Leu Gln Leu Ser Gly
465                 470                 475                 480

Met Asn Leu Asp Val Ala Lys Lys Pro Pro Arg Thr Ser Glu Arg Gln
                485                 490                 495

Ala Glu Ser Cys Gly Val Gly Gln Gly His Ala Glu Asn Gln Cys Val
            500                 505                 510

Ser Cys Arg Ala Gly Thr Tyr Tyr Asp Gly Ala Arg Glu Arg Cys Ile
        515                 520                 525

Leu Cys Pro Asn Gly Thr Phe Gln Asn Glu Glu Gly Gln Met Thr Cys
    530                 535                 540

Glu Pro Cys Pro Arg Pro Gly Asn Ser Gly Ala Leu Lys Thr Pro Glu
545                 550                 555                 560

Ala Trp Asn Met Ser Glu Cys Gly Gly Leu Cys Gln Pro Gly Glu Tyr
                565                 570                 575

Ser Ala Asp Gly Phe Ala Pro Cys Gln Leu Cys Ala Leu Gly Thr Phe
            580                 585                 590

Gln Pro Glu Ala Gly Arg Thr Ser Cys Phe Pro Cys Gly Gly Gly Leu
        595                 600                 605

Ala Thr Lys His Gln Gly Ala Thr Ser Phe Gln Asp Cys Glu Thr Arg
    610                 615                 620

Val Gln Cys Ser Pro Gly His Phe Tyr Asn Thr Thr Thr His Arg Cys
625                 630                 635                 640

Ile Arg Cys Pro Val Gly Thr Tyr Gln Pro Glu Phe Gly Lys Asn Asn
                645                 650                 655

Cys Val Ser Cys Pro Gly Asn Thr Thr Thr Asp Phe Asp Gly Ser Thr
            660                 665                 670

Asn Ile Thr Gln Cys Lys Asn Arg Arg Cys Gly Gly Glu Leu Gly Asp
        675                 680                 685

Phe Thr Gly Tyr Ile Glu Ser Pro Asn Tyr Pro Gly Asn Tyr Pro Ala
    690                 695                 700

Asn Thr Glu Cys Thr Trp Thr Ile Asn Pro Pro Pro Lys Arg Arg Ile
705                 710                 715                 720

Leu Ile Val Val Pro Glu Ile Phe Leu Pro Ile Glu Asp Asp Cys Gly
                725                 730                 735

Asp Tyr Leu Val Met Arg Lys Thr Ser Ser Ser Asn Ser Val Thr Thr
            740                 745                 750

Tyr Glu Thr Cys Gln Thr Tyr Glu Arg Pro Ile Ala Phe Thr Ser Arg
        755                 760                 765
```

-continued

```
Ser Lys Lys Leu Trp Ile Gln Phe Lys Ser Asn Glu Gly Asn Ser Ala
    770                 775                 780

Arg Gly Phe Gln Val Pro Tyr Val Thr Tyr Asp Glu Asp Tyr Gln Glu
785                 790                 795                 800

Leu Ile Glu Asp Ile Val Arg Asp Gly Arg Leu Tyr Ala Ser Glu Asn
                805                 810                 815

His Gln Glu Ile Leu Lys Asp Lys Lys Leu Ile Lys Ala Leu Phe Asp
            820                 825                 830

Val Leu Ala His Pro Gln Asn Tyr Phe Lys Tyr Thr Ala Gln Glu Ser
        835                 840                 845

Arg Glu Met Phe Pro Arg Ser Phe Ile Arg Leu Leu Arg Ser Lys Val
    850                 855                 860

Ser Arg Phe Leu Arg Pro Tyr Lys
865                 870


<210> SEQ ID NO 59
<211> LENGTH: 3821
<212> TYPE: DNA
<213> ORGANISM: human
<220> FEATURE:
<221> NAME/KEY: CDS
<222> LOCATION: (81)...(3164)

<400> SEQUENCE: 59

ggcgtccgcg cacacctccc cgcgccgccg ccgccaccgc ccgcactccg ccgcctctgc      60

ccgcaaccgc tgagccatcc atg ggg gtc gcg ggc cgc aac cgt ccc ggg gcg     113
                      Met Gly Val Ala Gly Arg Asn Arg Pro Gly Ala
                      1               5                   10

gcc tgg gcg gtg ctg ctg ctg ctg ctg ctg cta cca ctg ctg ctg ctg       161
Ala Trp Ala Val Leu Leu Leu Leu Leu Leu Leu Pro Leu Leu Leu Leu
            15                  20                  25

gtg ggg gcc gtc ccg ccg ggt cgg ggc cgt gcc gcg ggg ccg cag gag       209
Val Gly Ala Val Pro Pro Gly Arg Gly Arg Ala Ala Gly Pro Gln Glu
        30                  35                  40

gat gta gat gag tgt gcc caa ggg cta gat gac tgc cat gcc gac gcc       257
Asp Val Asp Glu Cys Ala Gln Gly Leu Asp Asp Cys His Ala Asp Ala
    45                  50                  55

ctg tgt cag aac aca ccc acc tcc tac aag tgc tcc tgc aag cct ggc       305
Leu Cys Gln Asn Thr Pro Thr Ser Tyr Lys Cys Ser Cys Lys Pro Gly
 60                  65                  70                  75

tac caa ggg gaa ggc agg cag tgt gag gac atc gat gaa tgt gga aat       353
Tyr Gln Gly Glu Gly Arg Gln Cys Glu Asp Ile Asp Glu Cys Gly Asn
                80                  85                  90

gag ctc aat gga ggc tgt gtc cat gac tgt ttg aat att cca ggc aat       401
Glu Leu Asn Gly Gly Cys Val His Asp Cys Leu Asn Ile Pro Gly Asn
            95                  100                 105

tat cgt tgc act tgt ttt gat ggc ttc atg ttg gct cat gac ggt cat       449
Tyr Arg Cys Thr Cys Phe Asp Gly Phe Met Leu Ala His Asp Gly His
        110                 115                 120

aat tgt ctt gat gtg gac gag tgc ctg gag aac aat ggc ggc tgc cag       497
Asn Cys Leu Asp Val Asp Glu Cys Leu Glu Asn Asn Gly Gly Cys Gln
    125                 130                 135

cat acc tgt gtc aac gtc atg ggg agc tat gag tgc tgc tgc aag gag       545
His Thr Cys Val Asn Val Met Gly Ser Tyr Glu Cys Cys Cys Lys Glu
140                 145                 150                 155

ggg ttt ttc ctg agt gac aat cag cac acc tgc att cac cgc tcg gaa       593
Gly Phe Phe Leu Ser Asp Asn Gln His Thr Cys Ile His Arg Ser Glu
                160                 165                 170
```

-continued

```
gag ggc ctg agc tgc atg aat aag gat cac ggc tgt agt cac atc tgc      641
Glu Gly Leu Ser Cys Met Asn Lys Asp His Gly Cys Ser His Ile Cys
            175                 180                 185

aag gag gcc cca agg ggc agc gtc gcc tgt gag tgc agg cct ggt ttt      689
Lys Glu Ala Pro Arg Gly Ser Val Ala Cys Glu Cys Arg Pro Gly Phe
        190                 195                 200

gag ctg gcc aag aac cag aga gac tgc atc ttg acc tgt aac cat ggg      737
Glu Leu Ala Lys Asn Gln Arg Asp Cys Ile Leu Thr Cys Asn His Gly
    205                 210                 215

aac ggt ggg tgc cag cac tcc tgt gac gat aca gcc gat ggc cca gag      785
Asn Gly Gly Cys Gln His Ser Cys Asp Asp Thr Ala Asp Gly Pro Glu
220                 225                 230                 235

tgc agc tgc cat cca cag tac aag atg cac aca gat ggg agg agc tgc      833
Cys Ser Cys His Pro Gln Tyr Lys Met His Thr Asp Gly Arg Ser Cys
                240                 245                 250

ctt gag cga gag gac act gtc ctg gag gtg aca gag agc aac acc aca      881
Leu Glu Arg Glu Asp Thr Val Leu Glu Val Thr Glu Ser Asn Thr Thr
            255                 260                 265

tca gtg gtg gat ggg gat aaa cgg gtg aaa cgg cgg ctg ctc atg gaa      929
Ser Val Val Asp Gly Asp Lys Arg Val Lys Arg Arg Leu Leu Met Glu
        270                 275                 280

acg tgt gct gtc aac aat gga ggc tgt gac cgc acc tgt aag gat act      977
Thr Cys Ala Val Asn Asn Gly Gly Cys Asp Arg Thr Cys Lys Asp Thr
    285                 290                 295

tcg aca ggt gtc cac tgc agt tgt cct gtt gga ttc act ctc cag ttg     1025
Ser Thr Gly Val His Cys Ser Cys Pro Val Gly Phe Thr Leu Gln Leu
300                 305                 310                 315

gat ggg aag aca tgt aaa gat att gat gag tgc cag acc cgc aat gga     1073
Asp Gly Lys Thr Cys Lys Asp Ile Asp Glu Cys Gln Thr Arg Asn Gly
                320                 325                 330

ggt tgt gat cat ttc tgc aaa aac atc gtg ggc agt ttt gac tgc ggc     1121
Gly Cys Asp His Phe Cys Lys Asn Ile Val Gly Ser Phe Asp Cys Gly
            335                 340                 345

tgc aag aaa gga ttt aaa tta tta aca gat gag aag tct tgc caa gat     1169
Cys Lys Lys Gly Phe Lys Leu Leu Thr Asp Glu Lys Ser Cys Gln Asp
        350                 355                 360

gtg gat gag tgc tct ttg gat agg acc tgt gac cac agc tgc atc aac     1217
Val Asp Glu Cys Ser Leu Asp Arg Thr Cys Asp His Ser Cys Ile Asn
    365                 370                 375

cac cct ggc aca ttt gct tgt gct tgc aac cga ggg tac acc ctg tat     1265
His Pro Gly Thr Phe Ala Cys Ala Cys Asn Arg Gly Tyr Thr Leu Tyr
380                 385                 390                 395

ggc ttc acc cac tgt gga gac acc aat gag tgc agc atc aac aac gga     1313
Gly Phe Thr His Cys Gly Asp Thr Asn Glu Cys Ser Ile Asn Asn Gly
                400                 405                 410

ggc tgt cag cag gtc tgt gtg aac aca gtg ggc agc tat gaa tgc cag     1361
Gly Cys Gln Gln Val Cys Val Asn Thr Val Gly Ser Tyr Glu Cys Gln
            415                 420                 425

tgc cac cct ggg tac aag ctc cac tgg aat aaa aaa gac tgt gtg gaa     1409
Cys His Pro Gly Tyr Lys Leu His Trp Asn Lys Lys Asp Cys Val Glu
        430                 435                 440

gtg aag ggg ctc ctg ccc aca agt gtg tca ccc cgt gtg tcc ctg cac     1457
Val Lys Gly Leu Leu Pro Thr Ser Val Ser Pro Arg Val Ser Leu His
    445                 450                 455

tgc ggt aag agt ggt gga gga gac ggg tgc ttc ctc aga tgt cac tct     1505
Cys Gly Lys Ser Gly Gly Gly Asp Gly Cys Phe Leu Arg Cys His Ser
460                 465                 470                 475

ggc att cac ctc tct tca gga ctg caa ggg gcc tac tct gtc acc tgt     1553
Gly Ile His Leu Ser Ser Gly Leu Gln Gly Ala Tyr Ser Val Thr Cys
                480                 485                 490
```

-continued

```
ggc tct tcc tct cct ctc agg aac aaa caa caa aaa tca aat gac tct      1601
Gly Ser Ser Ser Pro Leu Arg Asn Lys Gln Gln Lys Ser Asn Asp Ser
            495                 500                 505

gct ttt ggg gat gtc acc acc atc agg aca agt gta acc ttt aag cta      1649
Ala Phe Gly Asp Val Thr Thr Ile Arg Thr Ser Val Thr Phe Lys Leu
        510                 515                 520

aat gaa ggc aag tgt agt ttg aaa aat gct gag ctg ttt ccc gag ggt      1697
Asn Glu Gly Lys Cys Ser Leu Lys Asn Ala Glu Leu Phe Pro Glu Gly
    525                 530                 535

ctg cga cca gca cta cca gag aag cac agc tca gta aaa gag agc ttc      1745
Leu Arg Pro Ala Leu Pro Glu Lys His Ser Ser Val Lys Glu Ser Phe
540                 545                 550                 555

cgc tac gta aac ctt aca tgc agc tct ggc aag caa gtc cca gga gcc      1793
Arg Tyr Val Asn Leu Thr Cys Ser Ser Gly Lys Gln Val Pro Gly Ala
                560                 565                 570

cct ggc cga cca agc acc cct aag gaa atg ttt atc act gtt gag ttt      1841
Pro Gly Arg Pro Ser Thr Pro Lys Glu Met Phe Ile Thr Val Glu Phe
            575                 580                 585

gag ctt gaa act aac caa aag gag gtg aca gct tct tgt gac ctg agc      1889
Glu Leu Glu Thr Asn Gln Lys Glu Val Thr Ala Ser Cys Asp Leu Ser
        590                 595                 600

tgc atc gta aag cga acc gag aag cgg ctc cgt aaa gcc atc cgc acg      1937
Cys Ile Val Lys Arg Thr Glu Lys Arg Leu Arg Lys Ala Ile Arg Thr
    605                 610                 615

ctc aga aag gcc gtc cac agg gag cag ttt cac ctc cag ctc tca ggc      1985
Leu Arg Lys Ala Val His Arg Glu Gln Phe His Leu Gln Leu Ser Gly
620                 625                 630                 635

atg aac ctc gac gtg gct aaa aag cct ccc aga aca tct gaa cgc cag      2033
Met Asn Leu Asp Val Ala Lys Lys Pro Pro Arg Thr Ser Glu Arg Gln
                640                 645                 650

gca gag tcc tgt gga gtg ggc cag ggt cat gca gaa aac caa tgt gtc      2081
Ala Glu Ser Cys Gly Val Gly Gln Gly His Ala Glu Asn Gln Cys Val
            655                 660                 665

agt tgc agg gct ggg acc tat tat gat gga gca cga gaa cgc tgc att      2129
Ser Cys Arg Ala Gly Thr Tyr Tyr Asp Gly Ala Arg Glu Arg Cys Ile
        670                 675                 680

tta tgt cca aat gga acc ttc caa aat gag gaa gga caa atg act tgt      2177
Leu Cys Pro Asn Gly Thr Phe Gln Asn Glu Glu Gly Gln Met Thr Cys
    685                 690                 695

gaa cca tgc cca aga cca gga aat tct ggg gcc ctg aag acc cca gaa      2225
Glu Pro Cys Pro Arg Pro Gly Asn Ser Gly Ala Leu Lys Thr Pro Glu
700                 705                 710                 715

gct tgg aat atg tct gaa tgt gga ggt ctg tgt caa cct ggt gaa tat      2273
Ala Trp Asn Met Ser Glu Cys Gly Gly Leu Cys Gln Pro Gly Glu Tyr
                720                 725                 730

tct gca gat ggc ttt gca cct tgc cag ctc tgt gcc ctg ggc acg ttc      2321
Ser Ala Asp Gly Phe Ala Pro Cys Gln Leu Cys Ala Leu Gly Thr Phe
            735                 740                 745

cag cct gaa gct ggt cga act tcc tgc ttc ccc tgt gga gga ggc ctt      2369
Gln Pro Glu Ala Gly Arg Thr Ser Cys Phe Pro Cys Gly Gly Gly Leu
        750                 755                 760

gcc acc aaa cat cag gga gct act tcc ttt cag gac tgt gaa acc aga      2417
Ala Thr Lys His Gln Gly Ala Thr Ser Phe Gln Asp Cys Glu Thr Arg
    765                 770                 775

gtt caa tgt tca cct gga cat ttc tac aac acc acc act cac cga tgt      2465
Val Gln Cys Ser Pro Gly His Phe Tyr Asn Thr Thr Thr His Arg Cys
780                 785                 790                 795

att cgt tgc cca gtg gga aca tac cag cct gaa ttt gga aaa aat aat      2513
Ile Arg Cys Pro Val Gly Thr Tyr Gln Pro Glu Phe Gly Lys Asn Asn
```

-continued

```
                800                 805                 810

tgt gtt tct tgc cca gga aat act acg act gac ttt gat ggc tcc aca      2561
Cys Val Ser Cys Pro Gly Asn Thr Thr Thr Asp Phe Asp Gly Ser Thr
            815                 820                 825

aac ata acc cag tgt aaa aac aga aga tgt gga ggg gag ctg gga gat      2609
Asn Ile Thr Gln Cys Lys Asn Arg Arg Cys Gly Gly Glu Leu Gly Asp
        830                 835                 840

ttc act ggg tac att gaa tcc cca aac tac cca ggc aat tac cca gcc      2657
Phe Thr Gly Tyr Ile Glu Ser Pro Asn Tyr Pro Gly Asn Tyr Pro Ala
    845                 850                 855

aac acc gag tgt acg tgg acc atc aac cca ccc ccc aag cgc cgc atc      2705
Asn Thr Glu Cys Thr Trp Thr Ile Asn Pro Pro Pro Lys Arg Arg Ile
860                 865                 870                 875

ctg atc gtg gtc cct gag atc ttc ctg ccc ata gag gac gac tgt ggg      2753
Leu Ile Val Val Pro Glu Ile Phe Leu Pro Ile Glu Asp Asp Cys Gly
                880                 885                 890

gac tat ctg gtg atg cgg aaa acc tct tca tcc aat tct gtg aca aca      2801
Asp Tyr Leu Val Met Arg Lys Thr Ser Ser Ser Asn Ser Val Thr Thr
            895                 900                 905

tat gaa acc tgc cag acc tac gaa cgc ccc atc gcc ttc acc tcc agg      2849
Tyr Glu Thr Cys Gln Thr Tyr Glu Arg Pro Ile Ala Phe Thr Ser Arg
        910                 915                 920

tca aag aag ctg tgg att cag ttc aag tcc aat gaa ggg aac agc gct      2897
Ser Lys Lys Leu Trp Ile Gln Phe Lys Ser Asn Glu Gly Asn Ser Ala
    925                 930                 935

aga ggg ttc cag gtc cca tac gtg aca tat gat gag gac tac cag gaa      2945
Arg Gly Phe Gln Val Pro Tyr Val Thr Tyr Asp Glu Asp Tyr Gln Glu
940                 945                 950                 955

ctc att gaa gac ata gtt cga gat ggc agg ctc tat gca tct gag aac      2993
Leu Ile Glu Asp Ile Val Arg Asp Gly Arg Leu Tyr Ala Ser Glu Asn
                960                 965                 970

cat cag gaa ata ctt aag gat aag aaa ctt atc aag gct ctg ttt gat      3041
His Gln Glu Ile Leu Lys Asp Lys Lys Leu Ile Lys Ala Leu Phe Asp
            975                 980                 985

gtc ctg gcc cat ccc cag aac tat ttc aag tac aca gcc cag gag tcc      3089
Val Leu Ala His Pro Gln Asn Tyr Phe Lys Tyr Thr Ala Gln Glu Ser
        990                 995                 1000

cga gag atg ttt cca aga tcg ttc atc cga ttg cta cgt tcc aaa gtg      3137
Arg Glu Met Phe Pro Arg Ser Phe Ile Arg Leu Leu Arg Ser Lys Val
    1005                1010                1015

tcc agg ttt ttg aga cct tac aaa tga ctcagcccac gtgccactca            3184
Ser Arg Phe Leu Arg Pro Tyr Lys  *
1020                1025

atacaaatgt tctgctatag ggttggtggg acagagctgt cttccttctg catgtcagca    3244

cagtcgggta ttgctgcctc ccgtatcagt gactcattag agttcaattt ttatagataa    3304

tacagatatt ttggtaaatt gaacttggtt tttctttccc agcatcgtgg atgtagactg    3364

agaatggctt tgagtggcat cagcttctca ctgctgtggg cggatgtctt ggatagatca    3424

cgggctggct gagctggact ttggtcagcc taggtgagac tcacctgtcc ttctggggtc    3484

ttactcctcc tcaaggagtc tgtagtggaa aggaggccac agaataagct gcttattctg    3544

aaacttcagc ttcctctagc ccggccctct ctaagggagc cctctgcact cgtgtgcagg    3604

ctctgaccag gcagaacagg caagagggga gggaaggaga cccctgcagg ctccctccac    3664

ccaccttgag acctgggagg actcagtttc tccacagcct tctccagcct gtgtgataca    3724

agtttgatcc caggaacttg agttctaagc agtgctcgtg aaaaaaaaaa gcagaaagaa    3784

ttagaaataa ataaaaacta agcacttctg gagacat                             3821
```

<210> SEQ ID NO 60
<211> LENGTH: 1027
<212> TYPE: PRT
<213> ORGANISM: human

<400> SEQUENCE: 60

```
Met Gly Val Ala Gly Arg Asn Arg Pro Gly Ala Ala Trp Ala Val Leu
 1               5                  10                  15

Leu Leu Leu Leu Leu Leu Pro Leu Leu Leu Leu Val Gly Ala Val Pro
            20                  25                  30

Pro Gly Arg Gly Arg Ala Ala Gly Pro Gln Glu Asp Val Asp Glu Cys
        35                  40                  45

Ala Gln Gly Leu Asp Asp Cys His Ala Asp Ala Leu Cys Gln Asn Thr
    50                  55                  60

Pro Thr Ser Tyr Lys Cys Ser Cys Lys Pro Gly Tyr Gln Gly Glu Gly
65                  70                  75                  80

Arg Gln Cys Glu Asp Ile Asp Glu Cys Gly Asn Glu Leu Asn Gly Gly
                85                  90                  95

Cys Val His Asp Cys Leu Asn Ile Pro Gly Asn Tyr Arg Cys Thr Cys
            100                 105                 110

Phe Asp Gly Phe Met Leu Ala His Asp Gly His Asn Cys Leu Asp Val
        115                 120                 125

Asp Glu Cys Leu Glu Asn Asn Gly Gly Cys Gln His Thr Cys Val Asn
    130                 135                 140

Val Met Gly Ser Tyr Glu Cys Cys Cys Lys Glu Gly Phe Phe Leu Ser
145                 150                 155                 160

Asp Asn Gln His Thr Cys Ile His Arg Ser Glu Glu Gly Leu Ser Cys
                165                 170                 175

Met Asn Lys Asp His Gly Cys Ser His Ile Cys Lys Glu Ala Pro Arg
            180                 185                 190

Gly Ser Val Ala Cys Glu Cys Arg Pro Gly Phe Glu Leu Ala Lys Asn
        195                 200                 205

Gln Arg Asp Cys Ile Leu Thr Cys Asn His Gly Asn Gly Gly Cys Gln
    210                 215                 220

His Ser Cys Asp Asp Thr Ala Asp Gly Pro Glu Cys Ser Cys His Pro
225                 230                 235                 240

Gln Tyr Lys Met His Thr Asp Gly Arg Ser Cys Leu Glu Arg Glu Asp
                245                 250                 255

Thr Val Leu Glu Val Thr Glu Ser Asn Thr Thr Ser Val Val Asp Gly
            260                 265                 270

Asp Lys Arg Val Lys Arg Arg Leu Leu Met Glu Thr Cys Ala Val Asn
        275                 280                 285

Asn Gly Gly Cys Asp Arg Thr Cys Lys Asp Thr Ser Thr Gly Val His
    290                 295                 300

Cys Ser Cys Pro Val Gly Phe Thr Leu Gln Leu Asp Gly Lys Thr Cys
305                 310                 315                 320

Lys Asp Ile Asp Glu Cys Gln Thr Arg Asn Gly Gly Cys Asp His Phe
                325                 330                 335

Cys Lys Asn Ile Val Gly Ser Phe Asp Cys Gly Cys Lys Lys Gly Phe
            340                 345                 350

Lys Leu Leu Thr Asp Glu Lys Ser Cys Gln Asp Val Asp Glu Cys Ser
        355                 360                 365

Leu Asp Arg Thr Cys Asp His Ser Cys Ile Asn His Pro Gly Thr Phe
```

-continued

```
    370                 375                 380

Ala Cys Ala Cys Asn Arg Gly Tyr Thr Leu Tyr Gly Phe Thr His Cys
385                 390                 395                 400

Gly Asp Thr Asn Glu Cys Ser Ile Asn Asn Gly Gly Cys Gln Gln Val
                405                 410                 415

Cys Val Asn Thr Val Gly Ser Tyr Glu Cys Gln Cys His Pro Gly Tyr
            420                 425                 430

Lys Leu His Trp Asn Lys Lys Asp Cys Val Glu Val Lys Gly Leu Leu
        435                 440                 445

Pro Thr Ser Val Ser Pro Arg Val Ser Leu His Cys Gly Lys Ser Gly
    450                 455                 460

Gly Gly Asp Gly Cys Phe Leu Arg Cys His Ser Gly Ile His Leu Ser
465                 470                 475                 480

Ser Gly Leu Gln Gly Ala Tyr Ser Val Thr Cys Gly Ser Ser Ser Pro
                485                 490                 495

Leu Arg Asn Lys Gln Gln Lys Ser Asn Asp Ser Ala Phe Gly Asp Val
            500                 505                 510

Thr Thr Ile Arg Thr Ser Val Thr Phe Lys Leu Asn Glu Gly Lys Cys
        515                 520                 525

Ser Leu Lys Asn Ala Glu Leu Phe Pro Glu Gly Leu Arg Pro Ala Leu
    530                 535                 540

Pro Glu Lys His Ser Ser Val Lys Glu Ser Phe Arg Tyr Val Asn Leu
545                 550                 555                 560

Thr Cys Ser Ser Gly Lys Gln Val Pro Gly Ala Pro Gly Arg Pro Ser
                565                 570                 575

Thr Pro Lys Glu Met Phe Ile Thr Val Glu Phe Glu Leu Glu Thr Asn
            580                 585                 590

Gln Lys Glu Val Thr Ala Ser Cys Asp Leu Ser Cys Ile Val Lys Arg
        595                 600                 605

Thr Glu Lys Arg Leu Arg Lys Ala Ile Arg Thr Leu Arg Lys Ala Val
    610                 615                 620

His Arg Glu Gln Phe His Leu Gln Leu Ser Gly Met Asn Leu Asp Val
625                 630                 635                 640

Ala Lys Lys Pro Pro Arg Thr Ser Glu Arg Gln Ala Glu Ser Cys Gly
                645                 650                 655

Val Gly Gln Gly His Ala Glu Asn Gln Cys Val Ser Cys Arg Ala Gly
            660                 665                 670

Thr Tyr Tyr Asp Gly Ala Arg Glu Arg Cys Ile Leu Cys Pro Asn Gly
        675                 680                 685

Thr Phe Gln Asn Glu Glu Gly Gln Met Thr Cys Glu Pro Cys Pro Arg
    690                 695                 700

Pro Gly Asn Ser Gly Ala Leu Lys Thr Pro Glu Ala Trp Asn Met Ser
705                 710                 715                 720

Glu Cys Gly Gly Leu Cys Gln Pro Gly Glu Tyr Ser Ala Asp Gly Phe
                725                 730                 735

Ala Pro Cys Gln Leu Cys Ala Leu Gly Thr Phe Gln Pro Glu Ala Gly
            740                 745                 750

Arg Thr Ser Cys Phe Pro Cys Gly Gly Gly Leu Ala Thr Lys His Gln
        755                 760                 765

Gly Ala Thr Ser Phe Gln Asp Cys Glu Thr Arg Val Gln Cys Ser Pro
    770                 775                 780

Gly His Phe Tyr Asn Thr Thr Thr His Arg Cys Ile Arg Cys Pro Val
785                 790                 795                 800
```

```
Gly Thr Tyr Gln Pro Glu Phe Gly Lys Asn Asn Cys Val Ser Cys Pro
                805                 810                 815

Gly Asn Thr Thr Thr Asp Phe Asp Gly Ser Thr Asn Ile Thr Gln Cys
            820                 825                 830

Lys Asn Arg Arg Cys Gly Gly Glu Leu Gly Asp Phe Thr Gly Tyr Ile
        835                 840                 845

Glu Ser Pro Asn Tyr Pro Gly Asn Tyr Pro Ala Asn Thr Glu Cys Thr
    850                 855                 860

Trp Thr Ile Asn Pro Pro Pro Lys Arg Arg Ile Leu Ile Val Val Pro
865                 870                 875                 880

Glu Ile Phe Leu Pro Ile Glu Asp Asp Cys Gly Asp Tyr Leu Val Met
                885                 890                 895

Arg Lys Thr Ser Ser Ser Asn Ser Val Thr Thr Tyr Glu Thr Cys Gln
            900                 905                 910

Thr Tyr Glu Arg Pro Ile Ala Phe Thr Ser Arg Ser Lys Lys Leu Trp
        915                 920                 925

Ile Gln Phe Lys Ser Asn Glu Gly Asn Ser Ala Arg Gly Phe Gln Val
    930                 935                 940

Pro Tyr Val Thr Tyr Asp Glu Asp Tyr Gln Glu Leu Ile Glu Asp Ile
945                 950                 955                 960

Val Arg Asp Gly Arg Leu Tyr Ala Ser Glu Asn His Gln Glu Ile Leu
                965                 970                 975

Lys Asp Lys Lys Leu Ile Lys Ala Leu Phe Asp Val Leu Ala His Pro
            980                 985                 990

Gln Asn Tyr Phe Lys Tyr Thr Ala Gln Glu Ser Arg Glu Met Phe Pro
        995                 1000                1005

Arg Ser Phe Ile Arg Leu Leu Arg Ser Lys Val Ser Arg Phe Leu Arg
    1010                1015                1020

Pro Tyr Lys
1025


<210> SEQ ID NO 61
<211> LENGTH: 540
<212> TYPE: DNA
<213> ORGANISM: human
<220> FEATURE:
<221> NAME/KEY: CDS
<222> LOCATION: (41)...(295)

<400> SEQUENCE: 61

atccctgact cggggtcgcc tttggagcag agaggaggca atg gcc acc atg gag       55
                                             Met Ala Thr Met Glu
                                              1               5

aac aag gtg atc tgc gcc ctg gtc ctg gtg tcc atg ctg gcc ctc ggc      103
Asn Lys Val Ile Cys Ala Leu Val Leu Val Ser Met Leu Ala Leu Gly
                 10                  15                  20

acc ctg gcc gag gcc cag aca gag acg tgt aca gtg gcc ccc cgt gaa      151
Thr Leu Ala Glu Ala Gln Thr Glu Thr Cys Thr Val Ala Pro Arg Glu
             25                  30                  35

aga cag aat tgt ggt ttt cct ggt gtc acg ccc tcc cag tgt gca aat      199
Arg Gln Asn Cys Gly Phe Pro Gly Val Thr Pro Ser Gln Cys Ala Asn
         40                  45                  50

aag ggc tgc tgt ttc gac gac acc gtt cgt ggg gtc ccc tgg tgc ttc      247
Lys Gly Cys Cys Phe Asp Asp Thr Val Arg Gly Val Pro Trp Cys Phe
     55                  60                  65

tat cct aat acc atc gac gtc cct cca gaa gag gag tgt gaa ttt tag      295
Tyr Pro Asn Thr Ile Asp Val Pro Pro Glu Glu Glu Cys Glu Phe  *
```

-continued

```
 70                  75                  80

acacttctgc agggatctgc ctgcatcctg acggggtgcc gtccccagca cggtgattag    355

tcccagagct cggctgccac ctccaccgga cacctcagac acgcttctgc agctgtgcct    415

cggctcacaa cacagattga ctgctctgac tttgactact caaaattggc ctaaaaatta    475

aaagagatcg atattaaaaa aaaaaaaaaa aaaaaaaaaa aaaaaaaaaa aaaaaaaaaa    535

aaaaa                                                                540


<210> SEQ ID NO 62
<211> LENGTH: 84
<212> TYPE: PRT
<213> ORGANISM: human

<400> SEQUENCE: 62

Met Ala Thr Met Glu Asn Lys Val Ile Cys Ala Leu Val Leu Val Ser
 1               5                  10                  15
Met Leu Ala Leu Gly Thr Leu Ala Glu Ala Gln Thr Glu Thr Cys Thr
            20                  25                  30
Val Ala Pro Arg Glu Arg Gln Asn Cys Gly Phe Pro Gly Val Thr Pro
        35                  40                  45
Ser Gln Cys Ala Asn Lys Gly Cys Cys Phe Asp Asp Thr Val Arg Gly
    50                  55                  60
Val Pro Trp Cys Phe Tyr Pro Asn Thr Ile Asp Val Pro Pro Glu Glu
65                  70                  75                  80
Glu Cys Glu Phe


<210> SEQ ID NO 63
<211> LENGTH: 590
<212> TYPE: DNA
<213> ORGANISM: human
<220> FEATURE:
<221> NAME/KEY: CDS
<222> LOCATION: (28)...(402)

<400> SEQUENCE: 63

acctgcaccc cgcccgggca tagcacc atg cct gct tgt cgc cta ggc ccg cta     54
                              Met Pro Ala Cys Arg Leu Gly Pro Leu
                               1               5

gcc gcc gcc ctc ctc ctc agc ctg ctg ctg ttc ggc ttc acc cta gtc      102
Ala Ala Ala Leu Leu Leu Ser Leu Leu Leu Phe Gly Phe Thr Leu Val
 10                  15                  20                  25

tca ggc aca gga gca gag aag act ggc gtg tgc ccc gag ctc cag gct      150
Ser Gly Thr Gly Ala Glu Lys Thr Gly Val Cys Pro Glu Leu Gln Ala
                30                  35                  40

gac cag aac tgc acg caa gag tgc gtc tcg gac agc gaa tgc gcc gac      198
Asp Gln Asn Cys Thr Gln Glu Cys Val Ser Asp Ser Glu Cys Ala Asp
            45                  50                  55

aac ctc aag tgc tgc agc gcg ggc tgt gcc acc ttc tgc tct ctg ccc      246
Asn Leu Lys Cys Cys Ser Ala Gly Cys Ala Thr Phe Cys Ser Leu Pro
        60                  65                  70

aat gat aag gag ggt tcc tgc ccc cag gtg aac att aac ttt ccc cag      294
Asn Asp Lys Glu Gly Ser Cys Pro Gln Val Asn Ile Asn Phe Pro Gln
     75                  80                  85

ctc ggc ctc tgt cgg gac cag tgc cag gtg gac agc cag tgt cct ggc      342
Leu Gly Leu Cys Arg Asp Gln Cys Gln Val Asp Ser Gln Cys Pro Gly
 90                  95                 100                 105

cag atg aaa tgc tgc cgc aat ggc tgt ggg aag gtg tcc tgt gtc act      390
Gln Met Lys Cys Cys Arg Asn Gly Cys Gly Lys Val Ser Cys Val Thr
                110                 115                 120

ccc aat ttc tga gctccagcca ccaccaggct gagcagtgag gagagaaagt          442
Pro Asn Phe  *

ttctgcctgg ccctgcatct ggttccagcc cacctgccct cccctttttc gggactctgt    502
```

-continued

```
attccctctt gggctgacca cagcttctcc ctttcccaac caataaagta accactttca    562

gcaaaaaaaa aaaaaaaaaa aaaaaaaa                                       590
```

<210> SEQ ID NO 64
<211> LENGTH: 124
<212> TYPE: PRT
<213> ORGANISM: human

<400> SEQUENCE: 64

```
Met Pro Ala Cys Arg Leu Gly Pro Leu Ala Ala Ala Leu Leu Leu Ser
 1               5                  10                  15
Leu Leu Leu Phe Gly Phe Thr Leu Val Ser Gly Thr Gly Ala Glu Lys
            20                  25                  30
Thr Gly Val Cys Pro Glu Leu Gln Ala Asp Gln Asn Cys Thr Gln Glu
        35                  40                  45
Cys Val Ser Asp Ser Glu Cys Ala Asp Asn Leu Lys Cys Cys Ser Ala
    50                  55                  60
Gly Cys Ala Thr Phe Cys Ser Leu Pro Asn Asp Lys Glu Gly Ser Cys
65                  70                  75                  80
Pro Gln Val Asn Ile Asn Phe Pro Gln Leu Gly Leu Cys Arg Asp Gln
                85                  90                  95
Cys Gln Val Asp Ser Gln Cys Pro Gly Gln Met Lys Cys Cys Arg Asn
            100                 105                 110
Gly Cys Gly Lys Val Ser Cys Val Thr Pro Asn Phe
        115                 120
```

<210> SEQ ID NO 65
<211> LENGTH: 450
<212> TYPE: DNA
<213> ORGANISM: human
<220> FEATURE:
<221> NAME/KEY: CDS
<222> LOCATION: (67)...(288)

<400> SEQUENCE: 65

```
cccaagatgg actcaggcag gcagctctgc tgtatgtgaa gcccagtgag gggcagtggg     60

ggggcc atg ctg cag gta caa gtt aat ctc cct gta tcg cct ctg ccc       108
       Met Leu Gln Val Gln Val Asn Leu Pro Val Ser Pro Leu Pro
        1               5                  10

act tac cct tac tcc ttt ttc tac cca gat aag gag ggt tcc tgc ccc      156
Thr Tyr Pro Tyr Ser Phe Phe Tyr Pro Asp Lys Glu Gly Ser Cys Pro
 15                  20                  25                  30

cag gtg aac att aac ttt ccc cag ctc ggc ctc tgt cgg gac cag tgc      204
Gln Val Asn Ile Asn Phe Pro Gln Leu Gly Leu Cys Arg Asp Gln Cys
                 35                  40                  45

cag gtg gac agc cag tgt cct ggc cag atg aaa tgc tgc cgc aat ggc      252
Gln Val Asp Ser Gln Cys Pro Gly Gln Met Lys Cys Cys Arg Asn Gly
             50                  55                  60

tgt ggg aag gtg tcc tgt gtc act ccc aat ttc tga ggtccagcca           298
Cys Gly Lys Val Ser Cys Val Thr Pro Asn Phe  *
         65                  70

ccaccaggct gagcagtgag gagagaaagt ttctgcctgg ccctgcatct ggttccagcc    358

cacctgccct ccccttttc gggactctgt attccctctt gggctgacca cagcttctcc     418

ctttcccaac caataaagta accactttca gc                                  450
```

<210> SEQ ID NO 66
<211> LENGTH: 73
<212> TYPE: PRT
<213> ORGANISM: human

<400> SEQUENCE: 66

```
Met Leu Gln Val Gln Val Asn Leu Pro Val Ser Pro Leu Pro Thr Tyr
 1               5                  10                  15
```

-continued

```
Pro Tyr Ser Phe Phe Tyr Pro Asp Lys Glu Gly Ser Cys Pro Gln Val
            20                  25                  30

Asn Ile Asn Phe Pro Gln Leu Gly Leu Cys Arg Asp Gln Cys Gln Val
        35                  40                  45

Asp Ser Gln Cys Pro Gly Gln Met Lys Cys Cys Arg Asn Gly Cys Gly
    50                  55                  60

Lys Val Ser Cys Val Thr Pro Asn Phe
65                  70


<210> SEQ ID NO 67
<211> LENGTH: 1595
<212> TYPE: DNA
<213> ORGANISM: human
<220> FEATURE:
<221> NAME/KEY: CDS
<222> LOCATION: (81)...(1319)

<400> SEQUENCE: 67

ggcacgaggc ttataacctg ggatgggcac ccctgccagt cctgctctgc cgcctgccac      60

cgctgcccga gcccgacgct atg tcc agc aaa ggc tcc gtg gtt ctg gcc tac    113
                       Met Ser Ser Lys Gly Ser Val Val Leu Ala Tyr
                        1               5                  10

agt ggc ggc ctg gac acc tcg tgc atc ctc gtg tgg ctg aag gaa caa      161
Ser Gly Gly Leu Asp Thr Ser Cys Ile Leu Val Trp Leu Lys Glu Gln
             15                  20                  25

ggc tat gac gtc att gcc tat ctg gcc aac att ggc cag aag gaa gac      209
Gly Tyr Asp Val Ile Ala Tyr Leu Ala Asn Ile Gly Gln Lys Glu Asp
         30                  35                  40

ttc gag gaa gcc agg aag aag gca ctg aag ctt ggg gcc aaa aag gtg      257
Phe Glu Glu Ala Arg Lys Lys Ala Leu Lys Leu Gly Ala Lys Lys Val
     45                  50                  55

ttc att gag gat gtc agc agg gag ttt gtg gag gag ttc atc tgg ccg      305
Phe Ile Glu Asp Val Ser Arg Glu Phe Val Glu Glu Phe Ile Trp Pro
 60                  65                  70                  75

gcc atc cag tcc agc gca ctg tat gag gac cgc tac ctc ctg ggc acc      353
Ala Ile Gln Ser Ser Ala Leu Tyr Glu Asp Arg Tyr Leu Leu Gly Thr
                 80                  85                  90

tct ctt gcc agg ccc tgc atc gcc cgc aaa caa gtg gaa atc gcc cag      401
Ser Leu Ala Arg Pro Cys Ile Ala Arg Lys Gln Val Glu Ile Ala Gln
             95                 100                 105

cgg gag ggg gcc aag tat gtg tcc cac ggc gcc aca gga aag ggg aac      449
Arg Glu Gly Ala Lys Tyr Val Ser His Gly Ala Thr Gly Lys Gly Asn
        110                 115                 120

gat cag gtc cgg ttt gag ctc agc tgc tac tca ctg gcc ccc cag ata      497
Asp Gln Val Arg Phe Glu Leu Ser Cys Tyr Ser Leu Ala Pro Gln Ile
    125                 130                 135

aag gtc att gct ccc tgg agg atg cct gaa ttc tac aac cgg ttc aag      545
Lys Val Ile Ala Pro Trp Arg Met Pro Glu Phe Tyr Asn Arg Phe Lys
140                 145                 150                 155

ggc cgc aat gac ctg atg gag tac gca aag caa cac ggg att ccc atc      593
Gly Arg Asn Asp Leu Met Glu Tyr Ala Lys Gln His Gly Ile Pro Ile
                160                 165                 170

ccg gtc act ccc aag aac ccg tgg agc atg gat gag aac ctc atg cac      641
Pro Val Thr Pro Lys Asn Pro Trp Ser Met Asp Glu Asn Leu Met His
            175                 180                 185

atc agc tac gag gct gga atc ctg gag aac ccc aag aac caa gcg cct      689
Ile Ser Tyr Glu Ala Gly Ile Leu Glu Asn Pro Lys Asn Gln Ala Pro
        190                 195                 200

cca ggt ctc tac acg aag acc cag gac cca gcc aaa gcc ccc aac acc      737
```

-continued

```
Pro Gly Leu Tyr Thr Lys Thr Gln Asp Pro Ala Lys Ala Pro Asn Thr
    205                 210                 215

cct gac att ctc gag atc gag ttc aaa aaa ggg gtc cct gtg aag gtg      785
Pro Asp Ile Leu Glu Ile Glu Phe Lys Lys Gly Val Pro Val Lys Val
220                 225                 230                 235

acc aac gtc aag gat ggc acc acc cac cag acc tcc ttg gag ctc ttc      833
Thr Asn Val Lys Asp Gly Thr Thr His Gln Thr Ser Leu Glu Leu Phe
                240                 245                 250

atg tac ctg aac gaa gtc gcg ggc aag cat ggc gtg ggc cgt att gac      881
Met Tyr Leu Asn Glu Val Ala Gly Lys His Gly Val Gly Arg Ile Asp
            255                 260                 265

atc gtg gag aac cgc ttc att gga atg aag tcc cga ggt atc tac gag      929
Ile Val Glu Asn Arg Phe Ile Gly Met Lys Ser Arg Gly Ile Tyr Glu
        270                 275                 280

acc cca gca ggc acc atc ctt tac cac gct cat tta gac atc gag gcc      977
Thr Pro Ala Gly Thr Ile Leu Tyr His Ala His Leu Asp Ile Glu Ala
    285                 290                 295

ttc acc atg gac cgg gaa gtg cgc aaa atc aaa caa ggc ctg ggc ttg     1025
Phe Thr Met Asp Arg Glu Val Arg Lys Ile Lys Gln Gly Leu Gly Leu
300                 305                 310                 315

aaa ttt gct gag ctg gtg tat acc ggt ttc tgg cac agc cct gag tgt     1073
Lys Phe Ala Glu Leu Val Tyr Thr Gly Phe Trp His Ser Pro Glu Cys
                320                 325                 330

gaa ttt gtc cgc cac tgc atc gcc aag tcc cag gag cga gtg gaa ggg     1121
Glu Phe Val Arg His Cys Ile Ala Lys Ser Gln Glu Arg Val Glu Gly
            335                 340                 345

aaa gtg cag gtg tcc gtc ctc aag ggc cag gtg tac atc ctc ggc cgg     1169
Lys Val Gln Val Ser Val Leu Lys Gly Gln Val Tyr Ile Leu Gly Arg
        350                 355                 360

gag tcc cca ctg tct ctc tac aat gag gag ctg gtg agc atg aac gtg     1217
Glu Ser Pro Leu Ser Leu Tyr Asn Glu Glu Leu Val Ser Met Asn Val
    365                 370                 375

cag ggt gat tat gag cca act gat gcc acc ggg ttc atc aac atc aat     1265
Gln Gly Asp Tyr Glu Pro Thr Asp Ala Thr Gly Phe Ile Asn Ile Asn
380                 385                 390                 395

tcc ctc agg ctg aag gaa tat cat cgt ctc cag agc aag gtc act gcc     1313
Ser Leu Arg Leu Lys Glu Tyr His Arg Leu Gln Ser Lys Val Thr Ala
                400                 405                 410

aaa tag acccgtgtac aatgaggagc tggggcctcc tcaatttgca gatcccccaa      1369
Lys  *

gtacaggcgc taattgttgt gataatttgt aattgtgact tgttctcccc ggctggcagc   1429

gtagtggggc tgccaggccc cagctttgtt ccctggtccc cctgaagcct gcaaacgttg   1489

tcatcgaagg gaagggtggg gggcagctgc ggtggggagc tataaaaatg acaattaaaa   1549

gagacactag tcttttattt ctaaaaaaaa aaaaaaaaaa aaaaaa                  1595


<210> SEQ ID NO 68
<211> LENGTH: 412
<212> TYPE: PRT
<213> ORGANISM: human

<400> SEQUENCE: 68

Met Ser Ser Lys Gly Ser Val Val Leu Ala Tyr Ser Gly Gly Leu Asp
 1               5                  10                  15

Thr Ser Cys Ile Leu Val Trp Leu Lys Glu Gln Gly Tyr Asp Val Ile
            20                  25                  30

Ala Tyr Leu Ala Asn Ile Gly Gln Lys Glu Asp Phe Glu Glu Ala Arg
        35                  40                  45
```

-continued

```
Lys Lys Ala Leu Lys Leu Gly Ala Lys Lys Val Phe Ile Glu Asp Val
    50                  55                  60

Ser Arg Glu Phe Val Glu Glu Phe Ile Trp Pro Ala Ile Gln Ser Ser
65                  70                  75                  80

Ala Leu Tyr Glu Asp Arg Tyr Leu Leu Gly Thr Ser Leu Ala Arg Pro
                85                  90                  95

Cys Ile Ala Arg Lys Gln Val Glu Ile Ala Gln Arg Glu Gly Ala Lys
            100                 105                 110

Tyr Val Ser His Gly Ala Thr Gly Lys Gly Asn Asp Gln Val Arg Phe
        115                 120                 125

Glu Leu Ser Cys Tyr Ser Leu Ala Pro Gln Ile Lys Val Ile Ala Pro
    130                 135                 140

Trp Arg Met Pro Glu Phe Tyr Asn Arg Phe Lys Gly Arg Asn Asp Leu
145                 150                 155                 160

Met Glu Tyr Ala Lys Gln His Gly Ile Pro Ile Pro Val Thr Pro Lys
                165                 170                 175

Asn Pro Trp Ser Met Asp Glu Asn Leu Met His Ile Ser Tyr Glu Ala
            180                 185                 190

Gly Ile Leu Glu Asn Pro Lys Asn Gln Ala Pro Pro Gly Leu Tyr Thr
        195                 200                 205

Lys Thr Gln Asp Pro Ala Lys Ala Pro Asn Thr Pro Asp Ile Leu Glu
    210                 215                 220

Ile Glu Phe Lys Lys Gly Val Pro Val Lys Val Thr Asn Val Lys Asp
225                 230                 235                 240

Gly Thr Thr His Gln Thr Ser Leu Glu Leu Phe Met Tyr Leu Asn Glu
                245                 250                 255

Val Ala Gly Lys His Gly Val Gly Arg Ile Asp Ile Val Glu Asn Arg
            260                 265                 270

Phe Ile Gly Met Lys Ser Arg Gly Ile Tyr Glu Thr Pro Ala Gly Thr
        275                 280                 285

Ile Leu Tyr His Ala His Leu Asp Ile Glu Ala Phe Thr Met Asp Arg
    290                 295                 300

Glu Val Arg Lys Ile Lys Gln Gly Leu Gly Leu Lys Phe Ala Glu Leu
305                 310                 315                 320

Val Tyr Thr Gly Phe Trp His Ser Pro Glu Cys Glu Phe Val Arg His
                325                 330                 335

Cys Ile Ala Lys Ser Gln Glu Arg Val Glu Gly Lys Val Gln Val Ser
            340                 345                 350

Val Leu Lys Gly Gln Val Tyr Ile Leu Gly Arg Glu Ser Pro Leu Ser
        355                 360                 365

Leu Tyr Asn Glu Glu Leu Val Ser Met Asn Val Gln Gly Asp Tyr Glu
    370                 375                 380

Pro Thr Asp Ala Thr Gly Phe Ile Asn Ile Asn Ser Leu Arg Leu Lys
385                 390                 395                 400

Glu Tyr His Arg Leu Gln Ser Lys Val Thr Ala Lys
                405                 410
```

<210> SEQ ID NO 69
<211> LENGTH: 2682
<212> TYPE: DNA
<213> ORGANISM: human
<220> FEATURE:
<221> NAME/KEY: CDS
<222> LOCATION: (18)...(980)

<400> SEQUENCE: 69

-continued

```
cgagccaggg agaaagg atg gcc ggc ctg gcg gcg cgg ttg gtc ctg cta        50
                  Met Ala Gly Leu Ala Ala Arg Leu Val Leu Leu
                  1               5                   10

gct ggg gca gcg gcg ctg gcg agc ggc tcc cag ggc gac cgt gag ccg       98
Ala Gly Ala Ala Ala Leu Ala Ser Gly Ser Gln Gly Asp Arg Glu Pro
            15                  20                  25

gtg tac cgc gac tgc gta ctg cag tgc gaa gag cag aac tgc tct ggg      146
Val Tyr Arg Asp Cys Val Leu Gln Cys Glu Glu Gln Asn Cys Ser Gly
        30                  35                  40

ggc gct ctg aat cac ttc cgc tcc cgc cag cca atc tac atg agt cta      194
Gly Ala Leu Asn His Phe Arg Ser Arg Gln Pro Ile Tyr Met Ser Leu
    45                  50                  55

gca ggc tgg acc tgt cgg gac gac tgt aag tat gag tgt atg tgg gtc      242
Ala Gly Trp Thr Cys Arg Asp Asp Cys Lys Tyr Glu Cys Met Trp Val
 60                 65                  70                  75

acc gtt ggg ctc tac ctc cag gaa ggt cac aaa gtg cct cag ttc cat      290
Thr Val Gly Leu Tyr Leu Gln Glu Gly His Lys Val Pro Gln Phe His
                80                  85                  90

ggc aag tgg ccc ttc tcc cgg ttc ctg ttc ttt caa gag ccg gca tcg      338
Gly Lys Trp Pro Phe Ser Arg Phe Leu Phe Phe Gln Glu Pro Ala Ser
            95                 100                 105

gcc gtg gcc tcg ttt ctc aat ggc ctg gcc agc ctg gtg atg ctc tgc      386
Ala Val Ala Ser Phe Leu Asn Gly Leu Ala Ser Leu Val Met Leu Cys
        110                 115                 120

cgc tac cgc acc ttc gtg cca gcc tcc tcc ccc atg tac cac acc tgt      434
Arg Tyr Arg Thr Phe Val Pro Ala Ser Ser Pro Met Tyr His Thr Cys
    125                 130                 135

gtg gcc ttc gcc tgg gtg tcc ctc aat gca tgg ttc tgg tcc aca gtt      482
Val Ala Phe Ala Trp Val Ser Leu Asn Ala Trp Phe Trp Ser Thr Val
140                 145                 150                 155

ttc cac acc agg gac act gac ctc aca gag aaa atg gac tac ttc tgt      530
Phe His Thr Arg Asp Thr Asp Leu Thr Glu Lys Met Asp Tyr Phe Cys
                160                 165                 170

gcc tcc act gtc atc cta cac tca atc tac ctg tgc tgc gtc agg acc      578
Ala Ser Thr Val Ile Leu His Ser Ile Tyr Leu Cys Cys Val Arg Thr
            175                 180                 185

gtg ggg ctg cag cac cca gct gtg gtc agt gcc ttc cgg gct ctc ctg      626
Val Gly Leu Gln His Pro Ala Val Val Ser Ala Phe Arg Ala Leu Leu
        190                 195                 200

ctg ctc atg ctg acc gtg cac gtc tcc tac ctg agc ctc atc cgc ttc      674
Leu Leu Met Leu Thr Val His Val Ser Tyr Leu Ser Leu Ile Arg Phe
    205                 210                 215

gac tat ggc tac aac ctg gtg gcc aac gtg gct att ggc ctg gtc aac      722
Asp Tyr Gly Tyr Asn Leu Val Ala Asn Val Ala Ile Gly Leu Val Asn
220                 225                 230                 235

gtg gtg tgg tgg ctg gcc tgg tgc ctg tgg aac cag cgg cgg ctg cct      770
Val Val Trp Trp Leu Ala Trp Cys Leu Trp Asn Gln Arg Arg Leu Pro
                240                 245                 250

cac gtg cgc aag tgc gtg gtg gtg gtc ttg ctg ctg cag ggg ctg tcc      818
His Val Arg Lys Cys Val Val Val Val Leu Leu Leu Gln Gly Leu Ser
            255                 260                 265

ctg ctc gag ctg ctt gac ttc cca ccg ctc ttc tgg gtc ctg gat gcc      866
Leu Leu Glu Leu Leu Asp Phe Pro Pro Leu Phe Trp Val Leu Asp Ala
        270                 275                 280

cat gcc atc tgg cac atc agc acc atc cct gtc cac gtc ctc ttt ttc      914
His Ala Ile Trp His Ile Ser Thr Ile Pro Val His Val Leu Phe Phe
    285                 290                 295

agc ttt ctg gaa gat gac agc ctg tac ctg ctg aag gaa tca gag gac      962
Ser Phe Leu Glu Asp Asp Ser Leu Tyr Leu Leu Lys Glu Ser Glu Asp
```

-continued

```
300                 305                 310                 315

aag ttc aag ctg gac tga agaccttgga gcgagtctgc cccagtgggg            1010
Lys Phe Lys Leu Asp  *
                320

atcctgcccc cgccctgctg gcctcccttc tcccctcaac ccttgagatg attttctctt   1070

ttcaacttct tgaacttgga catgaaggat gtgggcccag aatcatgtgg ccagcccacc   1130

ccctgttggc cctcaccagc cttggagtct gttctaggga aggcctccca gcatctggga   1190

ctcgagagtg ggcagcccct ctacctcctg gagctgaact ggggtggaac tgagtgtgct   1250

cttagctcta ccgggaggac agctgcctgt ttcctcccca tcagcctcct ccccacatcc   1310

ccagctgcct ggctgggtcc tgaagccctc tgtctacctg ggagaccagg gaccacaggc   1370

cttagggata caggggggtcc ccttctgtta ccacccccca ccctcctcca ggacaccact  1430

aggtggtgct ggatgcttgt tctttggcca gccaaggttc acggcgattc tccccatggg   1490

atcttgaggg accaagctgc tgggattggg aaggagtttc accctgacca ttgccctagc   1550

caggttccca ggaggcctca ccatactccc tttcagggcc agggctccag caagcccagg   1610

gcaaggatcc tgtgctgctg tctggttgag agcctgccac cgtgtgtcgg gagtgtgggc   1670

caggctgagt gcataggtga cagggccgtg agcatgggcc tgggtgtgtg tgagctcagg   1730

cctaggtgcg cagtgtggag acgggtgttg tcggggaaga ggtgtggctt caaagtgtgt   1790

gtgtgcaggg ggtgggtgtg ttagcgtggg ttaggggaac gtgtgtgcgc gtgctggtgg   1850

gcatgtgaga tgagtgactg ccggtgaatg tgtccacagt tgagaggttg gagcaggatg   1910

agggaatcct gtcaccatca ataatcactt gtggagcgcc agctctgccc aaggcgccac   1970

ctgggcggac agccaggagc tctccatggc caggctgcct gtgtgcatgt tccctgtctg   2030

gtgcccccttt gcccgcctcc tgcaaacctc acagggtccc cacacaacag tgccctccag  2090

aagcagcccc tcggaggcag aggaaggaaa atggggatgg ctggggctct ctccatcctc   2150

cttttctcct tgccttcgca tggctggcct tcccctccaa aacctccatt cccctgctgc   2210

cagcccctttt gccatagcct gattttgggg aggaggaagg ggcgatttga gggagaaggg  2270

gagaaagctt atggctgggt ctggtttctt cccttcccag agggtcttac tgttccaggg   2330

tggccccagg gcaggcaggg gccacactat gcctgcgccc tggtaaaggt gacccctgcc   2390

atttaccagc agccctggca tgttcctgcc ccacaggaat agaatggagg gagctccaga   2450

aactttccat cccaaaggca gtctccgtgg ttgaagcaga ctggattttt gctctgcccc   2510

tgacccccttg tccctctttg agggagggga gctatgctag gactccaacc tcagggactc  2570

gggtggcctg cgctagcttc ttttgatact gaaaactttt aaggtgggag ggtggcaagg   2630

gatgtgctta ataaatcaat tccaagcctc aaaaaaaaaa aaaaaaaaaa aa           2682


<210> SEQ ID NO 70
<211> LENGTH: 320
<212> TYPE: PRT
<213> ORGANISM: human

<400> SEQUENCE: 70

Met Ala Gly Leu Ala Ala Arg Leu Val Leu Leu Ala Gly Ala Ala Ala
 1               5                  10                  15

Leu Ala Ser Gly Ser Gln Gly Asp Arg Glu Pro Val Tyr Arg Asp Cys
            20                  25                  30

Val Leu Gln Cys Glu Glu Gln Asn Cys Ser Gly Gly Ala Leu Asn His
        35                  40                  45
```

-continued

```
Phe Arg Ser Arg Gln Pro Ile Tyr Met Ser Leu Ala Gly Trp Thr Cys
    50                  55                  60

Arg Asp Asp Cys Lys Tyr Glu Cys Met Trp Val Thr Val Gly Leu Tyr
65                  70                  75                  80

Leu Gln Glu Gly His Lys Val Pro Gln Phe His Gly Lys Trp Pro Phe
                85                  90                  95

Ser Arg Phe Leu Phe Phe Gln Glu Pro Ala Ser Ala Val Ala Ser Phe
            100                 105                 110

Leu Asn Gly Leu Ala Ser Leu Val Met Leu Cys Arg Tyr Arg Thr Phe
        115                 120                 125

Val Pro Ala Ser Ser Pro Met Tyr His Thr Cys Val Ala Phe Ala Trp
    130                 135                 140

Val Ser Leu Asn Ala Trp Phe Trp Ser Thr Val Phe His Thr Arg Asp
145                 150                 155                 160

Thr Asp Leu Thr Glu Lys Met Asp Tyr Phe Cys Ala Ser Thr Val Ile
                165                 170                 175

Leu His Ser Ile Tyr Leu Cys Cys Val Arg Thr Val Gly Leu Gln His
            180                 185                 190

Pro Ala Val Val Ser Ala Phe Arg Ala Leu Leu Leu Leu Met Leu Thr
        195                 200                 205

Val His Val Ser Tyr Leu Ser Leu Ile Arg Phe Asp Tyr Gly Tyr Asn
    210                 215                 220

Leu Val Ala Asn Val Ala Ile Gly Leu Val Asn Val Val Trp Trp Leu
225                 230                 235                 240

Ala Trp Cys Leu Trp Asn Gln Arg Arg Leu Pro His Val Arg Lys Cys
                245                 250                 255

Val Val Val Val Leu Leu Leu Gln Gly Leu Ser Leu Leu Glu Leu Leu
            260                 265                 270

Asp Phe Pro Pro Leu Phe Trp Val Leu Asp Ala His Ala Ile Trp His
        275                 280                 285

Ile Ser Thr Ile Pro Val His Val Leu Phe Phe Ser Phe Leu Glu Asp
    290                 295                 300

Asp Ser Leu Tyr Leu Leu Lys Glu Ser Glu Asp Lys Phe Lys Leu Asp
305                 310                 315                 320


<210> SEQ ID NO 71
<211> LENGTH: 2116
<212> TYPE: DNA
<213> ORGANISM: human
<220> FEATURE:
<221> NAME/KEY: CDS
<222> LOCATION: (57)...(299)

<400> SEQUENCE: 71

cggttctcca agcacccagc atcctgctag acgcgccgcg caccgacgga ggggac atg      59
                                                              Met
                                                               1

ggc aga gca atg gtg gcc agg ctg ggg ctg ggg ctg ctg ctg ctg gca      107
Gly Arg Ala Met Val Ala Arg Leu Gly Leu Gly Leu Leu Leu Leu Ala
            5                   10                  15

ctg ctc cta ccc acg cag att tat tcc agt gaa aca aca act gga act      155
Leu Leu Leu Pro Thr Gln Ile Tyr Ser Ser Glu Thr Thr Thr Gly Thr
        20                  25                  30

tca agt aac tcc tcc cag agt act tcc aac tct ggg ttg gcc cca aat      203
Ser Ser Asn Ser Ser Gln Ser Thr Ser Asn Ser Gly Leu Ala Pro Asn
     35                  40                  45

cca act aat gcc acc acc aag gcg gct ggt ggt gcc ctg cag tca aca      251
```

-continued

```
Pro Thr Asn Ala Thr Thr Lys Ala Ala Gly Gly Ala Leu Gln Ser Thr
 50                  55                  60                  65

gcc agt ctc ttc gtg gtc tca ctc tct ctt ctg cat ctc tac tct taa      299
Ala Ser Leu Phe Val Val Ser Leu Ser Leu Leu His Leu Tyr Ser  *
                70                  75                  80

gagactcagg ccaagaaacg tcttctaaat ttccccatct tctaaaccca atccaaatgg    359

cgtctggaag tccaatgtgg caaggaaaaa caggtcttca tcgaatctac taattccaca    419

ccttttattg acacagaaaa tgttgagaat cccaaatttg attgatttga agaacatgtg    479

agaggtttga ctagatgatg aatgccaata ttaaatctgc tggagtttca tgtacaagat    539

gaaggagagg caacatccaa aatagttaag acatgatttc cttgaatgtg gcttgagaaa    599

tatggacact taatactacc ttgaaaataa gaatagaaat aaaggatggg attgtggaat    659

ggagattcag ttttcattgg ttcattaatt ctataaggcc ataaaacagg taatataaaa    719

agcttccatc gatctattta tatgtacatg agaaggaatc cccaggtgtt actgtaattc    779

ctcaacgtat tgtttcgacg gcactaattt aatgccgata tactctagat gaatgtttac    839

attgttgagc tattgctgtt ctcttgggaa ctgaactcac tttcctcctg aggctttgga    899

tttgacattg catttgacct tttaggtagt aattgacatg tgccagggca atgatgaatg    959

agaatctacc ccagatccaa gcatcctgag caactcttga ttatccatat tgagtcaaat   1019

ggtaggcatt tcctatcacc tgtttccatt caacaagagc actacattct tttagctaaa   1079

cggattccaa agagtagaat tgcattgacc acgactaatt tcaaaatgct ttttattatt   1139

attatttttt agacagtctc actttgtcgc ccaggccgga gtgcagtggt gcgatctcag   1199

atcagtgtac catttgcctc ccgggctcaa gcgattctcc tgcctcagcc tcccaagtag   1259

ctgggattac aggcacctgc caccatgccc ggctaatttt tgtaatttta gtagagacag   1319

ggtttcacca tgttgcccag gctggtttag aactcctgac ctcaggtgat ccacccgcct   1379

cggcctccca aagtgctggg attacaggct tgagcccccg cgcccagcca tcaaaatgct   1439

ttttatttct gcatatgttt gaatactttt tacaatttaa aaaaatgatc tgttttgaag   1499

gcaaaattgc aaatcttgaa attaagaagg caaaatgtaa aggagtcaaa ctataaatca   1559

agtatttggg aagtgaagac tggaagctaa tttgcataaa ttcacaaact tttatactct   1619

ttctgtatat acattttttt tctttaaaaa acaactatgg atcagaatag caacatttag   1679

aacacttttt gttatcagtc aatattttta gatagttaga acctggtcct aagcctaaaa   1739

gtgggcttga ttctgcagta aatcttttac aactgcctcg acacacataa accttttttaa   1799

aaatagacac tccccgaagt cttttgtttg tatggtcaca cactgatgct tagatgttcc   1859

agtaatctaa tatggccaca gtagtcttga tgaccaaagt cctttttttc catctttaga   1919

aaactacatg ggaacaaaca gatcgaacag ttttgaagct actgtgtgtg tgaatgaaca   1979

ctcttgcttt attccagaat gctgtacatc tattttggat tgtatattgt ggttgtgtat   2039

ttacgctttg attcatagta acttcttatg gaattgattt gcattgaacg acaaactgta   2099

aataaaaaga aacggtg                                                   2116

<210> SEQ ID NO 72
<211> LENGTH: 80
<212> TYPE: PRT
<213> ORGANISM: human

<400> SEQUENCE: 72

Met Gly Arg Ala Met Val Ala Arg Leu Gly Leu Gly Leu Leu Leu Leu
 1               5                  10                  15
```

-continued

```
Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Ser Gly Leu Ala Pro
        35                  40                  45

Asn Pro Thr Asn Ala Thr Thr Lys Ala Ala Gly Gly Ala Leu Gln Ser
    50                  55                  60

Thr Ala Ser Leu Phe Val Val Ser Leu Ser Leu Leu His Leu Tyr Ser
65                  70                  75                  80


<210> SEQ ID NO 73
<211> LENGTH: 1513
<212> TYPE: DNA
<213> ORGANISM: human
<220> FEATURE:
<221> NAME/KEY: CDS
<222> LOCATION: (236)...(742)

<400> SEQUENCE: 73

attcacttct cacaaggact gggtgaagag ttctgcagcc ttacagagac tggaaaagaa      60

gcccaaacca aggcccccag agaggtcccc caggcccctt tgggtccctg agcctcagct     120

ggaggtgggg ggtgcctgca gtgcgctggc tcagtctcct tctgaaaagc tggatccagc     180

ttgtttgaag cccttgagct gatcttagat ccggcgcagg agaccaacgc ctgcc atg      238
                                                             Met
                                                              1

ctg ttc cgg ctc tca gag cac tcc tca cca gag gag gaa gcc tcc ccc       286
Leu Phe Arg Leu Ser Glu His Ser Ser Pro Glu Glu Glu Ala Ser Pro
             5                  10                  15

cac cag aga gcc tca gga gag ggg cac cat ctc aag tcg aag aga ccc       334
His Gln Arg Ala Ser Gly Glu Gly His His Leu Lys Ser Lys Arg Pro
         20                  25                  30

aac ccc tgt gcc tac aca cca cct tcg ctg aaa gct gtg cag cgc att       382
Asn Pro Cys Ala Tyr Thr Pro Pro Ser Leu Lys Ala Val Gln Arg Ile
     35                  40                  45

gct gag tct cac ctg cag tct atc agc aat ttg aat gag aac cag gcc       430
Ala Glu Ser His Leu Gln Ser Ile Ser Asn Leu Asn Glu Asn Gln Ala
 50                  55                  60                  65

tca gag gag gag gat gag ctg ggg gag ctt cgg gag ctg ggt tat cca       478
Ser Glu Glu Glu Asp Glu Leu Gly Glu Leu Arg Glu Leu Gly Tyr Pro
                 70                  75                  80

aga gag gaa gat gag gag gaa gag gag gat gat gaa gaa gag gaa gaa       526
Arg Glu Glu Asp Glu Glu Glu Glu Glu Asp Asp Glu Glu Glu Glu Glu
             85                  90                  95

gaa gag gac agc cag gct gaa gtc ctg aag gtc atc agg cag tct gct       574
Glu Glu Asp Ser Gln Ala Glu Val Leu Lys Val Ile Arg Gln Ser Ala
        100                 105                 110

ggg caa aag aca acc tgt ggc cag ggt ctg gaa ggg ccc tgg gag cgc       622
Gly Gln Lys Thr Thr Cys Gly Gln Gly Leu Glu Gly Pro Trp Glu Arg
    115                 120                 125

cca ccc cct ctg gat gag tcc gag aga gat gga ggc tct gag gac caa       670
Pro Pro Pro Leu Asp Glu Ser Glu Arg Asp Gly Gly Ser Glu Asp Gln
130                 135                 140                 145

gtg gaa gac cca gca cta agt gag cct ggg gag gaa cct cag cgc cct       718
Val Glu Asp Pro Ala Leu Ser Glu Pro Gly Glu Glu Pro Gln Arg Pro
                150                 155                 160

tcc ccc tct gag cct ggc aca tag gcacccagcc tgcatctccc aggaggaagt      772
Ser Pro Ser Glu Pro Gly Thr  *
            165

ggaggggaca tcgctgttcc ccagaaaccc actctatcct caccctgttt tgtgctcttc     832
```

-continued

```
ccctcgcctg ctagggctgc ggcttctgac ttctagaaga ctaaggctgg tctgtgtttg    892

cttgtttgcc cacctttggc tgatacccag agaacctggg cacttgctgc ctgatgccca    952

cccctgccag tcattcctcc attcacccag cgggaggtgg gatgtgagac agcccacatt   1012

ggaaaatcca gaaaaccggg aacagggatt tgcccttcac aattctactc cccagatcct   1072

ctcccctgga cacaggagac ccacagggca ggaccctaag atctggggaa aggaggtcct   1132

gagaaccttg aggtaccctt agatcctttt ctacccactt tcctatggag gattccaagt   1192

caccacttct ctcaccggct tctaccaggg tccaggacta aggcgttttt ctccatagcc   1252

tcaacatttt gggaatcttc ccttaatcac ccttgctcct cctgggtgcc tggaagatgg   1312

actggcagag acctctttgt tgcgttttgt gctttgatgc caggaatgcc gcctagttta   1372

tgtccccggt ggggcacaca gcggggggcg ccaggttttc cttgtccccc agctgctctg   1432

cccctttccc cttcttccct gactccaggc ctgaacccct cccgtgctgt aataaatctt   1492

tgtaaataac aaaaaaaaaa a                                             1513
```

<210> SEQ ID NO 74
<211> LENGTH: 168
<212> TYPE: PRT
<213> ORGANISM: human

<400> SEQUENCE: 74

```
Met Leu Phe Arg Leu Ser Glu His Ser Ser Pro Glu Glu Glu Ala Ser
 1               5                  10                  15

Pro His Gln Arg Ala Ser Gly Glu Gly His His Leu Lys Ser Lys Arg
            20                  25                  30

Pro Asn Pro Cys Ala Tyr Thr Pro Pro Ser Leu Lys Ala Val Gln Arg
        35                  40                  45

Ile Ala Glu Ser His Leu Gln Ser Ile Ser Asn Leu Asn Glu Asn Gln
    50                  55                  60

Ala Ser Glu Glu Glu Asp Glu Leu Gly Glu Leu Arg Glu Leu Gly Tyr
65                  70                  75                  80

Pro Arg Glu Glu Asp Glu Glu Glu Glu Glu Asp Asp Glu Glu Glu Glu
                85                  90                  95

Glu Glu Glu Asp Ser Gln Ala Glu Val Leu Lys Val Ile Arg Gln Ser
            100                 105                 110

Ala Gly Gln Lys Thr Thr Cys Gly Gln Gly Leu Glu Gly Pro Trp Glu
        115                 120                 125

Arg Pro Pro Pro Leu Asp Glu Ser Glu Arg Asp Gly Gly Ser Glu Asp
    130                 135                 140

Gln Val Glu Asp Pro Ala Leu Ser Glu Pro Gly Glu Glu Pro Gln Arg
145                 150                 155                 160

Pro Ser Pro Ser Glu Pro Gly Thr
                165
```

<210> SEQ ID NO 75
<211> LENGTH: 1841
<212> TYPE: DNA
<213> ORGANISM: human
<220> FEATURE:
<221> NAME/KEY: CDS
<222> LOCATION: (468)...(1082)

<400> SEQUENCE: 75

```
agctgggacc ggagggtgag cccggcagag gcagagacac acgcggagag gaggagaggc     60
```

-continued

```
tgagggaggg aggtggagaa ggacgggaga ggcagagaga ggagacacgc agagacactc    120

aggaggggag agacaccgag acgcagagac actcaggagg ggagagacac cgagacgcag    180

agacacccag gccggggagc gcgagggagc gaggcacaga cctggctcag cgagcgcggg    240

gggcgagccc cgagtcccga gagcctgggg gcgcgcccag cccgggcgcc gaccctcctc    300

ccgctcccgc gccctcccct cggcgggcac ggtattttta tccgtgcgcg aacagccctc    360

ctcctcctct cgccgcacag cccgccgcct gcgcggggga gcccagcaca gaccgccgcc    420

gggaccccga gtcgcgcacc ccagccccac cgcccacccc gcgcgcc atg gac ccc      476
                                                    Met Asp Pro
                                                    1

aag gac cgc aag aag atc cag ttc tcg gtg ccc gcg ccc cct agc cag      524
Lys Asp Arg Lys Lys Ile Gln Phe Ser Val Pro Ala Pro Pro Ser Gln
    5                   10                  15

ctc gac ccc cgc cag gtg gag atg atc cgg cgc agg aga cca acg cct      572
Leu Asp Pro Arg Gln Val Glu Met Ile Arg Arg Arg Arg Pro Thr Pro
 20                 25                  30                  35

gcc atg ctg ttc cgg ctc tca gag cac tcc tca cca gag gag gaa gcc      620
Ala Met Leu Phe Arg Leu Ser Glu His Ser Ser Pro Glu Glu Glu Ala
                40                  45                  50

tcc ccc cac cag aga gcc tca gga gag ggg cac cat ctc aag tcg aag      668
Ser Pro His Gln Arg Ala Ser Gly Glu Gly His His Leu Lys Ser Lys
            55                  60                  65

aga ccc aac ccc tgt gcc tac aca cca cct tcg ctg aaa gct gtg cag      716
Arg Pro Asn Pro Cys Ala Tyr Thr Pro Pro Ser Leu Lys Ala Val Gln
        70                  75                  80

cgc att gct gag tct cac ctg cag tct atc agc aat ttg aat gag aac      764
Arg Ile Ala Glu Ser His Leu Gln Ser Ile Ser Asn Leu Asn Glu Asn
    85                  90                  95

cag gcc tca gag gag gag gat gag ctg ggg gag ctt cgg gag ctg ggt      812
Gln Ala Ser Glu Glu Glu Asp Glu Leu Gly Glu Leu Arg Glu Leu Gly
100                 105                 110                 115

tat cca aga gag gaa gat gag gag gaa gag gag gat gat gaa gaa gag      860
Tyr Pro Arg Glu Glu Asp Glu Glu Glu Glu Glu Asp Asp Glu Glu Glu
                120                 125                 130

gaa gaa gaa gag gac agc cag gct gaa gtc ctg aag gtc atc agg cag      908
Glu Glu Glu Glu Asp Ser Gln Ala Glu Val Leu Lys Val Ile Arg Gln
            135                 140                 145

tct gct ggg caa aag aca acc tgt ggc cag ggt ctg gaa ggg ccc tgg      956
Ser Ala Gly Gln Lys Thr Thr Cys Gly Gln Gly Leu Glu Gly Pro Trp
        150                 155                 160

gag cgc cca ccc cct ctg gat gag tcc gag aga gat gga ggc tct gag     1004
Glu Arg Pro Pro Pro Leu Asp Glu Ser Glu Arg Asp Gly Gly Ser Glu
    165                 170                 175

gac caa gtg gaa gac cca gca cta agt gag cct ggg gag gaa cct cag     1052
Asp Gln Val Glu Asp Pro Ala Leu Ser Glu Pro Gly Glu Glu Pro Gln
180                 185                 190                 195

cgc cct tcc ccc tct gag cct ggc aca tag gcacccagcc tgcatctccc       1102
Arg Pro Ser Pro Ser Glu Pro Gly Thr  *
                200

aggaggaagt ggaggggaca tcgctgttcc ccagaaaccc actctatcct caccctgttt   1162

tgtgctcttc ccctcgcctg ctagggctgc ggcttctgac ttctagaaga ctaaggctgg   1222

tctgtgtttg cttgtttgcc cacctttggc tgatacccag agaacctggg cacttgctgc   1282

ctgatgccca cccctgccag tcattcctcc attcacccag cgggaggtgg gatgtgagac   1342

agcccacatt ggaaaatcca gaaaaccggg aacagggatt tgcccttcac aattctactc   1402

cccagatcct ctcccctgga cacaggagac ccacagggca ggaccctaag atctggggaa   1462
```

-continued

```
aggaggtcct gagaaccttg aggtaccctt agatcctttt ctacccactt tcctatggag   1522

gattccaagt caccacttct ctcaccggct tctaccaggg tccaggacta aggcgttttt   1582

ctccatagcc tcaacatttt gggaatcttc ccttaatcac ccttgctcct cctgggtgcc   1642

tggaagatgg actggcagag acctctttgt tgcgttttgt gctttgatgc caggaatgcc   1702

gcctagttta tgtccccggt ggggcacaca gcggggggcg ccaggttttc cttgtccccc   1762

agctgctctg cccctttccc cttcttccct gactccaggc ctgaacccct cccgtgctgt   1822

aataaatctt tgtaaataa                                                1841


<210> SEQ ID NO 76
<211> LENGTH: 204
<212> TYPE: PRT
<213> ORGANISM: human

<400> SEQUENCE: 76

Met Asp Pro Lys Asp Arg Lys Lys Ile Gln Phe Ser Val Pro Ala Pro
 1               5                  10                  15

Pro Ser Gln Leu Asp Pro Arg Gln Val Glu Met Ile Arg Arg Arg Arg
            20                  25                  30

Pro Thr Pro Ala Met Leu Phe Arg Leu Ser Glu His Ser Ser Pro Glu
        35                  40                  45

Glu Glu Ala Ser Pro His Gln Arg Ala Ser Gly Glu Gly His His Leu
    50                  55                  60

Lys Ser Lys Arg Pro Asn Pro Cys Ala Tyr Thr Pro Pro Ser Leu Lys
65                  70                  75                  80

Ala Val Gln Arg Ile Ala Glu Ser His Leu Gln Ser Ile Ser Asn Leu
                85                  90                  95

Asn Glu Asn Gln Ala Ser Glu Glu Glu Asp Glu Leu Gly Glu Leu Arg
            100                 105                 110

Glu Leu Gly Tyr Pro Arg Glu Glu Asp Glu Glu Glu Glu Glu Asp Asp
        115                 120                 125

Glu Glu Glu Glu Glu Glu Glu Asp Ser Gln Ala Glu Val Leu Lys Val
    130                 135                 140

Ile Arg Gln Ser Ala Gly Gln Lys Thr Thr Cys Gly Gln Gly Leu Glu
145                 150                 155                 160

Gly Pro Trp Glu Arg Pro Pro Pro Leu Asp Glu Ser Glu Arg Asp Gly
                165                 170                 175

Gly Ser Glu Asp Gln Val Glu Asp Pro Ala Leu Ser Glu Pro Gly Glu
            180                 185                 190

Glu Pro Gln Arg Pro Ser Pro Ser Glu Pro Gly Thr
        195                 200


<210> SEQ ID NO 77
<211> LENGTH: 3745
<212> TYPE: DNA
<213> ORGANISM: human
<220> FEATURE:
<221> NAME/KEY: CDS
<222> LOCATION: (124)...(2220)

<400> SEQUENCE: 77

agcggcgcct taaatagcat ccagagccgg cgcggggcag ggagtgggct gcagtgacag     60

ccggcggcgg agcggccggt ccacggagga gaattcagct tagagaacta tcaacacagg    120

aca atg caa gcc cat gag ctg ttc cgg tat ttt cga atg cca gag ctg      168
    Met Gln Ala His Glu Leu Phe Arg Tyr Phe Arg Met Pro Glu Leu
```

-continued

```
     1               5                   10                  15

gtt gac ttc cga cag tac gtg cgt act ctt ccg acc aac acg ctt atg      216
Val Asp Phe Arg Gln Tyr Val Arg Thr Leu Pro Thr Asn Thr Leu Met
                 20                  25                  30

ggc ttc gga gct ttt gca gca ctc acc acc ttc tgg tac gcc acg aga      264
Gly Phe Gly Ala Phe Ala Ala Leu Thr Thr Phe Trp Tyr Ala Thr Arg
             35                  40                  45

ccc aaa ccc ctg aag ccg cca tgc gac ctc tcc atg cag tca gtg gaa      312
Pro Lys Pro Leu Lys Pro Pro Cys Asp Leu Ser Met Gln Ser Val Glu
         50                  55                  60

gtg gcg ggt agt ggt ggt gca cga aga tcc gca cta ctt gac agc gac      360
Val Ala Gly Ser Gly Gly Ala Arg Arg Ser Ala Leu Leu Asp Ser Asp
     65                  70                  75

gag ccc ttg gtg tat ttc tat gat gat gtc aca aca tta tac gaa ggt      408
Glu Pro Leu Val Tyr Phe Tyr Asp Asp Val Thr Thr Leu Tyr Glu Gly
 80                  85                  90                  95

ttc cag agg gga ata cag gtg tca aat aat ggc cct tgt tta ggc tct      456
Phe Gln Arg Gly Ile Gln Val Ser Asn Asn Gly Pro Cys Leu Gly Ser
                100                 105                 110

cgg aaa cca gac caa ccc tat gaa tgg ctt tca tat aaa cag gtt gca      504
Arg Lys Pro Asp Gln Pro Tyr Glu Trp Leu Ser Tyr Lys Gln Val Ala
            115                 120                 125

gaa ttg tcg gag tgc ata ggc tca gca ctg atc cag aag ggc ttc aag      552
Glu Leu Ser Glu Cys Ile Gly Ser Ala Leu Ile Gln Lys Gly Phe Lys
        130                 135                 140

act gcc cca gat cag ttc att ggc atc ttt gct caa aat aga cct gag      600
Thr Ala Pro Asp Gln Phe Ile Gly Ile Phe Ala Gln Asn Arg Pro Glu
    145                 150                 155

tgg gtg att att gaa caa gga tgc ttt gct tat tcg atg gtg atc gtt      648
Trp Val Ile Ile Glu Gln Gly Cys Phe Ala Tyr Ser Met Val Ile Val
160                 165                 170                 175

cca ctt tat gat acc ctt gga aat gaa gcc atc acg tac ata gtc aac      696
Pro Leu Tyr Asp Thr Leu Gly Asn Glu Ala Ile Thr Tyr Ile Val Asn
                180                 185                 190

aaa gct gaa ctc tct ctg gtt ttt gtt gac aag cca gag aag gcc aaa      744
Lys Ala Glu Leu Ser Leu Val Phe Val Asp Lys Pro Glu Lys Ala Lys
            195                 200                 205

ctc tta tta gag ggt gta gaa aat aag tta ata cca ggc ctt aaa atc      792
Leu Leu Leu Glu Gly Val Glu Asn Lys Leu Ile Pro Gly Leu Lys Ile
        210                 215                 220

ata gtt gtc atg gat gcc tac ggc agt gaa ctg gtg gaa cga ggc cag      840
Ile Val Val Met Asp Ala Tyr Gly Ser Glu Leu Val Glu Arg Gly Gln
    225                 230                 235

agg tgt ggg gtg gaa gtc acc agc atg aag gcg atg gag gac ctg gga      888
Arg Cys Gly Val Glu Val Thr Ser Met Lys Ala Met Glu Asp Leu Gly
240                 245                 250                 255

aga gcc aac aga cgg aag ccc aag cct cca gca cct gaa gat ctt gca      936
Arg Ala Asn Arg Arg Lys Pro Lys Pro Pro Ala Pro Glu Asp Leu Ala
                260                 265                 270

gta att tgt ttc aca agt gga act aca ggc aac ccc aaa gga gca atg      984
Val Ile Cys Phe Thr Ser Gly Thr Thr Gly Asn Pro Lys Gly Ala Met
            275                 280                 285

gtc act cac cga aac ata gtg agc gat tgt tca gct ttt gtg aaa gca     1032
Val Thr His Arg Asn Ile Val Ser Asp Cys Ser Ala Phe Val Lys Ala
        290                 295                 300

aca gag aaa gca ctt ccc ttg agt gcc agt gac aca cac att tca tat     1080
Thr Glu Lys Ala Leu Pro Leu Ser Ala Ser Asp Thr His Ile Ser Tyr
    305                 310                 315

tta cca ctt gct cac att tat gaa cag tta ttg aag tgt gta atg ctg     1128
```

-continued

```
Leu Pro Leu Ala His Ile Tyr Glu Gln Leu Leu Lys Cys Val Met Leu
320                 325                 330                 335

tgt cat gga gct aaa atc gga ttt ttc caa gga gat atc agg ctg ctc     1176
Cys His Gly Ala Lys Ile Gly Phe Phe Gln Gly Asp Ile Arg Leu Leu
                340                 345                 350

atg gat gac ctc aag gtg ctt caa ccc act gtc ttc ccc gtg gtt cca     1224
Met Asp Asp Leu Lys Val Leu Gln Pro Thr Val Phe Pro Val Val Pro
            355                 360                 365

aga ctg ctg aac cgg atg ttt gac cga att ttc gga caa gca aac acc     1272
Arg Leu Leu Asn Arg Met Phe Asp Arg Ile Phe Gly Gln Ala Asn Thr
        370                 375                 380

acg ctg aag cga tgg ctc ttg gac ttt gcc tcc aag agg aaa gaa gca     1320
Thr Leu Lys Arg Trp Leu Leu Asp Phe Ala Ser Lys Arg Lys Glu Ala
    385                 390                 395

gag ctt cgc agc ggc atc atc aga aac aac agc ctg tgg gac cgg ctg     1368
Glu Leu Arg Ser Gly Ile Ile Arg Asn Asn Ser Leu Trp Asp Arg Leu
400                 405                 410                 415

atc ttc cac aaa gta cag tcg agc ctg ggc gga aga gtc cgg ctg atg     1416
Ile Phe His Lys Val Gln Ser Ser Leu Gly Gly Arg Val Arg Leu Met
                420                 425                 430

gtg aca gga gcc gcc ccg gtg tct gcc act gtg ctg acg ttc ctc aga     1464
Val Thr Gly Ala Ala Pro Val Ser Ala Thr Val Leu Thr Phe Leu Arg
            435                 440                 445

gca gcc ctg ggc tgt cag ttt tat gaa gga tac gga cag aca gag tgc     1512
Ala Ala Leu Gly Cys Gln Phe Tyr Glu Gly Tyr Gly Gln Thr Glu Cys
        450                 455                 460

act gcc ggg tgc tgc cta acc atg cct gga gac tgg acc gca ggc cat     1560
Thr Ala Gly Cys Cys Leu Thr Met Pro Gly Asp Trp Thr Ala Gly His
    465                 470                 475

gtt ggg gcc ccg atg ccg tgc aat ttg ata aaa ctt gtt gat gtg gaa     1608
Val Gly Ala Pro Met Pro Cys Asn Leu Ile Lys Leu Val Asp Val Glu
480                 485                 490                 495

gaa atg aat tac atg gct gcc gag ggc gag ggc gag gtg tgt gtg aaa     1656
Glu Met Asn Tyr Met Ala Ala Glu Gly Glu Gly Glu Val Cys Val Lys
                500                 505                 510

ggg cca aat gta ttt cag ggc tac ttg aag gac cca gcg aaa aca gca     1704
Gly Pro Asn Val Phe Gln Gly Tyr Leu Lys Asp Pro Ala Lys Thr Ala
            515                 520                 525

gaa gct ttg gac aaa gac ggc tgg tta cac aca ggg gac att gga aaa     1752
Glu Ala Leu Asp Lys Asp Gly Trp Leu His Thr Gly Asp Ile Gly Lys
        530                 535                 540

tgg tta cca aat ggc acc ttg aaa att atc gac cgg aaa aag cac ata     1800
Trp Leu Pro Asn Gly Thr Leu Lys Ile Ile Asp Arg Lys Lys His Ile
    545                 550                 555

ttt aag ctg gca caa gga gaa tac ata gcc cct gaa aag att gaa aat     1848
Phe Lys Leu Ala Gln Gly Glu Tyr Ile Ala Pro Glu Lys Ile Glu Asn
560                 565                 570                 575

atc tac atg cga agt gag cct gtt gct cag gtg ttt gtc cac gga gaa     1896
Ile Tyr Met Arg Ser Glu Pro Val Ala Gln Val Phe Val His Gly Glu
                580                 585                 590

agc ctg cag gca ttt ctc att gca att gtg gta cca gat gtt gag aca     1944
Ser Leu Gln Ala Phe Leu Ile Ala Ile Val Val Pro Asp Val Glu Thr
            595                 600                 605

tta tgt tcc tgg gcc caa aag aga gga ttt gaa ggg tcg ttt gag gaa     1992
Leu Cys Ser Trp Ala Gln Lys Arg Gly Phe Glu Gly Ser Phe Glu Glu
        610                 615                 620

ctg tgc aga aat aag gat gtc aaa aaa gct atc ctc gaa gat atg gtg     2040
Leu Cys Arg Asn Lys Asp Val Lys Lys Ala Ile Leu Glu Asp Met Val
    625                 630                 635
```

-continued

```
aga ctt ggg aag gat tct ggt ctg aaa cca ttt gaa cag gtc aaa ggc     2088
Arg Leu Gly Lys Asp Ser Gly Leu Lys Pro Phe Glu Gln Val Lys Gly
640                 645                 650                 655

atc aca ttg cac cct gaa tta ttt tct atc gac aat ggc ctt ctg act     2136
Ile Thr Leu His Pro Glu Leu Phe Ser Ile Asp Asn Gly Leu Leu Thr
                660                 665                 670

cca aca atg aag gcg aaa agg cca gag ctg cgg aac tat ttc agg tcg     2184
Pro Thr Met Lys Ala Lys Arg Pro Glu Leu Arg Asn Tyr Phe Arg Ser
            675                 680                 685

cag ata gat gac ctc tat tcc act atc aag gtt tag tgtgaagaag          2230
Gln Ile Asp Asp Leu Tyr Ser Thr Ile Lys Val  *
        690                 695

aaagctcaga ggaaatggca cagttccaca atctcttctc ctgctgatgg ccttcatgtt   2290

gttaattttg aatacagcaa gtgtagggaa ggaagcgttc gtgtttgact tgtccattcg   2350

gggttcttct cataggaatg ctagaggaaa cagaacaccg ccttacagtc acctcatgtt   2410

gcagaccatg tttatggtaa tacacacttt ccaaaatgag ccttaaaaat tgtaaagggg   2470

atactataaa tgtgctaagt tatttgagac ttcctcagtt taaaaagtgg gttttaaatc   2530

ttctgtctcc ctgcttttct aatcaagggg ttaggacttt gctatctctg agatgtctgc   2590

tacttgctgc aaattctgca gctgtctgct gctctaaaga gtacagtgca ctagagggaa   2650

gtgttccctt taaaaataag aacaactgtc ctggctggag aatctcacaa gcggaccaga   2710

gatcttttta aatccctgct actgtccctt ctcacaggca ttcacagaac ccttctgatt   2770

cgtaagggtt acgaaactca tgttcttctc cagtcccctg tggtttctgt tggagcataa   2830

ggtttccagt aagcgggagg gcagatccaa ctcagaacca tgcagataag gagcctctgg   2890

caaatgggtg ctcatcagaa cgcgtggatt ctctttcatg gcagaatgct cttggactcg   2950

gttctccagg cctgattccc cgactccatc ctttttcagg ggttatttaa aaatctgcct   3010

tagattctat agtgaagaca agcatttcaa gaaagagtta cctggatcag ccatgctcag   3070

ctgtgacgcc tgaataactg tctactttat cttcactgaa ccactcactc tgtgtaaagg   3130

ccaacagatt tttaatgtgg ttttcatatc aaaagatcat gttgggatta acttgccttt   3190

ttccccaaaa aataaactct caggcaagca tttctttaaa gctattaagg gagtatatac   3250

ttgagtactt attgaaatgg acagtaataa gcaaatgttc ttataatgct acctgatttc   3310

tatgaaatgt gtttgacaag ccaaaattct aggatgtaga aatctggaaa gttcatttcc   3370

tgggattcac ttctccaggg attttttaaa gttaatttgg gaaattaaca gcagttcact   3430

ttattgtgag tctttgccac atttgactga attgagctgt catttgtaca tttaaagcag   3490

ctgttttggg gtctgtgaga gtacatgtat tatatacaag cacaacaggg cttgcactaa   3550

agaattgtca ttgtaataac actacttggt agcctaactt catatatgta ttcttaattg   3610

cacaaaaagt caataatttg tcaccttggg gttttgaatg tttgctttaa gtgttggcta   3670

tttctatgtt ttataaacca aaacaaaatt tccaaaaaca atgaaggaaa ccaaaataaa   3730

tatttctgca tttcg                                                    3745


<210> SEQ ID NO 78
<211> LENGTH: 698
<212> TYPE: PRT
<213> ORGANISM: human

<400> SEQUENCE: 78

Met Gln Ala His Glu Leu Phe Arg Tyr Phe Arg Met Pro Glu Leu Val
 1               5                  10                  15
```

-continued

```
Asp Phe Arg Gln Tyr Val Arg Thr Leu Pro Thr Asn Thr Leu Met Gly
            20                  25                  30

Phe Gly Ala Phe Ala Ala Leu Thr Thr Phe Trp Tyr Ala Thr Arg Pro
        35                  40                  45

Lys Pro Leu Lys Pro Pro Cys Asp Leu Ser Met Gln Ser Val Glu Val
    50                  55                  60

Ala Gly Ser Gly Gly Ala Arg Arg Ser Ala Leu Leu Asp Ser Asp Glu
65                  70                  75                  80

Pro Leu Val Tyr Phe Tyr Asp Asp Val Thr Thr Leu Tyr Glu Gly Phe
                85                  90                  95

Gln Arg Gly Ile Gln Val Ser Asn Asn Gly Pro Cys Leu Gly Ser Arg
            100                 105                 110

Lys Pro Asp Gln Pro Tyr Glu Trp Leu Ser Tyr Lys Gln Val Ala Glu
        115                 120                 125

Leu Ser Glu Cys Ile Gly Ser Ala Leu Ile Gln Lys Gly Phe Lys Thr
    130                 135                 140

Ala Pro Asp Gln Phe Ile Gly Ile Phe Ala Gln Asn Arg Pro Glu Trp
145                 150                 155                 160

Val Ile Ile Glu Gln Gly Cys Phe Ala Tyr Ser Met Val Ile Val Pro
                165                 170                 175

Leu Tyr Asp Thr Leu Gly Asn Glu Ala Ile Thr Tyr Ile Val Asn Lys
            180                 185                 190

Ala Glu Leu Ser Leu Val Phe Val Asp Lys Pro Glu Lys Ala Lys Leu
        195                 200                 205

Leu Leu Glu Gly Val Glu Asn Lys Leu Ile Pro Gly Leu Lys Ile Ile
    210                 215                 220

Val Val Met Asp Ala Tyr Gly Ser Glu Leu Val Glu Arg Gly Gln Arg
225                 230                 235                 240

Cys Gly Val Glu Val Thr Ser Met Lys Ala Met Glu Asp Leu Gly Arg
                245                 250                 255

Ala Asn Arg Arg Lys Pro Lys Pro Pro Ala Pro Glu Asp Leu Ala Val
            260                 265                 270

Ile Cys Phe Thr Ser Gly Thr Thr Gly Asn Pro Lys Gly Ala Met Val
        275                 280                 285

Thr His Arg Asn Ile Val Ser Asp Cys Ser Ala Phe Val Lys Ala Thr
    290                 295                 300

Glu Lys Ala Leu Pro Leu Ser Ala Ser Asp Thr His Ile Ser Tyr Leu
305                 310                 315                 320

Pro Leu Ala His Ile Tyr Glu Gln Leu Leu Lys Cys Val Met Leu Cys
                325                 330                 335

His Gly Ala Lys Ile Gly Phe Phe Gln Gly Asp Ile Arg Leu Leu Met
            340                 345                 350

Asp Asp Leu Lys Val Leu Gln Pro Thr Val Phe Pro Val Val Pro Arg
        355                 360                 365

Leu Leu Asn Arg Met Phe Asp Arg Ile Phe Gly Gln Ala Asn Thr Thr
    370                 375                 380

Leu Lys Arg Trp Leu Leu Asp Phe Ala Ser Lys Arg Lys Glu Ala Glu
385                 390                 395                 400

Leu Arg Ser Gly Ile Ile Arg Asn Asn Ser Leu Trp Asp Arg Leu Ile
                405                 410                 415

Phe His Lys Val Gln Ser Ser Leu Gly Gly Arg Val Arg Leu Met Val
            420                 425                 430

Thr Gly Ala Ala Pro Val Ser Ala Thr Val Leu Thr Phe Leu Arg Ala
```

-continued

```
        435                 440                 445

Ala Leu Gly Cys Gln Phe Tyr Glu Gly Tyr Gly Gln Thr Glu Cys Thr
    450                 455                 460

Ala Gly Cys Cys Leu Thr Met Pro Gly Asp Trp Thr Ala Gly His Val
465                 470                 475                 480

Gly Ala Pro Met Pro Cys Asn Leu Ile Lys Leu Val Asp Val Glu Glu
                485                 490                 495

Met Asn Tyr Met Ala Ala Glu Gly Glu Gly Glu Val Cys Val Lys Gly
            500                 505                 510

Pro Asn Val Phe Gln Gly Tyr Leu Lys Asp Pro Ala Lys Thr Ala Glu
        515                 520                 525

Ala Leu Asp Lys Asp Gly Trp Leu His Thr Gly Asp Ile Gly Lys Trp
    530                 535                 540

Leu Pro Asn Gly Thr Leu Lys Ile Ile Asp Arg Lys Lys His Ile Phe
545                 550                 555                 560

Lys Leu Ala Gln Gly Glu Tyr Ile Ala Pro Glu Lys Ile Glu Asn Ile
                565                 570                 575

Tyr Met Arg Ser Glu Pro Val Ala Gln Val Phe Val His Gly Glu Ser
            580                 585                 590

Leu Gln Ala Phe Leu Ile Ala Ile Val Val Pro Asp Val Glu Thr Leu
        595                 600                 605

Cys Ser Trp Ala Gln Lys Arg Gly Phe Glu Gly Ser Phe Glu Glu Leu
    610                 615                 620

Cys Arg Asn Lys Asp Val Lys Lys Ala Ile Leu Glu Asp Met Val Arg
625                 630                 635                 640

Leu Gly Lys Asp Ser Gly Leu Lys Pro Phe Glu Gln Val Lys Gly Ile
                645                 650                 655

Thr Leu His Pro Glu Leu Phe Ser Ile Asp Asn Gly Leu Leu Thr Pro
            660                 665                 670

Thr Met Lys Ala Lys Arg Pro Glu Leu Arg Asn Tyr Phe Arg Ser Gln
        675                 680                 685

Ile Asp Asp Leu Tyr Ser Thr Ile Lys Val
    690                 695


<210> SEQ ID NO 79
<211> LENGTH: 3809
<212> TYPE: DNA
<213> ORGANISM: human
<220> FEATURE:
<221> NAME/KEY: CDS
<222> LOCATION: (188)...(2284)

<400> SEQUENCE: 79

agcggatcgt ggctcagccg cggcggtggc gggggcgcaa ccagcgggcc gaggcggcgg      60

cgccagcggc gccttaaata gcatccagag ccggcgcggg gcagggagtg ggctgcagtg     120

acagccggcg gcggagcggc cggtccacgg aggagaattc agcttagaga actatcaaca     180

caggaca atg caa gcc cat gag ctg ttc cgg tat ttt cga atg cca gag       229
        Met Gln Ala His Glu Leu Phe Arg Tyr Phe Arg Met Pro Glu
         1               5                  10

ctg gtt gac ttc cga cag tac gtg cgt act ctt ccg acc aac acg ctt       277
Leu Val Asp Phe Arg Gln Tyr Val Arg Thr Leu Pro Thr Asn Thr Leu
 15                  20                  25                  30

atg ggc ttc gga gct ttt gca gca ctc acc acc ttc tgg tac gcc acg       325
Met Gly Phe Gly Ala Phe Ala Ala Leu Thr Thr Phe Trp Tyr Ala Thr
                 35                  40                  45
```

-continued

```
aga ccc aaa ccc ctg aag ccg cca tgc gac ctc tcc atg cag tca gtg      373
Arg Pro Lys Pro Leu Lys Pro Pro Cys Asp Leu Ser Met Gln Ser Val
                50                  55                  60

gaa gtg gcg ggt agt ggt ggt gca cga aga tcc gca cta ctt gac agc      421
Glu Val Ala Gly Ser Gly Gly Ala Arg Arg Ser Ala Leu Leu Asp Ser
            65                  70                  75

gac gag ccc ttg gtg tat ttc tat gat gat gtc aca aca tta tac gaa      469
Asp Glu Pro Leu Val Tyr Phe Tyr Asp Asp Val Thr Thr Leu Tyr Glu
        80                  85                  90

ggt ttc cag agg gga ata cag gtg tca aat aat ggc cct tgt tta ggc      517
Gly Phe Gln Arg Gly Ile Gln Val Ser Asn Asn Gly Pro Cys Leu Gly
 95                 100                 105                 110

tct cgg aaa cca gac caa ccc tat gaa tgg ctt tca tat aaa cag gtt      565
Ser Arg Lys Pro Asp Gln Pro Tyr Glu Trp Leu Ser Tyr Lys Gln Val
                115                 120                 125

gca gaa ttg tcg gag tgc ata ggc tca gca ctg atc cag aag ggc ttc      613
Ala Glu Leu Ser Glu Cys Ile Gly Ser Ala Leu Ile Gln Lys Gly Phe
            130                 135                 140

aag act gcc cca gat cag ttc att ggc atc ttt gct caa aat aga cct      661
Lys Thr Ala Pro Asp Gln Phe Ile Gly Ile Phe Ala Gln Asn Arg Pro
        145                 150                 155

gag tgg gtg att att gaa caa gga tgc ttt gct tat tcg atg gtg atc      709
Glu Trp Val Ile Ile Glu Gln Gly Cys Phe Ala Tyr Ser Met Val Ile
    160                 165                 170

gtt cca ctt tat gat acc ctt gga aat gaa gcc atc acg tac ata gtc      757
Val Pro Leu Tyr Asp Thr Leu Gly Asn Glu Ala Ile Thr Tyr Ile Val
175                 180                 185                 190

aac aaa gct gaa ctc tct ctg gtt ttt gtt gac aag cca gag aag gcc      805
Asn Lys Ala Glu Leu Ser Leu Val Phe Val Asp Lys Pro Glu Lys Ala
                195                 200                 205

aaa ctc tta tta gag ggt gta gaa aat aag tta ata cca ggc ctt aaa      853
Lys Leu Leu Leu Glu Gly Val Glu Asn Lys Leu Ile Pro Gly Leu Lys
            210                 215                 220

atc ata gtt gtc atg gat gcc tac ggc agt gaa ctg gtg gaa cga ggc      901
Ile Ile Val Val Met Asp Ala Tyr Gly Ser Glu Leu Val Glu Arg Gly
        225                 230                 235

cag agg tgt ggg gtg gaa gtc acc agc atg aag gcg atg gag gac ctg      949
Gln Arg Cys Gly Val Glu Val Thr Ser Met Lys Ala Met Glu Asp Leu
    240                 245                 250

gga aga gcc aac aga cgg aag ccc aag cct cca gca cct gaa gat ctt      997
Gly Arg Ala Asn Arg Arg Lys Pro Lys Pro Pro Ala Pro Glu Asp Leu
255                 260                 265                 270

gca gta att tgt ttc aca agt gga act aca ggc aac ccc aaa gga gca     1045
Ala Val Ile Cys Phe Thr Ser Gly Thr Thr Gly Asn Pro Lys Gly Ala
                275                 280                 285

atg gtc act cac cga aac ata gtg agc gat tgt tca gct ttt gtg aaa     1093
Met Val Thr His Arg Asn Ile Val Ser Asp Cys Ser Ala Phe Val Lys
            290                 295                 300

gca aca gag aat aca gtc aat cct tgc cca gat gat act ttg ata tct     1141
Ala Thr Glu Asn Thr Val Asn Pro Cys Pro Asp Asp Thr Leu Ile Ser
        305                 310                 315

ttc ttg cct ctc gcc cat atg ttt gag aga gtt gta gag tgt gta atg     1189
Phe Leu Pro Leu Ala His Met Phe Glu Arg Val Val Glu Cys Val Met
    320                 325                 330

ctg tgt cat gga gct aaa atc gga ttt ttc caa gga gat atc agg ctg     1237
Leu Cys His Gly Ala Lys Ile Gly Phe Phe Gln Gly Asp Ile Arg Leu
335                 340                 345                 350

ctc atg gat gac ctc aag gtg ctt caa ccc act gtc ttc ccc gtg gtt     1285
Leu Met Asp Asp Leu Lys Val Leu Gln Pro Thr Val Phe Pro Val Val
                355                 360                 365
```

-continued

```
cca aga ctg ctg aac cgg atg ttt gac cga att ttc gga caa gca aac     1333
Pro Arg Leu Leu Asn Arg Met Phe Asp Arg Ile Phe Gly Gln Ala Asn
            370                 375                 380

acc acg ctg aag cga tgg ctc ttg gac ttt gcc tcc aag agg aaa gaa     1381
Thr Thr Leu Lys Arg Trp Leu Leu Asp Phe Ala Ser Lys Arg Lys Glu
        385                 390                 395

gca gag ctt cgc agc ggc atc atc aga aac aac agc ctg tgg gac cgg     1429
Ala Glu Leu Arg Ser Gly Ile Ile Arg Asn Asn Ser Leu Trp Asp Arg
    400                 405                 410

ctg atc ttc cac aaa gta cag tcg agc ctg ggc gga aga gtc cgg ctg     1477
Leu Ile Phe His Lys Val Gln Ser Ser Leu Gly Gly Arg Val Arg Leu
415                 420                 425                 430

atg gtg aca gga gcc gcc ccg gtg tct gcc act gtg ctg acg ttc ctc     1525
Met Val Thr Gly Ala Ala Pro Val Ser Ala Thr Val Leu Thr Phe Leu
                435                 440                 445

aga gca gcc ctg ggc tgt cag ttt tat gaa gga tac gga cag aca gag     1573
Arg Ala Ala Leu Gly Cys Gln Phe Tyr Glu Gly Tyr Gly Gln Thr Glu
            450                 455                 460

tgc act gcc ggg tgc tgc cta acc atg cct gga gac tgg acc gca ggc     1621
Cys Thr Ala Gly Cys Cys Leu Thr Met Pro Gly Asp Trp Thr Ala Gly
        465                 470                 475

cat gtt ggg gcc ccg atg ccg tgc aat ttg ata aaa ctt gtt gat gtg     1669
His Val Gly Ala Pro Met Pro Cys Asn Leu Ile Lys Leu Val Asp Val
    480                 485                 490

gaa gaa atg aat tac atg gct gcc gag ggc gag ggc gag gtg tgt gtg     1717
Glu Glu Met Asn Tyr Met Ala Ala Glu Gly Glu Gly Glu Val Cys Val
495                 500                 505                 510

aaa ggg cca aat gta ttt cag ggc tac ttg aag gac cca gcg aaa aca     1765
Lys Gly Pro Asn Val Phe Gln Gly Tyr Leu Lys Asp Pro Ala Lys Thr
                515                 520                 525

gca gaa gct ttg gac aaa gac ggc tgg tta cac aca ggg gac att gga     1813
Ala Glu Ala Leu Asp Lys Asp Gly Trp Leu His Thr Gly Asp Ile Gly
            530                 535                 540

aaa tgg tta cca aat ggc acc ttg aaa att atc gac cgg aaa aag cac     1861
Lys Trp Leu Pro Asn Gly Thr Leu Lys Ile Ile Asp Arg Lys Lys His
        545                 550                 555

ata ttt aag ctg gca caa gga gaa tac ata gcc cct gaa aag att gaa     1909
Ile Phe Lys Leu Ala Gln Gly Glu Tyr Ile Ala Pro Glu Lys Ile Glu
    560                 565                 570

aat atc tac atg cga agt gag cct gtt gct cag gtg ttt gtc cac gga     1957
Asn Ile Tyr Met Arg Ser Glu Pro Val Ala Gln Val Phe Val His Gly
575                 580                 585                 590

gaa agc ctg cag gca ttt ctc att gca att gtg gta cca gat gtt gag     2005
Glu Ser Leu Gln Ala Phe Leu Ile Ala Ile Val Val Pro Asp Val Glu
                595                 600                 605

aca tta tgt tcc tgg gcc caa aag aga gga ttt gaa ggg tcg ttt gag     2053
Thr Leu Cys Ser Trp Ala Gln Lys Arg Gly Phe Glu Gly Ser Phe Glu
            610                 615                 620

gaa ctg tgc aga aat aag gat gtc aaa aaa gct atc ctc gaa gat atg     2101
Glu Leu Cys Arg Asn Lys Asp Val Lys Lys Ala Ile Leu Glu Asp Met
        625                 630                 635

gtg aga ctt ggg aag gat tct ggt ctg aaa cca ttt gaa cag gtc aaa     2149
Val Arg Leu Gly Lys Asp Ser Gly Leu Lys Pro Phe Glu Gln Val Lys
    640                 645                 650

ggc atc aca ttg cac cct gaa tta ttt tct atc gac aat ggc ctt ctg     2197
Gly Ile Thr Leu His Pro Glu Leu Phe Ser Ile Asp Asn Gly Leu Leu
655                 660                 665                 670

act cca aca atg aag gcg aaa agg cca gag ctg cgg aac tat ttc agg     2245
Thr Pro Thr Met Lys Ala Lys Arg Pro Glu Leu Arg Asn Tyr Phe Arg
```

-continued

```
            675                 680                 685

tcg cag ata gat gac ctc tat tcc act atc aag gtt tag tgtgaagaag      2294
Ser Gln Ile Asp Asp Leu Tyr Ser Thr Ile Lys Val  *
            690                 695

aaagctcaga ggaaatggca cagttccaca atctcttctc ctgctgatgg ccttcatgtt   2354

gttaattttg aatacagcaa gtgtagggaa ggaagcgttc gtgtttgact tgtccattcg   2414

gggttcttct cataggaatg ctagaggaaa cagaacaccg ccttacagtc acctcatgtt   2474

gcagaccatg tttatggtaa tacacacttt ccaaaatgag ccttaaaaat tgtaaagggg   2534

atactataaa tgtgctaagt tatttgagac ttcctcagtt taaaaagtgg gttttaaatc   2594

ttctgtctcc ctgcttttct aatcaagggg ttaggacttt gctatctctg agatgtctgc   2654

tacttgctgc aaattctgca gctgtctgct gctctaaaga gtacagtgca ctagagggaa   2714

gtgttccctt taaaaataag aacaactgtc ctggctggag aatctcacaa gcggaccaga   2774

gatcttttta aatccctgct actgtccctt ctcacaggca ttcacagaac ccttctgatt   2834

cgtaagggtt acgaaactca tgttcttctc cagtcccctg tggtttctgt tggagcataa   2894

ggtttccagt aagcgggagg gcagatccaa ctcagaacca tgcagataag gagcctctgg   2954

caaatgggtg ctcatcagaa cgcgtggatt ctctttcatg gcagaatgct cttggactcg   3014

gttctccagg cctgattccc cgactccatc ctttttcagg ggttatttaa aaatctgcct   3074

tagattctat agtgaagaca agcatttcaa gaaagagtta cctggatcag ccatgctcag   3134

ctgtgacgcc tgaataactg tctactttat cttcactgaa ccactcactc tgtgtaaagg   3194

ccaacagatt tttaatgtgg ttttcatatc aaaagatcat gttgggatta acttgccttt   3254

ttccccaaaa aataaactct caggcaagca tttctttaaa gctattaagg gagtatatac   3314

ttgagtactt attgaaatgg acagtaataa gcaaatgttc ttataatgct acctgatttc   3374

tatgaaatgt gtttgacaag ccaaaattct aggatgtaga aatctggaaa gttcatttcc   3434

tgggattcac ttctccaggg attttttaaa gttaatttgg gaaattaaca gcagttcact   3494

ttattgtgag tctttgccac atttgactga attgagctgt catttgtaca tttaaagcag   3554

ctgttttggg gtctgtgaga gtacatgtat tatatacaag cacaacaggg cttgcactaa   3614

agaattgtca ttgtaataac actacttggt agcctaactt catatatgta ttcttaattg   3674

cacaaaaagt caataatttg tcaccttggg gttttgaatg tttgctttaa gtgttggcta   3734

tttctatgtt ttataaacca aaacaaaatt tccaaaaaca atgaaggaaa ccaaaataaa   3794

tatttctgca tttcg                                                    3809
```

<210> SEQ ID NO 80
<211> LENGTH: 698
<212> TYPE: PRT
<213> ORGANISM: human

<400> SEQUENCE: 80

```
Met Gln Ala His Glu Leu Phe Arg Tyr Phe Arg Met Pro Glu Leu Val
 1               5                  10                  15

Asp Phe Arg Gln Tyr Val Arg Thr Leu Pro Thr Asn Thr Leu Met Gly
            20                  25                  30

Phe Gly Ala Phe Ala Ala Leu Thr Thr Phe Trp Tyr Ala Thr Arg Pro
        35                  40                  45

Lys Pro Leu Lys Pro Pro Cys Asp Leu Ser Met Gln Ser Val Glu Val
    50                  55                  60

Ala Gly Ser Gly Gly Ala Arg Arg Ser Ala Leu Leu Asp Ser Asp Glu
```

-continued

```
65                  70                  75                  80

Pro Leu Val Tyr Phe Tyr Asp Asp Val Thr Thr Leu Tyr Glu Gly Phe
                85                  90                  95

Gln Arg Gly Ile Gln Val Ser Asn Asn Gly Pro Cys Leu Gly Ser Arg
            100                 105                 110

Lys Pro Asp Gln Pro Tyr Glu Trp Leu Ser Tyr Lys Gln Val Ala Glu
        115                 120                 125

Leu Ser Glu Cys Ile Gly Ser Ala Leu Ile Gln Lys Gly Phe Lys Thr
    130                 135                 140

Ala Pro Asp Gln Phe Ile Gly Ile Phe Ala Gln Asn Arg Pro Glu Trp
145                 150                 155                 160

Val Ile Ile Glu Gln Gly Cys Phe Ala Tyr Ser Met Val Ile Val Pro
                165                 170                 175

Leu Tyr Asp Thr Leu Gly Asn Glu Ala Ile Thr Tyr Ile Val Asn Lys
            180                 185                 190

Ala Glu Leu Ser Leu Val Phe Val Asp Lys Pro Glu Lys Ala Lys Leu
        195                 200                 205

Leu Leu Glu Gly Val Glu Asn Lys Leu Ile Pro Gly Leu Lys Ile Ile
    210                 215                 220

Val Val Met Asp Ala Tyr Gly Ser Glu Leu Val Glu Arg Gly Gln Arg
225                 230                 235                 240

Cys Gly Val Glu Val Thr Ser Met Lys Ala Met Glu Asp Leu Gly Arg
                245                 250                 255

Ala Asn Arg Arg Lys Pro Lys Pro Pro Ala Pro Glu Asp Leu Ala Val
            260                 265                 270

Ile Cys Phe Thr Ser Gly Thr Thr Gly Asn Pro Lys Gly Ala Met Val
        275                 280                 285

Thr His Arg Asn Ile Val Ser Asp Cys Ser Ala Phe Val Lys Ala Thr
    290                 295                 300

Glu Asn Thr Val Asn Pro Cys Pro Asp Asp Thr Leu Ile Ser Phe Leu
305                 310                 315                 320

Pro Leu Ala His Met Phe Glu Arg Val Val Glu Cys Val Met Leu Cys
                325                 330                 335

His Gly Ala Lys Ile Gly Phe Phe Gln Gly Asp Ile Arg Leu Leu Met
            340                 345                 350

Asp Asp Leu Lys Val Leu Gln Pro Thr Val Phe Pro Val Val Pro Arg
        355                 360                 365

Leu Leu Asn Arg Met Phe Asp Arg Ile Phe Gly Gln Ala Asn Thr Thr
    370                 375                 380

Leu Lys Arg Trp Leu Leu Asp Phe Ala Ser Lys Arg Lys Glu Ala Glu
385                 390                 395                 400

Leu Arg Ser Gly Ile Ile Arg Asn Asn Ser Leu Trp Asp Arg Leu Ile
                405                 410                 415

Phe His Lys Val Gln Ser Ser Leu Gly Gly Arg Val Arg Leu Met Val
            420                 425                 430

Thr Gly Ala Ala Pro Val Ser Ala Thr Val Leu Thr Phe Leu Arg Ala
        435                 440                 445

Ala Leu Gly Cys Gln Phe Tyr Glu Gly Tyr Gly Gln Thr Glu Cys Thr
    450                 455                 460

Ala Gly Cys Cys Leu Thr Met Pro Gly Asp Trp Thr Ala Gly His Val
465                 470                 475                 480

Gly Ala Pro Met Pro Cys Asn Leu Ile Lys Leu Val Asp Val Glu Glu
                485                 490                 495
```

-continued

```
Met Asn Tyr Met Ala Ala Glu Gly Glu Gly Glu Val Cys Val Lys Gly
            500                 505                 510

Pro Asn Val Phe Gln Gly Tyr Leu Lys Asp Pro Ala Lys Thr Ala Glu
        515                 520                 525

Ala Leu Asp Lys Asp Gly Trp Leu His Thr Gly Asp Ile Gly Lys Trp
    530                 535                 540

Leu Pro Asn Gly Thr Leu Lys Ile Ile Asp Arg Lys Lys His Ile Phe
545                 550                 555                 560

Lys Leu Ala Gln Gly Glu Tyr Ile Ala Pro Glu Lys Ile Glu Asn Ile
                565                 570                 575

Tyr Met Arg Ser Glu Pro Val Ala Gln Val Phe Val His Gly Glu Ser
            580                 585                 590

Leu Gln Ala Phe Leu Ile Ala Ile Val Val Pro Asp Val Glu Thr Leu
        595                 600                 605

Cys Ser Trp Ala Gln Lys Arg Gly Phe Glu Gly Ser Phe Glu Glu Leu
    610                 615                 620

Cys Arg Asn Lys Asp Val Lys Lys Ala Ile Leu Glu Asp Met Val Arg
625                 630                 635                 640

Leu Gly Lys Asp Ser Gly Leu Lys Pro Phe Glu Gln Val Lys Gly Ile
                645                 650                 655

Thr Leu His Pro Glu Leu Phe Ser Ile Asp Asn Gly Leu Leu Thr Pro
            660                 665                 670

Thr Met Lys Ala Lys Arg Pro Glu Leu Arg Asn Tyr Phe Arg Ser Gln
        675                 680                 685

Ile Asp Asp Leu Tyr Ser Thr Ile Lys Val
    690                 695


<210> SEQ ID NO 81
<211> LENGTH: 737
<212> TYPE: DNA
<213> ORGANISM: human
<220> FEATURE:
<221> NAME/KEY: CDS
<222> LOCATION: (30)...(662)

<400> SEQUENCE: 81

ggagtttcgc cgccgcagtc ttcgccacc atg ccg ccc tac acc gtg gtc tat       53
                                Met Pro Pro Tyr Thr Val Val Tyr
                                 1               5

ttc cca gtt cga ggc cgc tgc gcg gcc ctg cgc atg ctg ctg gca gat      101
Phe Pro Val Arg Gly Arg Cys Ala Ala Leu Arg Met Leu Leu Ala Asp
     10                  15                  20

cag ggc cag agc tgg aag gag gag gtg gtg acc gtg gag acg tgg cag      149
Gln Gly Gln Ser Trp Lys Glu Glu Val Val Thr Val Glu Thr Trp Gln
 25                  30                  35                  40

gag ggc tca ctc aaa gcc tcc tgc cta tac ggg cag ctc ccc aag ttc      197
Glu Gly Ser Leu Lys Ala Ser Cys Leu Tyr Gly Gln Leu Pro Lys Phe
                 45                  50                  55

cag gac gga gac ctc acc ctg tac cag tcc aat acc atc ctg cgt cac      245
Gln Asp Gly Asp Leu Thr Leu Tyr Gln Ser Asn Thr Ile Leu Arg His
             60                  65                  70

ctg ggc cgc acc ctt ggg ctc tat ggg aag gac cag cag gag gca gcc      293
Leu Gly Arg Thr Leu Gly Leu Tyr Gly Lys Asp Gln Gln Glu Ala Ala
         75                  80                  85

ctg gtg gac atg gtg aat gac ggc gtg gag gac ctc cgc tgc aaa tac      341
Leu Val Asp Met Val Asn Asp Gly Val Glu Asp Leu Arg Cys Lys Tyr
     90                  95                 100
```

-continued

```
atc tcc ctc atc tac acc aac tat gag gcg ggc aag gat gac tat gtg      389
Ile Ser Leu Ile Tyr Thr Asn Tyr Glu Ala Gly Lys Asp Asp Tyr Val
105                 110                 115                 120

aag gca ctg ccc ggg caa ctg aag cct ttt gag acc ctg ctg tcc cag      437
Lys Ala Leu Pro Gly Gln Leu Lys Pro Phe Glu Thr Leu Leu Ser Gln
                125                 130                 135

aac cag gga ggc aag acc ttc att gtg gga gac cag atc tcc ttc gct      485
Asn Gln Gly Gly Lys Thr Phe Ile Val Gly Asp Gln Ile Ser Phe Ala
            140                 145                 150

gac tac aac ctg ctg gac ttg ctg ctg atc cat gag gtc cta gcc cct      533
Asp Tyr Asn Leu Leu Asp Leu Leu Leu Ile His Glu Val Leu Ala Pro
        155                 160                 165

ggc tgc ctg gat gcg ttc ccc ctg ctc tca gca tat gtg ggg cgc ctc      581
Gly Cys Leu Asp Ala Phe Pro Leu Leu Ser Ala Tyr Val Gly Arg Leu
    170                 175                 180

agc gcc cgg ccc aag ctc aag gcc ttc ctg gcc tcc cct gag tac gtg      629
Ser Ala Arg Pro Lys Leu Lys Ala Phe Leu Ala Ser Pro Glu Tyr Val
185                 190                 195                 200

aac ctc ccc atc aat ggc aac ggg aaa cag tga gggttggggg gactctgagc    682
Asn Leu Pro Ile Asn Gly Asn Gly Lys Gln  *
                205                 210

gggaggcaga gtttgccttc ctttctccag gaccaataaa atttctaaga gagct         737


<210> SEQ ID NO 82
<211> LENGTH: 210
<212> TYPE: PRT
<213> ORGANISM: human

<400> SEQUENCE: 82

Met Pro Pro Tyr Thr Val Val Tyr Phe Pro Val Arg Gly Arg Cys Ala
 1               5                  10                  15

Ala Leu Arg Met Leu Leu Ala Asp Gln Gly Gln Ser Trp Lys Glu Glu
            20                  25                  30

Val Val Thr Val Glu Thr Trp Gln Glu Gly Ser Leu Lys Ala Ser Cys
        35                  40                  45

Leu Tyr Gly Gln Leu Pro Lys Phe Gln Asp Gly Asp Leu Thr Leu Tyr
    50                  55                  60

Gln Ser Asn Thr Ile Leu Arg His Leu Gly Arg Thr Leu Gly Leu Tyr
65                  70                  75                  80

Gly Lys Asp Gln Gln Glu Ala Ala Leu Val Asp Met Val Asn Asp Gly
                85                  90                  95

Val Glu Asp Leu Arg Cys Lys Tyr Ile Ser Leu Ile Tyr Thr Asn Tyr
            100                 105                 110

Glu Ala Gly Lys Asp Asp Tyr Val Lys Ala Leu Pro Gly Gln Leu Lys
        115                 120                 125

Pro Phe Glu Thr Leu Leu Ser Gln Asn Gln Gly Gly Lys Thr Phe Ile
    130                 135                 140

Val Gly Asp Gln Ile Ser Phe Ala Asp Tyr Asn Leu Leu Asp Leu Leu
145                 150                 155                 160

Leu Ile His Glu Val Leu Ala Pro Gly Cys Leu Asp Ala Phe Pro Leu
                165                 170                 175

Leu Ser Ala Tyr Val Gly Arg Leu Ser Ala Arg Pro Lys Leu Lys Ala
            180                 185                 190

Phe Leu Ala Ser Pro Glu Tyr Val Asn Leu Pro Ile Asn Gly Asn Gly
        195                 200                 205

Lys Gln
    210
```

-continued

```
<210> SEQ ID NO 83
<211> LENGTH: 704
<212> TYPE: DNA
<213> ORGANISM: human
<220> FEATURE:
<221> NAME/KEY: CDS
<222> LOCATION: (104)...(568)

<400> SEQUENCE: 83

tgcagcggtg gtcggctgtt gggtgtggag tttcccagcg cccctcgggt ccgacccttt     60

gagcgttctg ctccggcgcc agcctacctc gctcctcggc gcc atg acc aca acc      115
                                                Met Thr Thr Thr
                                                 1

acc acc ttc aag gga gtc gac ccc aac agc agg aat agc tcc cga gtt      163
Thr Thr Phe Lys Gly Val Asp Pro Asn Ser Arg Asn Ser Ser Arg Val
 5                  10                  15                  20

ttg cgg cct cca ggt ggt gga tcc aat ttt tca tta ggt ttt gat gaa      211
Leu Arg Pro Pro Gly Gly Gly Ser Asn Phe Ser Leu Gly Phe Asp Glu
                25                  30                  35

cca aca gaa caa cct gtg agg aag aac aaa atg gcc tct aat atc ttt      259
Pro Thr Glu Gln Pro Val Arg Lys Asn Lys Met Ala Ser Asn Ile Phe
            40                  45                  50

ggg aca cct gaa gaa aat caa gct tct tgg gcc aag tca gca ggt gcc      307
Gly Thr Pro Glu Glu Asn Gln Ala Ser Trp Ala Lys Ser Ala Gly Ala
        55                  60                  65

aag tct agt ggt ggc agg gaa gac ttg gag tca tct gga ctg cag aga      355
Lys Ser Ser Gly Gly Arg Glu Asp Leu Glu Ser Ser Gly Leu Gln Arg
    70                  75                  80

agg aac tcc tct gaa gca agc tcc gga gac ttc tta gat ctg aag gga      403
Arg Asn Ser Ser Glu Ala Ser Ser Gly Asp Phe Leu Asp Leu Lys Gly
 85                  90                  95                 100

gaa ggt gat att cat gaa aat gtg gac aca gac ttg cca ggc agc ctg      451
Glu Gly Asp Ile His Glu Asn Val Asp Thr Asp Leu Pro Gly Ser Leu
                105                 110                 115

ggg cag agt gaa gag aag ccc gtg cct gct gcg cct gtg ccc agc ccg      499
Gly Gln Ser Glu Glu Lys Pro Val Pro Ala Ala Pro Val Pro Ser Pro
            120                 125                 130

gtg gcc ccg gcc cca gtg cca tcc aga aga aat ccc cct ggc ggc aag      547
Val Ala Pro Ala Pro Val Pro Ser Arg Arg Asn Pro Pro Gly Gly Lys
        135                 140                 145

tcc agc ctc gtc ttg ggt tag ctctgactgt cctgaacgct gtcgttctgt         598
Ser Ser Leu Val Leu Gly  *
    150

ctgtttcctc catgcttgag aactgcacaa cttgagcctg actgtacatc ttcttggatt    658

tgtttcatta aaaagaagca ctttatgtaa aaaaaaaaaa aaaaaa                   704


<210> SEQ ID NO 84
<211> LENGTH: 154
<212> TYPE: PRT
<213> ORGANISM: human

<400> SEQUENCE: 84

Met Thr Thr Thr Thr Thr Phe Lys Gly Val Asp Pro Asn Ser Arg Asn
 1               5                  10                  15

Ser Ser Arg Val Leu Arg Pro Pro Gly Gly Gly Ser Asn Phe Ser Leu
            20                  25                  30

Gly Phe Asp Glu Pro Thr Glu Gln Pro Val Arg Lys Asn Lys Met Ala
        35                  40                  45
```

-continued

```
Ser Asn Ile Phe Gly Thr Pro Glu Glu Asn Gln Ala Ser Trp Ala Lys
    50                  55                  60

Ser Ala Gly Ala Lys Ser Ser Gly Gly Arg Glu Asp Leu Glu Ser Ser
65                  70                  75                  80

Gly Leu Gln Arg Arg Asn Ser Ser Glu Ala Ser Ser Gly Asp Phe Leu
                85                  90                  95

Asp Leu Lys Gly Glu Gly Asp Ile His Glu Asn Val Asp Thr Asp Leu
            100                 105                 110

Pro Gly Ser Leu Gly Gln Ser Glu Glu Lys Pro Val Pro Ala Ala Pro
        115                 120                 125

Val Pro Ser Pro Val Ala Pro Ala Pro Val Pro Ser Arg Arg Asn Pro
    130                 135                 140

Pro Gly Gly Lys Ser Ser Leu Val Leu Gly
145                 150


<210> SEQ ID NO 85
<211> LENGTH: 748
<212> TYPE: DNA
<213> ORGANISM: human
<220> FEATURE:
<221> NAME/KEY: CDS
<222> LOCATION: (8)...(355)

<400> SEQUENCE: 85

ggccgcg atg agc ggg gag ccg ggg cag acg tcc gta gcg ccc cct ccc       49
        Met Ser Gly Glu Pro Gly Gln Thr Ser Val Ala Pro Pro Pro
          1               5                  10

gag gag gtc gag ccg ggc agt ggg gtc cgc atc gtg gtg gag tac tgt       97
Glu Glu Val Glu Pro Gly Ser Gly Val Arg Ile Val Val Glu Tyr Cys
 15                  20                  25                  30

gaa ccc tgc ggc ttc gag gcg acc tac ctg gag ctg gcc agt gct gtg      145
Glu Pro Cys Gly Phe Glu Ala Thr Tyr Leu Glu Leu Ala Ser Ala Val
                35                  40                  45

aag gag cag tat ccg ggc atc gag atc gag tcg cgc ctc ggg ggc aca      193
Lys Glu Gln Tyr Pro Gly Ile Glu Ile Glu Ser Arg Leu Gly Gly Thr
            50                  55                  60

ggt gcc ttt gag ata gag ata aat gga cag ctg gtg ttc tcc aag ctg      241
Gly Ala Phe Glu Ile Glu Ile Asn Gly Gln Leu Val Phe Ser Lys Leu
         65                  70                  75

gag aat ggg ggc ttt ccc tat gag aaa gat ctc att gag gcc atc cga      289
Glu Asn Gly Gly Phe Pro Tyr Glu Lys Asp Leu Ile Glu Ala Ile Arg
     80                  85                  90

aga gcc agt aat gga gaa acc cta gaa aag atc acc aac agc cgt cct      337
Arg Ala Ser Asn Gly Glu Thr Leu Glu Lys Ile Thr Asn Ser Arg Pro
 95                 100                 105                 110

ccc tgc gtc atc ctg tga ctgcacagga ctctgggttc ctgctctgtt             385
Pro Cys Val Ile Leu  *
                115

ctggggtcca aaccttggtc tccctttggt cctgctggga gctccccctg cctctttccc    445

ctacttagct ccttagcaaa gagaccctgg cctccacttt gccctttggg tacaaagaag    505

gaatagaaga ttccgtggcc ttgggggcag gagagagaca ctctccatga acacttctcc    565

agccacctca taccccttc ccagggtaag tgcccacgaa agcccagtcc actcttcgcc     625

tcggtaatac ctgtctgatg ccacagattt tatttattct cccctaaccc agggcaatgt    685

cagctattgg cagtaaagtg gcgctacaaa cactaaaaaa aaaaaaaaaa aaaaaaaaaa    745

aaa                                                                   748
```

-continued

<210> SEQ ID NO 86
<211> LENGTH: 115
<212> TYPE: PRT
<213> ORGANISM: human

<400> SEQUENCE: 86

```
Met Ser Gly Glu Pro Gly Gln Thr Ser Val Ala Pro Pro Pro Glu Glu
 1               5                  10                  15

Val Glu Pro Gly Ser Gly Val Arg Ile Val Val Glu Tyr Cys Glu Pro
            20                  25                  30

Cys Gly Phe Glu Ala Thr Tyr Leu Glu Leu Ala Ser Ala Val Lys Glu
        35                  40                  45

Gln Tyr Pro Gly Ile Glu Ile Glu Ser Arg Leu Gly Gly Thr Gly Ala
    50                  55                  60

Phe Glu Ile Glu Ile Asn Gly Gln Leu Val Phe Ser Lys Leu Glu Asn
65                  70                  75                  80

Gly Gly Phe Pro Tyr Glu Lys Asp Leu Ile Glu Ala Ile Arg Arg Ala
                85                  90                  95

Ser Asn Gly Glu Thr Leu Glu Lys Ile Thr Asn Ser Arg Pro Pro Cys
            100                 105                 110

Val Ile Leu
        115
```

<210> SEQ ID NO 87
<211> LENGTH: 3020
<212> TYPE: DNA
<213> ORGANISM: human
<220> FEATURE:
<221> NAME/KEY: CDS
<222> LOCATION: (111)...(1295)

<400> SEQUENCE: 87

```
tgaagctcgt cagttcacca tccgccctcg gcttccgcgg ggcgctgggc cgccagcctc      60

ggcaccgtcc tttcctttct ccctcgcgtt aggcaggtga cagcagggac atg tct        116
                                                       Met Ser
                                                        1

cgg gag atg cag gat gta gac ctc gct gag gtg aag cct ttg gtg gag       164
Arg Glu Met Gln Asp Val Asp Leu Ala Glu Val Lys Pro Leu Val Glu
         5                  10                  15

aaa ggg gag acc atc acc ggc ctc ctg caa gag ttt gat gtc cag gag       212
Lys Gly Glu Thr Ile Thr Gly Leu Leu Gln Glu Phe Asp Val Gln Glu
     20                  25                  30

cag gac atc gag act tta cat ggc tct gtt cac gtc acg ctg tgt ggg       260
Gln Asp Ile Glu Thr Leu His Gly Ser Val His Val Thr Leu Cys Gly
 35                  40                  45                  50

act ccc aag gga aac cgg cct gtc atc ctc acc tac cat gac atc ggc       308
Thr Pro Lys Gly Asn Arg Pro Val Ile Leu Thr Tyr His Asp Ile Gly
                55                  60                  65

atg aac cac aaa acc tgc tac aac ccc ctc ttc aac tac gag gac atg       356
Met Asn His Lys Thr Cys Tyr Asn Pro Leu Phe Asn Tyr Glu Asp Met
            70                  75                  80

cag gag atc acc cag cac ttt gcc gtc tgc cac gtg gac gcc cct ggc       404
Gln Glu Ile Thr Gln His Phe Ala Val Cys His Val Asp Ala Pro Gly
         85                  90                  95

cag cag gac ggc gca gcc tcc ttc ccc gca ggg tac atg tac ccc tcc       452
Gln Gln Asp Gly Ala Ala Ser Phe Pro Ala Gly Tyr Met Tyr Pro Ser
    100                 105                 110

atg gat cag ctg gct gaa atg ctt cct gga gtc ctt caa cag ttt ggg       500
Met Asp Gln Leu Ala Glu Met Leu Pro Gly Val Leu Gln Gln Phe Gly
115                 120                 125                 130
```

-continued

```
ctg aaa agc att att ggc atg gga aca gga gca ggc gcc tac acc cta      548
Leu Lys Ser Ile Ile Gly Met Gly Thr Gly Ala Gly Ala Tyr Thr Leu
                135                 140                 145

act cga ttt gct cta aac aac cct gag atg gtg gag ggc ctt gtc ctt      596
Thr Arg Phe Ala Leu Asn Asn Pro Glu Met Val Glu Gly Leu Val Leu
            150                 155                 160

atc aac gtg aac cct tgt gcg gaa ggc tgg atg gac tgg gcc gcc tcc      644
Ile Asn Val Asn Pro Cys Ala Glu Gly Trp Met Asp Trp Ala Ala Ser
        165                 170                 175

aag atc tca gga tgg acc caa gct ctg ccg gac atg gtg gtg tcc cac      692
Lys Ile Ser Gly Trp Thr Gln Ala Leu Pro Asp Met Val Val Ser His
    180                 185                 190

ctt ttt ggg aag gaa gaa atg cag agt aac gtg gaa gtg gtc cac acc      740
Leu Phe Gly Lys Glu Glu Met Gln Ser Asn Val Glu Val Val His Thr
195                 200                 205                 210

tac cgc cag cac att gtg aat gac atg aac ccc ggc aac ctg cac ctg      788
Tyr Arg Gln His Ile Val Asn Asp Met Asn Pro Gly Asn Leu His Leu
                215                 220                 225

ttc atc aat gcc tac aac agc cgg cgc gac ctg gag att gag cga cca      836
Phe Ile Asn Ala Tyr Asn Ser Arg Arg Asp Leu Glu Ile Glu Arg Pro
            230                 235                 240

atg ccg gga acc cac aca gtc acc ctg cag tgc cct gct ctg ttg gtg      884
Met Pro Gly Thr His Thr Val Thr Leu Gln Cys Pro Ala Leu Leu Val
        245                 250                 255

gtt ggg gac agc tcg cct gca gtg gat gcc gtg gtg gag tgc aac tca      932
Val Gly Asp Ser Ser Pro Ala Val Asp Ala Val Val Glu Cys Asn Ser
    260                 265                 270

aaa ttg gac cca aca aag acc act ctc ctc aag atg gcg gac tgt ggc      980
Lys Leu Asp Pro Thr Lys Thr Thr Leu Leu Lys Met Ala Asp Cys Gly
275                 280                 285                 290

ggc ctc ccg cag atc tcc cag ccg gcc aag ctc gct gag gcc ttc aag     1028
Gly Leu Pro Gln Ile Ser Gln Pro Ala Lys Leu Ala Glu Ala Phe Lys
                295                 300                 305

tac ttc gtg cag ggc atg gga tac atg ccc tcg gct agc atg acc cgc     1076
Tyr Phe Val Gln Gly Met Gly Tyr Met Pro Ser Ala Ser Met Thr Arg
            310                 315                 320

ctg atg cgg tcc cgc aca gcc tct ggt tcc agc gtc act tct ctg gat     1124
Leu Met Arg Ser Arg Thr Ala Ser Gly Ser Ser Val Thr Ser Leu Asp
        325                 330                 335

ggc acc cgc agc cgc tcc cac acc agc gag ggc acc cga agc cgc tcc     1172
Gly Thr Arg Ser Arg Ser His Thr Ser Glu Gly Thr Arg Ser Arg Ser
    340                 345                 350

cac acc agc gag ggc acc cgc agc cgc tcg cac acc agc gag ggg gcc     1220
His Thr Ser Glu Gly Thr Arg Ser Arg Ser His Thr Ser Glu Gly Ala
355                 360                 365                 370

cac ctg gac atc acc ccc aac tcg ggt gct gct ggg aac agc gcc ggg     1268
His Leu Asp Ile Thr Pro Asn Ser Gly Ala Ala Gly Asn Ser Ala Gly
                375                 380                 385

ccc aag tcc atg gag gtc tcc tgc tag gcggcctgcc cagctgccgc           1315
Pro Lys Ser Met Glu Val Ser Cys  *
            390

ccccggactc tgatctctgt agtggccccc tcctccccgg ccccttttcg ccccctgcct   1375

gccatactgc gcctaactcg gtattaatcc aaagcttatt ttgtaagagt gagctctggt   1435

ggagacaaat gaggtctatt acgtgggtgc cctctccaaa ggcggggtgg cggtggacca   1495

aaggaaggaa gcaagcatct ccgcatcgca tcctcttcca ttaaccagtg gccggttgcc   1555

actctcctcc cctccctcag agacaccaaa ctgccaaaaa caagacgcgt agcagcacac   1615
```

-continued

```
acttcacaaa gccaagccta ggccgccctg agcatcctgg ttcaaacggg tgcctggtca   1675

gaaggccagc cgcccacttc ccgtttcctc tttaactgag gagaagctga tccagctttc   1735

cggaaacaaa atccttttct tcatttgggg aggggggtaa tagtgacatg caggcacctc   1795

ttttaaacag gcaaaacagg aagggggaaa aggtgggatt catgtcgagg ctagaggcat   1855

ttggaacaac aaatctacgt agttaacttg aagaaaccga tttttaaagt tggtgcatct   1915

agaaagcttt gaatgcagaa gcaaacaagc ttgatttttc tagcatcctc ttaatgtgca   1975

gcaaaagcag gcaacaaaat ctcctggctt tacagacaaa aatatttcag caaacgttgg   2035

gcatcatggt ttttgaaggc tttagttctg ctttctgcct ctcctccaca gccccaacct   2095

cccacccctg atacatgagc cagtgattat tcttgttcag ggagaagatc atttagattt   2155

gttttgcatt ccttagaatg gagggcaaca ttccacagct gccctggctg tgatgagtgt   2215

ccttgcaggg gccggagtag gagcactggg gtgggggcgg aattggggtt actcgatgta   2275

agggattcct tgttgttgtg ttgagatcca gtgcagttgt gatttctgtg gatcccagct   2335

tggtccagga attttgagag attggcttaa atccagtttt caatcttcga cagctgggct   2395

ggaacgtgaa ctcagtagct gaacctgtct gacccggtca cgttcttgga tcctcagaac   2455

tctttgctct tgtcggggtg ggggtgggaa ctcacgtggg gagcggtggc tgagaaaatg   2515

taaggattct ggaatacata ttccatggac tttccttccc tctcctgctt cctcttttcc   2575

tgctccctaa cctttcgccg aatggggcag acaaacactg acgtttctgg gtggccagtg   2635

cggctgccag gttcctgtac tactgccttg tacttttcat tttggctcac cgtggatttt   2695

ctcataggaa gtttggtcag agtgaattga atattgtaag tcagccactg ggacccgagg   2755

atttctggga ccccgcagtt gggaggagga agtagtccag ccttccaggt gggcgtgaga   2815

ggcaatgact cgttacctgc cgcccatcac cttggaggcc ttccctggcc ttgagtagaa   2875

aagtcgggga tcggggcaag agaggctgag tacggatggg aaactattgt gcacaagtct   2935

ttccagagga gtttcttaat gagatatttg tatttatttc cagaccaata aatttgtaac   2995

tttgcaaaaa aaaaaaaaaa aaaaa                                         3020
```

<210> SEQ ID NO 88
<211> LENGTH: 394
<212> TYPE: PRT
<213> ORGANISM: human

<400> SEQUENCE: 88

```
Met Ser Arg Glu Met Gln Asp Val Asp Leu Ala Glu Val Lys Pro Leu
 1               5                  10                  15

Val Glu Lys Gly Glu Thr Ile Thr Gly Leu Leu Gln Glu Phe Asp Val
            20                  25                  30

Gln Glu Gln Asp Ile Glu Thr Leu His Gly Ser Val His Val Thr Leu
        35                  40                  45

Cys Gly Thr Pro Lys Gly Asn Arg Pro Val Ile Leu Thr Tyr His Asp
    50                  55                  60

Ile Gly Met Asn His Lys Thr Cys Tyr Asn Pro Leu Phe Asn Tyr Glu
65                  70                  75                  80

Asp Met Gln Glu Ile Thr Gln His Phe Ala Val Cys His Val Asp Ala
                85                  90                  95

Pro Gly Gln Gln Asp Gly Ala Ala Ser Phe Pro Ala Gly Tyr Met Tyr
            100                 105                 110

Pro Ser Met Asp Gln Leu Ala Glu Met Leu Pro Gly Val Leu Gln Gln
        115                 120                 125
```

-continued

```
Phe Gly Leu Lys Ser Ile Ile Gly Met Gly Thr Gly Ala Gly Ala Tyr
    130                 135                 140

Thr Leu Thr Arg Phe Ala Leu Asn Asn Pro Glu Met Val Glu Gly Leu
145                 150                 155                 160

Val Leu Ile Asn Val Asn Pro Cys Ala Glu Gly Trp Met Asp Trp Ala
                165                 170                 175

Ala Ser Lys Ile Ser Gly Trp Thr Gln Ala Leu Pro Asp Met Val Val
            180                 185                 190

Ser His Leu Phe Gly Lys Glu Glu Met Gln Ser Asn Val Glu Val Val
        195                 200                 205

His Thr Tyr Arg Gln His Ile Val Asn Asp Met Asn Pro Gly Asn Leu
    210                 215                 220

His Leu Phe Ile Asn Ala Tyr Asn Ser Arg Arg Asp Leu Glu Ile Glu
225                 230                 235                 240

Arg Pro Met Pro Gly Thr His Thr Val Thr Leu Gln Cys Pro Ala Leu
                245                 250                 255

Leu Val Val Gly Asp Ser Ser Pro Ala Val Asp Ala Val Val Glu Cys
            260                 265                 270

Asn Ser Lys Leu Asp Pro Thr Lys Thr Thr Leu Leu Lys Met Ala Asp
        275                 280                 285

Cys Gly Gly Leu Pro Gln Ile Ser Gln Pro Ala Lys Leu Ala Glu Ala
    290                 295                 300

Phe Lys Tyr Phe Val Gln Gly Met Gly Tyr Met Pro Ser Ala Ser Met
305                 310                 315                 320

Thr Arg Leu Met Arg Ser Arg Thr Ala Ser Gly Ser Ser Val Thr Ser
                325                 330                 335

Leu Asp Gly Thr Arg Ser Arg Ser His Thr Ser Glu Gly Thr Arg Ser
            340                 345                 350

Arg Ser His Thr Ser Glu Gly Thr Arg Ser Arg Ser His Thr Ser Glu
        355                 360                 365

Gly Ala His Leu Asp Ile Thr Pro Asn Ser Gly Ala Ala Gly Asn Ser
    370                 375                 380

Ala Gly Pro Lys Ser Met Glu Val Ser Cys
385                 390


<210> SEQ ID NO 89
<211> LENGTH: 2401
<212> TYPE: DNA
<213> ORGANISM: human
<220> FEATURE:
<221> NAME/KEY: CDS
<222> LOCATION: (301)...(762)

<400> SEQUENCE: 89

gcgtccccga agaggccggg aacggagccc aggaaaaact acaactccca ggaggcgtcg      60

ggagggccgg cccggagcca gcggaagaaa ctacaactcc cagaaggcgt cgggcgtgcc     120

ggcgcggggc ggtgacgtac ggggaccggc gcggagcgct gattcggccg gagctgccag     180

cggggaggct gcagccgcgg gttgttacag ctgctggagc agcagcggcc cccgctcccg     240

ggaaccgttc ccgggccgtt gatcttcggc cccacacgaa cagcagagag gggcagcagg     300

atg aat gtg ggc aca gcg cac agc gag gtg aac ccc aac acg cgg gtg       348
Met Asn Val Gly Thr Ala His Ser Glu Val Asn Pro Asn Thr Arg Val
 1               5                  10                  15

atg aac agc cgt ggc atc tgg ctc tcc tac gtg ctg gcc atc ggt ctc       396
Met Asn Ser Arg Gly Ile Trp Leu Ser Tyr Val Leu Ala Ile Gly Leu
```

-continued

```
            20                  25                  30

ctc cac atc gtg ctg ctg agc atc ccg ttt gtg agt gtc cct gtc gtc      444
Leu His Ile Val Leu Leu Ser Ile Pro Phe Val Ser Val Pro Val Val
        35                  40                  45

tgg acc ctc acc aac ctc att cac aac atg ggc atg tat atc ttc ctg      492
Trp Thr Leu Thr Asn Leu Ile His Asn Met Gly Met Tyr Ile Phe Leu
    50                  55                  60

cac acg gtg aag ggg aca ccc ttt gag acc ccg gac cag ggc aag gcg      540
His Thr Val Lys Gly Thr Pro Phe Glu Thr Pro Asp Gln Gly Lys Ala
 65                  70                  75                  80

agg ctg cta acc cac tgg gag cag atg gat tat ggg gtc cag ttc acg      588
Arg Leu Leu Thr His Trp Glu Gln Met Asp Tyr Gly Val Gln Phe Thr
                85                  90                  95

gcc tct cgg aag ttc ttg acc atc aca ccc atc gtg ctg tac ttc ctc      636
Ala Ser Arg Lys Phe Leu Thr Ile Thr Pro Ile Val Leu Tyr Phe Leu
            100                 105                 110

acc agc ttc tac act aag tac gac cag atc cat ttt gtg ctc aac acc      684
Thr Ser Phe Tyr Thr Lys Tyr Asp Gln Ile His Phe Val Leu Asn Thr
        115                 120                 125

gtg tcc ctg atg agc gtg ctt atc ccc aag ctg ccc cag ctc cac gga      732
Val Ser Leu Met Ser Val Leu Ile Pro Lys Leu Pro Gln Leu His Gly
    130                 135                 140

gtc cgg att ttt gga atc aat aag tac tga gagtgcagcc ccttcccctg        782
Val Arg Ile Phe Gly Ile Asn Lys Tyr  *
145                 150

cccagggtgg caggggaggg gtagggtaaa aggcatgtgc tgcaacactg aagacagaaa    842

gaagaagcct ctggacactg ccagagatgg gggttgagcc tctggcctaa tttccccccct   902

cgcttccccc agtagccaac ttggagtagc ttgtagtggg gttggggtag gccccctggg    962

ctctgacctt ttctgaattt tttgatcttt tccttttgct ttttgaatag agactccatg   1022

gagttggtca tggaatgggc tgggctcctg ggctgaacat ggaccacgca gttgcgacag   1082

gaggccaggg gaaaaacccc tgctcacttg tttgccctca ggcagccaaa gcactttaac   1142

ccctgcatag ggagcagagg gcggtacggc ttctggattg tttcactgtg attcctaggt   1202

tttttcgatg ccacgcagtg tgtgcttttg tgtatggaag caagtgtggg atgggtcttt   1262

gcctttctgg gtagggagct gtctaatcca agtcccaggc ttttggcagc ttctctgcaa   1322

cccaccgtgg gtcctggttg ggagtgggga gggtcaggtt ggggaaagat ggggtagagt   1382

gtagatggct tggttccaga ggtgaggggg ccagggctgc tgccatcctg gcctggtgga   1442

ggttggggag ctgtaggaga gctagtgagt cgagacttag aagaatgggg ccacatagca   1502

gcagaggact ggtgtaaggg agggaggggt agggacagaa gctagaccca atctcctttg   1562

ggatgtgggc agggagggaa gcaggcttgg agggttaatt tacccacaga atgtgatagt   1622

aataggggag ggaggctgct gtgggtttaa ctcctgggtt ggctgttggg tagacaggtg   1682

gggaaaaggc ccgtgagtca ttgtaagcac aggtccaact tggccctgac tcctgcgggg   1742

gtatggggaa gctgtgacag aaacgatggg tgctgtggtc ctctgcaggc cctcacccct   1802

taacttcctc atacagactg gcactgggca gggcctctca tgtggcagcc acatgtggcg   1862

ttgtgaggcc accccatgtg gggtctgtgg tgagagtcct gtaggatccc tgctcaagca   1922

gcacagagga aggggcaaga cgtggcctgt aggcactgtc tcagcctgca gagaagaaag   1982

tgaggccggg agcctgagcc tgggctggag ccttctcccc tccccagttg gactaggggc   2042

agtgttaatt ttgaaaaggt gtgggtccct gtgtcctctt ccaggggtcc aagggaacag   2102

gagaggtcac tgggcctgtt ttctccctcc tgaccctgca tctcccaccc cgtgtatcat   2162
```

-continued

```
agggaacttt caccttaaaa tctttctaag caaagtgtga ataggatttt tactcccttt   2222

gtacagtatt ctgagaaacg caaataaaag ggcaacatgt ttctgtttcc ctgtgtctgg   2282

ccttcgcttc ctggaaggct gaggggaggg ggcaggggtg tgggcagcgg ctcccgctga   2342

ggtgctggtg gggcatcagt gcagctctga cggtggcagg aggggcgctg ggactgctg    2401
```

```
<210> SEQ ID NO 90
<211> LENGTH: 153
<212> TYPE: PRT
<213> ORGANISM: human

<400> SEQUENCE: 90

Met Asn Val Gly Thr Ala His Ser Glu Val Asn Pro Asn Thr Arg Val
 1               5                  10                  15

Met Asn Ser Arg Gly Ile Trp Leu Ser Tyr Val Leu Ala Ile Gly Leu
            20                  25                  30

Leu His Ile Val Leu Leu Ser Ile Pro Phe Val Ser Val Pro Val Val
        35                  40                  45

Trp Thr Leu Thr Asn Leu Ile His Asn Met Gly Met Tyr Ile Phe Leu
    50                  55                  60

His Thr Val Lys Gly Thr Pro Phe Glu Thr Pro Asp Gln Gly Lys Ala
65                  70                  75                  80

Arg Leu Leu Thr His Trp Glu Gln Met Asp Tyr Gly Val Gln Phe Thr
                85                  90                  95

Ala Ser Arg Lys Phe Leu Thr Ile Thr Pro Ile Val Leu Tyr Phe Leu
            100                 105                 110

Thr Ser Phe Tyr Thr Lys Tyr Asp Gln Ile His Phe Val Leu Asn Thr
        115                 120                 125

Val Ser Leu Met Ser Val Leu Ile Pro Lys Leu Pro Gln Leu His Gly
    130                 135                 140

Val Arg Ile Phe Gly Ile Asn Lys Tyr
145                 150
```

```
<210> SEQ ID NO 91
<211> LENGTH: 778
<212> TYPE: DNA
<213> ORGANISM: human
<220> FEATURE:
<221> NAME/KEY: CDS
<222> LOCATION: (52)...(711)

<400> SEQUENCE: 91

caggttggaa accagtgccc caggcggcga ggagagcggt gccttgcagg g atg ctg      57
                                                          Met Leu
                                                           1

cgg gcg gga gca cca acc ggg gac tta ccc cgg gcg gga gaa gtc cac      105
Arg Ala Gly Ala Pro Thr Gly Asp Leu Pro Arg Ala Gly Glu Val His
         5                  10                  15

acc ggg acc acc atc atg gca gtg gag ttt gac ggg ggc gtt gtg atg      153
Thr Gly Thr Thr Ile Met Ala Val Glu Phe Asp Gly Gly Val Val Met
     20                  25                  30

ggt tct gat tcc cga gtg tct gca ggc gag gcg gtg gtg aac cga gtg      201
Gly Ser Asp Ser Arg Val Ser Ala Gly Glu Ala Val Val Asn Arg Val
 35                  40                  45                  50

ttt gac aag ctg tcc ccg ctg cac gag cgc atc tac tgt gca ctc tct      249
Phe Asp Lys Leu Ser Pro Leu His Glu Arg Ile Tyr Cys Ala Leu Ser
                55                  60                  65

ggt tca gct gct gat gcc caa gcc gtg gcc gac atg gcc gcc tac cag      297
```

-continued

```
Gly Ser Ala Ala Asp Ala Gln Ala Val Ala Asp Met Ala Ala Tyr Gln
            70                  75                  80

ctg gag ctc cat ggg ata gaa ctg gag gaa cct cca ctt gtt ttg gct      345
Leu Glu Leu His Gly Ile Glu Leu Glu Glu Pro Pro Leu Val Leu Ala
        85                  90                  95

gct gca aat gtg gtg aga aat atc agc tat aaa tat cga gag gac ttg      393
Ala Ala Asn Val Val Arg Asn Ile Ser Tyr Lys Tyr Arg Glu Asp Leu
    100                 105                 110

tct gca cat ctc atg gta gct ggc tgg gac caa cgt gaa gga ggt cag      441
Ser Ala His Leu Met Val Ala Gly Trp Asp Gln Arg Glu Gly Gly Gln
115                 120                 125                 130

gta tat gga acc ctg gga gga atg ctg act cga cag cct ttt gcc att      489
Val Tyr Gly Thr Leu Gly Gly Met Leu Thr Arg Gln Pro Phe Ala Ile
                135                 140                 145

ggt ggc tcc ggc agc acc ttt atc tat ggt tat gtg gat gca gca tat      537
Gly Gly Ser Gly Ser Thr Phe Ile Tyr Gly Tyr Val Asp Ala Ala Tyr
            150                 155                 160

aag cca ggc atg tct ccc gag gag tgc agg cgc ttc acc aca gac gct      585
Lys Pro Gly Met Ser Pro Glu Glu Cys Arg Arg Phe Thr Thr Asp Ala
        165                 170                 175

att gct ctg gcc atg agc cgg gat ggc tca agc ggg ggt gtc atc tac      633
Ile Ala Leu Ala Met Ser Arg Asp Gly Ser Ser Gly Gly Val Ile Tyr
    180                 185                 190

ctg gtc act att aca gct gcc ggt gtg gac cat cga gtc atc ttg ggc      681
Leu Val Thr Ile Thr Ala Ala Gly Val Asp His Arg Val Ile Leu Gly
195                 200                 205                 210

aat gaa ctg cca aaa ttc tat gat gag tga accttcccca gacttctctt        731
Asn Glu Leu Pro Lys Phe Tyr Asp Glu  *
                215

tcttattttg taataaactc tctagggcca aaaaaaaaaa aaaaaaa                  778


<210> SEQ ID NO 92
<211> LENGTH: 219
<212> TYPE: PRT
<213> ORGANISM: human

<400> SEQUENCE: 92

Met Leu Arg Ala Gly Ala Pro Thr Gly Asp Leu Pro Arg Ala Gly Glu
 1               5                  10                  15

Val His Thr Gly Thr Thr Ile Met Ala Val Glu Phe Asp Gly Gly Val
            20                  25                  30

Val Met Gly Ser Asp Ser Arg Val Ser Ala Gly Glu Ala Val Val Asn
        35                  40                  45

Arg Val Phe Asp Lys Leu Ser Pro Leu His Glu Arg Ile Tyr Cys Ala
    50                  55                  60

Leu Ser Gly Ser Ala Ala Asp Ala Gln Ala Val Ala Asp Met Ala Ala
65                  70                  75                  80

Tyr Gln Leu Glu Leu His Gly Ile Glu Leu Glu Glu Pro Pro Leu Val
                85                  90                  95

Leu Ala Ala Ala Asn Val Val Arg Asn Ile Ser Tyr Lys Tyr Arg Glu
            100                 105                 110

Asp Leu Ser Ala His Leu Met Val Ala Gly Trp Asp Gln Arg Glu Gly
        115                 120                 125

Gly Gln Val Tyr Gly Thr Leu Gly Gly Met Leu Thr Arg Gln Pro Phe
    130                 135                 140

Ala Ile Gly Gly Ser Gly Ser Thr Phe Ile Tyr Gly Tyr Val Asp Ala
145                 150                 155                 160
```

-continued

```
Ala Tyr Lys Pro Gly Met Ser Pro Glu Glu Cys Arg Arg Phe Thr Thr
                165                 170                 175

Asp Ala Ile Ala Leu Ala Met Ser Arg Asp Gly Ser Ser Gly Gly Val
            180                 185                 190

Ile Tyr Leu Val Thr Ile Thr Ala Ala Gly Val Asp His Arg Val Ile
        195                 200                 205

Leu Gly Asn Glu Leu Pro Lys Phe Tyr Asp Glu
    210                 215


<210> SEQ ID NO 93
<211> LENGTH: 1374
<212> TYPE: DNA
<213> ORGANISM: human
<220> FEATURE:
<221> NAME/KEY: CDS
<222> LOCATION: (103)...(1047)

<400> SEQUENCE: 93

ggacagcttg gagatagggc ccggaattgc gggcgtcact ctgctcctgc gacctagcca      60

ggcgtgaggg agtgacagca gcgcattcgc gggacgagag cg atg agt gag aac        114
                                               Met Ser Glu Asn
                                                 1

gcc gca cca ggt ctg atc tca gag ctg aag ctg gct gtg ccc tgg ggc       162
Ala Ala Pro Gly Leu Ile Ser Glu Leu Lys Leu Ala Val Pro Trp Gly
 5                  10                  15                  20

cac atc gca gcc aaa gcc tgg ggc tcc ctg cag ggc cct cca gtt ctc       210
His Ile Ala Ala Lys Ala Trp Gly Ser Leu Gln Gly Pro Pro Val Leu
                25                  30                  35

tgc ctg cac ggc tgg ctg gac aat gcc agc tcc ttc gac aga ctc atc       258
Cys Leu His Gly Trp Leu Asp Asn Ala Ser Ser Phe Asp Arg Leu Ile
            40                  45                  50

cct ctt ctc ccg caa gac ttt tat tac gtt gcc atg gat ttc gga ggt       306
Pro Leu Leu Pro Gln Asp Phe Tyr Tyr Val Ala Met Asp Phe Gly Gly
        55                  60                  65

cat ggg ctc tcg tcc cat tac agc cca ggt gtc cca tat tac ctc cag       354
His Gly Leu Ser Ser His Tyr Ser Pro Gly Val Pro Tyr Tyr Leu Gln
     70                  75                  80

act ttt gtg agt gag atc cga aga gtt gtg gca gcc ttg aaa tgg aat       402
Thr Phe Val Ser Glu Ile Arg Arg Val Val Ala Ala Leu Lys Trp Asn
 85                  90                  95                 100

cga ttc tcc att ctg ggc cac agc ttc ggt ggc gtc gtg ggc gga atg       450
Arg Phe Ser Ile Leu Gly His Ser Phe Gly Gly Val Val Gly Gly Met
                105                 110                 115

ttt ttc tgt acc ttc ccc gag atg gtg gat aaa ctt atc ttg ctg gac       498
Phe Phe Cys Thr Phe Pro Glu Met Val Asp Lys Leu Ile Leu Leu Asp
            120                 125                 130

acg ccg ctc ttt ctc ctg gaa tca gat gaa atg gag aac ttg ctg acc       546
Thr Pro Leu Phe Leu Leu Glu Ser Asp Glu Met Glu Asn Leu Leu Thr
        135                 140                 145

tac aag cgg aga gcc ata gag cac gtg ctg cag gta gag gcc tcc cag       594
Tyr Lys Arg Arg Ala Ile Glu His Val Leu Gln Val Glu Ala Ser Gln
    150                 155                 160

gag ccc tcg cac gtg ttc agc ctg aag cag ctg ctg cag agg tta ctg       642
Glu Pro Ser His Val Phe Ser Leu Lys Gln Leu Leu Gln Arg Leu Leu
165                 170                 175                 180

aag agc aat agc cac ttg agt gag gag tgc ggg gag ctt ctc ctg caa       690
Lys Ser Asn Ser His Leu Ser Glu Glu Cys Gly Glu Leu Leu Leu Gln
                185                 190                 195

aga gga acc acg aag gtg gcc aca ggt ctg gtt ctg aac aga gac cag       738
Arg Gly Thr Thr Lys Val Ala Thr Gly Leu Val Leu Asn Arg Asp Gln
```

-continued

```
            200                 205                 210

agg ctc gcc tgg gca gag aac agc att gac ttc atc agc agg gag ctg      786
Arg Leu Ala Trp Ala Glu Asn Ser Ile Asp Phe Ile Ser Arg Glu Leu
        215                 220                 225

tgt gcg cat tcc atc agg aag ctg cag gcc cat gtc ctg ttg atc aaa      834
Cys Ala His Ser Ile Arg Lys Leu Gln Ala His Val Leu Leu Ile Lys
    230                 235                 240

gca gtc cac gga tat ttt gat tca aga cag aat tac tct gag aag gag      882
Ala Val His Gly Tyr Phe Asp Ser Arg Gln Asn Tyr Ser Glu Lys Glu
245                 250                 255                 260

tcc ctg tcg ttc atg ata gac acg atg aaa tcc acc ctc aaa gag cag      930
Ser Leu Ser Phe Met Ile Asp Thr Met Lys Ser Thr Leu Lys Glu Gln
                265                 270                 275

ttc cag ttt gtg gaa gtc cca ggc aat cac tgt gtc cac atg agc gaa      978
Phe Gln Phe Val Glu Val Pro Gly Asn His Cys Val His Met Ser Glu
            280                 285                 290

ccc cag cac gtg gcc agt atc atc agc tcc ttc tta cag tgc aca cac     1026
Pro Gln His Val Ala Ser Ile Ile Ser Ser Phe Leu Gln Cys Thr His
        295                 300                 305

atg ctc cca gcc cag ctg tag ctctgggcct ggaactatga agacctagtg        1077
Met Leu Pro Ala Gln Leu  *
    310

ctcccagact caacactggg actctgagtt cctgagcccc acaacaaggc cagggatggt   1137

ggggacaggc ctcactagtc ttgaggccca gcctaggatg gtagtcaggg gaaggagcga   1197

gattccaact tcaacatctg tgacctcaag gggagacag agtctgggtt ccagggctgc    1257

tttctcctgg ctaataataa atatccagcc agctggagga aggaagggca ggctgggccc   1317

acctagcctt tccctgctgc ccaactggat ggaaaataaa aggttcttgt attctca      1374


<210> SEQ ID NO 94
<211> LENGTH: 314
<212> TYPE: PRT
<213> ORGANISM: human

<400> SEQUENCE: 94

Met Ser Glu Asn Ala Ala Pro Gly Leu Ile Ser Glu Leu Lys Leu Ala
 1               5                  10                  15

Val Pro Trp Gly His Ile Ala Ala Lys Ala Trp Gly Ser Leu Gln Gly
            20                  25                  30

Pro Pro Val Leu Cys Leu His Gly Trp Leu Asp Asn Ala Ser Ser Phe
        35                  40                  45

Asp Arg Leu Ile Pro Leu Leu Pro Gln Asp Phe Tyr Tyr Val Ala Met
    50                  55                  60

Asp Phe Gly Gly His Gly Leu Ser Ser His Tyr Ser Pro Gly Val Pro
65                  70                  75                  80

Tyr Tyr Leu Gln Thr Phe Val Ser Glu Ile Arg Arg Val Val Ala Ala
                85                  90                  95

Leu Lys Trp Asn Arg Phe Ser Ile Leu Gly His Ser Phe Gly Gly Val
            100                 105                 110

Val Gly Gly Met Phe Phe Cys Thr Phe Pro Glu Met Val Asp Lys Leu
        115                 120                 125

Ile Leu Leu Asp Thr Pro Leu Phe Leu Leu Glu Ser Asp Glu Met Glu
    130                 135                 140

Asn Leu Leu Thr Tyr Lys Arg Arg Ala Ile Glu His Val Leu Gln Val
145                 150                 155                 160

Glu Ala Ser Gln Glu Pro Ser His Val Phe Ser Leu Lys Gln Leu Leu
```

-continued

```
                165                 170                 175

Gln Arg Leu Leu Lys Ser Asn Ser His Leu Ser Glu Glu Cys Gly Glu
            180                 185                 190

Leu Leu Leu Gln Arg Gly Thr Thr Lys Val Ala Thr Gly Leu Val Leu
        195                 200                 205

Asn Arg Asp Gln Arg Leu Ala Trp Ala Glu Asn Ser Ile Asp Phe Ile
    210                 215                 220

Ser Arg Glu Leu Cys Ala His Ser Ile Arg Lys Leu Gln Ala His Val
225                 230                 235                 240

Leu Leu Ile Lys Ala Val His Gly Tyr Phe Asp Ser Arg Gln Asn Tyr
                245                 250                 255

Ser Glu Lys Glu Ser Leu Ser Phe Met Ile Asp Thr Met Lys Ser Thr
            260                 265                 270

Leu Lys Glu Gln Phe Gln Phe Val Glu Val Pro Gly Asn His Cys Val
        275                 280                 285

His Met Ser Glu Pro Gln His Val Ala Ser Ile Ile Ser Ser Phe Leu
    290                 295                 300

Gln Cys Thr His Met Leu Pro Ala Gln Leu
305                 310


<210> SEQ ID NO 95
<211> LENGTH: 598
<212> TYPE: DNA
<213> ORGANISM: human
<220> FEATURE:
<221> NAME/KEY: CDS
<222> LOCATION: (23)...(421)

<400> SEQUENCE: 95

cagagtcact cctgccttca cc atg aag tcc agc ggc ctc ttc ccc ttc ctg      52
                         Met Lys Ser Ser Gly Leu Phe Pro Phe Leu
                          1               5                  10

gtg ctg ctt gcc ctg gga act ctg gca cct tgg gct gtg gaa ggc tct      100
Val Leu Leu Ala Leu Gly Thr Leu Ala Pro Trp Ala Val Glu Gly Ser
                15                  20                  25

gga aag tcc ttc aaa gct gga gtc tgt cct cct aag aaa tct gcc cag      148
Gly Lys Ser Phe Lys Ala Gly Val Cys Pro Pro Lys Lys Ser Ala Gln
            30                  35                  40

tgc ctt aga tac aag aaa cct gag tgc cag agt gac tgg cag tgt cca      196
Cys Leu Arg Tyr Lys Lys Pro Glu Cys Gln Ser Asp Trp Gln Cys Pro
        45                  50                  55

ggg aag aag aga tgt tgt cct gac act tgt ggc atc aaa tgc ctg gat      244
Gly Lys Lys Arg Cys Cys Pro Asp Thr Cys Gly Ile Lys Cys Leu Asp
    60                  65                  70

cct gtt gac acc cca aac cca aca agg agg aag cct ggg aag tgc cca      292
Pro Val Asp Thr Pro Asn Pro Thr Arg Arg Lys Pro Gly Lys Cys Pro
 75                  80                  85                  90

gtg act tat ggc caa tgt ttg atg ctt aac ccc ccc aat ttc tgt gag      340
Val Thr Tyr Gly Gln Cys Leu Met Leu Asn Pro Pro Asn Phe Cys Glu
                95                  100                 105

atg gat ggc cag tgc aag cgt gac ttg aag tgt tgc atg ggc atg tgt      388
Met Asp Gly Gln Cys Lys Arg Asp Leu Lys Cys Cys Met Gly Met Cys
            110                 115                 120

ggg aaa tcc tgc gtt tcc cct gtg aaa gct tga ttcctgccat atggaggagg    441
Gly Lys Ser Cys Val Ser Pro Val Lys Ala  *
        125                 130

ctctggagtc ctgctctgtg tggtccaggt cctttccacc ctgagacttg gctccaccac    501

tgatatcctc ctttggggaa aggcttggca cacagcaggc tttcaagaag tgccagttga    561
```

-continued

```
tcaatgaata aataaacgag cctatttctc tttgcac                        598


<210> SEQ ID NO 96
<211> LENGTH: 132
<212> TYPE: PRT
<213> ORGANISM: human

<400> SEQUENCE: 96

Met Lys Ser Ser Gly Leu Phe Pro Phe Leu Val Leu Leu Ala Leu Gly
 1               5                  10                  15

Thr Leu Ala Pro Trp Ala Val Glu Gly Ser Gly Lys Ser Phe Lys Ala
            20                  25                  30

Gly Val Cys Pro Pro Lys Lys Ser Ala Gln Cys Leu Arg Tyr Lys Lys
        35                  40                  45

Pro Glu Cys Gln Ser Asp Trp Gln Cys Pro Gly Lys Lys Arg Cys Cys
    50                  55                  60

Pro Asp Thr Cys Gly Ile Lys Cys Leu Asp Pro Val Asp Thr Pro Asn
65                  70                  75                  80

Pro Thr Arg Arg Lys Pro Gly Lys Cys Pro Val Thr Tyr Gly Gln Cys
                85                  90                  95

Leu Met Leu Asn Pro Pro Asn Phe Cys Glu Met Asp Gly Gln Cys Lys
            100                 105                 110

Arg Asp Leu Lys Cys Cys Met Gly Met Cys Gly Lys Ser Cys Val Ser
        115                 120                 125

Pro Val Lys Ala
    130
```